US011759563B2

(12) United States Patent
Zollinger et al.

(10) Patent No.: US 11,759,563 B2
(45) Date of Patent: Sep. 19, 2023

(54) MANIFOLDS FOR A MEDICAL WASTE COLLECTION ASSEMBLY AND METHODS OF COLLECTING A TISSUE SAMPLE WITH THE SAME

(71) Applicant: Stryker Corporation, Kalamazoo, MI (US)

(72) Inventors: Michael Zollinger, Chelsea, MI (US); Michael Peterson, Richland, MI (US)

(73) Assignee: STRYKER CORPORATION, Kalamazoo, MI (US)

( * ) Notice: Subject to any disclaimer, the term of this patent is extended or adjusted under 35 U.S.C. 154(b) by 281 days.

(21) Appl. No.: 17/053,246

(22) PCT Filed: May 17, 2019

(86) PCT No.: PCT/US2019/032911
§ 371 (c)(1),
(2) Date: Nov. 5, 2020

(87) PCT Pub. No.: WO2019/222655
PCT Pub. Date: Nov. 21, 2019

(65) Prior Publication Data
US 2021/0162101 A1    Jun. 3, 2021

Related U.S. Application Data

(60) Provisional application No. 62/746,802, filed on Oct. 17, 2018, provisional application No. 62/685,792, (Continued)

(51) Int. Cl.
*A61M 1/00*        (2006.01)
(52) U.S. Cl.
CPC ......... *A61M 1/79* (2021.05); *A61M 2205/125* (2013.01); *A61M 2210/1433* (2013.01)

(58) Field of Classification Search
CPC ....... A61B 10/0283; A61B 10/02; A61M 1/79
See application file for complete search history.

(56) References Cited

U.S. PATENT DOCUMENTS 4,376,053 A * 3/1983 Bullock ................. B01D 29/01
                                              D23/209
4,643,197 A   2/1987 Greene et al.
(Continued)

FOREIGN PATENT DOCUMENTS

WO    2005079947 A2   9/2005
WO    2013090579 A1   6/2013
(Continued)

OTHER PUBLICATIONS

Partial International Search Report for Application No. PCT/US2020/059288 dated Feb. 18, 2021, 2 pages.
(Continued)

*Primary Examiner* — Susan S Su
*Assistant Examiner* — Ted Yang
(74) *Attorney, Agent, or Firm* — Howard & Howard Attorneys PLLC

(57) ABSTRACT

A manifold for collecting a tissue sample with a medical waste collection assembly. A base portion of a housing is removably engaged with a manifold receiver to provide a suction path from an inlet fitting receiving a suction line. A tray may be removably positioned within an accessory sleeve. Locating features facilitate defining a gap between a base portion of the tray and a lower barrier of the accessory sleeve. The tray may include a control surface to move the manifold between a sealing configuration, and a bleed configuration in which a second suction path is provided through the gap and below the tray. A backflow prevention (Continued)

valve may be disposed within the suction path between the tray and a filter element. Methods for collecting the tissue sample are also disclosed.

7 Claims, 70 Drawing Sheets

Related U.S. Application Data filed on Jun. 15, 2018, provisional application No. 62/673,418, filed on May 18, 2018.

(56) References Cited

U.S. PATENT DOCUMENTS

| | | | |
|---|---|---|---|
| 5,256,160 A | 10/1993 | Clement | |
| 5,624,418 A | 4/1997 | Shepard | |
| 7,244,236 B2 | 7/2007 | Merkle | |
| 7,556,622 B2 | 7/2009 | Mark et al. | |
| 7,615,037 B2 | 11/2009 | Murray et al. | |
| 7,621,898 B2 | 11/2009 | Lalomia et al. | |
| 7,715,037 B2 | 5/2010 | Castellani et al. | |
| 7,775,973 B2 * | 8/2010 | Okada | A61B 1/00128 606/115 |
| 8,088,079 B2 * | 1/2012 | Kaye | A61B 10/0283 600/562 |
| 8,216,199 B2 | 7/2012 | Murray et al. | |
| 8,465,439 B2 * | 6/2013 | Parks | A61M 1/60 604/319 |
| 8,518,002 B2 | 8/2013 | Murray et al. | |
| 8,740,866 B2 | 6/2014 | Reasoner et al. | |
| 8,877,146 B2 | 11/2014 | Williamson, IV et al. | |
| 8,915,897 B2 | 12/2014 | Murray et al. | |
| 9,089,801 B1 | 7/2015 | Gavlak et al. | |
| 9,579,428 B1 | 2/2017 | Reasoner et al. | |
| 9,671,318 B1 * | 6/2017 | Bedoe | A61B 10/02 |
| 9,782,524 B2 | 10/2017 | Reasoner et al. | |
| 10,471,188 B1 | 11/2019 | Zollinger et al. | |
| 2006/0189950 A1 | 8/2006 | Rogers et al. | |
| 2007/0191731 A1 * | 8/2007 | Kaye | A61B 10/0283 600/565 |
| 2008/0082021 A1 * | 4/2008 | Ichikawa | A61B 10/0096 600/104 |
| 2009/0112118 A1 * | 4/2009 | Quick, Jr. | A61B 10/0275 600/564 |
| 2010/0160824 A1 * | 6/2010 | Parihar | A61B 10/0096 600/567 |
| 2015/0065913 A1 * | 3/2015 | Keller | A61B 10/0266 600/566 |
| 2017/0311935 A1 * | 11/2017 | Choung | A61B 10/0275 |
| 2019/0343493 A1 | 11/2019 | McCabe | |

FOREIGN PATENT DOCUMENTS

| | | | |
|---|---|---|---|
| WO | WO-2013090579 A1 * | 6/2013 | ......... A61B 10/0045 |
| WO | 2018170233 A1 | 9/2018 | |
| WO | 2019222655 A2 | 11/2019 | |
| WO | 2020209898 A1 | 10/2020 | |

OTHER PUBLICATIONS

International Search Report for Application No. PCT/US2019/032911 dated Dec. 3, 2019, 4 pages.

* cited by examiner

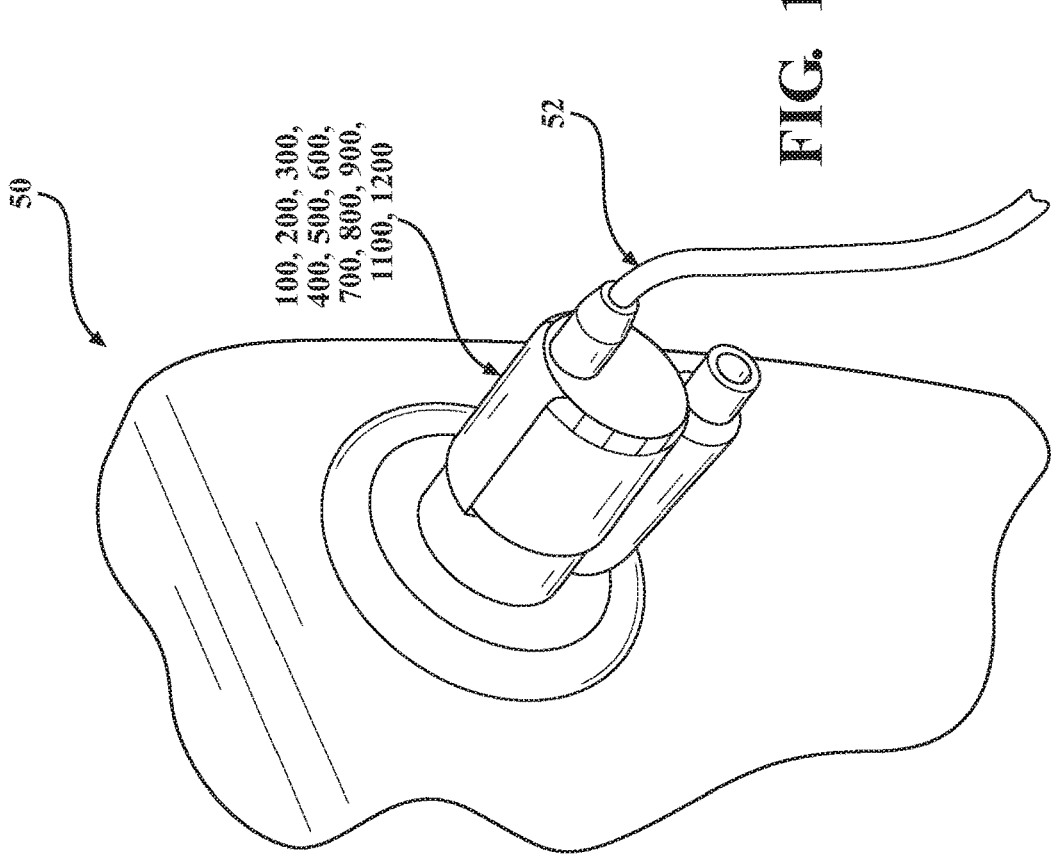

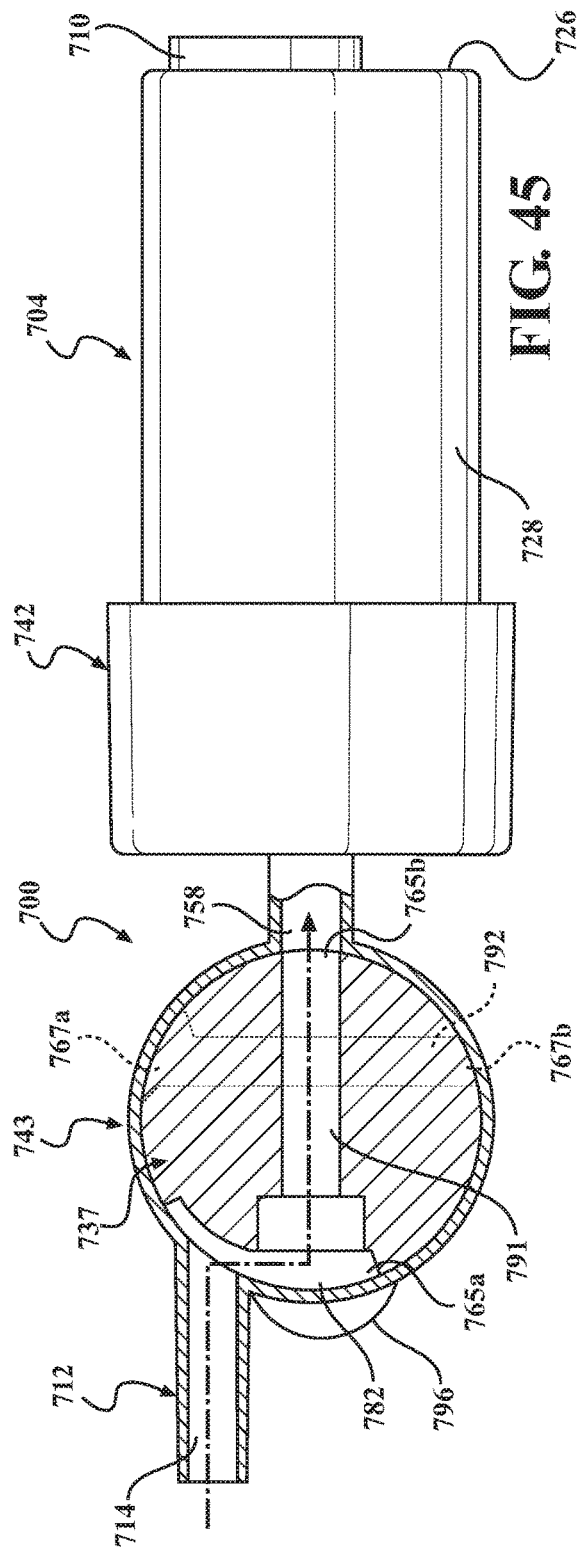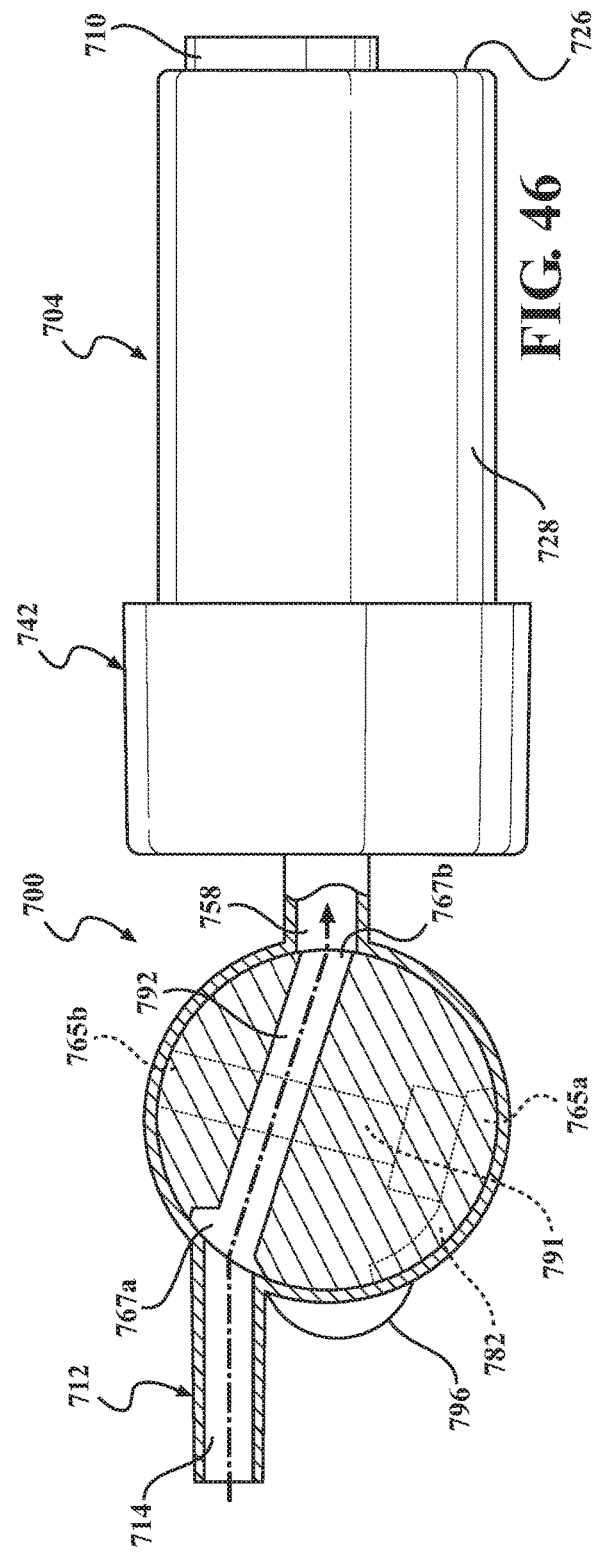

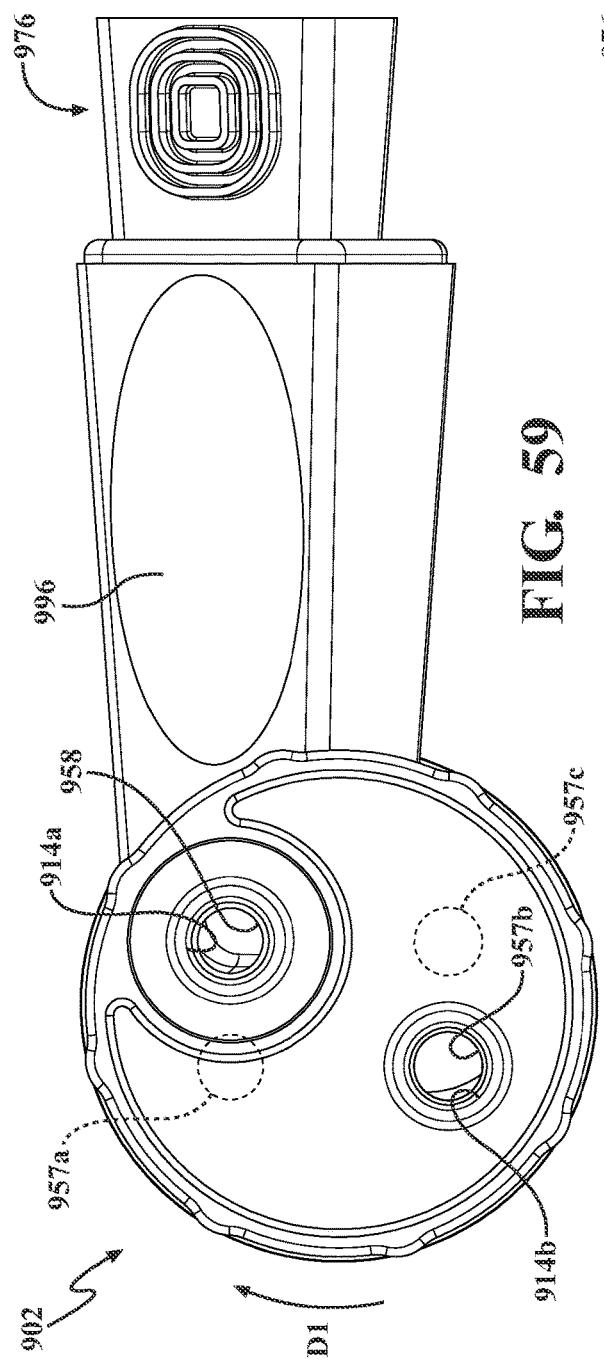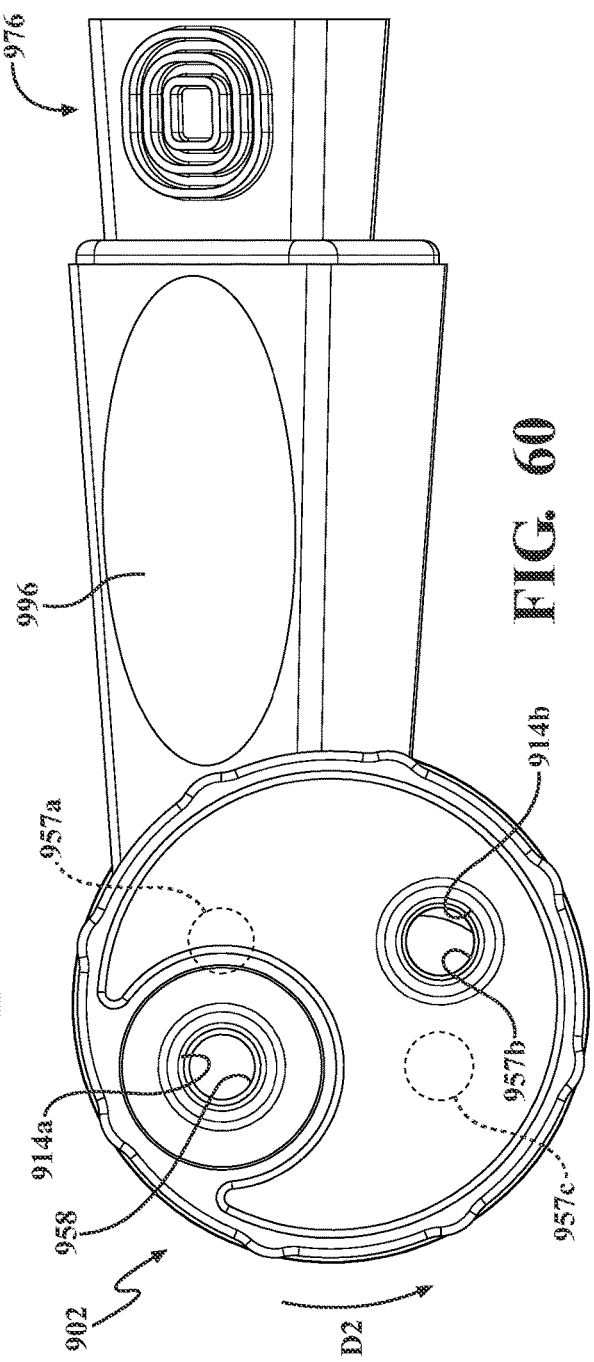

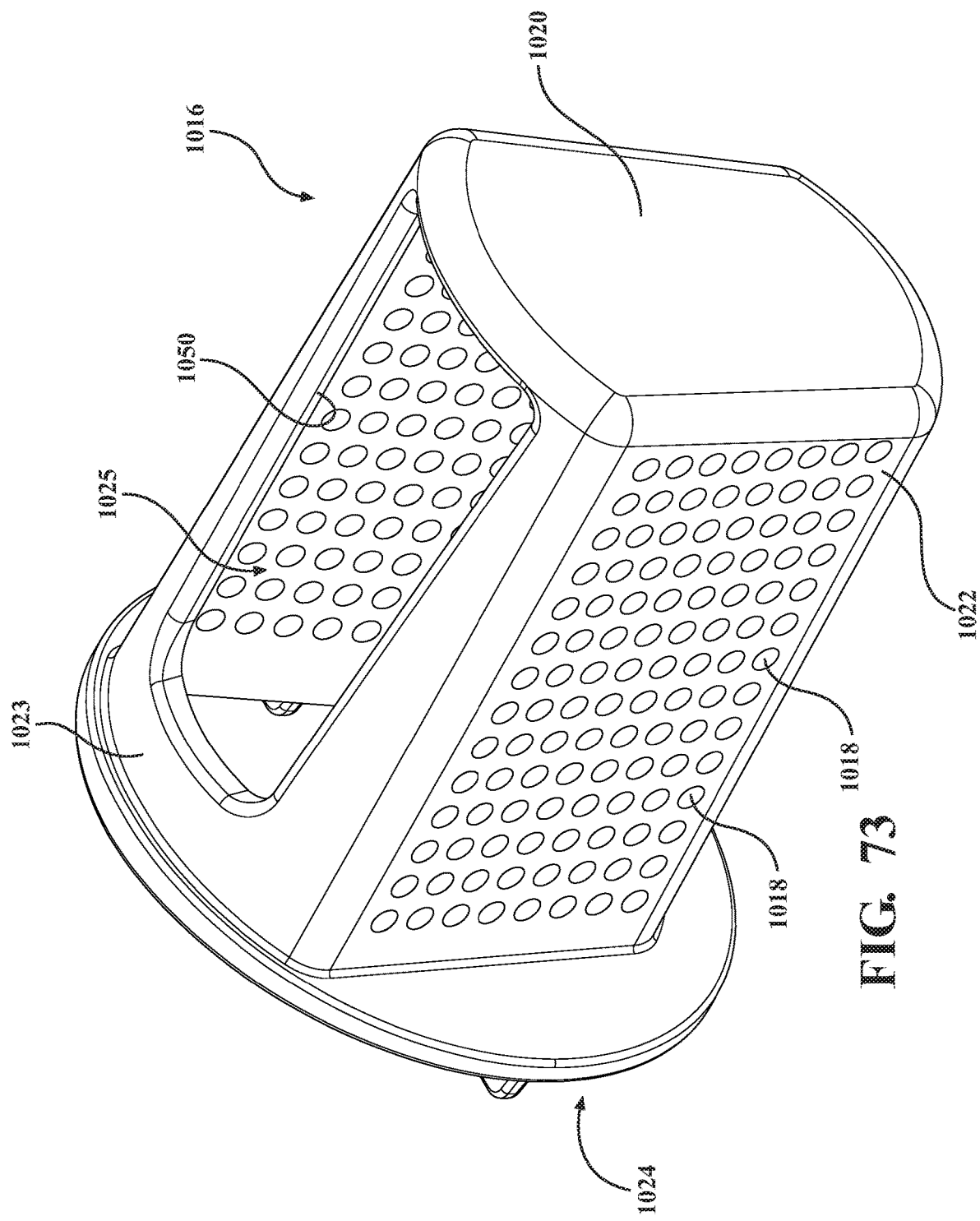

MANIFOLDS FOR A MEDICAL WASTE COLLECTION ASSEMBLY AND METHODS OF COLLECTING A TISSUE SAMPLE WITH THE SAME

CROSS REFERENCE TO RELATED APPLICATIONS

This is a national stage application of International Patent Application No. PCT/US2019/032911, filed on May 17, 2019, which claims priority to and all the benefits of U.S. Provisional Patent Application No. 62/673,418, filed on May 18, 2018, U.S. Provisional Patent Application No. 62/685,792, filed Jun. 15, 2018, and U.S. Provisional Patent Application No. 62/746,802, filed Oct. 17, 2018, the entire contents of each are hereby incorporated by reference.

TECHNICAL FIELD

The present disclosure is generally directed to devices, systems, and methods for surgical procedures, and more specifically, but not exclusively, surgical procedures involving collecting a tissue sample under suction with a medical waste collection assembly.

BACKGROUND

Certain surgical procedures include the removal of a tissue sample for evaluation. For example, a polypectomy procedure involves removal of a polyp from surgical site within the patient, such as the colon or the endometrial tissue that lines the uterus. Often the polyp is aspirated with suction applied at surgical site with a medical waste collection assembly. Retrieving the polyp once collected in the suction path is an area of particular interest and development. Many known systems and methods are associated with several shortcomings, including increased time and inconvenience during the surgical procedure, potential exposure to hazardous medical waste, inability to collect multiple tissue samples, among others. Therefore, there is a need in the art for an improved manifold and methods for collecting the tissue sample with the manifold and the medical waste collection assembly.

BRIEF DESCRIPTION OF THE DRAWINGS

Advantages of the present disclosure will be readily appreciated as the same becomes better understood by reference to the following detailed description when considered in connection with the accompanying drawings.

FIG. 1 is a schematic representation of a portion of a medical waste collection assembly with a manifold positioned within a manifold receiver of the medical waste collection assembly.

FIG. 2 is a partial sectional view of the manifold engaging the manifold receiver including a suction inlet.

FIG. 45 is a partial sectional view of the manifold of FIG. 41 with a schematic representation of the suction path with the rotor in the tissue collecting position.

FIG. 46 is a partial sectional view of the manifold of FIG. 41 with a schematic representation of the suction path with the rotor in the bypass position.

FIG. 59 is a front elevation view of the manifold of FIG. 55 with a schematic representation of the manifold in a tissue collecting position.

FIG. 60 is a front elevation view of the manifold of FIG. 55 with a schematic representation of the manifold in a bypass position.

FIG. 73 is a rear perspective view of a filter element including a window to permit retrieval of the tissue sample through the access feature.

SUMMARY OF THE DISCLOSURE

Figure 3:
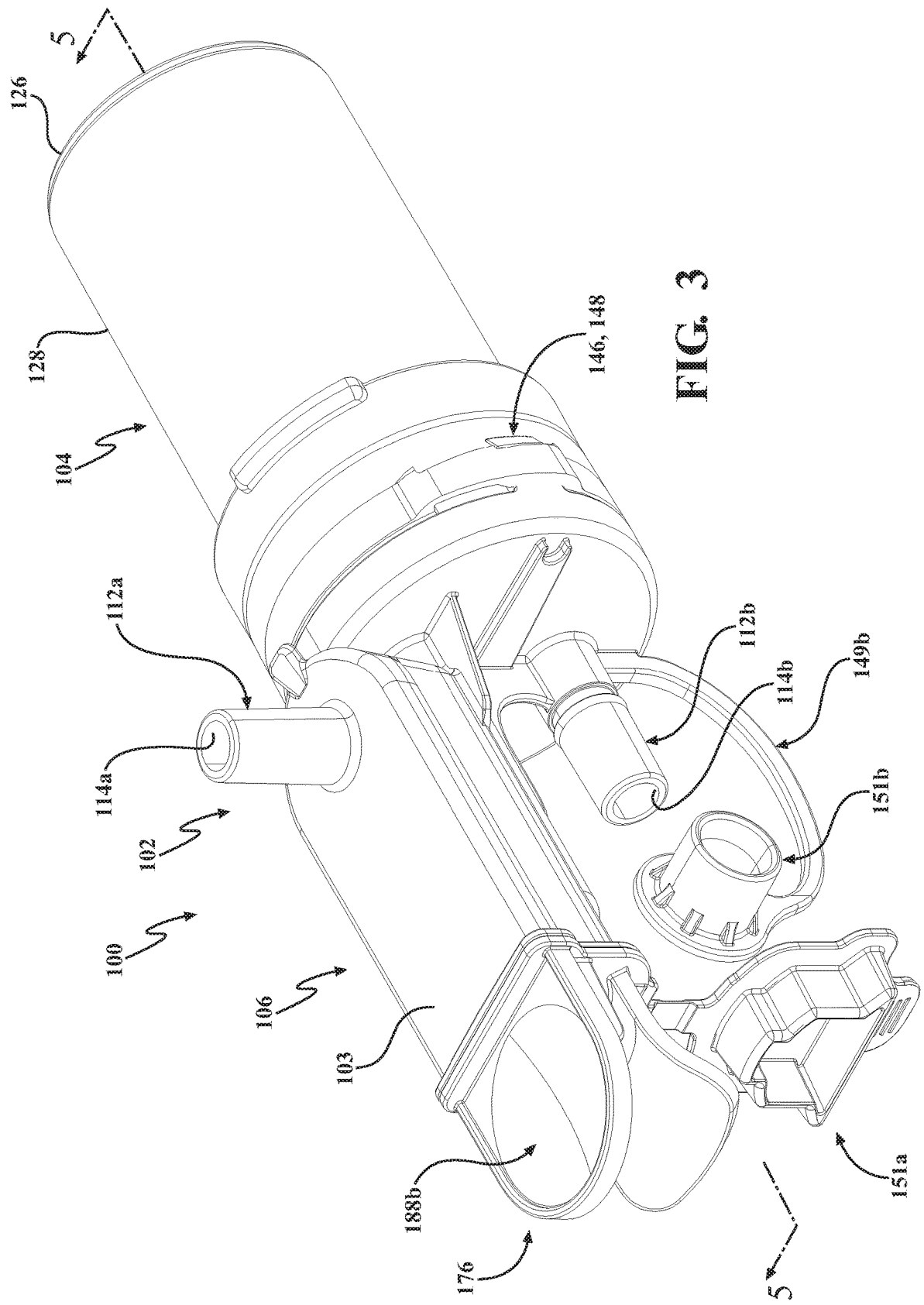
FIG. 3 is a perspective view of a manifold.

A manifold for collecting a tissue sample through a suction line. A housing defines a manifold volume, an inlet bore in fluid communication with the manifold volume and adapted to be in fluid communication with the suction line, an accessory opening into an accessory sleeve in fluid communication with the manifold volume, and an outlet opening adapted to be in fluid communication with a suction source to provide a first suction path from the suction line to the outlet opening through the accessory sleeve and the manifold volume. The housing includes locating features disposed within the accessory sleeve. The manifold includes a tray including a control surface, a sealing surface coupled to the control surface, a base portion, and side portion coupled to the base portion with the base and the side portions extending from the sealing surface and defining a tissue collecting cavity, and porous features within the base portion. The tray is adapted to be removably coupled with the housing such that (i) the sealing surface seals the accessory opening, (ii) the tissue collecting cavity is positioned within the accessory sleeve and opening towards the inlet bore, and (iii) the base portion and/or the side portion engages the locating features within the accessory sleeve to provide a gap between the base portion of the tray and a lower barrier of the housing defining the accessory sleeve. The tray is adapted to receive an input from a user to move the sealing surface away from a portion of the accessory opening near the lower barrier to provide and locate a second suction path from the accessory opening to the outlet opening through the gap between the base portion of the tray and the lower barrier of the housing defining the accessory sleeve.

A manifold for collecting a tissue sample through a suction line. The manifold includes a housing defining a manifold volume, an inlet bore in fluid communication with the manifold volume and adapted to be in fluid communication with the suction line, an accessory opening into an accessory sleeve in fluid communication with the manifold volume, a trough within the accessory sleeve extending to the accessory opening, and an outlet opening adapted to be in fluid communication a suction source to provide a suction path from the suction line to the outlet opening through the accessory sleeve and the manifold volume. The manifold includes a tray including a control surface, a sealing surface coupled to the control surface, a base portion, and side portion coupled to the base portion with the base and the side portions extending from the sealing surface and defining a tissue collecting cavity, and porous features within the base portion. The tray is adapted to be removably coupled with the housing in a sealing configuration in which (i) the sealing surface seals the accessory opening, (ii) the tissue collecting cavity is positioned within the accessory sleeve and opening towards the inlet bore, and (iii) a gap is defined between the base portion of the tray and the trough within the accessory sleeve. The control surface of the tray is adapted to receive an input from a user to actuate the manifold from the sealing configuration to a bleed configuration in which a portion of the sealing surface moves away from a portion of the accessory opening to provide and locate a second suction path from the accessory opening to the outlet opening through the trough and the manifold volume.

A method for collecting a tissue sample through a suction line coupled to a manifold. The manifold includes a housing defining a manifold volume, an inlet bore in fluid communication with the manifold volume in fluid communication with the suction line, an accessory opening into an accessory sleeve in fluid communication with the manifold volume, locating features disposed within the accessory sleeve, an outlet opening in fluid communication with a suction source. The manifold includes a tray including a control surface, a sealing surface coupled to the control surface, a base portion, and side portion coupled to the base portion with the base and the side portions extending from the sealing surface and defining a tissue collecting cavity, and porous features within the base portion. The tray is coupled with the housing such that tissue collecting cavity is within the accessory sleeve and opens towards the inlet bore, the sealing surface seals the accessory opening, and the base portion and/or the side portion engages the locating features within the accessory sleeve to provide a gap between the base portion of the tray and a lower barrier of the housing defining the accessory sleeve. A first suction path from the suction line to the outlet opening through the accessory sleeve and the manifold volume is provided. The suction source is operated to collect the tissue sample within the tissue collecting cavity of the tray with the porous features. An input is applied to the control surface of the tray to move at least a portion of the sealing surface away from a portion of the accessory opening near the lower barrier to provide and locate a second suction path from the accessory opening to the outlet opening through the gap between the base portion of the tray and the lower barrier of the housing.

DETAILED DESCRIPTION

The aspiration of a tissue sample from within the patient may be facilitated with a medical waste collection assembly 50, represented schematically in FIG. 1. Exemplary medical waste collection assemblies suitable for aspiration are the Neptune 2® and Neptune 3® Waste Management Systems manufactured by Stryker Corporation (Kalamazoo, Mich.), and disclosed in commonly owned U.S. Pat. Nos. 7,621,898, 8,216,199, 8,740,866, 8,915,897, 9,579,428, and 9,782,524, the entire contents of each are hereby incorporated by reference. The medical waste collection assembly 50, in a broadest sense, includes a vacuum pump adapted to be placed in fluid communication with a proximal end of a suction line 52. A distal end of the suction line 52 is coupled to an instrument positioned near the surgical site. The desired tissue sample is resected, for example with a snare technique, and the resected tissue sample is aspirated into suction line 52 towards the medical waste collection assembly 50.

The aspiration of semisolid and solid matter, including the tissue sample, must be captured or suitably filtered avoid potential clogging of components of the medical waste collection assembly 50. With concurrent reference to FIG. 2, the medical waste collection assembly 50 engages a manifold 100, 200, 300, 400, 500, 600, 700, 800, 900, 1000, 1100 (hereinafter 100-1100). The medical waste collection assembly 50 includes a manifold receiver 54 adapted to be removably engaged with the manifold 100-1100. The manifold receiver 54 may define a void 56 sized to receive a proximal portion of the manifold 100-1100. The medical waste collection assembly 50 further includes a suction inlet 58 adapted to be in fluid communication with an outlet opening of the manifold 100-1100 when the manifold 100-1100 is engaged with the manifold receiver 54. The manifold receiver 54 may include a valve disc 60 that is rotatable to align a bore 62 with the suction inlet 58 when the outlet opening engages and rotates a boss 64 defining the bore 62. Specifics of the interface between the manifold 100-1100 and the manifold receiver 54 are disclosed within commonly owned U.S. Pat. Nos. 7,615,037, 8,518,002, 8,915,897, and 9,579,428, the entire contents of each are hereby incorporated by reference.

The manifold 100-1100 is adapted to receive the suction line 52, as shown in FIG. 1. With the manifold 100-1100 engaging the manifold receiver 54, a suction path is established from the suction line 52 to the medical waste collection assembly 50 through the manifold 100-1100. The manifold 100-1100, among other functions to be described, captures the semisolid and solid matter entrained within the stream being aspirated from the surgical site.

Figure 4:
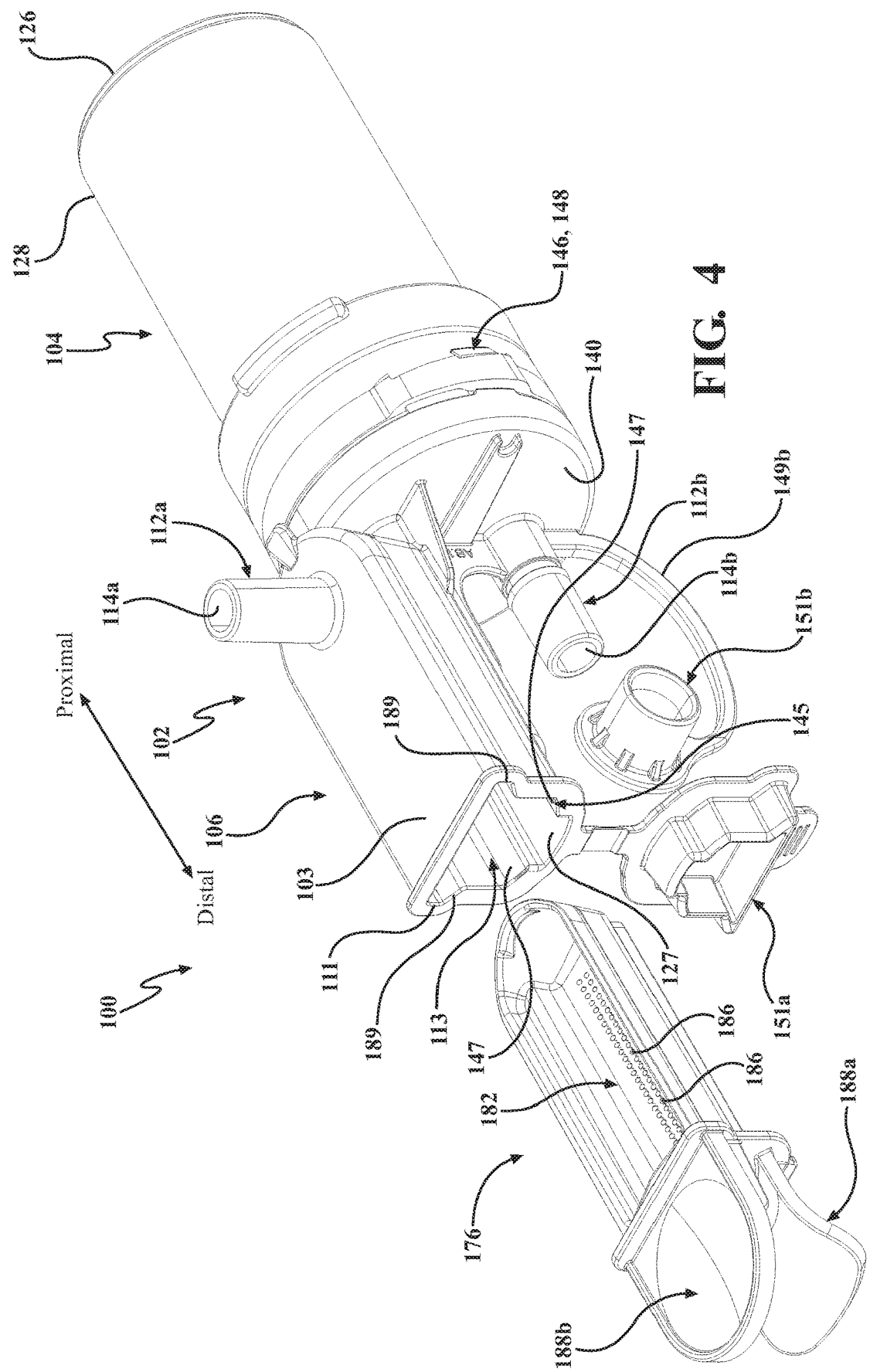
FIG. 4 is a perspective view of the manifold of FIG. 3 with a tray removed from an accessory sleeve.
Figure 5:
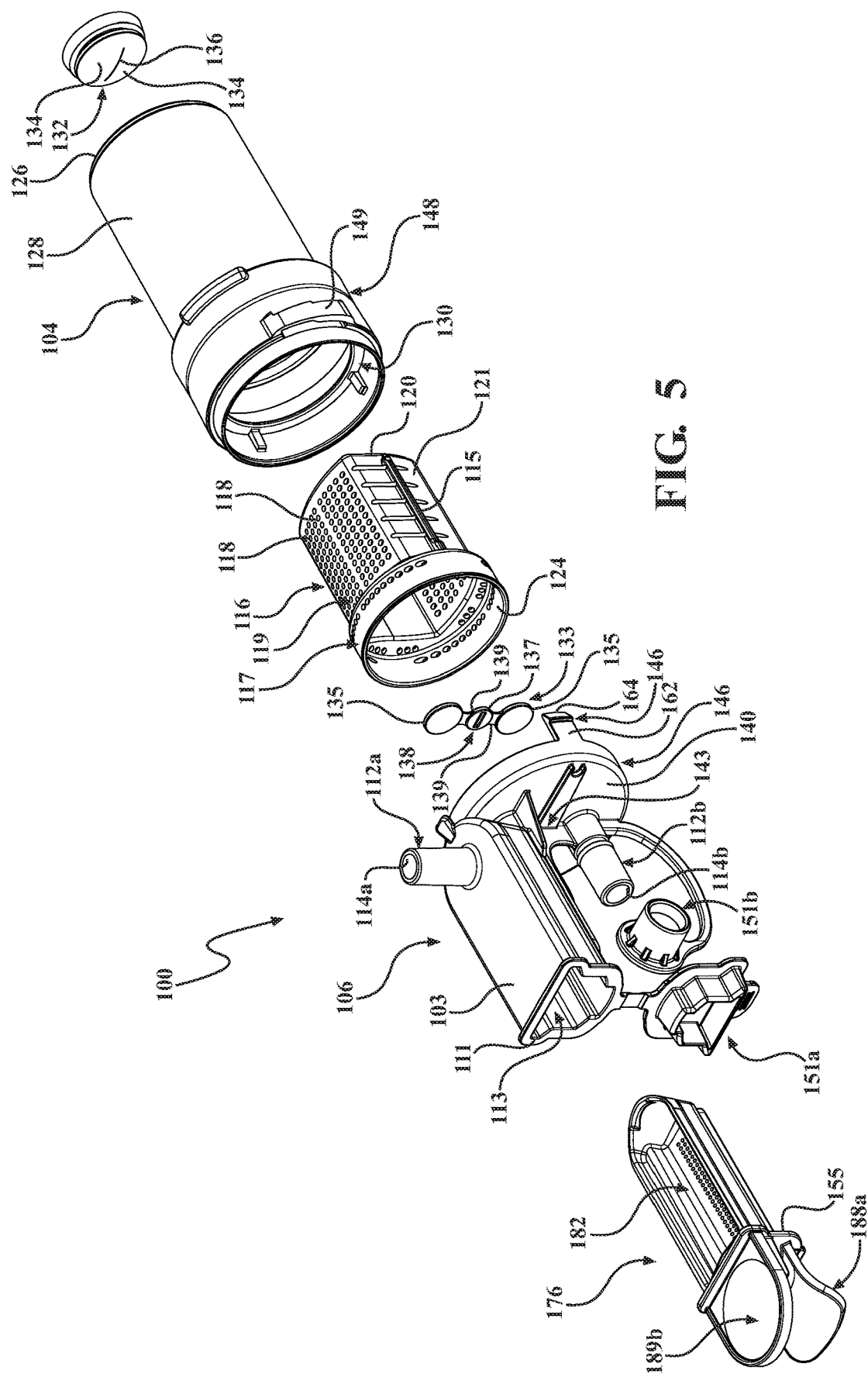
FIG. 5 is an exploded view of the manifold of FIG. 3.
Figure 6:
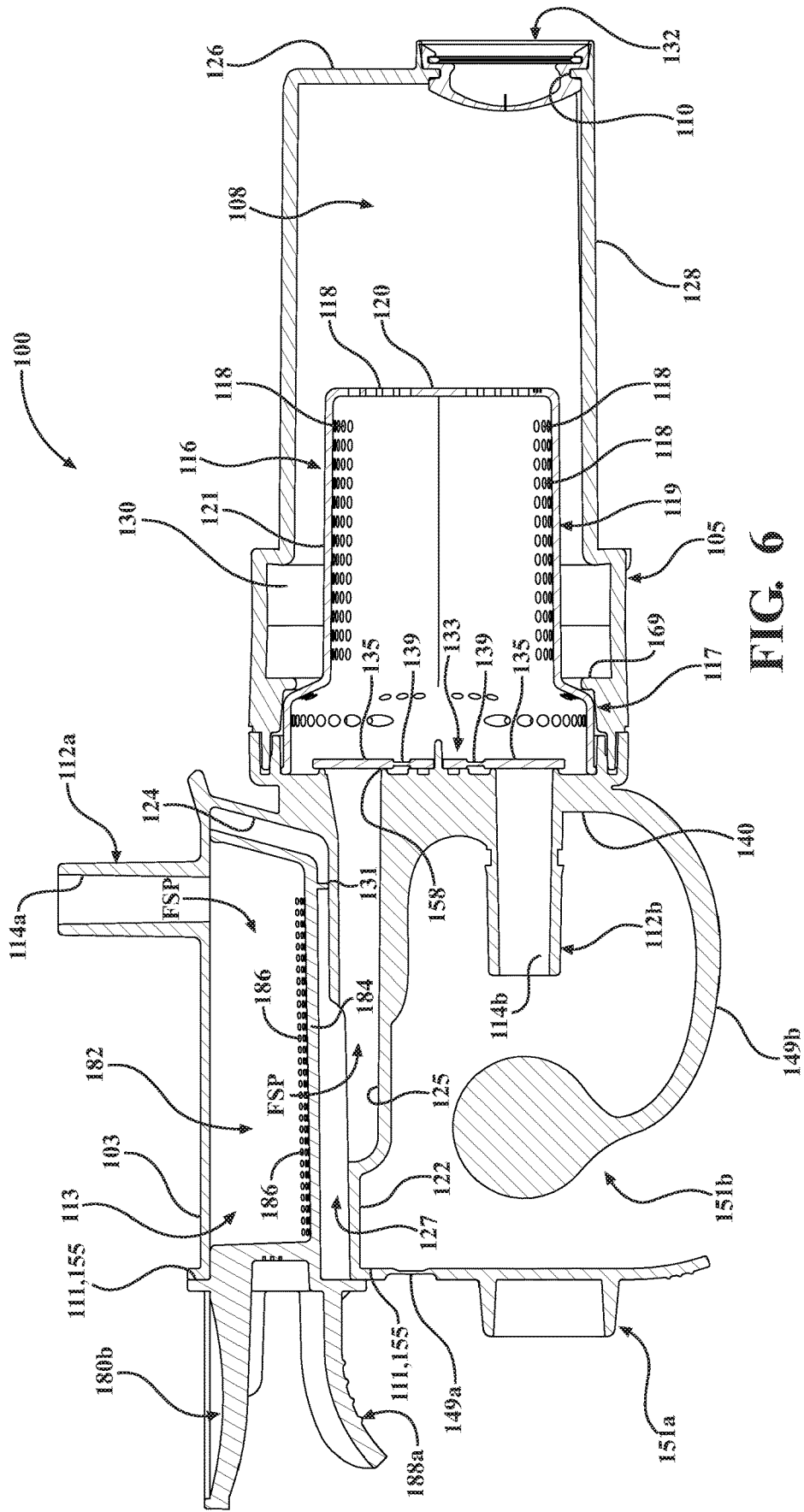
FIG. 6 is a sectional view of the manifold of FIG. 3 taken along section lines 6-6.
Figure 7:
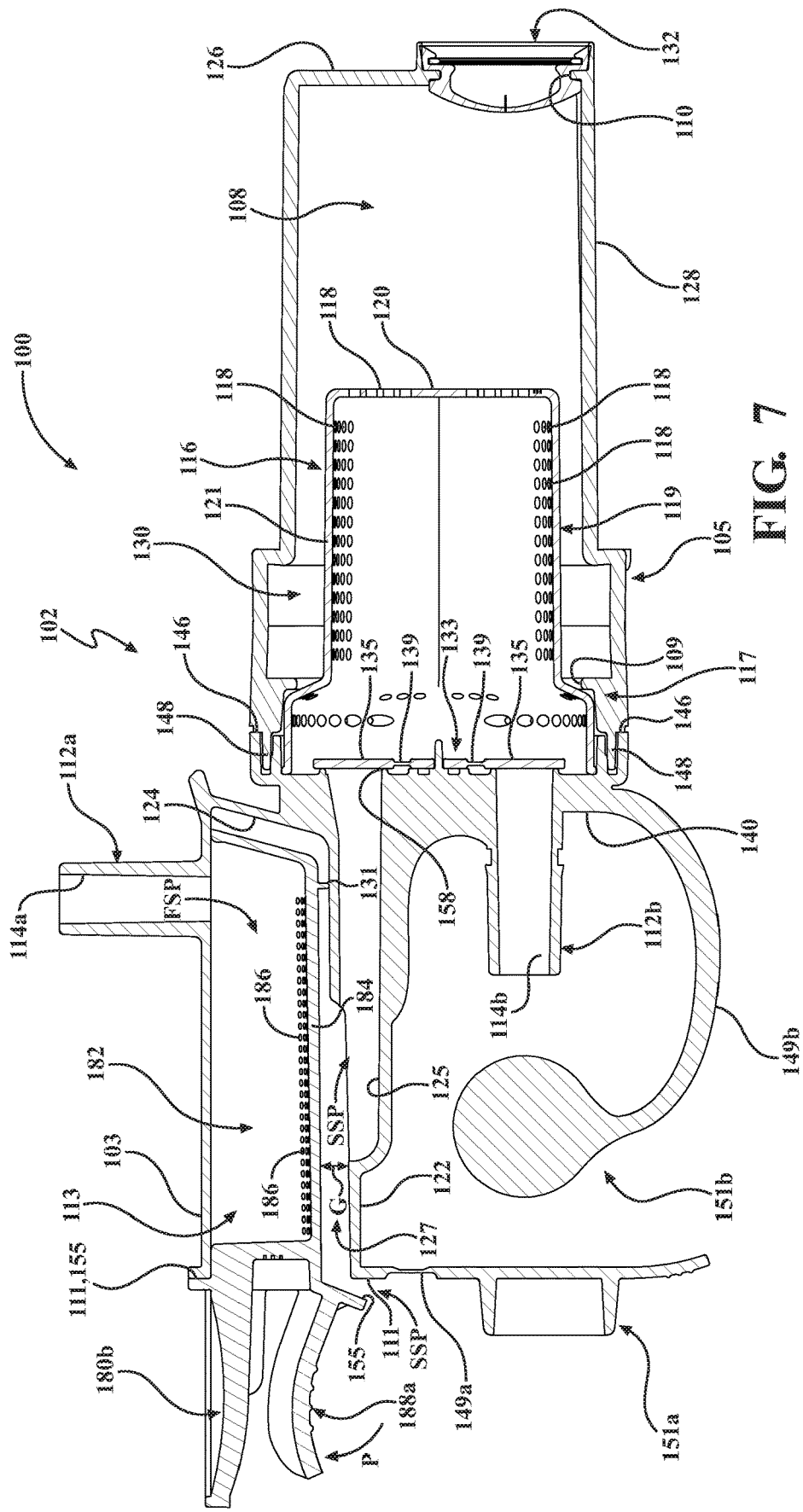
FIG. 7 is the sectional view of FIG. 6 with a control surface moved to a bleed configuration.

FIGS. 3-7 show an implementation of the manifold 100 for collecting a tissue sample. The manifold 100 includes a housing 102 adapted to be removably engaged with the manifold receiver 54. The housing 102 may include a body portion 104 and a cap portion 106. The cap portion 106 is coupled to the body portion 104 with removable or permanent joining means, but it is contemplated that the body and cap portions 104, 106 may be formed as a single piece of unitary construction. As best shown in FIGS. 6 and 7, the manifold 100 defines a manifold volume 108 and an outlet opening 110 in fluid communication with the manifold volume 108. The body portion 104 may include a proximal base 126 and at least one side 128 extending distally from the proximal base 126 to define a cavity 130 including a portion of the manifold volume 108. FIG. 3 shows the body portion 104 as being cylindrical and defining the cavity 130, but it is understood that other geometries are contemplated, including asymmetric shapes. As used herein, proximal (P) refers to a direction towards a rear of the manifold 100 and the medical waste collection assembly 50 when engaged with the manifold 100, and distal (D) refers to a direction towards a front of the manifold 100 and the surgical site (see FIG. 4). The outlet opening 110 may be disposed within the proximal base 126. Alternatively, the outlet opening 110 may be positioned at any suitable location of the housing 102, including but not limited to the side 128 of the body portion 104, and a cap faceplate 140 of the cap portion 106 to be described. The housing 102 includes at least one inlet fitting 112a, 112b is adapted to receive the suction line 52. The inlet fitting(s) 112a, 112b defines a respective inlet bore 114a, 114b in fluid communication with the manifold volume 108. The outlet opening 110 is adapted to be in fluid communication with the suction inlet 58 of the medical waste collection assembly 50 when the housing 102 is engaged with the manifold receiver 54 such that the suction path is provided from the inlet bore(s) 114a, 114b to the suction inlet 58.

The manifold 100 may include a drip valve 132 disposed within the outlet opening 110 to prevent egress of fluid from the outlet opening 110 when the housing 102 is disengaged from the manifold receiver 54, for example, subsequent to the surgical procedure. The drip valve 132 may include a pair of deflectable wings 134 defining a slit 136 therebetween. In a manner further detailed in previously incorporated U.S. Pat. Nos. 7,615,037, 8,518,002, 8,915,897, and 9,579,428, the boss 64 of the manifold receiver 54 (see FIG. 2) deflects the wings 134 and extends through the slit 136 of the drip valve 132 to provide fluid communication between the manifold volume 108 and the suction inlet 58 of the medical waste collection assembly 50.

Figure 10:
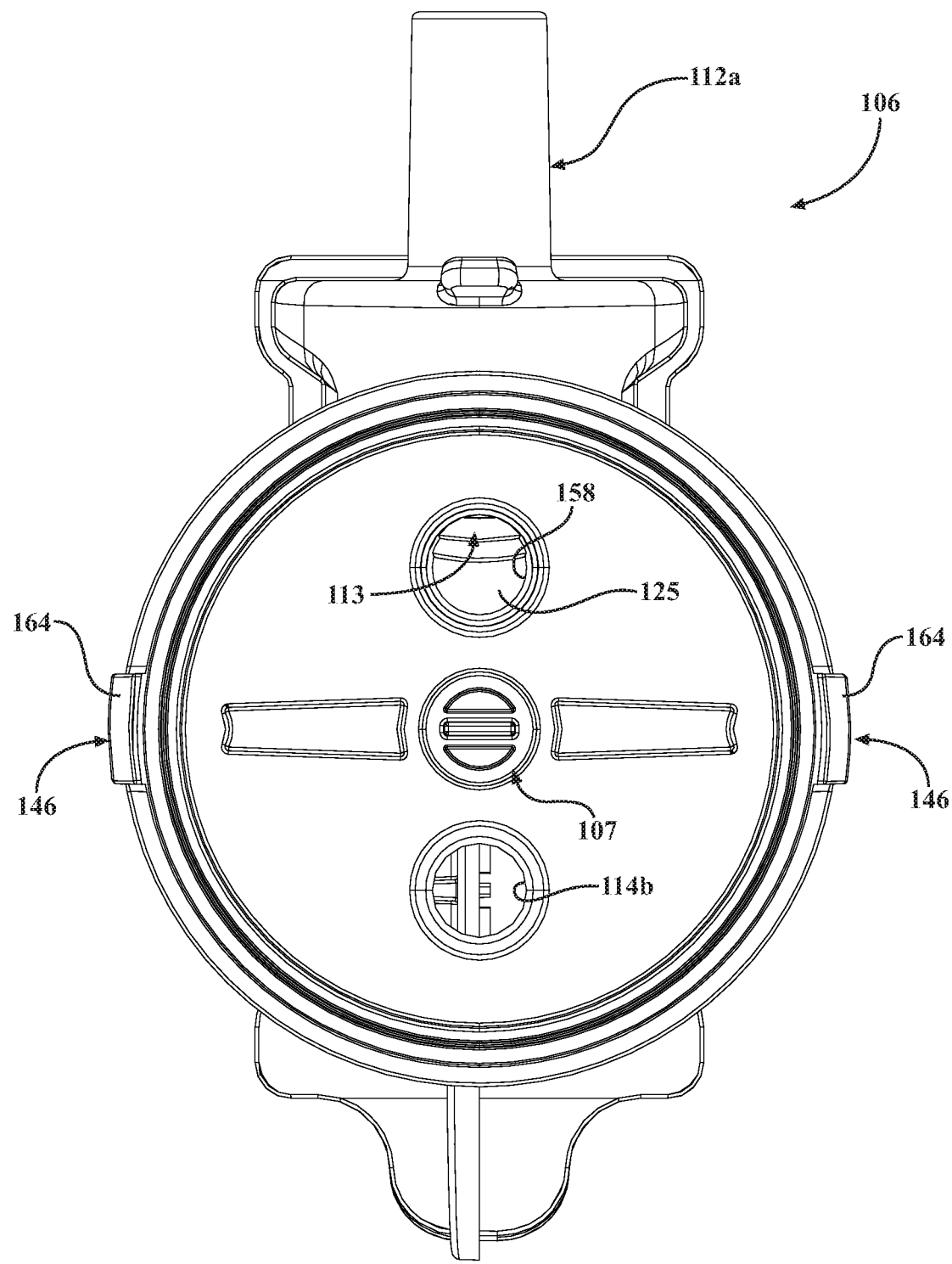
FIG. 10 is a rear elevation view of a cap portion of the manifold.

Referring again to FIG. 5, the manifold 100 may include at least one valve 133 configured to prevent backflow from the manifold volume 108. With further reference to FIGS. 5-7, the valve 133 may be coupled to the cap portion 106 and disposed within a cavity of the cap portion 106 defining at least a portion of the manifold volume 108. In particular, an inner or proximal surface of the cap portion 106 may include a coupler 107 (see FIG. 10), such as a protrusion extending proximally. The valve 133 includes a coupler 137 complementary to the coupler 107 of the cap portion 106. The coupler 137 may be a slot disposed within a central hub 138 of the valve 133 and sized to engage the protrusion with an interference arrangement. Additionally or alternatively, a suitable joining process such as adhesives, mechanical fastening, and the like, may be used to couple the valves 133 with the cap portion 106.

The valve 133 may include a pair of flappers 135 coupled to the central hub 138 with flexible wings 139. The flexible wings 139 include a length sufficient to space each of the pair of flappers 135 from the central hub 138 by a distance equal to a distance between the coupler 107 of the cap portion 106 and (i) a transfer bore 125 establishing communication between an accessory sleeve 113 and the manifold volume 108 (see FIGS. 6 and 7); and (ii) a second one of the inlet bores 114b. The flappers 135 are sized to cover the inlet bores 114 with the flappers 135 being circular in shape as shown in FIG. 5. The valve 133 may be formed with elastic material(s) such as a rubber or other polymers with suitable viscoelasticity. The dimensions and material(s) of the valve 133 are configured to facilitate resilient deformation about an axis transverse to the length of the valve 133. In other words, the dimensions and material(s) of the valve 133 are configured to facilitate the wings 139 resiliently deforming to permit movement of the flappers 135 in the proximal-to-distal direction. FIGS. 6 and 7 show the valve 133 in its natural or unstressed state. The flexural properties to the wings 139 may be tuned based on a desired magnitude of movement of the flappers 135 under anticipated levels of vacuum provided by the vacuum pump. Certain features of the valve 133 may be similar to those disclosed in U.S. Pat. No. 7,715,037, issued Nov. 10, 2009, the contents of which are hereby incorporated by reference in its entirety.

During assembly of the manifold 100, the valve 133 may be coupled to the housing 102, and more particularly to the cap portion 106. The complementary couplers 107, 137 are engaged, and the valve 133 are positioned directly adjacent or abutting the inner or proximal surface of the cap portion 106. In particular, with the valve 133 in the natural or unstressed state, the flappers 135 are abutting the inner or proximal surface of the cap portion 106 and covering the transfer bore 125 and the second of the inlet bores 114b. With the manifold 100 inserted into the manifold receiver 54 and with operation of the medical waste collection system 50, the vacuum is drawn on or through the manifold 100 in fluid communication with the suction inlet 58. Should no cap 151a, 151b be sealing a respective one of the inlet bores 114a, 114b from fluid communication with the ambient, the vacuum drawn on or through the manifold 100 is sufficient to resiliently deform the wings 139 to permit flexing of the wings 139 of the flappers 135 in the proximal direction. The movement of the flappers 135 away from the proximal end of one or both the inlet and transfer bores 114, 125 establishes the suction path from the inlet bore(s) 114a, 114b to the manifold volume 108, and thus to the suction inlet 58. Upon cessation of the vacuum drawn on or through the manifold 100, the valve 133 return to the natural or unstressed state in which the wings 139 resiliently move the flappers 135 into abutment with the inner or proximal surface of the cap portion 106 to cover and seal the proximal end of the inlet and transfer bores 114, 125. The sealing of the proximal end of the inlet and transfer bores 114, 125 prevent backflow from the manifold volume 108 to the accessory sleeve 113 and the inlet bore 114b, respectively, and thus possible egress of the waste material.

The manifold 100 may include a filter element 116 disposed within the housing 102 and in the suction path. The filter element 116 includes porous features or apertures 118 adapted to capture or otherwise filter the semisolid and solid matter entrained within the stream being aspirated along the suction path. In other words, the suction path is provided from the inlet bore 114a, 114b to the suction inlet 58 through each of the manifold volume 108, the filter element 116, and the outlet opening 110. The filter element 116 may include a base wall 120 and at least one sidewall 121 extending distally from the base wall 120 to form a basket-shaped structure 119 defining a mouth. The porous features may be are defined within the base wall 120, the sidewall 121, and/or a brim 117 to be described. To maintain the rotational orientation of the filter element 116 relative to the body portion 104, the filter element 116 and the body portion 104 may include several features including ribs 115 adapted to radially align the filter element 116 within the body portion 104. Further, the filter element 116 may be disposed in a location separate from the manifold volume 108 that is in fluid communication with the outlet opening 110 of the manifold 100. Shapes and configurations of the filter element 116 suitable for certain implementations of the manifold 100 are disclosed in commonly owned International Publication No. WO 2018/170233, filed Mar. 15, 2018, the entire contents of which are hereby incorporated by reference. Still further, the filter element 116 may be considered optional, and manifold designs that do not include a filter element are contemplated.

The filter element 116 may include the brim 117 coupled to the basket 119. The brim 117 may extend distally and radially outwardly from the basket 119. The brim 117 may include an outer diameter or dimension greater or larger than an outer diameter or dimension of the basket 119. With further reference to FIGS. 6 and 7, a length of the basket 119 may be such that the basket 119 is disposed within the body portion 104, and a length of the brim 117 may be such that the brim 117 is disposed within a neck 105 of the body portion 104. A step 109 extends radially inward from an inner surface of the neck 105. A flared wall of the filter element 116 defining at portion of the brim 117 may be positioned adjacent to or in abutment with the step 109 of the body portion 104. The resulting arrangement includes the basket 119 being secured within the manifold volume 108 by interference engagement when the body portion 104 is coupled with the cap portion 106. In other words, during assembly of the manifold 100, the brim 117 of the filter element 116 may be positioned in abutment with the inner surface of the cap portion 106, and the body portion 104 advanced over the basket 119 of the filter element 116. The body portion 104 is coupled to the cap portion 106 in a manner to be described, and the step 109 of the body portion 104 engages the flared wall defining a proximal side of the brim 117 to axially secure the filter basket 116 within the manifold volume 108. As previously mentioned, the ribs 115 engaging slots (not shown) within the body portion 104 radially align the filter element 116 within the body portion 104.

The filter element 116, in a broadest sense, includes structures configured to capture or collect the semisolid or solid waste material entrained within the liquid waste material being drawn through the manifold 100 under the influence of the vacuum provided by the medical waste collection system 50. The apertures of the filter element 116 may be shaped as holes, pores, and/or slots, among others. The holes, the pores, and/or the slots may be defined within any one or more of the base wall 120, the sidewall(s) 121, and the brim 117. The apertures—in type and position—are arranged in a manner to minimize clogging of the filter element 116. For example, the slots defined within the sidewalls 121 are positioned closer to an upper aspect of the filter element 116 than to a lower aspect. As the semisolid or solid waste material is collected, it will accumulate on bottom of the basket 119 under the influence of gravity with subsequent flow of the waste material passing above the accumulation. Upon accumulation of sufficient amounts of the semisolid or solid waste material, it may be desirable for the waste material to encounter the slots, which have a smallest dimension approximately equal to the pores (to capture the semisolid or solid waste material of the same size as the pores) with a greater or larger area of opening to permit greater volume flow through the slots. Further, the vertical arrangement of the slots is transverse to the suction path and parallel to gravity. Thus, with further accumulation of the semisolid or solid waste material, at least a portion of the slots remain unobstructed until substantially an entirety of the basket 119 is consumed with the waste material, thereby maximizing the operational lifecycle of the manifold 100.

The filter element 116 may include at least one overfill opening (not shown) positioned on an upper aspect of the filter element 116. The overfill opening(s) are configured to maximize the operational cycle of the manifold 100. As previously explained, as the semisolid or solid waste material is collected, it will accumulate on bottom of the basket 119 under the influence of gravity. Owing to the direction of the suction path (i.e., in the proximal direction), as the semisolid or solid waste material will accumulate on the base wall 120 of the basket 119. Should a sufficient amount of the semisolid or solid waste material be generated over the course of the surgical procedure, an entirety of the basket 119 may become consumed with the accumulated semisolid or solid waste material. In other words, most or all of the holes, the pores, and/or the slots of the filter element 116 may become clogged with the semisolid or solid waste material. The overfill opening(s) are sized and positioned to permit the suction path to be routed through the overfill opening(s) and external to the basket 119. In other words, owing to understood principles of fluid dynamics where fluid assumes the path of least resistance, the suction path in the aforementioned scenario extends from the inlet bore(s) 114a, 114b, through the cap portion 106, through the overfill opening(s), within the body portion 104 between the basket 119 and the inner surface of the body portion 104, and to the outlet opening 110 to be described.

Referring now to FIG. 5, the cap portion 106 includes the cap head 142 and a support frame 143. The support frame 143 may be integrally formed with the cap head 142. The support frame 143 is positioned distal to the cap head 142 and generally defines the front of the manifold 100. The cap portion 106 includes an upper barrier 103, the first inlet fitting 112a, and the second inlet fitting 112b. More particularly, the accessory sleeve 113 coupled to the support frame 143 includes the first inlet fitting 112a, and the cap head 142 includes the second inlet fitting 112b. The first inlet fitting 112a extends upwardly from the distal barrier 103 with the first inlet bore 114a extending through the distal barrier 103. The second inlet fitting 112b extends distally from the cap head 142 with the second inlet bore 114b (also referred to herein as a bypass bore) extending through the cap head 142.

The housing of the manifold 100 further defines an accessory opening 111 opening into the accessory sleeve 113. The accessory sleeve 113 may be at least partially defined by the upper barrier 103, a lower barrier 122, and opposing side barriers 123 extending between the upper barrier 103 and the lower barrier 122. The accessory sleeve 113 may be further defined by an end barrier 124 opposite the accessory opening 111. The accessory sleeve 113 is in fluid communication with the manifold volume 108 through the bore 125 (also referred to herein as a transfer bore) and an aperture 158 extending through the cap faceplate 140. More particularly, the bore 125 is defined between a first end within at least one of the lower barrier 122 and the side barrier(s) 123, and a second end opening into the manifold volume, for example, the aperture 158.

The manifold 100 includes a tray 176 configured to be removably positioned within the accessory sleeve 113. The tray 176 defines the tissue collecting cavity 182 and the porous features 186 within the tissue collecting cavity 182. With the tray 176 positioned within the accessory sleeve 113, the porous features 186 are in the suction path to collect the tissue sample. The tray 176 further includes a sealing surface 155 adapted to be in sealing engagement with the accessory opening 111 when the tray 176 is within the accessory sleeve 113. In particular, the tray 176 may include a flange defining the sealing surface 155 with the sealing surface 155 adapted to contact a perimeter of the accessory opening 111. Even more particularly, with the accessory opening 111 defined collectively by the upper, lower, and opposing side barriers 103, 122, 123, the sealing surface 155 adapted to contact ends of each of the upper, lower, and opposing side barriers 103, 122, 123. With the tray 176 within the accessory sleeve 113 and the sealing surface 155 covering the accessory opening 111, suction is maintained through the suction path during operation of the medical waste collection assembly 50.

Once it is desired to retrieve the collected tissue sample, the tray 176 may be slidably removed from the accessory sleeve 113 with the tissue sample disposed within the tissue collecting cavity 182. Yet, upon moving the sealing surface 155 out of sealing engagement with the accessory opening 111, a second suction path may be generated secondary to principles of fluid dynamics. The first suction path from the suction line to the outlet opening through the accessory sleeve 113 and the manifold volume may lessened, or eliminated, and the second suction path is generated from the accessory opening 111 to the outlet opening through the accessory sleeve 113 and the manifold volume. In other words, the bore 125 is common to both the first and second suction paths, and depending on the fluid itself (e.g., air versus liquid waste material) and the relative resistance encounter by the fluid in the first and second suction paths, the second suction path may include significant volume flow of fluid, typically air, through the accessory opening 111 and the accessory sleeve 113 as the tray 176 is being slidably removed from the accessory sleeve 113. In known systems, the tissue specimen may encounter the fluid volume flow and associated forces, and the tissue sample may undesirably be swept along the fluid flow and ejected from the tray. In other instances, it may be desirable to "bleed" or reduce suction through the first suction path, perhaps temporarily, without needing to remove the manifold from the medical waste collection assembly and/or cease operation of the medical waste collection assembly. Known systems do not adequately address this desire.

The manifold 100 advantageously provides for locating the second suction path in a manner that the likelihood of inadvertent loss of the tissue sample is minimized. Further, the manifold 100 advantageously provides for the second suction path being of sufficient volume flow such that the first suction path may be temporarily limited or eliminated.

Referring now to FIGS. 6 and 7, the housing of the manifold 100 includes locating features 145 disposed within the accessory sleeve 113. In a most broadest sense, the locating features 145 are configured to appropriately locate the tray 176 such that a gap (G) is defined between the base portion 184 (also referred to herein as the screen surface) of the tray 176 and at least a portion of the lower barrier 122 at least partially defining the accessory sleeve 113. As to be further explained, the gap (G) is sized such that the second suction path (SSP), owing to fluid dynamics, is directed through the gap (G) without encountering the tissue collecting cavity 182 of the tray 176, thereby minimizing the likelihood of loss of the tissue sample. The illustrated locating features 145 are plateaus 147 defining a trough 127 therebetween. It is appreciated that the trough 127 defines at least a portion of the accessory sleeve 113 and extends to the accessory opening 111.

Figure 8:
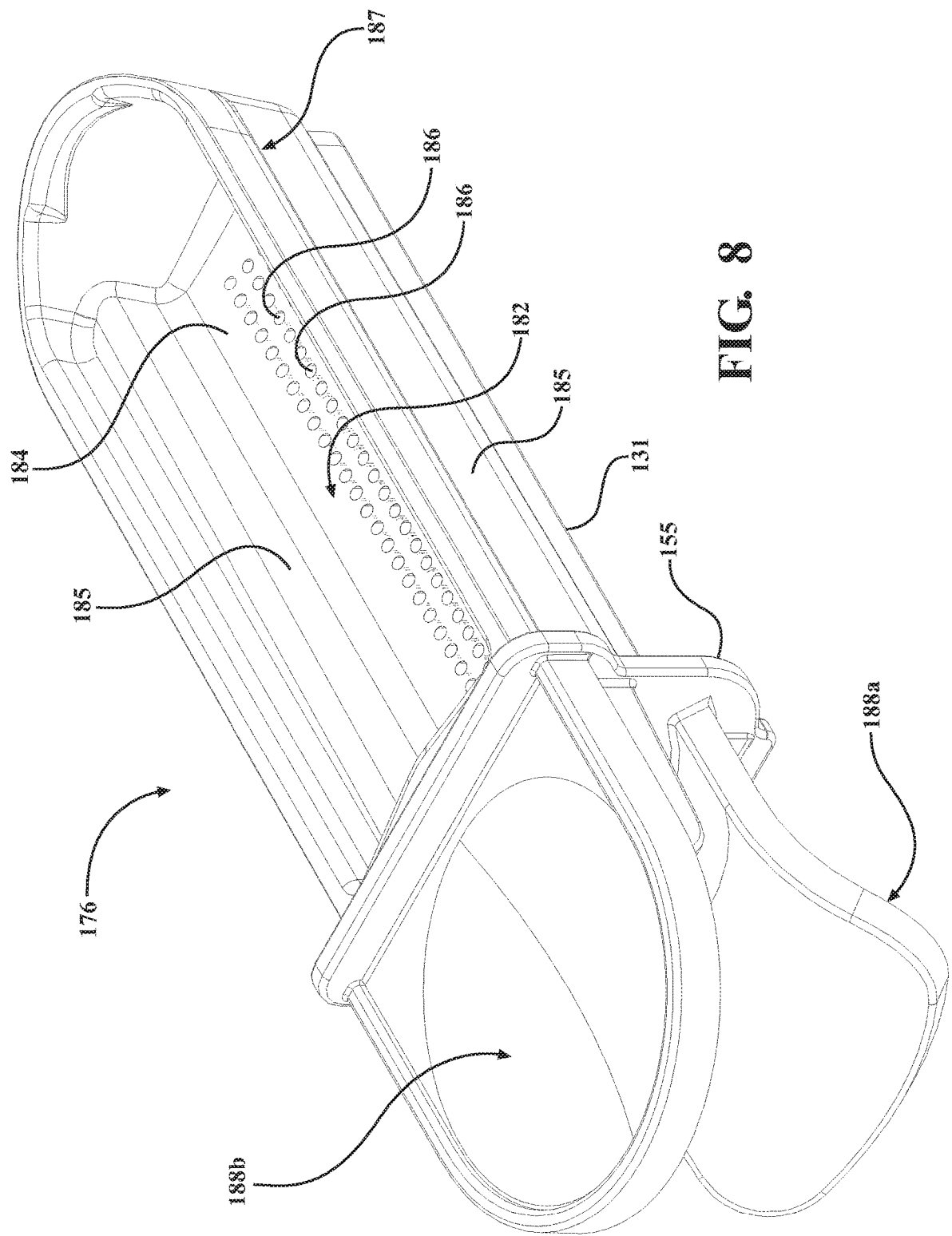
FIG. 8 is a top perspective view of the tray.
Figure 9:
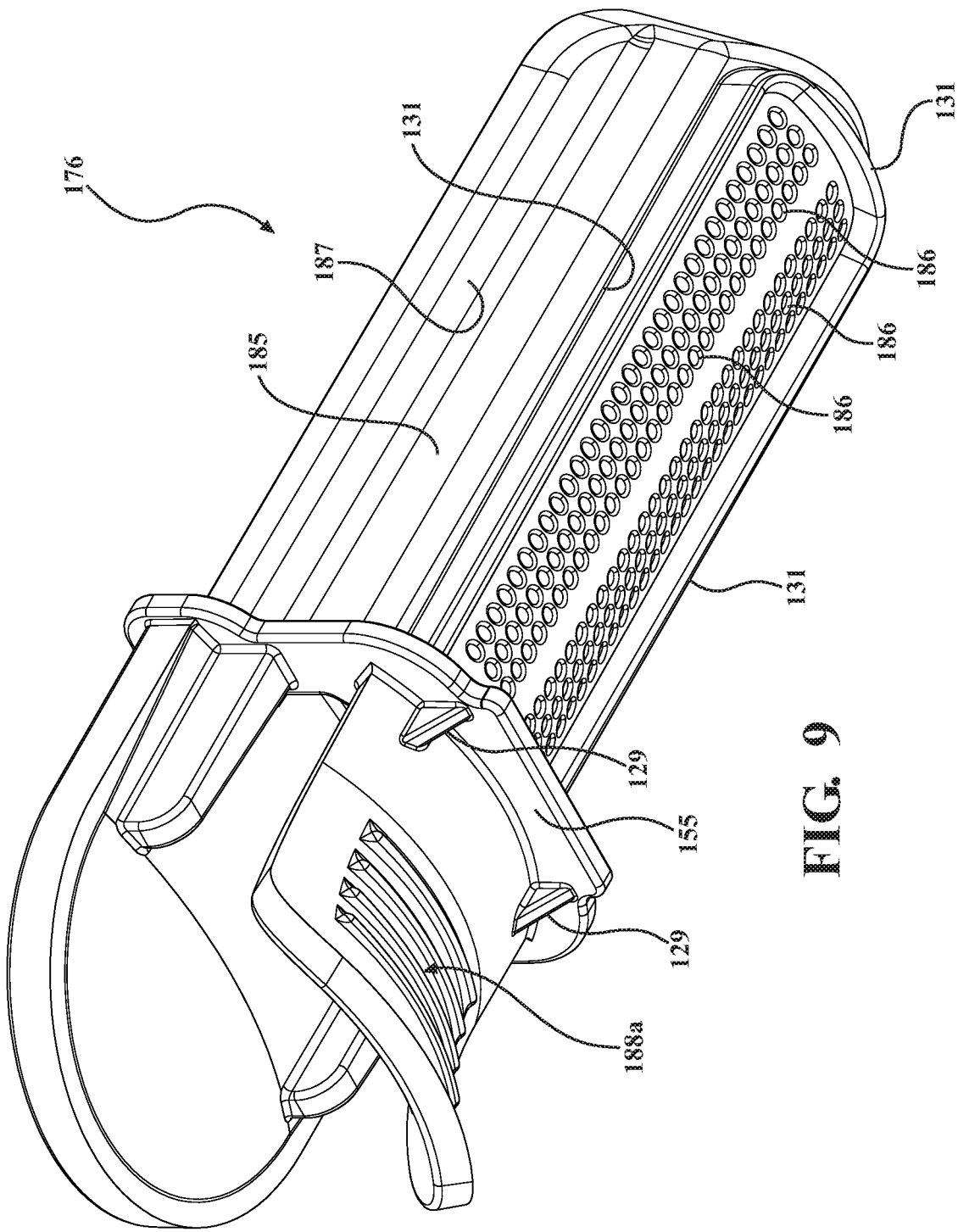
FIG. 9 is a bottom perspective view of the tray.

FIGS. 8 and 9 show the tray 176 including the base portion 184. The base portion 184 may be slightly arcuate, as shown, but alternatively may be planar or of any suitable profile. The tray 176 further includes side portion(s) 185 (also referred to herein as sides) coupled to the base portion 184. The base and side portions 184, 185 may extend from the sealing surface 155 and arranged to define the tissue collecting cavity 182. For convention, the tissue collecting cavity 182 is considered to be opening away from the base portion 184 in a direction parallel to the side portions 185. The porous features 186 are defined within the base portion 184.

The tray 176 includes one or more control surfaces 188a, 188b adapted to receive an input from the user. FIGS. 8 and 9 show two control surfaces 188a, 188b extending from the flange in a direction opposite the sealing surface 155. The control surface 188a, 188b may be formed as a grip to be pinched between fingers of the user. More specifically, the grip may include a first portion 188a and a second portion 188b collectively arranged to be pinched by the user to move the first portion 188a towards the second portion 188b for function to be described.

With the tray 176 removably coupled with the housing, as shown in FIG. 5, (i) the sealing member 155 seals the accessory opening 111, (ii) the tissue collecting cavity 182 is positioned within the accessory sleeve 113 and opening towards the inlet bore 112a, and (iii) the base portion 184 and/or the side portion 185 engages the locating features 145 within the accessory sleeve 113 to provide the aforementioned gap (G) between the base portion 184 of the tray 176 and the lower barrier 122. More specifically, the base portion 184 of the tray 176 may be arranged to rest upon or otherwise be supported by the plateaus 147 such that the gap (G) is defined between an underside of the base portion 184 of the tray 176 and the upper surface of the trough 127. The gap (G) may be considered to be beneath the tray 176 (i.e., opposite the tissue collecting cavity 182 in the aforementioned convention). With the tray 176 positioned within the accessory sleeve 113, the gap (G) is in communication with the bore 125 extending to the manifold volume 108. It is further noted that an upper aspect of the tray 176 is positioned adjacent to the upper barrier 103 with little distance therebetween.

At least a portion of the sealing surface 155 may be formed from resiliently flexible material. In particular, a lower aspect of sealing surface 155 (i.e., the aspect of the sealing surface 155 contacting the end of the lower barrier 122 at least partially defining the accessory opening 111) may be formed from the resiliently flexible material. The resiliently flexible material is rigidly coupled to the control surface 188, for example, with gussets 129. With concurrent reference to FIG. 9, the gussets 129 are triangular-like structures rigidly coupling the flange defining the sealing surface 155 and the second portion 188b of the grip defining the control surface 188.

In operation, should the user wish to reduce or eliminate the first suction path through the first inlet bore 114a, the accessory sleeve 113, and the bore 125, the user provides an input to the control surface 188. In particular, the user may pinch the first and second portions 188a, 188b of the grip defining the control surface 188. With particular reference to FIGS. 6 and 7, the first portion 188a moves or pivots (P) towards the second portion 188b to move the manifold 100 from a sealing configuration to a bleed configuration. Owing to the resiliently flexible material of the flange defining the sealing surface 155 and the rigid connection from the gussets 129, at least a portion of the sealing surface 155 moves away from a portion of the accessory opening 111 near the lower barrier 122. The trough 127 extending to the accessory opening 111 is exposed to atmosphere, and the second suction path (SSP) is provided. As shown in FIG. 7, the second suction path (SSP) is located from the accessory opening 111 to the bore 125 through the gap (G) between the base portion 184 of the tray 176 and the lower barrier 122 of the housing defining the accessory sleeve 113. Owing to the lesser resistance of the fluid (e.g., the air) entering the second suction path (SSP) relative to the end of the suction line disposed well upstream at the surgical site (as well as the density of the waste material in the suction line relative to air), fluid dynamics dictate that the second suction path (SSP) becomes the primary suction path in the bleed configuration, and negligible suction may be maintained through the suction line 52. Should the user wish to promptly reestablish the first suction path (FSP) as the primary (and only) suction path, the user simply releases the input provided to the control surface 188. The resilient nature of the sealing surface 155 as well as the second suction path (SSP) adjacent the sealing surface 155 results in the sealing surface 155 reengaging the accessory opening 111, and the manifold 100 reassumes the sealing configuration. Moving the manifold 100 between the sealing configuration and the bleed configuration may occur as many times as desired without undue difficulty and without needing to stop operation of the medical waste collection assembly 50.

Moreover, as mentioned, the second suction path (SSP) is located below the below the tray 176 (i.e., opposite the tissue collecting cavity 1082 in the aforementioned convention). As a result, should the user wish to retrieve the tissue sample collected in the tissue collecting cavity 182, the user maintains the input to the control surface 188 while withdrawing the tray 176 from the accessory sleeve 113. Since the gap (G) is relatively larger than any distance between the upper aspect of the tray 176 positioned adjacent to the upper barrier 103, nearly an entirely of the second suction path (SSP) remains below the tray 176 as the tray 176 is removed. It is appreciated that any fluid flow of the second suction path (SSP) travelling above the tray 176 to be drawn into the tissue collection cavity 182 is negligible. As a result, the user may confidently remove the tray 176 without risk of compromising a critical aspect of the surgical procedure by inadvertently losing the collected tissue sample.

Returning to FIGS. 8 and 9, the tray 176 may include a foot 131 extending from the base portion 184, and more particularly extending from the base portion 184 in a direction opposite the tissue collecting cavity 182. The foot 131 may be generally U-shaped and bound the porous features 186 within the base portion 184 when viewed in bottom plan (see FIG. 9). Alternatively, for example, the foot 131 may be a series of discontinuous protrusions extending from the base portion 184 near the side portions 185. It is appreciated that the generally U-shaped foot 131, when the tray 176 is fully positioned within the accessory sleeve 113, also bounds the bore 125 in communication with the manifold volume 108. In other words, each of side portions of the foot 131 may be supported on one of the plateaus 147, and a distal portion of the foot 131 may be supported on the lower barrier 122 near the end barrier 124 opposite the accessory opening 111. The relatively minimal clearance between the foot 131 and the lower barrier 122, particularly with the bounding of the bore 125, substantially isolates the second suction path (SSP) from the first suction path (FSP) when the manifold 100 is in the bleed configuration (except for through the porous features 186). The arrangement may further increase the disparity in resistance between the second suction path (SSP) and the first suction path (FSP) when the manifold 100 is in the bleed configuration such that the second suction path (SSP) becomes the primary suction path in the bleed configuration, and negligible suction is maintained through the suction line 52.

The foot 131 is further configured to further locate the base portion 184 of the tray 176 within the accessory sleeve 113. More particularly, the foot 131 may be supported on or positioned adjacent the plateaus 147, as mentioned, and additional clearance may be provided between the base portion 184 and the lower barrier 122 defining the gap (G). FIG. 7 shows the distal portion of the foot 131 situated upon the lower barrier 122 such that the gap (G) extends above the level of the plateaus 147 to the base portion 184 of the tray 176. The maximizing of the size of the gap (G) (i.e., the distance from the base portion 184 to the lower barrier 122 defining the trough 127) increases the effectiveness of the bleed functionality and further reduces the likelihood of fluid flow of the second suction path (SSP) above the tray 176 to possibly dislodge or eject the collected tissue sample.

With continued reference to FIGS. 8 and 9, the tray 176 may include orientation features 187 configured to engage complementary orientation features 189 (shown in FIG. 4) of the accessory sleeve 113 to position the tray 176 within the accessory sleeve 113 in a singular relative orientation to the upper barrier 103, and in particular with the tissue collecting cavity 182 opening towards the upper barrier 103. The orientation features 189 of the accessory sleeve 113 may be considered a groove defined within each of the opposing side barriers 123. In other words, each of the side barriers 123 near the upper barrier 103 flare outwardly to define the groove. The orientation features 187 of the tray 176 may be considered rails extending from the side portions 185, and in particular, near an upper aspect of the tray 176. The complementary orientation features 187, 189 may be configured to be movably engaged by sliding the rails within the grooves. It is understood that the orientation features 187 of the tray 176 may further serve as locating features to define a vertical position of the base portion 184 relative to the lower barrier 122, and hence at least partially influencing the size of the gap (G).

Figure 11:
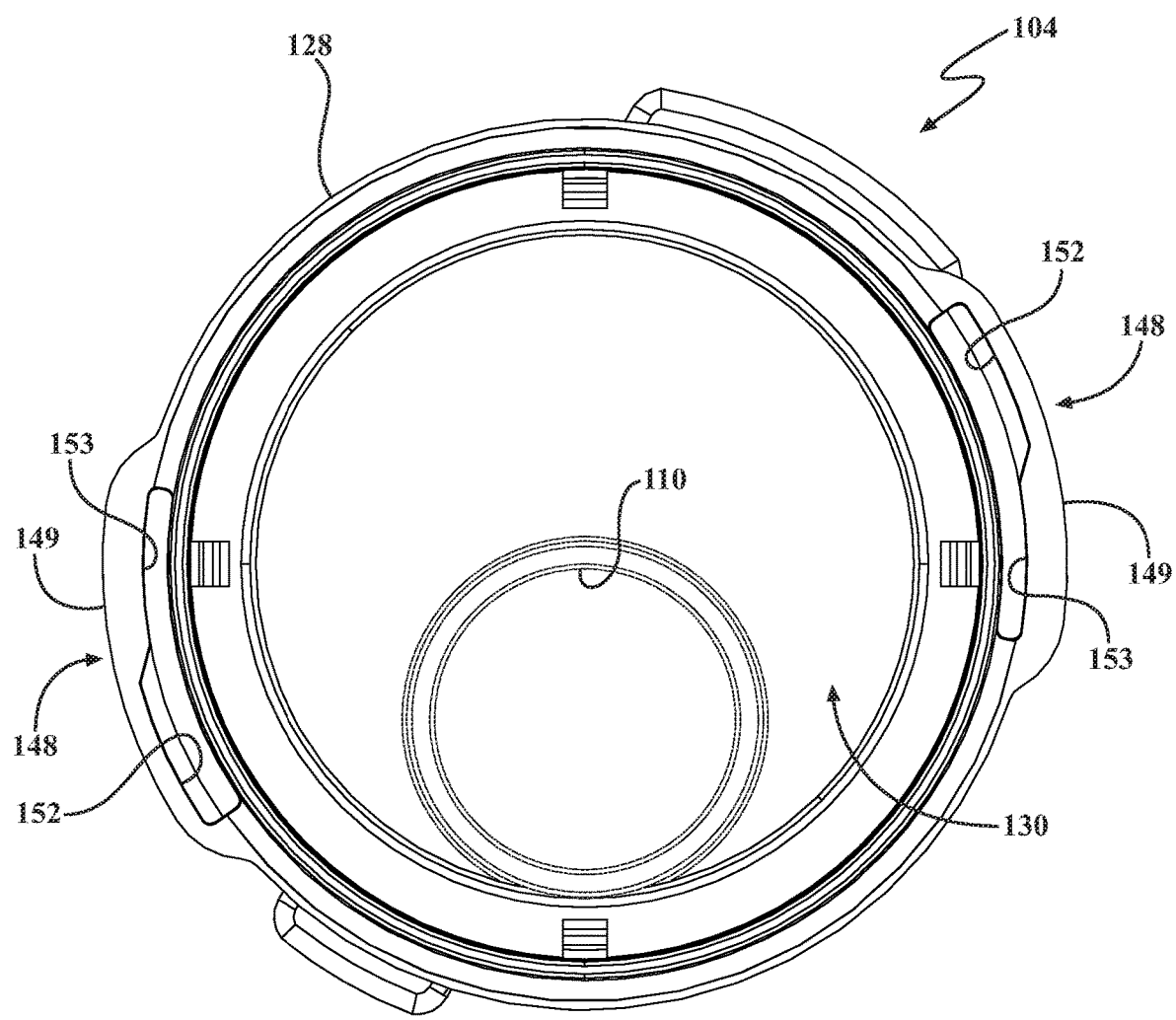
FIG. 11 is a front elevation view of a body portion of the manifold.

In certain implementations, the cap portion 106 and the body portion 104 are removably coupled to one another. Referring to FIGS. 3-5, the cap portion 106 includes at least one key 146 or head coupler configured to be removably coupled with at least one keyway 148 or trunk coupler of the body portion 104. The key 146 may be two keys 146 diametrically opposed to one another and extending proximally from the cap portion 106. The keyway 148 may be two keyways 148 diametrically opposed to one another and defined between at least one lip 149 extending radially outwardly from the neck 105 of the body portion 104. In another implementation, the keys 146 and the keyways 148 may be three keys 146 and three keyways 148, respectively, and spaced apart from one another by approximately 120 degrees. The keyway(s) 148 may include an insertion portion 152 and a locking portion 153 in communication with the insertion portion 152. As best shown in FIG. 11, the insertion portion 152 may be wider than the locking portion 153. In other words, a portion of the lip 149 defining the locking portion 153 may be thinner than a portion of the lip 149 defining the insertion portion 152. The key 146 may include a shank 162, and a barb 164 extending from the shank 162. The barb 164 may be thicker than the shank 162. The width of the insertion portion 152 is greater or larger than a thickness of the barb 164 and greater or larger than a thickness of the shank 162, and the width of the locking portion 153 is less than the thickness of the barb 164 and greater or larger than the thickness of the shank 162. Further, a length of the shank 162 may be at least equal to a length of the lip 149. More particularly, the length of the shank 162 may be greater or larger than the length of the portion of the lip 149 defining the insertion portion 152, and the length of the shank 162 may be approximately equal to the length of the portion of the lip 149 defining the locking portion 153. As a result, during assembly of the manifold 100 or when it is desired to couple the cap portion 106 with the body portion 104, the cap portion 106 is oriented relative to the body portion 104 such that the barb(s) 164 are rotationally aligned with the insertion portion(s) 152. The cap portion 106 is moved towards the body portion 104 such that the barb(s) 164 extend through the insertion portion(s) 152 to pass the lip 149, and the shank 162 is positioned within the insertion portion(s) 152. The cap portion 106 is rotated relative to the body portion 104, for example, clockwise in the view of FIG. 11, to move the key(s) 146 within the keyway(s) 148. The shank(s) 162 move from within the insertion portion(s) 152 to within the locking portion(s) 153 with the barb(s) 164 positioned in an interference arrangement with the portion of the lip(s) 166 defining the locking portion(s) 153. The interference prevents axial movement of the cap portion 106 relative to the body portion 104, and the cap portion 106 may be considered secured to the body portion 104 to form the housing 102 of the manifold 100.

The removable coupling between the cap portion 106 and the body portion 104 may provide access to the manifold volume 108 within which the filter element 116 is disposed. Among other advantages, accessing the filter element 116 may allow the user to retrieve waste material collected within the filter element 116, most notably a polyp or tissue sample, for further examination and processing during certain surgical procedures. Commonly owned International Publication No. WO 2013/090579, published Jun. 20, 2013, the entire contents of which is hereby incorporated by reference, discloses a manifold including a tissue trap for collecting the polyp or the tissue sample. In certain implementations, the manifold 100, including the cap portion 106, may include further features to facilitate collection of tissue sample(s).

When it is desired to decouple the cap portion 106 from the body portion 104, the aforementioned method steps are reversed. The cap portion 106 is rotated relative to the body portion 104, counterclockwise in the view of FIG. 11, to move the key(s) 146 within the keyway(s) 148. The shank(s) 162 move from within the locking portion(s) 153 to within the insertion portion(s) 152 with the barb(s) 164 removed from the interference arrangement with the portion of the lip(s) 149 defining the locking portion(s) 153. The cap portion 106 moves away from the body portion 104 such that the barb(s) 164 pass the lip(s) 149, and the keys(s) 146 may be considered disengaged from the keyway(s) 148. The cavity 130 of the cap portion 106 may be accessible, and/or the manifold volume 108 of the body portion 104 may be accessed, as generally shown in FIG. 5.

In certain implementations, the cap portion 106 and the body portion 104 are rigidly connected through a suitable joining process, for example, spin welding, solvent bonding, adhesives, mechanical fastening, and the like. As previously mentioned, the housing 102 may be of unitary or monolithic construction such that there is no discrete head and trunk. Suitable manufacturing processes for forming the housing 102 may include injection molding, three-dimensional printing, computer numerical control (CNC) machining, polymer casting, vacuum forming, blow molding, among others. Suitable materials for forming the housing 102 may include polymers, composites, metals, ceramics, and combinations thereof. The materials include sufficient anticorrosive properties to avoid degradation when exposed to the waste material and sufficient mechanical properties to maintain integrity under the vacuum levels to be provided by the medical waste collection system. The polymers of polyethylene, polypropylene, polyvinyl chloride, polyethylene terephthalate (PET, PETE), polystyrene, polycarbonate, and poly(methyl methacrylate) may be particularly well suited for the manifold 100 in low-cost and disposable implementations.

Figure 12:
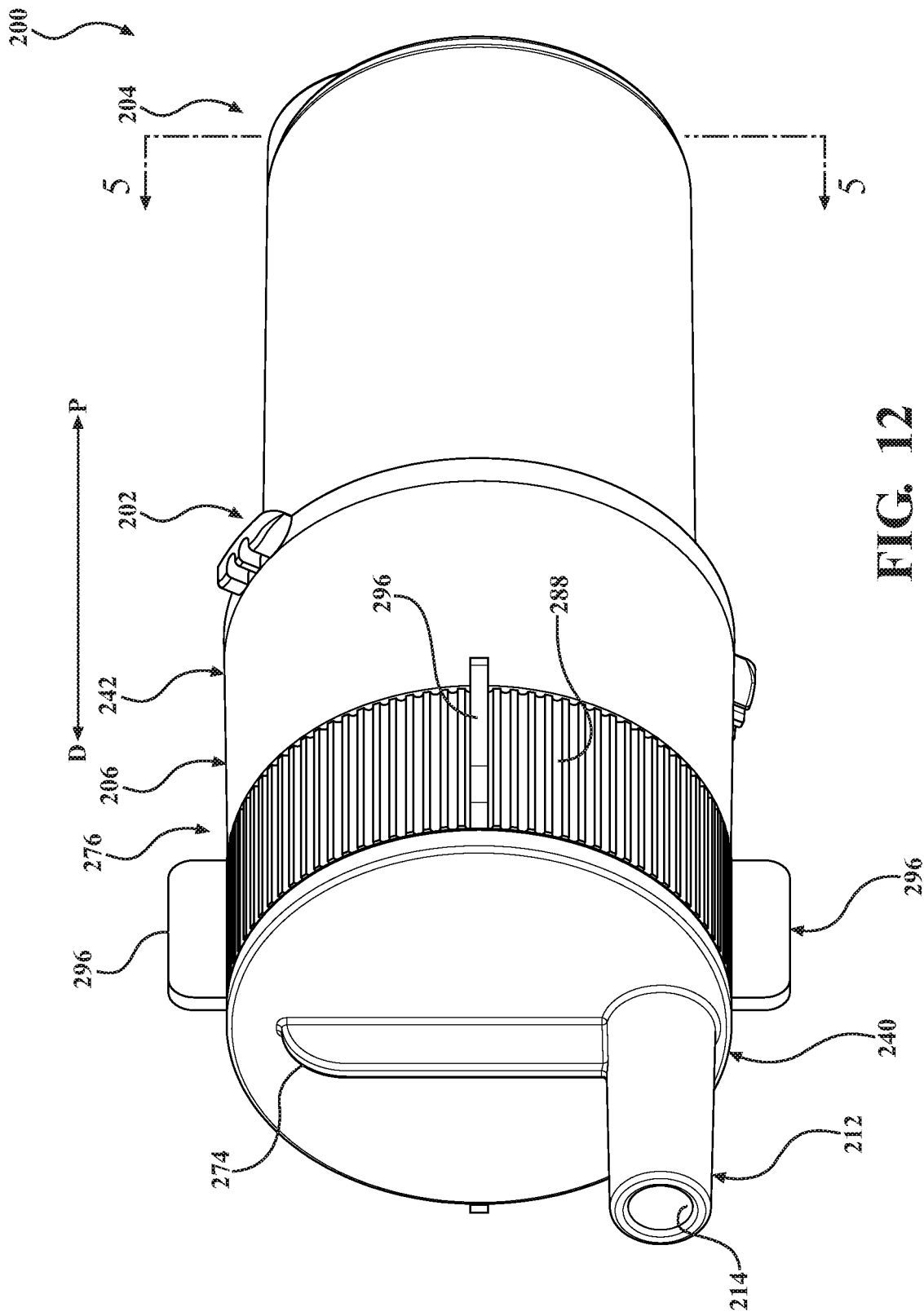
FIG. 12 is a perspective view of a manifold.
Figure 13:
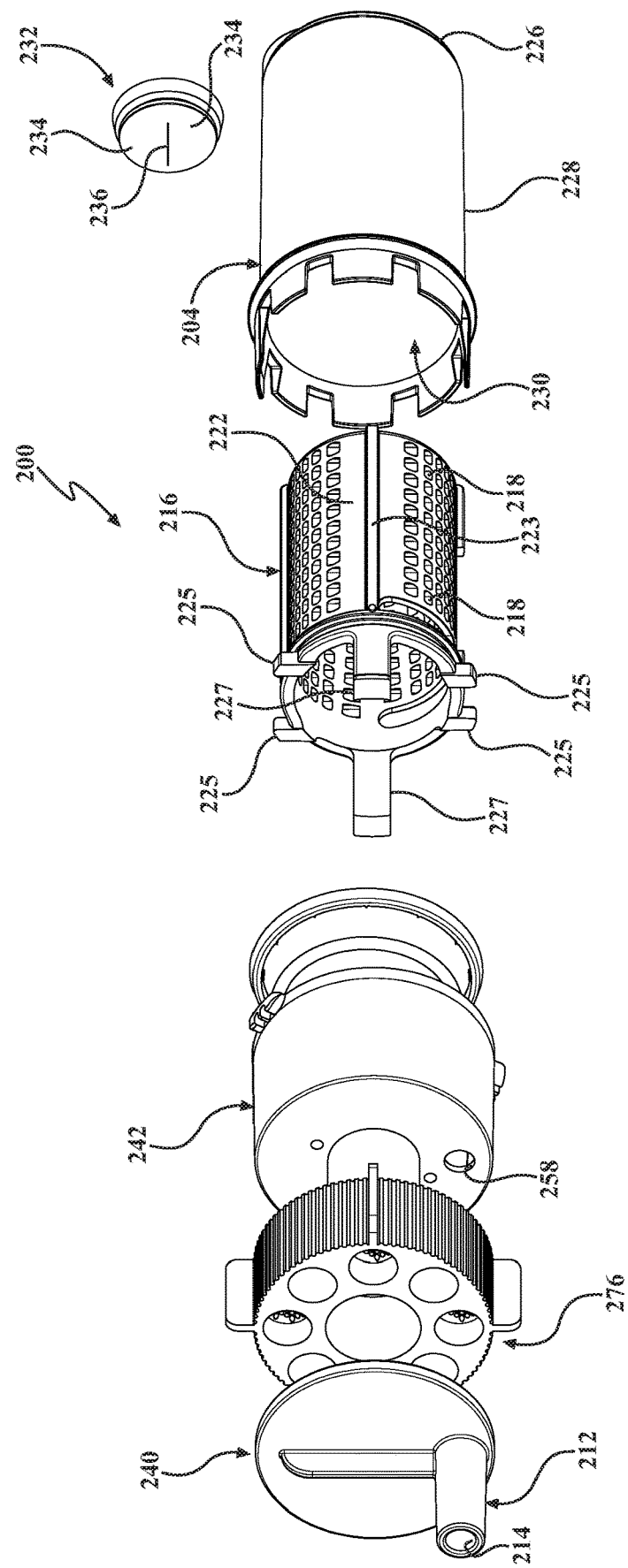
FIG. 13 is an exploded view of the manifold of FIG. 12.
Figure 14:
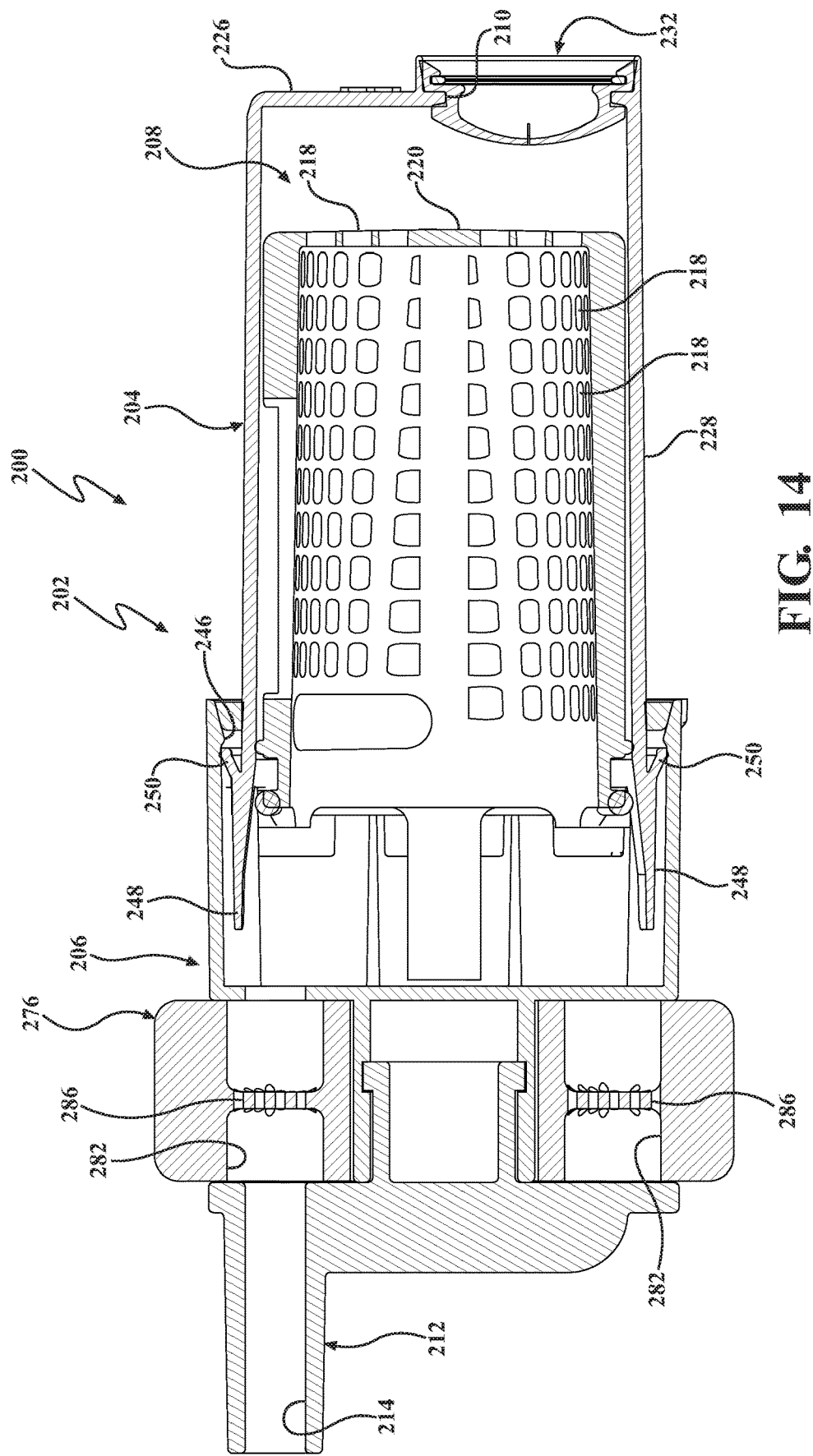
FIG. 14 is a sectional view of the manifold of FIG. 12 taken along section lines 5-5.

Referring now to FIGS. 12-14, another manifold 200 is illustrated that is, in at least some respects, similar to that previously described (and certain like components being indicated by like numerals plus one hundred (100)). The manifold 200 includes the housing 202 adapted to be removably engaged with the manifold receiver 54. The housing 202 includes the body portion 204 and the cap portion 206 coupled to the body portion 204. As best shown in FIG. 14, the housing 202 defines the manifold volume 208, and the outlet opening 210 in fluid communication with the manifold volume 208. The body portion 204 may include the proximal base 226 and the side 228 extending distally from the proximal base 226 to define the cavity 230 including a portion of the manifold volume 208. The outlet opening 210 may be positioned within the proximal base 226. The cap portion 206 includes the inlet fitting 212 defining the inlet bore 214 in fluid communication with the manifold volume 208. The drip valve 232 may be disposed within the outlet opening 210 in the manner previously described.

Figure 15:
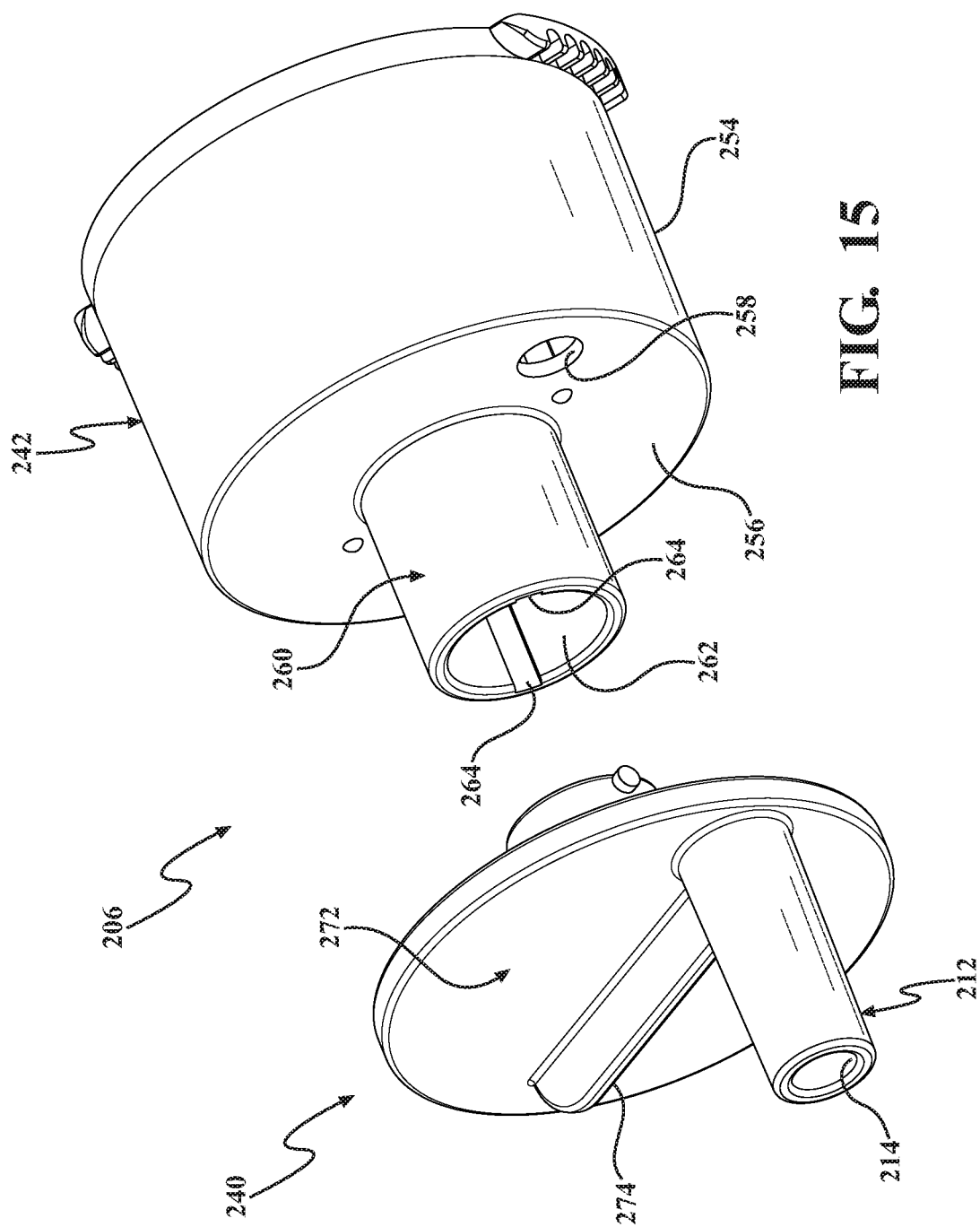
FIG. 15 is an exploded view of a cap portion of the manifold of FIG. 12.
Figure 16:
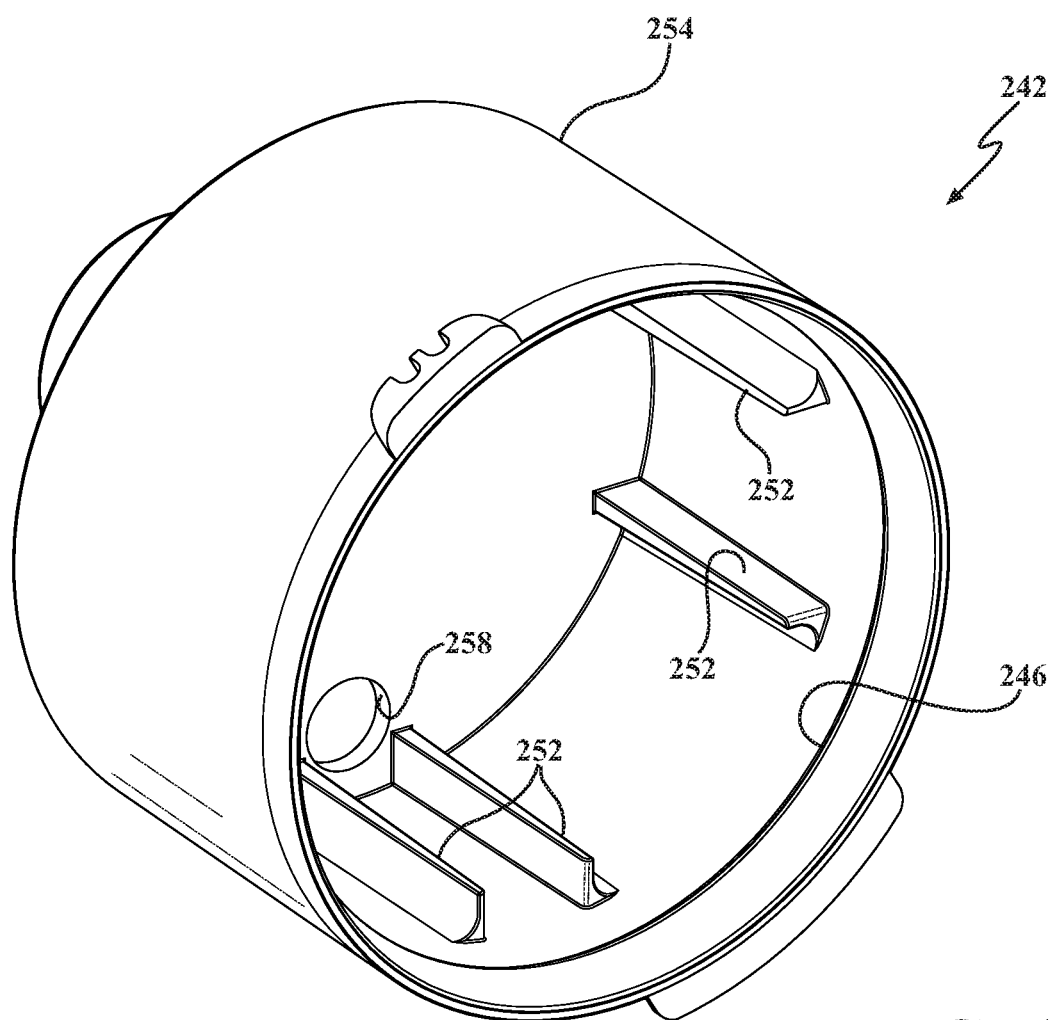
FIG. 16 is a rear perspective view of a cap head of the cap portion.
Figure 17:
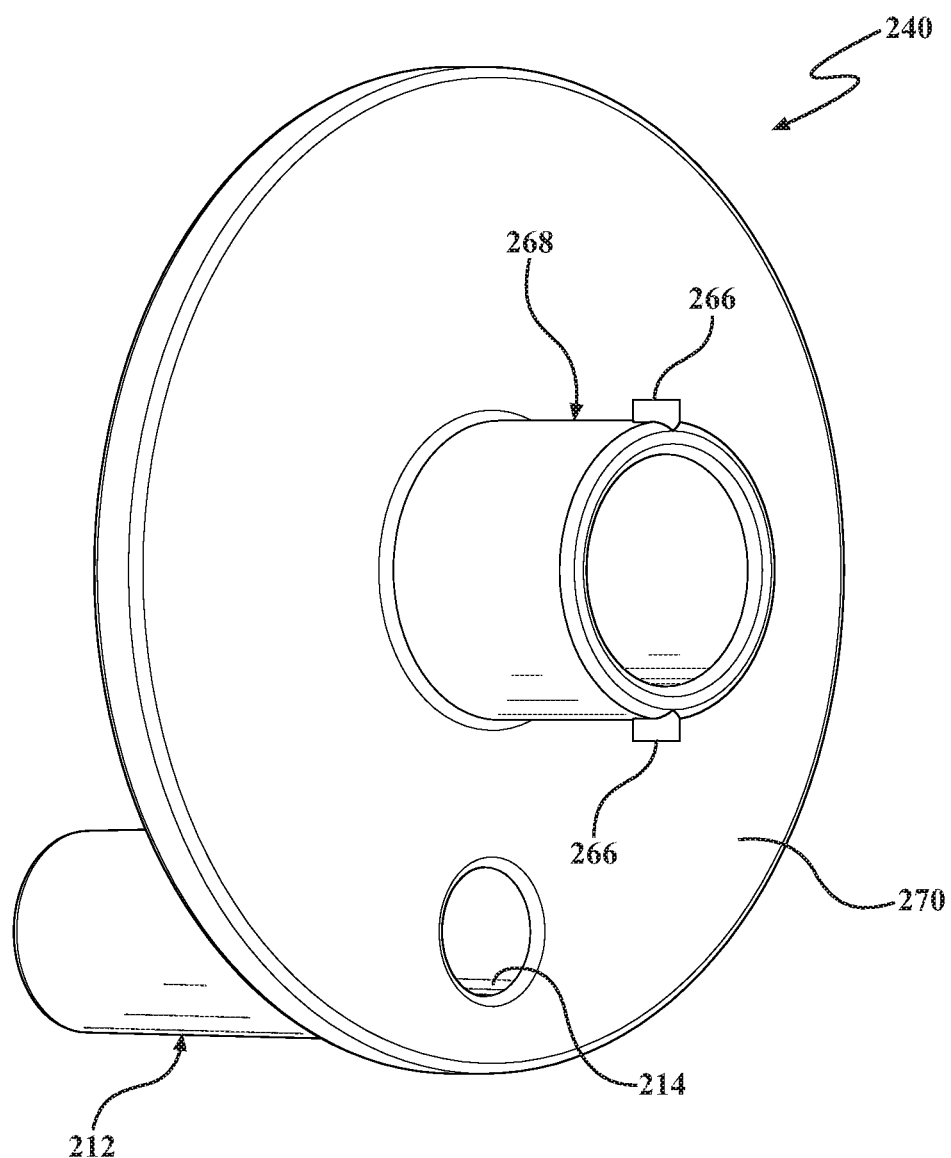
FIG. 17 is a rear perspective view of a cap faceplate of the cap portion of FIG. 18.

FIGS. 15-17 show the cap portion 206 including a cap faceplate 240 and a cap head 242. The cap head 242 may be coupled with the body portion 204. The cap head 242 may include an annular inclined surface terminating at an annular plateau 246. The annular inclined surface 244 is shaped to impart resilient deflection of flanges 248 of the body portion 204 as the body and cap portions 204, 206 are assembled. The flanges 248 are directed within the cap head 242 until a barbed feature 250 moves past the annular plateau 246 and resiliently deflects outwardly into interference engagement with the annular plateau 246. In such a construction, the body and cap portions 204, 206 are generally prevented from decoupling. Further, the cap head 242 includes one or more orientation features 252, for example one or more pairs of ribs extending radially inwardly from an inner annular surface. The ribs receive the flanges 248 therebetween to prevent rotation of the cap head 242 relative to the body portion 204. The ribs may also receive the tabs 227 of the filter element 216 to prevent rotation of the filter element 216 relative to the cap portion 206.

The cap head 242 includes at least one sidewall 254 extending distally and terminating at a distal face 256. An aperture 258 extends through the distal face 256 of the cap head 242. The cap head 242 includes a spindle 260 extending distally from the distal face 256 with the spindle 260 defining a cavity 262 and coupling features 264. The coupling features 264 are a pair of slots arranged to provide a bayonet mount with complementary coupling features 266 of the cap faceplate 240. The complementary coupling features 266 of the cap faceplate 240 are posts circumferentially arranged to be received within the slots. The complementary coupling features 266 extend radially from a tubular portion 268 adapted to be received within the cavity 242 of the spindle 260. The cap faceplate 240 may be disc-shaped including a proximal face 270 and a distal face 272 opposite the proximal face 270. The tubular portion 268 extends proximally from the proximal face 270. To facilitate decoupling of the cap faceplate 240 removably coupled with the cap head 242, the cap faceplate 240 may include a grip 274 adapted to be manipulated by the user (e.g., pinched).

The cap faceplate 240 of the cap portion 206 includes the inlet fitting 212. As shown in FIG. 15, the inlet fitting 212 extends distally from the distal face 272 of the cap faceplate 240 with the inlet bore 214 extending through the cap faceplate 240. As a result, with the manifold 200 assembled, the inlet fitting 212 is rotatably fixed relative to the body portion 204.

During operation of the medical waste collection assembly 50 with the manifold 200, the tissue sample may be collected with the porous features 218 of the filter element 216. Retrieval of the tissue sample from the filter element 216, however, may be cumbersome. As a result, the manifold advantageously provide for efficient retrieval of the tissue sample from the manifold 200, and further provide for efficient collection of multiple tissue samples as well as selective operation of the system without collection of the tissue sample (i.e., without replacing components). Referring again to FIGS. 12 and 13, the manifold 200 includes a tray 276 rotatably coupled to the housing 202. In particular and with concurrent reference to FIG. 19, the tray 276 defines a central lumen 280 sized to receive the spindle 260 of the cap head 242. With the tray 276 rotatably disposed about the spindle 260, the tray 276 is positioned between the cap faceplate 240 and the cap head 242, and in particular between the proximal face 270 of the cap faceplate 240 and the distal face 256 of the cap head 242. It is understood that the tray 276 may be monolithic, or constructed from multiple components to form a tray assembly. The tray 276 may be movably disposed within the housing 202 in ways other than being rotatable.

Figure 19:
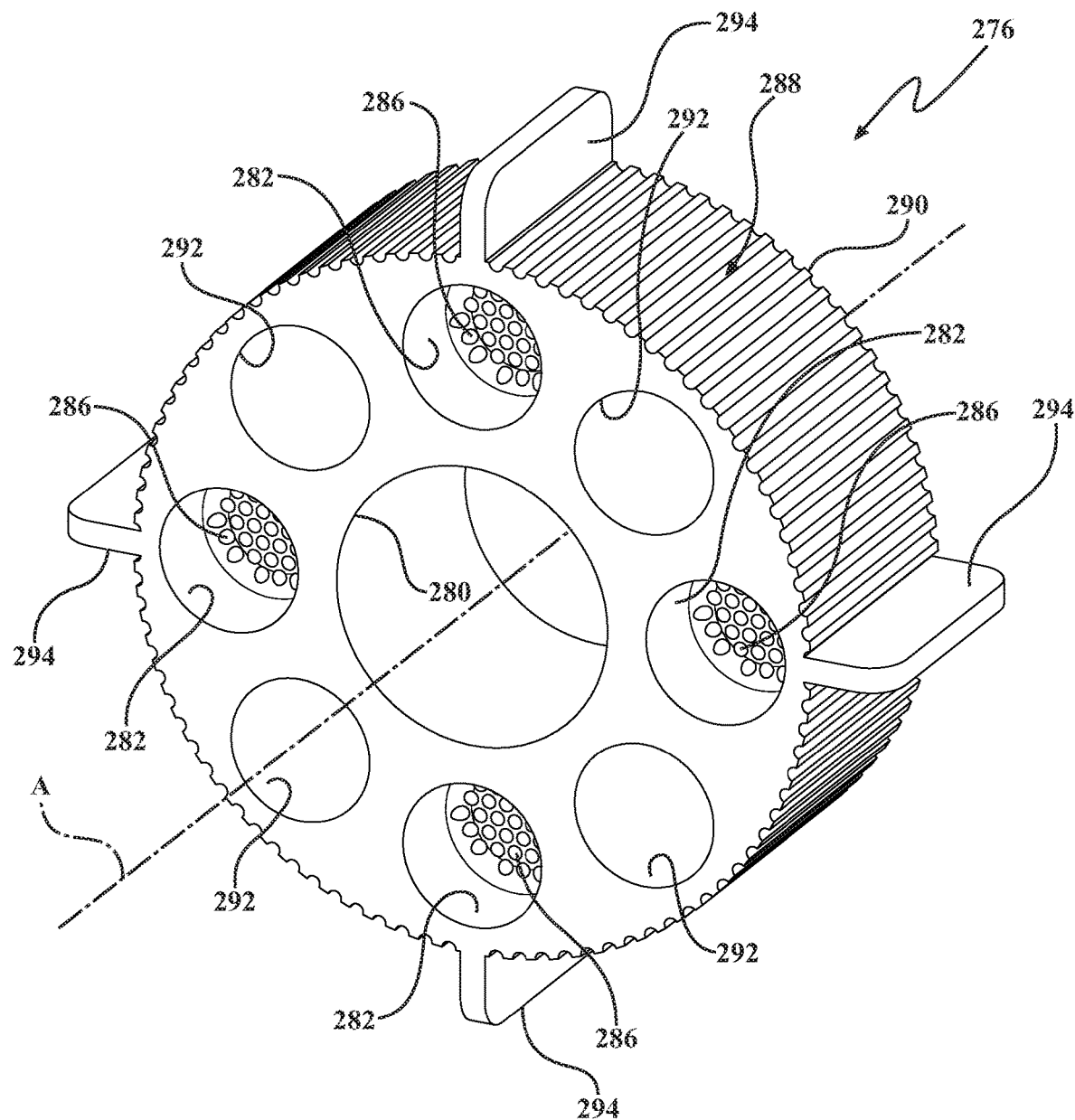
FIG. 19 is a perspective view of a tray of the manifold of FIG. 12 with the tray defining tissue collecting cavities and bypass channels.

The tray 276 defines a plurality of tissue collecting cavities 282. Each of the tissue collecting cavities 282 may extend at least partially through the tray 276. The tray 276 further defines porous features 286 within each of the tissue collecting cavities 282. Four tissue collecting cavities 282, but it is contemplated the tray 276 may include, one, two, three, five, or six or more of the tissue collecting cavities 282. The tissue collecting cavities 282 may be angularly spaced equally about an axis A extending coaxially through the tray 276. Alternate versions of the tray 276 may include unequal spacing, or a combination of equal and unequal spacing. While the tissue collecting cavities 282 are shown as being integral to the tray 276, the tissue collecting cavities 282 may be configured as modular inserts for the tray 276. The tray 276 includes a control surface 288 adapted to receive an input from the user. FIG. 19 shows the control surface 288 substantially defined by an outer annular surface 290 opposite the central lumen 280 to provide a generally cylindrical shape to the tray 276. The input to the control surface 288 rotates the tray 276 about the axis A to selectively provide fluid communication with one of the tissue collecting cavities 282 with the inlet bore 214 such that the porous features 286 are in the suction path to collect the tissue sample during operation of the medical waste collection assembly 50.

The distal face 256 of the cap head 242 may define the aperture 258 previously mentioned. The cap faceplate 240 is rotatably fixed relative to the cap head 242 with the inlet bore 214 aligned with the aperture 258. The tray 276 is axially positioned between the inlet bore 214 and the aperture 258. Should the user wish to collect the tissue sample with one of the tissue collecting cavities 282, the user provides the input to the control surface 288 to move (i.e., rotate) the tray 276 about the axis A to align one of the tissue collecting cavities 282 with the inlet bore 214 (and the aperture 258). The tissue collecting cavity 282 is in the suction path, and the tissue sample being aspirated through the suction path encounters the porous features 286 within the tissue collecting cavity 282. Should another tissue sample be desired, the user may simply provide another input to the control surface 288 to rotate the tray 276 about the axis A to align another one of the tissue collecting cavities 282 with the inlet bore 214. The method may be repeated up to the number of tissue collecting cavities 282.

For any number of reasons, the user may prefer to wait until a certain point in the surgical procedure to operate the manifold 200 in a manner to collect the tissue sample, but maintain the capability of aspirating the surgical site for other reasons (e.g., visualization). Moreover, once the tissue sample(s) are collected, the user may prefer to continue to aspirate the surgical site without needing to first retrieve the tissue sample from the manifold 200. Yet directing the stream over the previously collected tissue sample for any period of time may degrade the tissue sample itself. The manifold 200 advantageously accommodates the aforementioned considerations. Referring again to FIG. 19, the tray 276 further defines at least one bypass channel 292 separate from the tissue collecting cavities 282. Each of the bypass channels 292 may be shaped as a borehole extending axially through the tray 276. The illustrated implementation shows four of the bypass channels 292, but it is contemplated the tray 276 may define, one, two, three, five, or six or more of the bypass channels 292. The tissue collecting cavities 282 and the bypass channels 292 may be arranged in an alternating manner and equally spaced angularly about the axis A. Alternate versions of the tray 276 may include groupings of the tissue collecting cavities 282 and/or the bypass channels 292, and unequal spacing or a combination of equal and unequal spacing. It is further contemplated that the tray 276 may be formed to only define the tissue collecting cavities 282 with the bypass channel(s) 292 being defined between an outer surface of the tray 276 and an inner surface of the housing 202. For example, the tray 276 may be triangular-shaped to define the tissue collecting cavities 282. The inner surface of the housing 202 circumscribes the triangle and the area between the triangular-shaped tray 276 and the inner surface of the housing 302 constitutes the bypass channel 292.

The tray 276 is adapted to be rotated about the axis A to selectively align the bypass channel 292 with the inlet bore 214 and the aperture 258 to permit fluid to flow through the manifold 200 without collecting the tissue sample during operation of the medical waste collection assembly 50. In particular, the user provides the input to the control surface 288 to rotate the tray 276 about the axis A to align one of the bypass channels 292 with both the inlet bore 214 and the aperture 258. With the bypass channel 292 in the suction path, the tissue collecting cavity is not in the suction path, and therefore the stream does not encounter the porous features 286. In other words, when the bypass channel 292 is in fluid communication with the inlet bore 214, it is considered that the tissue collecting cavities 282 are not in fluid communication with the inlet bore 214. It should be appreciated that the stream is filtered with the filter element 216 of the manifold 200 regardless of whether the tissue sample is being collected with the tray 276.

Figure 20:
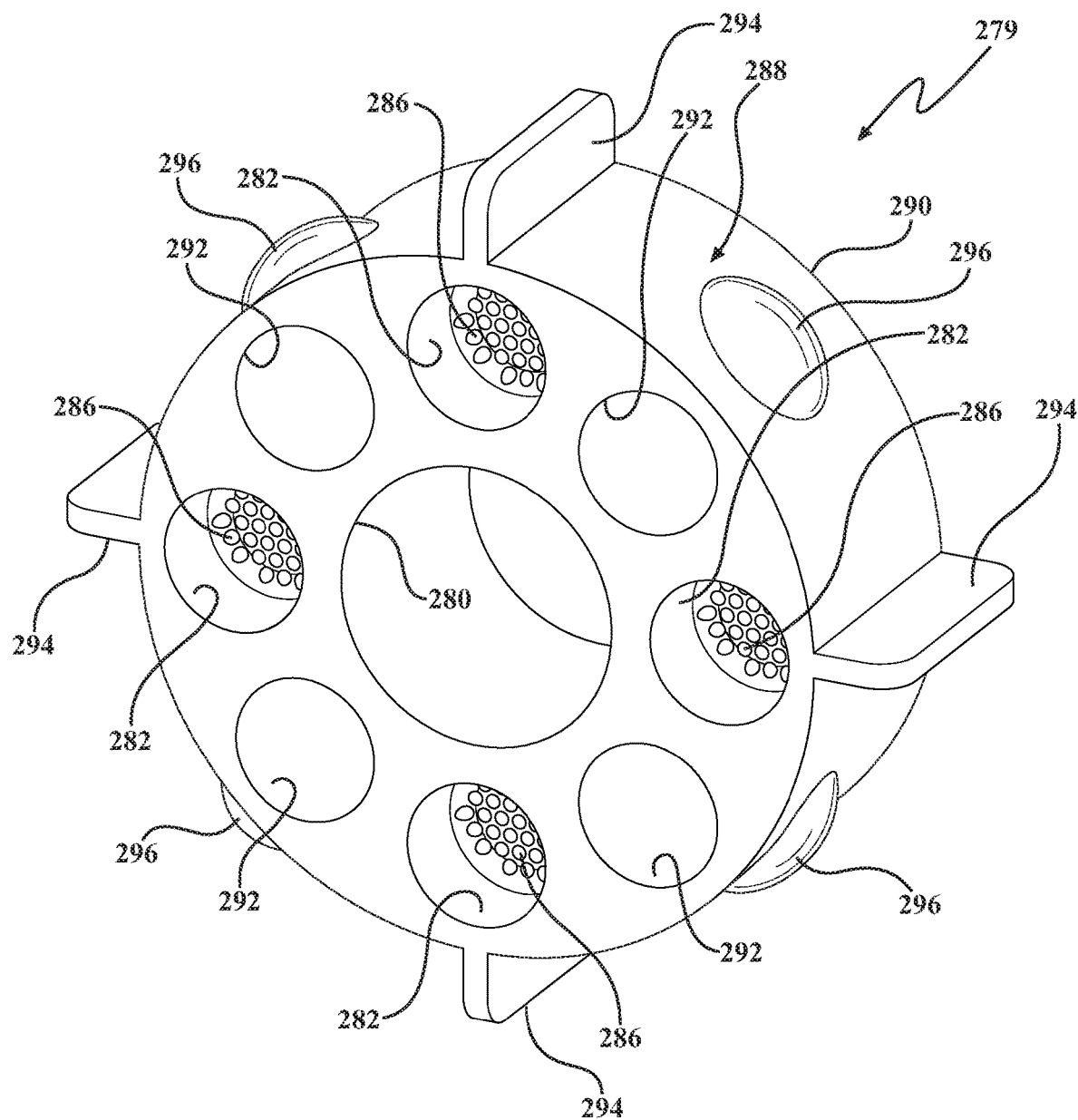
FIG. 20 is a perspective view of another tray for use with the manifold of FIG. 12 with the tray including magnifying lenses.

The tray 276 of the manifold 200 may include alignment features 294 adapted to provide visual indicia to the user as to the angular position of the tissue collecting cavities 282. FIGS. 19 and 20 show the alignment features 294 as tabs extending radially from the outer annular surface 290 of the tray 276. The alignment features 294 are shown as coplanar with a plane extending through the axis A and a bisecting each of the tissue collecting cavities 282. The alignment features 294 may also conveniently function to improve manipulation of the control surface 288 when providing the input to the control surface 288. The user provides the input to the control surface 288 (and/or the alignment features 294) until one of the alignment features 294 is generally aligned with a radial center of the inlet bore 214. The grip 274 may bisect the distal face 272 of the cap faceplate 240 such that when the tissue collecting cavity 282 is aligned with the inlet bore 214, an opposing pair of the alignment features 294 are coplanar with the grip 274. This added alignment may provide further visual confirmation to the user. It is contemplated that additional or alternate indicia may be provided on the manifold 200 in suitable locations to facilitate accurate orientating of the tray 276.

Figure 18:
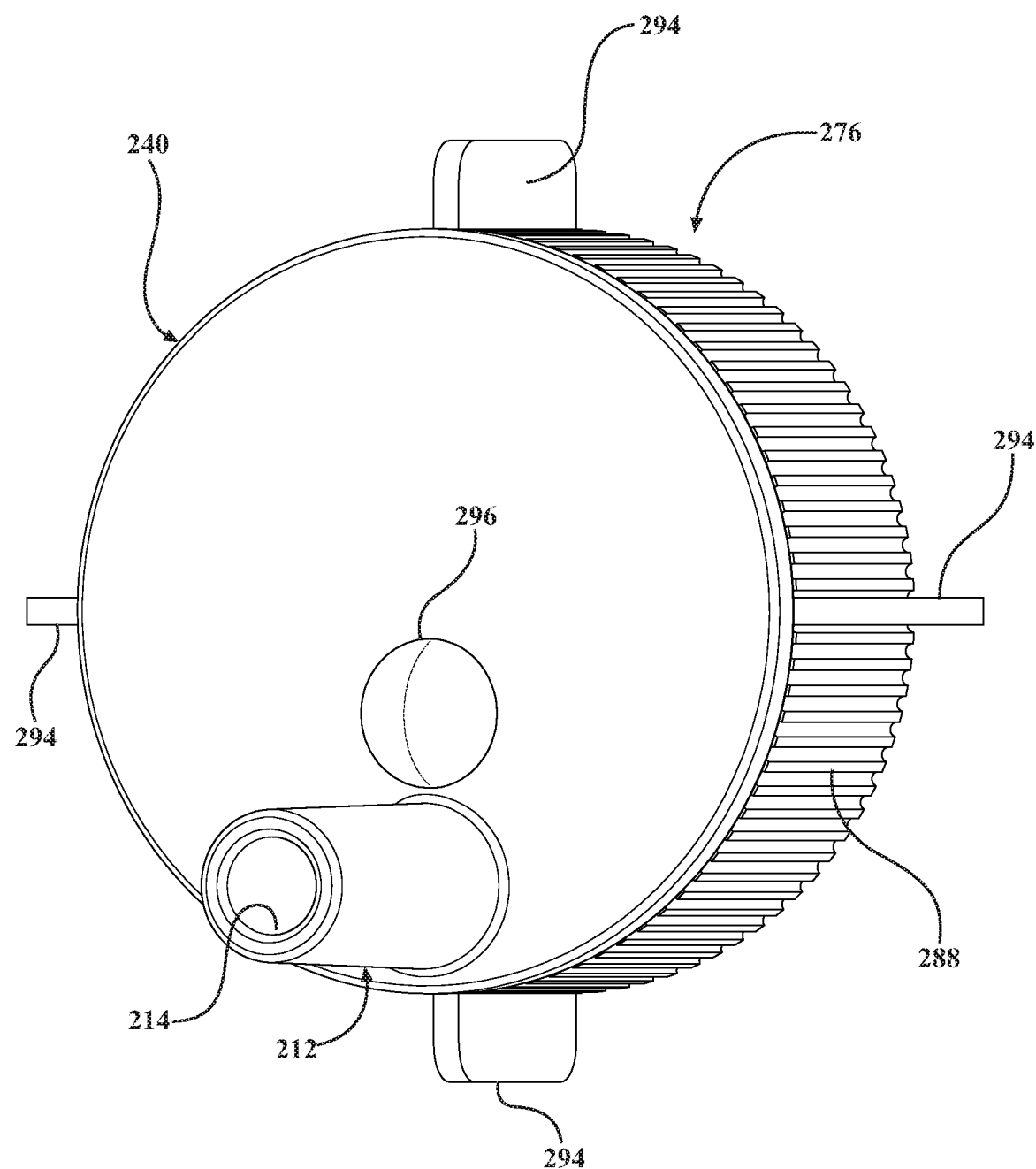
FIG. 18 is a perspective view of another cap faceplate and a tray of the manifold with the cap faceplate including a magnifying lens.

The manifold 200 may include one or more lenses 296 positioned to provide magnification within one or more of the tissue collecting cavities 282. Referring to FIG. 18, the lens 296 is disposed on the cap faceplate 240 of the cap portion 206. The lens 296 is positioned adjacent the inlet fitting 212 to provide visualization within the tissue collecting cavity 282 in fluid communication with the inlet bore 214. In another implementation (see FIG. 20), the lenses 296 are disposed on the tray 276. With the size of tissue samples often on the order of a few millimeters, and the lens(es) 296 magnifying within one or more of the tissue collecting cavities 282, the user is able to more efficiently and effectively determine whether a satisfactory tissue sample has been collected in one of the tissue collecting cavities 282. It is contemplated that lighting may be provided to illuminate the one or more of the tissue collecting cavities 282. A light source (not shown) may be suitably positioned on the manifold receiver 54 and/or the manifold 200 to direct light within the tissue collecting cavities 282.

As mentioned, the bypass channels 292 permit the user to continue to aspirate the surgical site without needing to first retrieve the tissue sample from the manifold 200 and without compromising the quality of the tissue sample as initially collected. As a result, the manifold 200 may remain engaged with the medical waste collection assembly 50 until the conclusion of the surgical procedure. Thereafter, the manifold 200 facilitates efficient retrieval of the tissue sample. The cap portion 206 is removably coupled to the tray 276 to provide access to the tissue collecting cavities 282. The user may support the manifold 200 in one hand while engaging the grip 274 with the other. The user manipulates the grip 274 to disengage the complementary coupling features 266, 267 (e.g., the bayonet mount) between the cap faceplate 240 and the cap head 242. The cap faceplate 240 is decoupled from the cap head 242, thereby exposing the tissue collecting cavities 282. Further, the tray 276 may be slidably removed from the spindle 260 of the cap head 242 to require the user to manage only the tray 276 during retrieval of the tissue sample(s). Further, with the tray 276 separable from the remainder of the manifold 200, the tray 276 may permit further processing of the tissue sample(s) prior to retrieval (e.g., positioning the tray 276 with the tissue sample(s) within a container of formalin).

Figure 21:
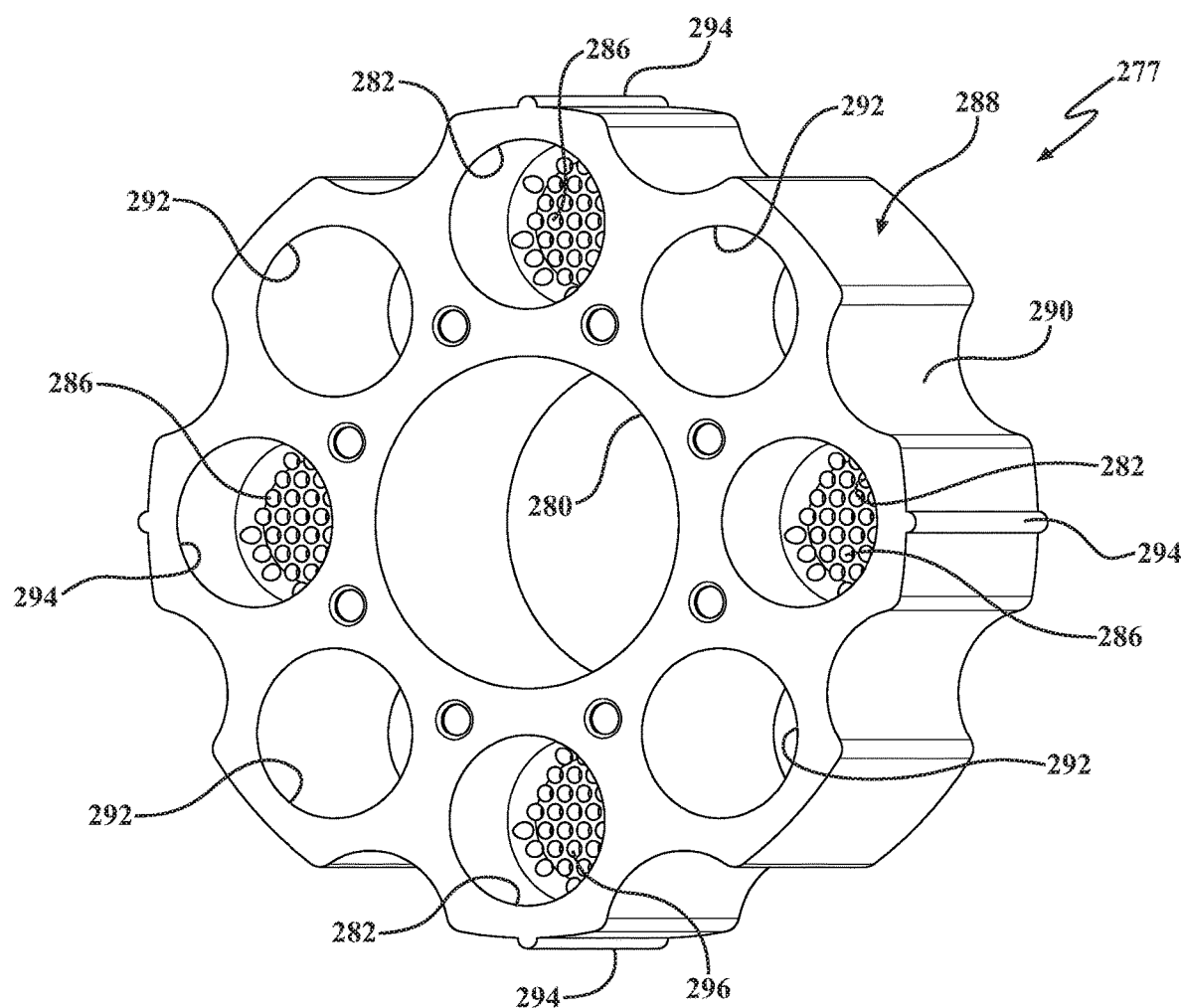
FIG. 21 is a perspective view of another tray for use with the manifold of FIG. 12.
Figure 22:
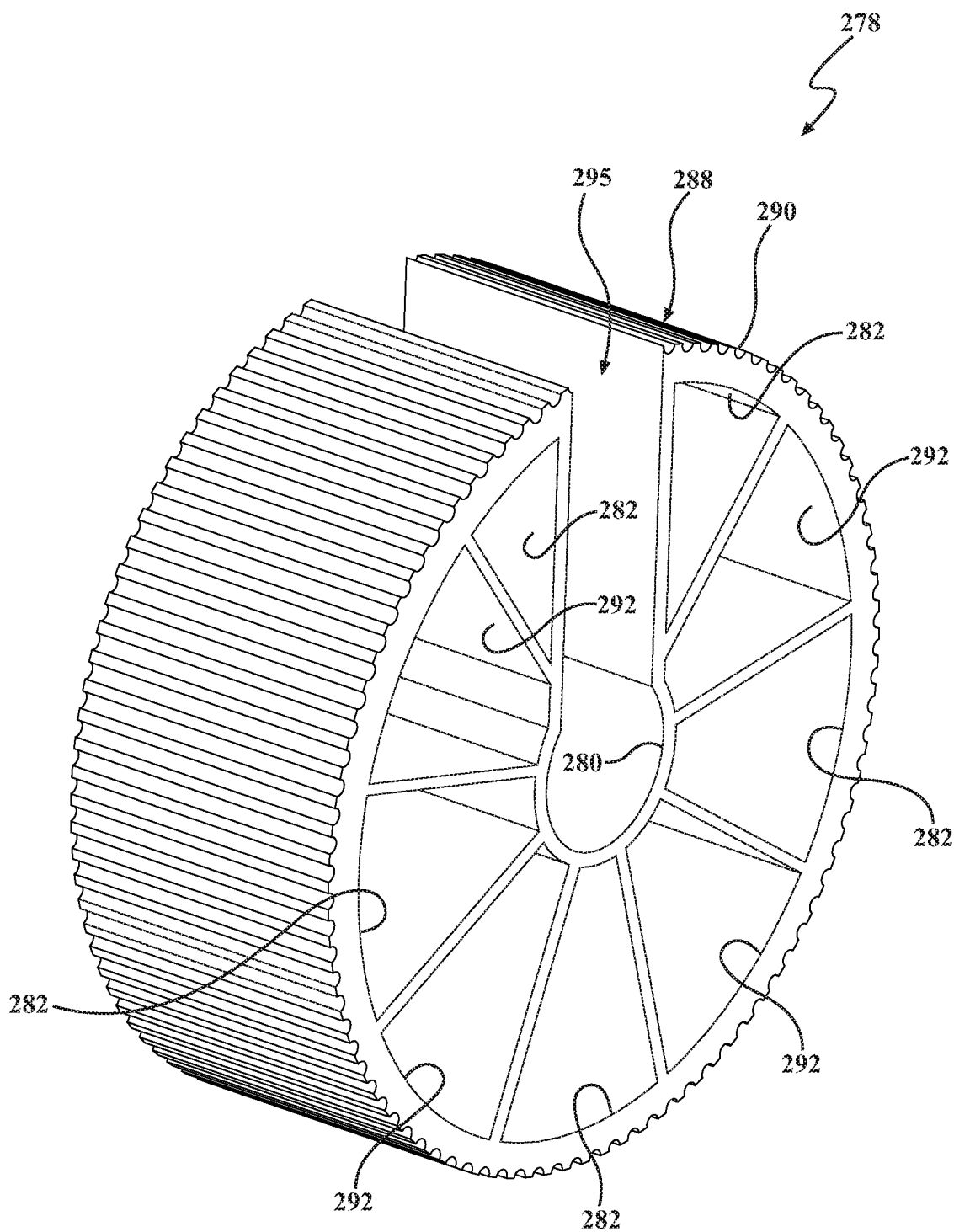
FIG. 22 is a perspective view of another tray for use with the manifold of FIG. 12.

FIGS. 20-22 illustrate alternative versions of the tray 277, 278, 279 for use with the manifold 200. In many respects the trays 277, 278, 279 are the same as the tray 276 previously described with like numerals indicating like components. FIG. 20 shows the lenses 296 disposed on and circumferentially arranged about the control surface 288. Each of the lenses 296 is angularly aligned with one of the tissue collecting cavities 282. It is noted that in FIG. 21, the alignment features 294 are angularly aligned with the bypass channels 292 as opposed to the tissue collecting cavities 282 to provide suitable space on the outer annular surface 290 for the lenses 296. FIG. 21 shows the outer annular surface 290 including a different contour to improve user manipulation of the control surface 288. In particular, the outer annular surface 290 includes a plurality of valleys separating a plurality of peaks corresponding to the angular position of the tissue collecting cavities 282 and the bypass channels 292. The alignment features 294 are disposed on every other one of the peaks and correspond to the angular position of the tissue collecting cavities 282. It is noted that the alignment features 294 are less pronounced than those previously described. The tray 278 of FIG. 22 shows, in particular, an alternative geometry for the tissue collecting cavities 282 and the bypass channels 292. The tissue collecting cavities 282 and the bypass channels 292 of FIG. 22 are defined by sectors that are generally pie-shaped. Further, the tray 278 includes a channel 295 extending radially from the central lumen 280 to the outer annular surface 290. The channel 295 includes a width defined between opposing sides that is approximately equal to or greater than a diameter of the spindle 260 of the cap portion 206. It is contemplated that the width of the channel 295 may be slightly less than the diameter of the spindle 260 so as to provide a defeatable interference fit between the tray 278 and a portion of the central lumen 280. The channel 295 permits the tray 278 to be decoupled from the remainder of the manifold 200 without requiring the cap faceplate 240 to be decoupled from the cap head 242.

Figure 23:
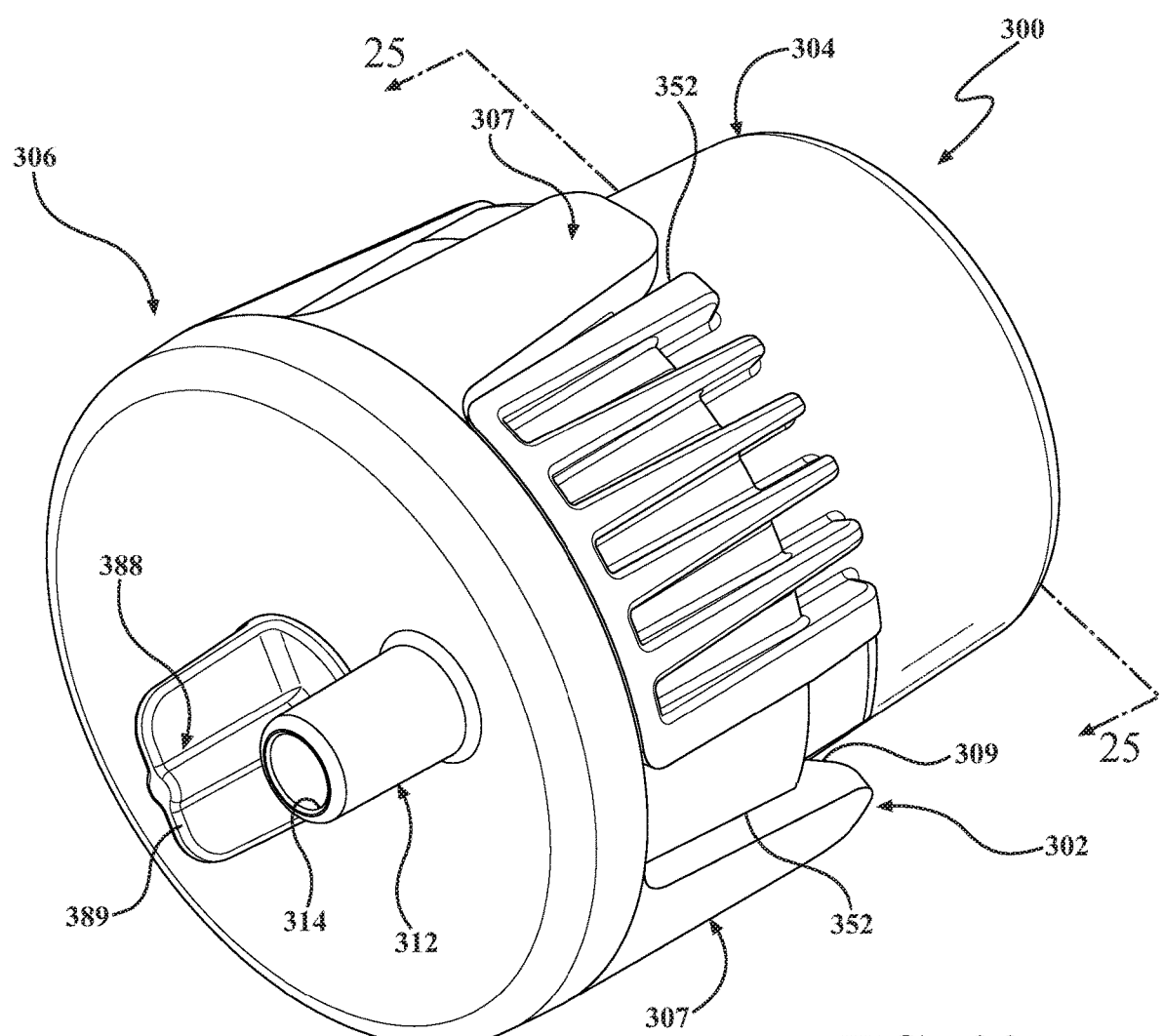
FIG. 23 is a perspective view of a manifold.
Figure 24:
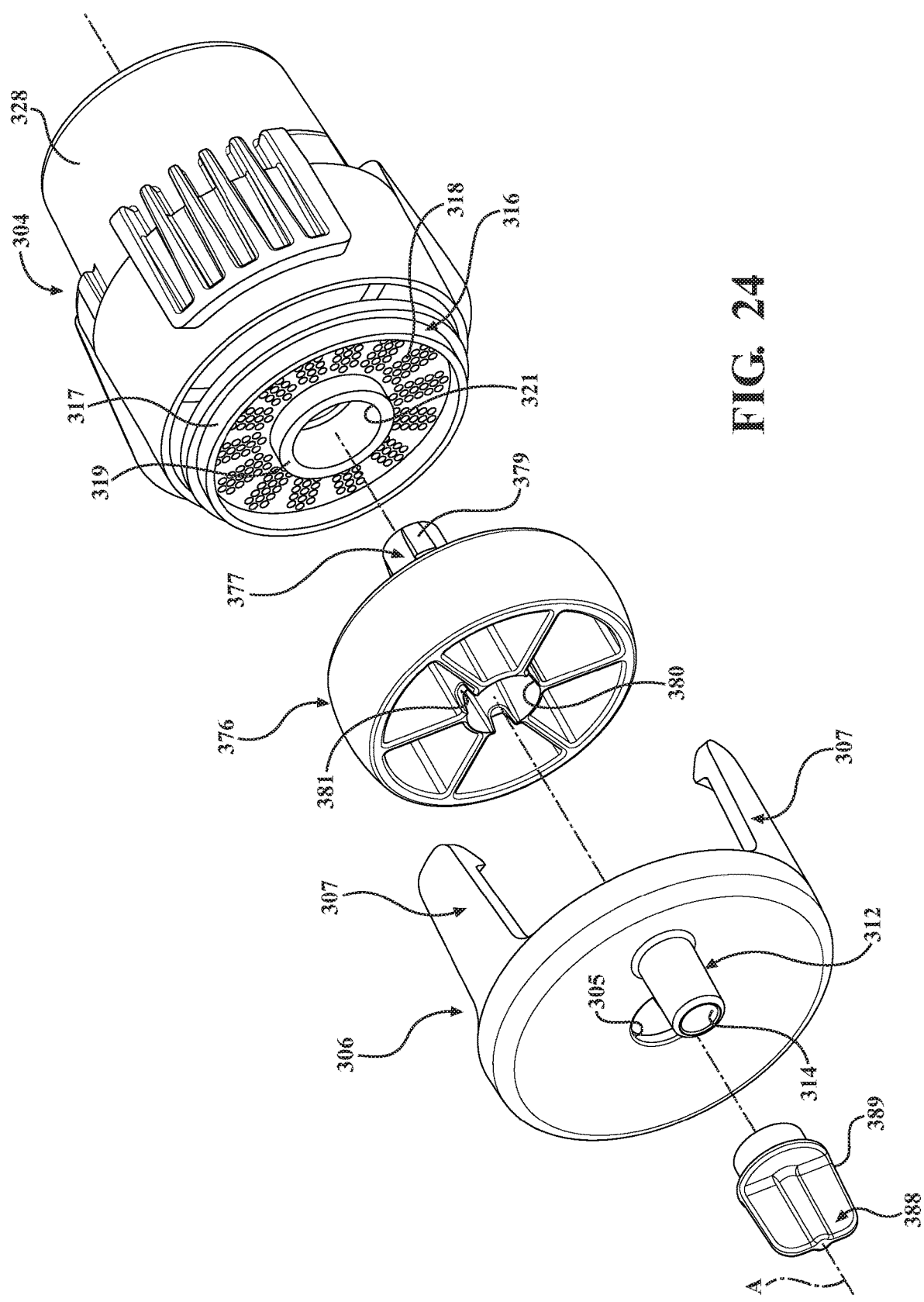
FIG. 24 is an exploded view of the manifold of FIG. 23.
Figure 25:
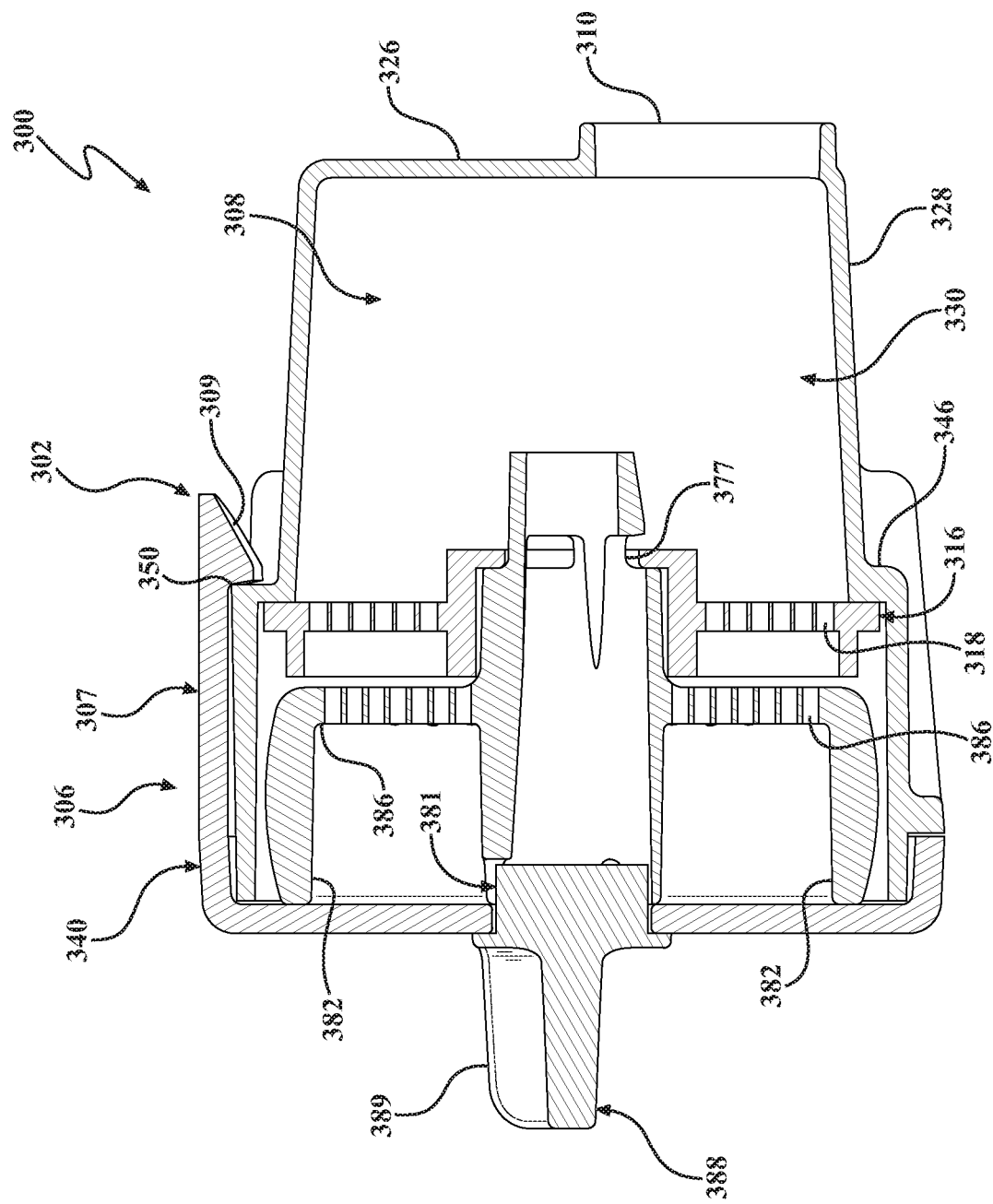
FIG. 25 is a sectional view of the manifold of FIG. 23 taken along section lines 25-25.

Referring now to FIGS. 23-25, another manifold 300 is illustrated that is, in at least some respects, similar to those previously described (and certain like components being indicated by like numerals plus one hundred (100)). The manifold 300 includes the housing 302 adapted to be removably engaged with the manifold receiver 54. The housing 302 includes the body portion 304 and the cap portion 306 coupled to the body portion 304. As best shown in FIG. 25, the housing 302 defines the manifold volume 308, and the outlet opening 310 in fluid communication with the manifold volume 308. The body portion 304 may include the proximal base 326 and the side 328 extending distally from the proximal base 326 to define the cavity 230 including a portion of the manifold volume 308. The outlet opening 310 may be positioned within the proximal base 326. The cap portion 306 includes the inlet fitting 312 defining the inlet bore 314 in fluid communication with the manifold volume 308. The drip valve (not shown) may be disposed within the outlet opening 310 in the manner previously described.

The cap portion 306 may be removably coupled to the body portion 304. With reference to FIGS. 23 and 24, the cap portion 306 includes flanges 307 circumferentially positioned near a rim of the cap faceplate 340. The flanges 307 each include an inclined surface 309 at a proximal end of the flange 307. The inclined surfaces 309 of the flanges 307 are shaped to impart resilient deflection of the flanges 307 as the body and cap portions 304, 306 are assembled. The flanges 307 are directed over the sidewall 328 of the body portion 304 until a barbed feature 350 moves past the annular plateau 346 of the body portion 304 and resiliently deflects inwardly into interference engagement with the annular plateau 346. Further, the body portion 304 includes one or more orientation features 352, for example one or more surfaces extending radially from the sidewall 328 to engage the flanges 307 and prevent rotation of the cap portion 306 relative to the body portion 304. In other words, the cap portion 306 is rotatably fixed relative to the body portion 304.

The manifold 300 may include the filter element 316 disposed within the housing 302 and in the suction path. The filter element 316 defines the porous features 318 adapted to capture the semisolid and solid matter entrained within the stream being aspirated along the suction path. The filter element 316 is illustrated as disc-shaped with an outer annular rim 317 opposite an inner annular rim 319 defining a lumen 321. As shown in FIGS. 24 and 25, the tray 376 includes an axle 377 extending proximally from a proximal side of the tray 376. The lumen 321 of the filter element 316 is sized to receive the axle 377 of the tray 376. Further, each of the tray 376 and the filter element 316 include complementary orientation features 379 adapted to prevent rotation of filter element 316 relative to the tray 376. In other words, when the tray 376 is rotated about the axis A in the manner to be described, the filter element 316 rotates correspondingly. The orientation features 379 may include a key disposed on the axle 377 and a corresponding keyhole (not shown) suitably disposed on the filter element 316.

Figure 26:
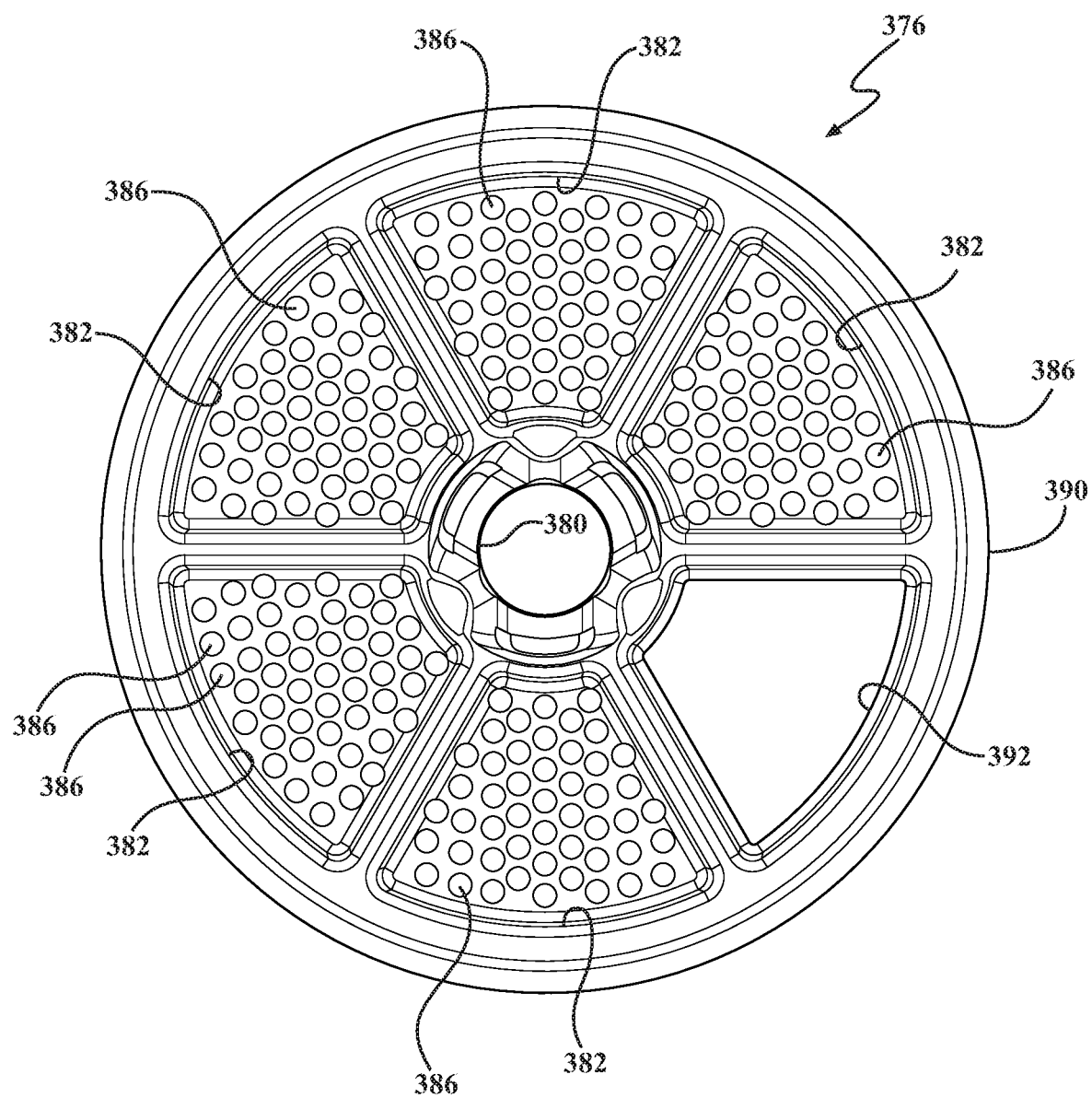
FIG. 26 is a front elevation view of a tray of the manifold of FIG. 23 with the tray defining tissue collecting cavities and a bypass channel.

The manifold 300 includes the tray 376 rotatably coupled to the housing 302. The tray 376 is positioned proximal to the cap faceplate 340 of the cap portion 306. With concurrent reference to FIG. 26, the tray 376 defines the tissue collecting cavities 382. Each of the tissue collecting cavities 382 may be formed as a sector and define porous features 386 within each of the tissue collecting cavities 382. The sectors may be generally pie-shaped. FIG. 26 also shows five of the tissue collecting cavities 382, but it is contemplated the tray 376 may include, one, two, three, four, or six or more of the tissue collecting cavities 382. Further, the tissue collecting cavities 382 may be equally sized, but alternate versions may include the unequal sizing, or a combination of equal and unequal sizing.

The manifold 300 includes the control surface 388 adapted to receive the input from the user. FIGS. 23-25 show the control surface 388 defined on a knob 389 positioned distal to the cap portion 306. In particular, the cap faceplate 340 of the cap portion 306 includes an opening 305 with the control surface 388 arranged to manipulated through the opening 305. Depending on the location of the tray 376, the body portion 304 may alternatively comprise such an opening. The knob 389 is coupled to the tray 376 with complementary orientation features 381. FIG. 24 shows the complementary orientation features 381 including keyways defined within the tray 376 near the central lumen 380, and FIG. 25 shows the complementary orientation feature including a key extending from a proximal region of the knob 389. The complementary orientation features 381 are adapted to preserve relative rotation between the control surface 388 and the tray 376 such that when the knob 389 is rotated about the axis A, the tray 376 rotates correspondingly.

In operation, should the user wish to collect the tissue sample in one of the tissue collecting cavities 382, the user provides the input to the control surface 388 to rotate the knob 389 and the tray 376 about the axis A to align one of the tissue collecting cavities 382 with the inlet bore 314. The aligned tissue collecting cavity 382 is in the suction path, and the tissue sample being aspirated through the suction path encounters the porous features 386 within the tissue collecting cavity 382. Should another tissue sample be desired, the user may simply provide another input to the control surface 388 to rotate the knob 389 and the tray 376 about the axis A to align another one of the tissue collecting cavities 382 with the inlet bore 314. The method may be repeated up to the number of tissue collecting cavities 382.

For reasons previously expressed, the tray 376 defines the bypass channel 392 separate from the tissue collecting cavities 382. The bypass channel 392, shown in FIG. 26, permits fluid to flow through the manifold 300 without collecting the tissue sample during operation of the medical waste collection assembly 50. The tray 376 is adapted to be rotated about the axis A to selectively align the bypass channel 392 with the inlet bore 314. In particular, the user provides the input to the control surface 388 to rotate the knob 389 and the tray 376 about the axis A to align the bypass channel 392 with the inlet bore 314. As mentioned, when the bypass channel 392 is in fluid communication with the inlet bore 314, it is considered that the tissue collecting cavities 382 are not in fluid communication with the inlet bore 314. The manifold 300 may include the lens(es) (not shown) and/or the illumination previously described to provide magnification and improved visualization within one or more of the tissue collecting cavities 382.

The manifold 300 facilitates efficient retrieval of the tissue sample from the manifold 300. The manifold 300 is decoupled from the medical waste collection assembly 50, most often after the relevant aspects of the surgical procedure have been completed. The user supports the body portion 304 with one hand, and overcomes the interference engagement between the barbed feature 350 at the proximal end of the flange 307 of the cap portion 306 and the annular plateau 346 of the body portion 304. The cap portion 306 is decoupled from the body portion 304, thereby exposing the tissue sample(s) collected in the tissue receiving cavities 382 of the tray 376.

Figure 27:
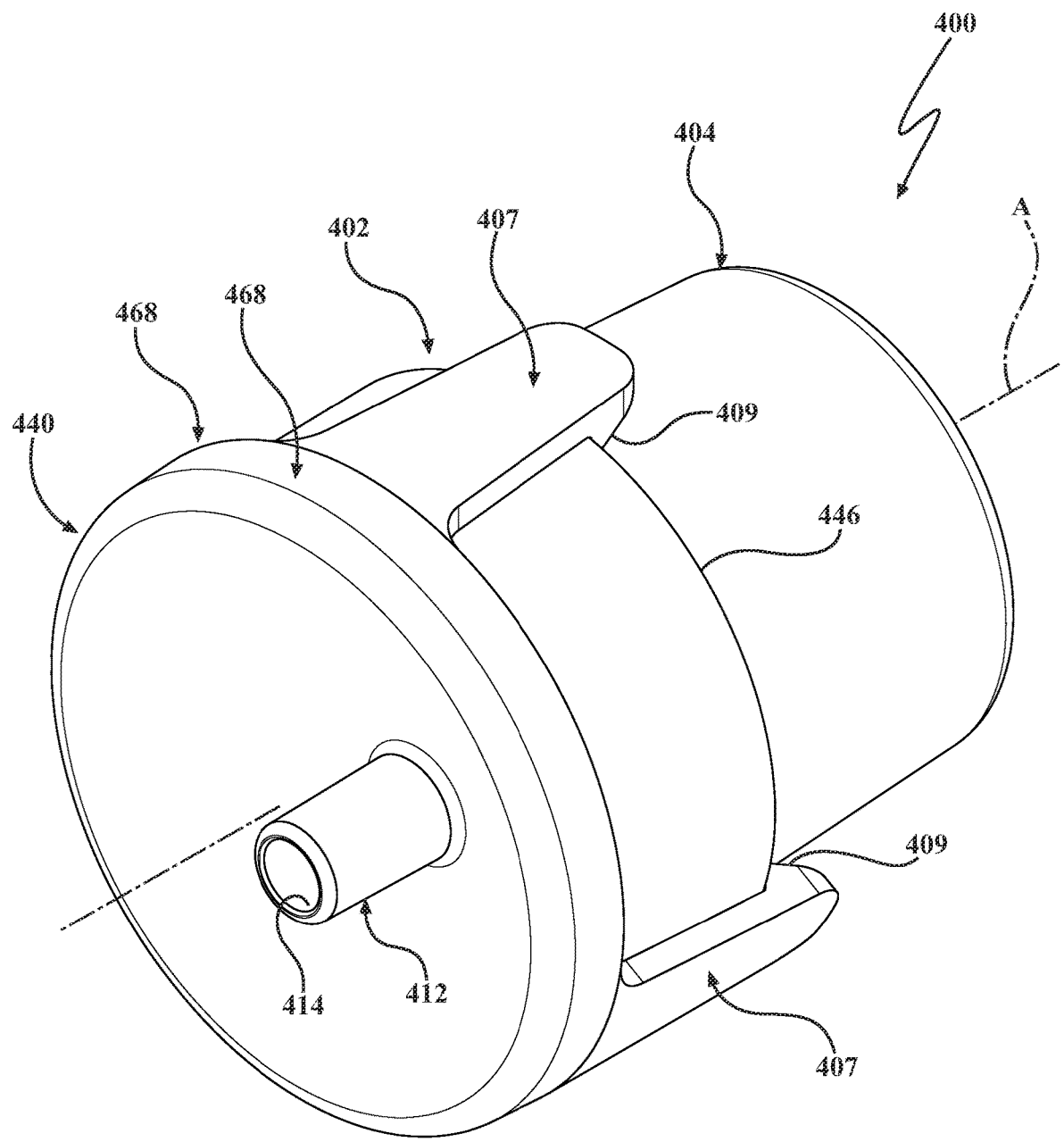
FIG. 27 is a perspective view of a manifold.
Figure 28:
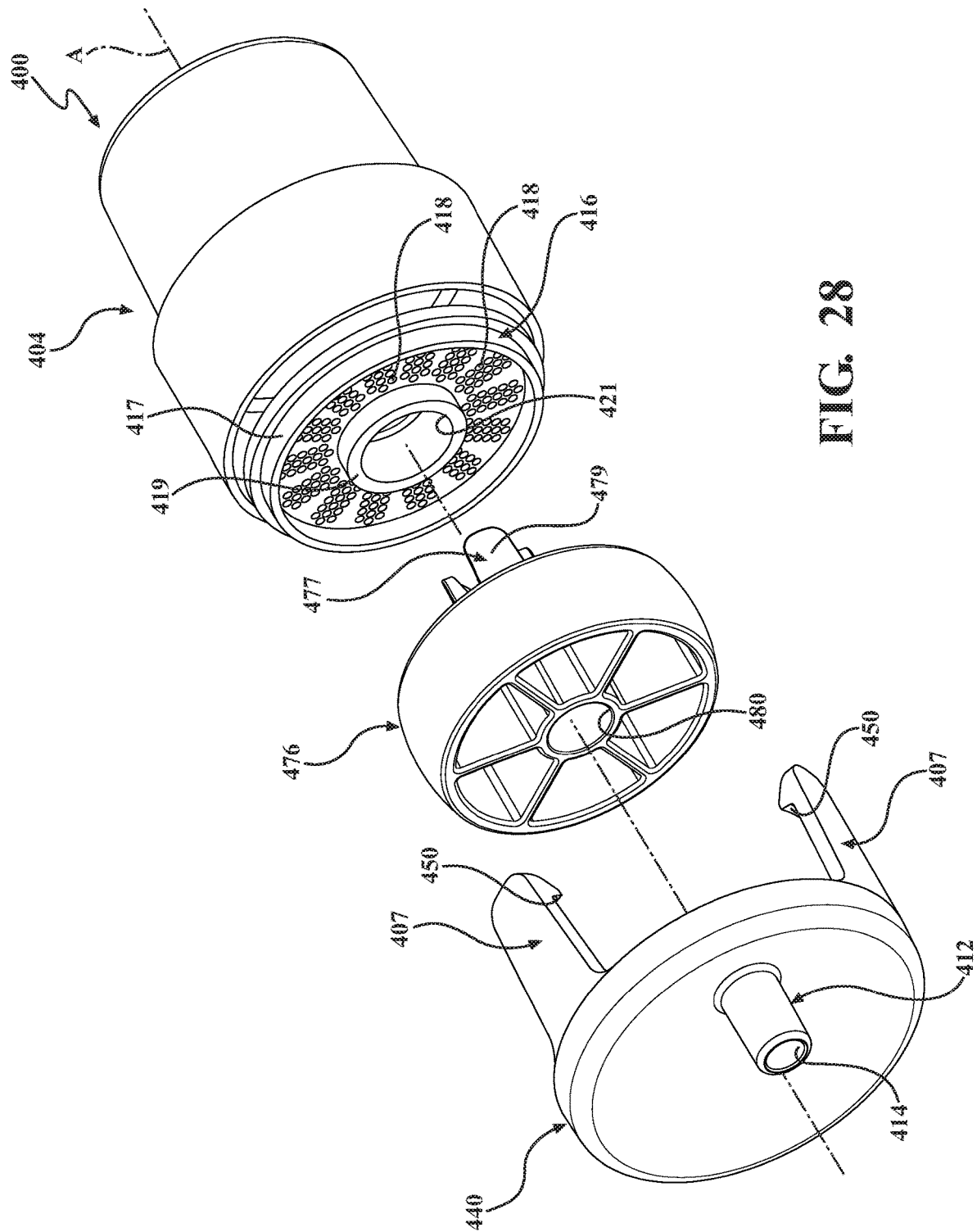
FIG. 28 is an exploded view of the manifold of FIG. 27.

Referring now to FIGS. 27 and 28, another manifold 400 is illustrated that is, in at least some respects, similar to those previously described (and certain like components being indicated by like numerals plus one hundred (100)) with only certain features being explicitly described in the interest of brevity. The manifold 400 includes the cap portion 406 being rotatably coupled to the body portion 404, and the tray 476 is rotatably fixed relative to the body portion 404. FIG. 28 shows the axle 477 extending proximally from the tray 476 and defining orientation features 479 adapted to engage complementary orientation features (not shown) of the body portion 404. The engagement of the complementary orientation features 479 prevents rotation of the tray 476 relative to the body portion 404.

The cap portion 406 includes the flanges 407 circumferentially positioned near a rim of the cap faceplate 440. The flanges 407 each include an inclined surface 409 shaped to impart resilient deflection of the flanges 407 as the body and cap portions 404, 406 are assembled. The flanges 407 are directed over the sidewall 408 of the body portion 404 until the barbed feature 450 moves past the annular plateau 446 of the body portion 404 and resiliently deflects inwardly into interference engagement with the annular plateau 446. The body portion 404 may not include the orientation features such that, once the body and cap portions 404, 406 are coupled in the above manner, the cap portion 406 may be rotated relative to the body portion 404. In particular, the barbed feature 450 may move along the annular plateau 446 while maintaining the axial position of the cap portion 406 relative to the body portion 404.

The cap portion 406 includes the inlet fitting 412, and therefore rotation of the cap portion 404 results in corresponding rotation of the inlet bore 414 of the inlet fitting 412, and in particular relative to the tray 476 rotatably fixed relative to the body portion 404. The tray 476 defines the tissue collecting cavities 482, the porous features 486 within the tissue collecting cavities 482, and the bypass channel(s) 492 may be separate from the tissue collecting cavities 482. In operation, should the user wish to collect the tissue sample in one of the tissue collecting cavities 482, the user provides the input to the control surface 488 to rotate the cap portion 406 and inlet fitting 412 about the axis A to align the inlet bore 414 with one of the tissue collecting cavities 482. The aligned tissue collecting cavity 482 is in the suction path, and the tissue sample being aspirated through the suction path encounters the porous features 486. Should another tissue sample be desired, the user may simply provide another input to the control surface 488 to rotate the cap portion 406 and the inlet fitting 412 about the axis A to align the inlet bore 414 with another one of the tissue collecting cavities 482. The method may be repeated up to the number of tissue collecting cavities 482. Likewise, the cap portion 406 may be rotated about the axis A to selectively align the inlet bore 414 with the bypass channel 492 to permit fluid to flow through the manifold 400 without collecting the tissue sample during operation of the medical waste collection assembly 50. The manifold 400 may include the lens(es) (not shown) and/or the illumination previously described to provide magnification and visualization within one or more of the tissue collecting cavities 482.

Figure 29:
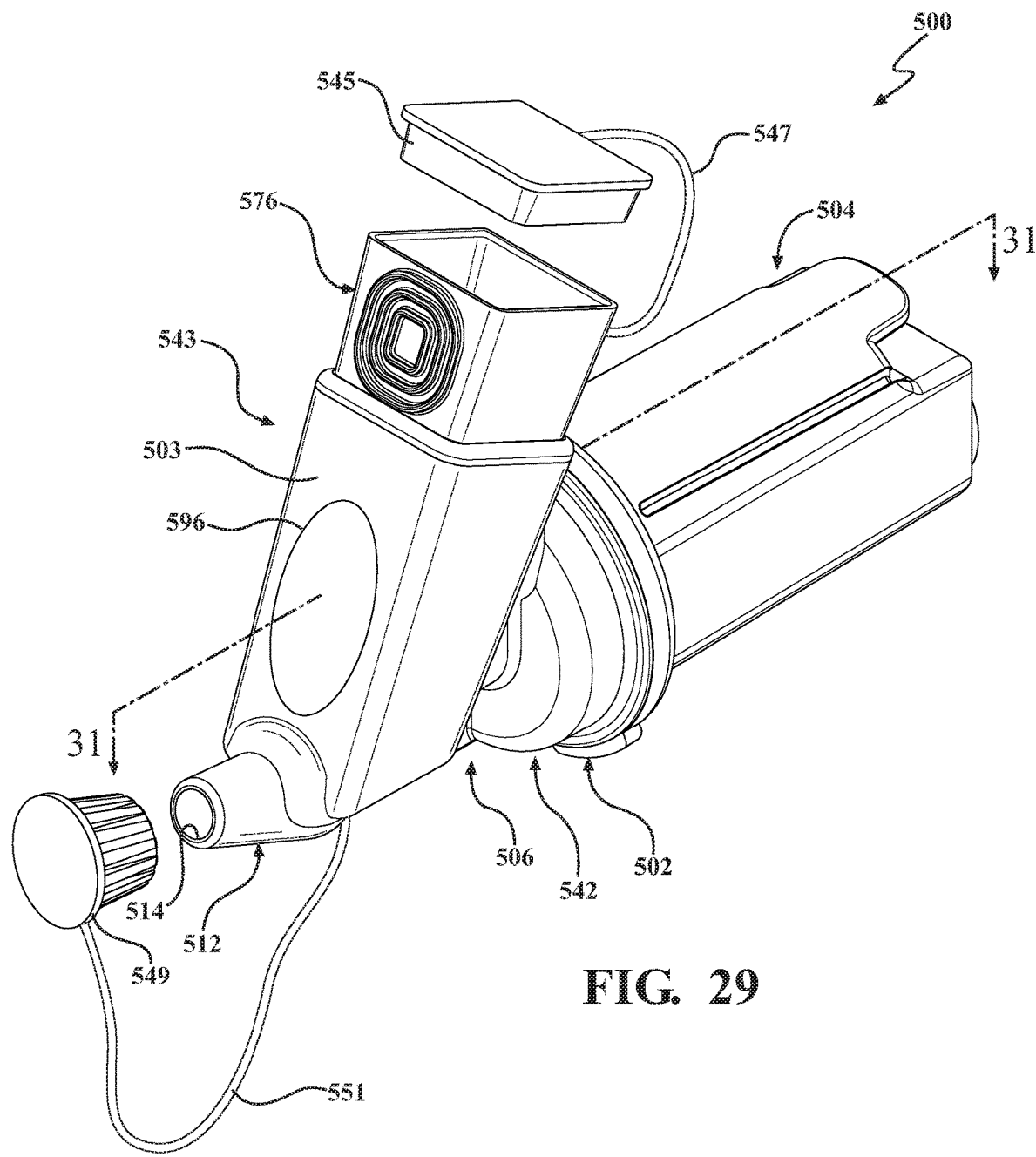
FIG. 29 is a perspective view of a manifold.
Figure 30:
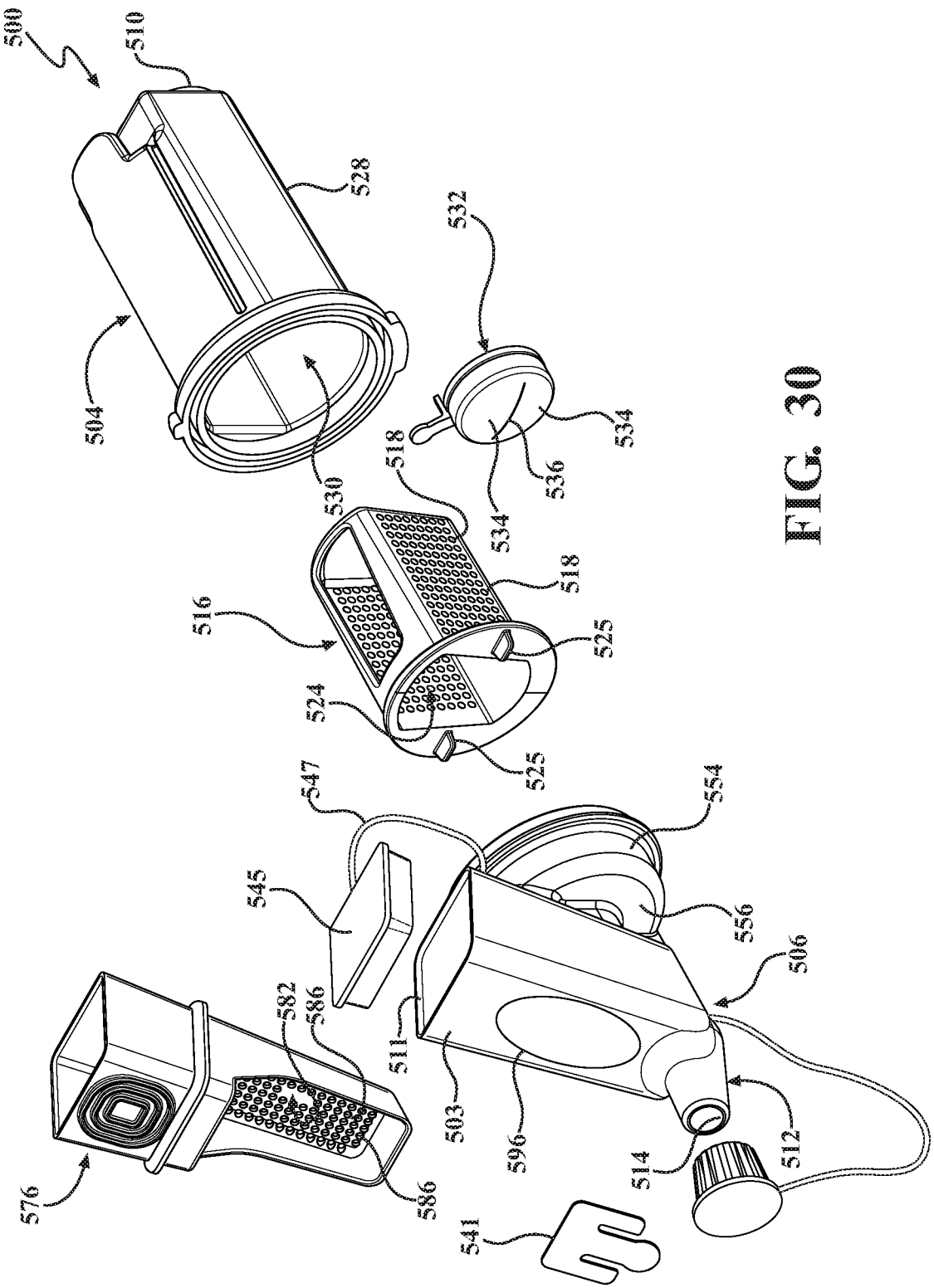
FIG. 30 is an exploded view of the manifold of FIG. 29.
Figure 31:
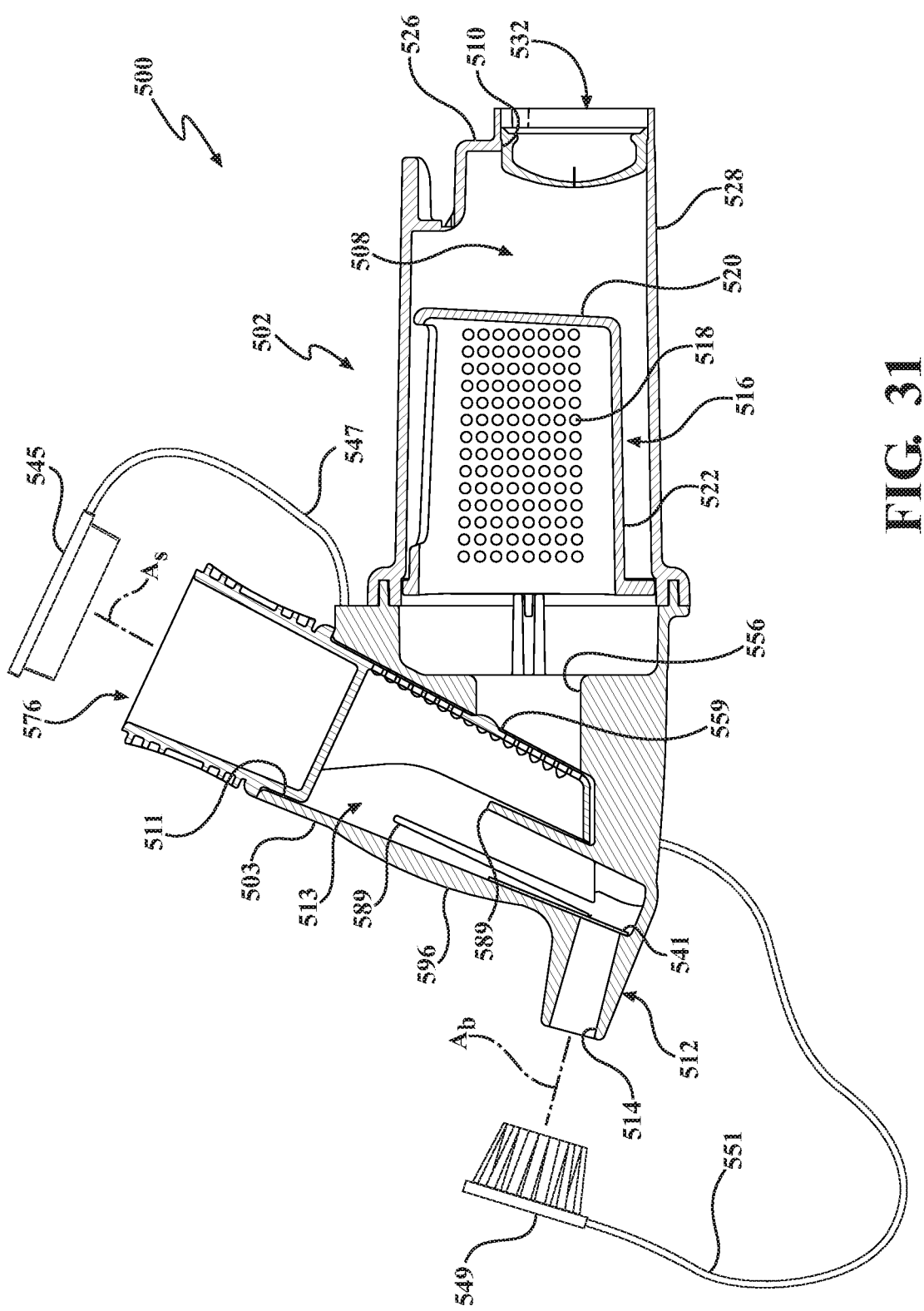
FIG. 31 is a sectional view of the manifold of FIG. 29 taken along section lines 31-31.

Referring now to FIGS. 29-31, another manifold 500 is illustrated that is, in at least some respects, similar to those previously described (and certain like components being indicated by like numerals plus one hundred (100)). The manifold 500 includes the housing 502 adapted to be removably engaged with the manifold receiver 54. The housing 502 includes the body portion 504 and the cap portion 506. As previously expressed, the cap portion 506 may be coupled to the body portion 504 with removable or permanent joining means, or the body and cap portions 504, 506 may be formed as a single piece of unitary construction. In one example, the body and cap portions 504, 506 are spin welded at an interface to prevent reuse. As best shown in FIG. 31, the housing 502 defines the manifold volume 508, and the outlet opening 510 in fluid communication with the manifold volume 508. The body portion 504 may include the proximal base 526 and the side 528 extending distally from the proximal base 526 to define the cavity 530 including a portion of the manifold volume 508. The housing 502 includes an inlet fitting 512 defining an inlet bore 514 in fluid communication with the manifold volume 508. As previously mentioned, the outlet opening 510 is adapted to be in fluid communication with the suction inlet 58 of the medical waste collection assembly 50 when the housing 502 is engaged with the manifold receiver 54 such that a suction path is provided from the inlet bore 514 to the suction inlet 58.

The manifold 500 may include a drip valve 532 positioned within the outlet opening 510 to prevent egress of material from the outlet opening 510 when the housing 502 is disengaged from the manifold receiver 54. The drip valve 532 may include the pair of deflectable wings 534 defining the slit 536 with the boss 64 of the manifold receiver 54 (see FIG. 2) adapted to deflect the wings 534 and extend through the slit 536 of the drip valve 532. The arrangement provides provide fluid communication between the manifold volume 508 and the suction inlet 58 of the medical waste collection assembly 50.

The manifold 500 may include the filter element 516 disposed within the housing 502 and in the suction path. The filter element 516 defines porous features 518 adapted to capture the semisolid and solid matter entrained within the stream being aspirated along the suction path. The suction path is provided from the inlet bore 514 to the suction inlet 52 through each of the manifold volume 508, the filter element 516, and the outlet opening 510. The filter element 516 may include the base wall 520 and the sidewall 522 extending from the base wall 520 to form the basket defining the mouth 524. The filter element 516 may includes certain features to be later described in detail (e.g., a window 715). It is appreciated that the filter element 216, 316 of previously described implementations may be used.

Figure 32:
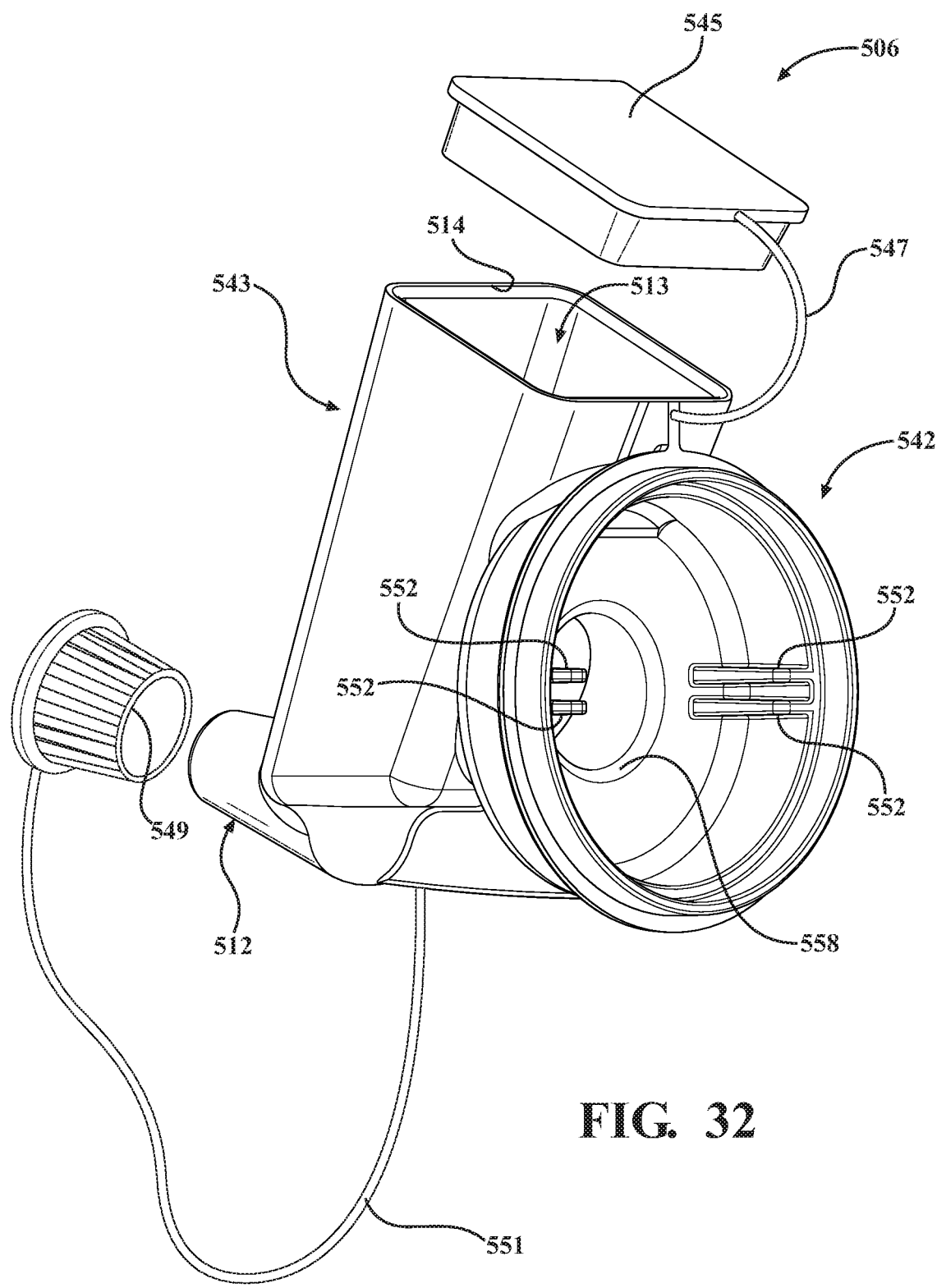
FIG. 32 is a rear perspective view of a cap portion of the manifold of FIG. 29.

With concurrent reference to FIG. 32, the cap portion 506 includes the cap head 542 and a support frame 543. The cap head 542 may include one or more orientation features 552, for example one or more pairs of rails extending radially inward from an inner annular surface. The rails receive tabs 552 disposed near the mouth 524 of the filter element 516 to prevent rotation of the filter element 516 relative to the cap portion 506. The cap head 542 includes at least one sidewall extending distally and terminating at the distal face 556. The aperture 558 extends through the distal face 556.

The support frame 543 may be integrally formed with the cap head 542. The support frame 543 is positioned distal to the cap head 542 and defines the front of the manifold 500. The cap portion 506 of the housing 502 defines a distal barrier 503 near the front of the manifold 500, as shown in FIGS. 29 and 30. The housing 502 includes the inlet fitting 512, and more particularly the support frame 543 of the cap portion 506 includes the inlet fitting 512. The inlet fitting 512 extends distally from the distal barrier 503 with the inlet bore 514 extending through the distal barrier 503.

The housing 502 further defines an accessory opening 511 opening into an accessory sleeve 513. The accessory sleeve 513 is in fluid communication with the manifold volume 508 through the aperture 558 extending through the distal face 556. The accessory sleeve 513 is disposed within the support frame 543 of the cap body 506. FIG. 29 shows the accessory opening 511 positioned at a superior aspect of the support frame 543 with the accessory sleeve 513 opening inferiorly within the support frame 543. The accessory sleeve 513 may be oriented on an axis $A_s$ angled away from a longitudinal axis of the housing 502, and more specifically angled proximally away from the front of the housing. With the tray 576 to be removably positioned within the accessory sleeve 513 in a manner to be described, the orientation of the accessory sleeve 513 limits or prevents inadvertent "splashing" of the medical waste from within the accessory sleeve 513 after removal of the tray 576 from the suction path. In one example, the axis $A_s$ of the accessory sleeve 513 relative to the longitudinal axis of the housing 502 is approximately within the range of 45 to 75 degrees, and more particularly within the range of 55 to 65 degrees.

The inlet bore 514 of the inlet fitting 512 may be inclined relative to horizontal. In particular, the inlet bore 514 is oriented on an axis Ab angled distally upward relative to the longitudinal axis of the housing 502. The inclination of the inlet bore 514 limits or prevents inadvertent "dripping" of the medical waste from the inlet bore 514 after removal of the suction line 52. Any remaining fluid within the inlet bore 514 flows towards the accessory sleeve 513 under the influence of gravity. A valve 541 may be coupled to the housing 502 and positioned within the accessory sleeve 513, as best shown in FIG. 30. The valve 541 may be a flapper valve adapted to be seated over a proximal end of the inlet bore 514 to prevent backflow of the fluid from the accessory sleeve 513 to the inlet bore 514. Other suitable valves are contemplated, for example, a duckbill valve.

As mentioned, the manifold 500 includes the tray 576 configured to be removably positioned within the accessory sleeve 513. The tray 576 defines a tissue collecting cavity 582 and porous features 586 within the tissue collecting cavity 582. With the tray 576 positioned within the accessory sleeve 513, the porous features 582 are in the suction path to collect the tissue sample. Once it is desired to retrieve the collected tissue sample, the tray 576 may be slidably removed from the accessory sleeve 513 with the tissue sample disposed within the tissue collecting cavity 582. It is to be understood that the tray 576 is optional, and the manifold 500 may be operated without the tray 576 within the accessory sleeve 513. The manifold 500 may include a cap 545 sized to be disposed in sealing engagement with the accessory opening 511. The cap 545 may be coupled to the housing 502 with a tether 547. FIG. 29 shows another cap 549 adapted to be coupled in sealing engagement with the inlet fitting 512 to cover the inlet bore 514. The cap 549 may also be coupled to the housing 502 with a tether 551.

Figure 33:
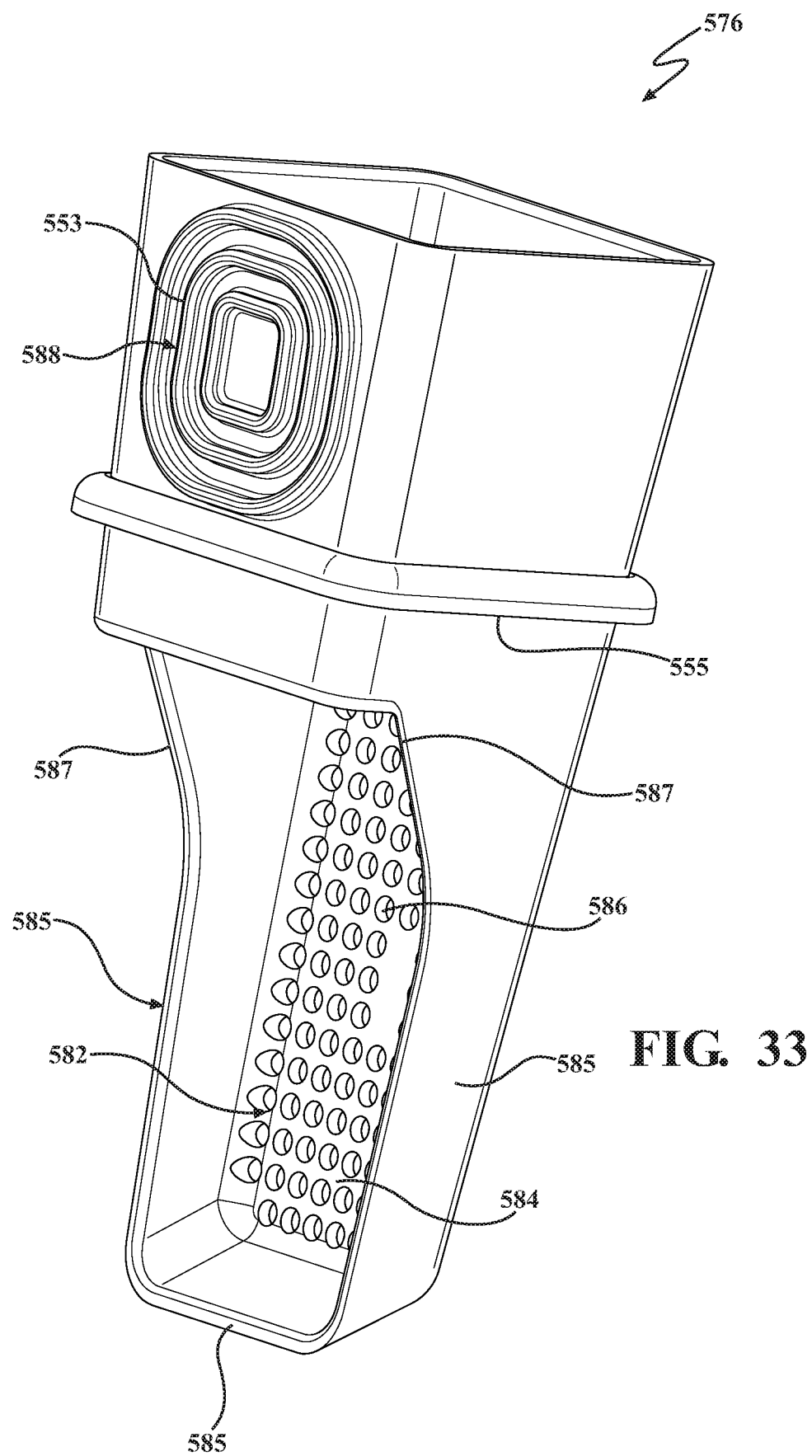
FIG. 33 is a perspective view of a tray of the manifold of FIG. 29 with the tray defining a tissue collecting cavity.

With concurrent reference to FIG. 33, the tray 576 may be formed from a single piece or multiple components. The tray 576 includes a control surface 588 adapted to receive the input from the user. The control surface 588 may be formed as a handle to be pinched between fingers of the user. FIG. 33 shows the handle being square-shaped with gripping features 553 disposed on one or more of the faces of the square-shaped handle. The tray 576 further includes a sealing surface 555 adapted to be in sealing engagement with the housing 502 when the tray 576 is within the accessory sleeve 513. In particular, the tray 576 may include a flange defining the sealing surface 555 with the sealing surface 555 adapted to contact a perimeter of the accessory opening 511. With the tray 576 within the accessory sleeve 513 and the sealing surface 555 covering the accessory opening 511, suction is maintained through the suction path during operation of the medical waste collection assembly 50. Likewise, the cap 545 is sized to cover the accessory opening 511 to maintain suction through the suction path.

The tray 576 may include a retention feature 559 adapted to defeatably engage a complementary retention feature of the housing 502. The retention feature 559 is adapted to be engaged concurrent with the sealing surface 555 being positioned adjacent to the perimeter of the accessory opening 511. FIG. 31 shows the retention feature 559 including a detent positioned on an underside of the tissue collecting cavity 582. The retention feature 559 engages a recess within the housing 502, namely a superior aspect of the aperture 558 of the cap head 542. As the retention feature 559 engages the complementary retention feature, a tactile and/or audible feedback may be provided to the user such that the user is confident the tray 576 is fully disposed or seated within the accessory sleeve 513. Further, with the retention feature 559 engaged, the sealing surface 555 is adjacent to the perimeter of the accessory opening 511 such that, once the medical waste collection assembly 50 is actuated, the suction path is successfully established. Once the tissue sample is collected within the tissue collecting cavity 582 and the user wishes to remove the tray 576, an input of sufficient force is provided to the control surface 588 of the tray 576 to disengage the retention feature 559 and the complementary retention feature (e.g., overcome the interference engagement between the detent and the housing 502).

The tray 576 may include a second retention feature (not shown) to engage a second complementary retention feature (not shown) of the housing 502. The second complementary retention features are on the tray 576 and the housing 502 in a suitable positon such that the tray 576 may be only partially disposed or seated within the accessory sleeve 513. Further sealing surfaces may be provided to cover the accessory opening 511 to maintain suction with the tray 576 only partially disposed within the accessory sleeve 513. Thus, the tray 576 may be "staged" in the bypass position and define the bypass channel 592 between a distal one of the sides 585 and a bottom of the accessory sleeve 513. The medical waste collection assembly 50 may be operated with the tray 576 in the bypass position such that fluid is permitted to flow through the suction path without the tray 576 collecting the tissue sample. Once the user wishes to collect the tissue sample, the user provides the further input to the control surface 588 (i.e., urge the tray 576 downwardly) to disengage the second complementary retention features and move the tray 576 from the bypass position to the tissue collection position in which the tissue collection cavity 582 is fully disposed in the accessory sleeve 513 such that the porous features 586 are in the suction path to collect the tissue sample.

As previously mentioned, it is desirable to visualize the tissue collecting cavity 582 during collection of the tissue sample. The quick visual confirmation afforded to the user once the tissue sample is within the tissue collecting cavity 582 permits the user to move onto any other aspects of the surgical procedure. The tissue collecting cavity 582 of the tray 576 opens towards the front of the manifold 500 when the tray 576 is within the accessory sleeve 513, and the distal barrier 503 includes a lens 596 providing magnification within the tissue collecting cavity when the tray is within the accessory sleeve 513.

With reference to FIG. 33, the tray 576 may include opposing pairs of sides 585 extending from a screen surface 584 defining the porous features 586. The sides 585 and the screen surface 584 collectively define the tissue collecting cavity 582 of the tray 576. For convention, the tissue collecting cavity 582 of FIG. 33 is considered to be opening away from the screen surface 584 in a direction parallel to the sides 585. The tray 576 further includes orientation features 587 configured to engage complementary orientation features 589 of the accessory sleeve 513 to position the tray 576 within the accessory sleeve 513 in a predetermined orientation relative to the distal barrier 503, and in particular with the tissue collecting cavity 582 opening towards the distal barrier 503. FIG. 33 shows the orientation features 587 including tapering portions of the sides 585 of the tray 576. The orientation features 587 result in the sides 585 of the tray 576 tapering to a designed thickness. The complementary orientation features 589 include protrusions positioned within the accessory sleeve 513 such that in only one orientation of the tray 576 relative to the distal barrier 503 may the tray 576 be fully seated within the accessory sleeve 513. As best shown in FIG. 31, one of the protrusions is spaced from a proximal surface of the accessory sleeve 513 by a distance slightly greater than the designed thickness of the sides 585 of the tray 576. As a result, as the tray 576 is slidably moved downwardly within the accessory sleeve 513 in the predetermined orientation, a distal portion of the tray 576 becomes situated within a portion of the accessory sleeve 513 between the protrusion and a proximal surface defining the accessory sleeve 513. FIG. 31 shows another one of the protrusions obstructing a distal portion of the accessory sleeve 513 to prevent the tray 576 from being disposed within the accessory sleeve 513 in any orientation other than the predetermined orientation. With the tray 576 being disposed within the accessory sleeve 513 in the predetermined orientation, the tissue collecting cavity 582 opens towards the front of the manifold 500, for example towards the distal barrier 503 defining a distal surface of the accessory sleeve 513.

FIGS. 29-31 show the distal barrier 503 including the lens 596. The lens 596 is shown oval-shaped, but other suitable geometries are contemplated. The lens 596 is shaped to maximize visualization of the tissue collecting cavity 582 and to provide magnification to the same. The combined effect of the angularity of the accessory sleeve 513, the forward-opening tissue collecting cavity 582 of the tray 576, and the lens 596 of the distal barrier 503 provides for the user to glance at the manifold 500 from a reasonable distance and without undue maneuvering about the manifold 500 to quickly ascertain whether a suitable tissue sample has been captured. In addition, the tray 576 being inserted into the manifold 500 on a different face of the manifold 500 than the inlet bore 514 further facilitates visualization. It is contemplated that lighting may be provided to illuminate the tissue collecting cavity 582.

Figure 34:
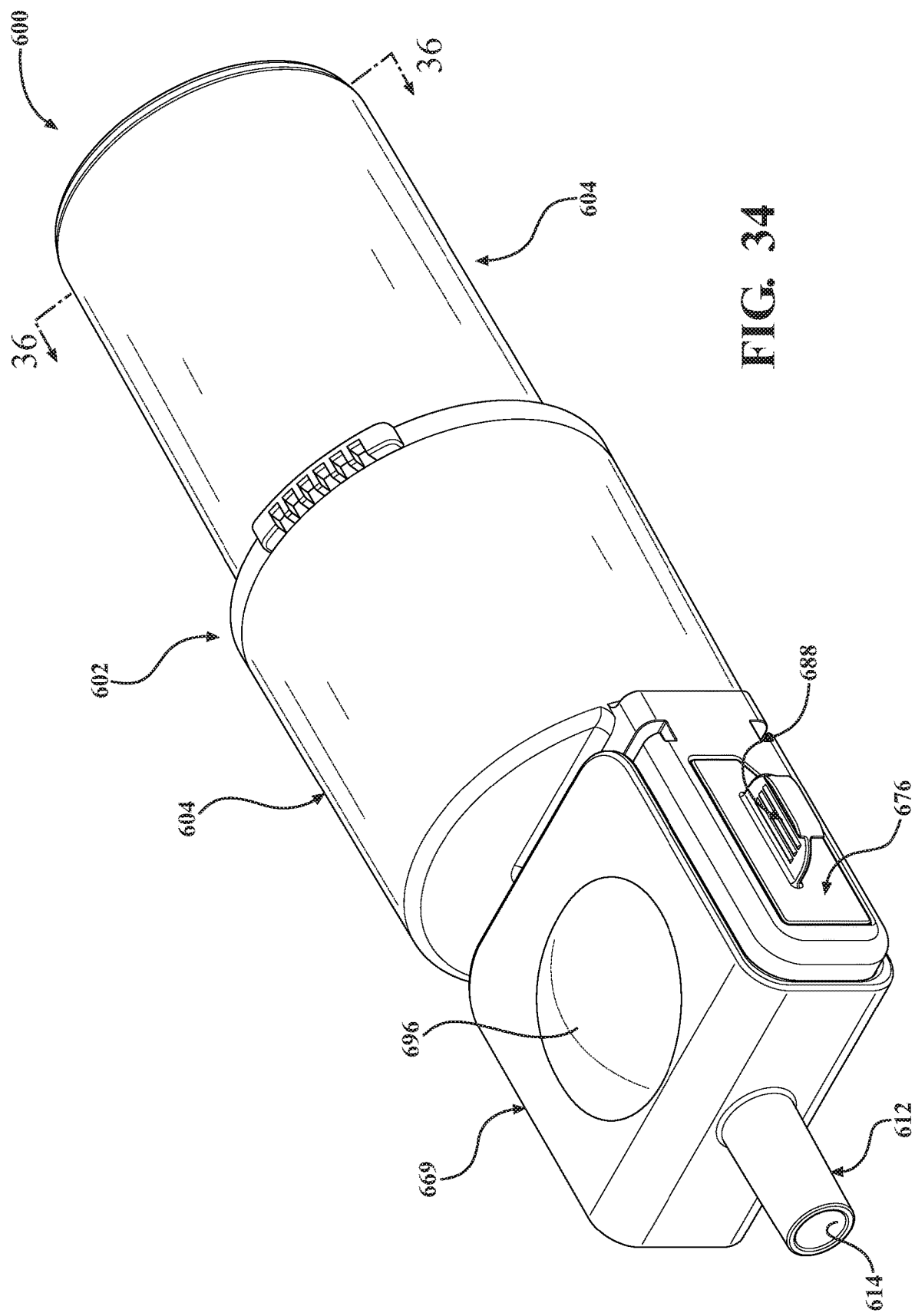
FIG. 34 is a perspective view of a manifold.
Figure 35:
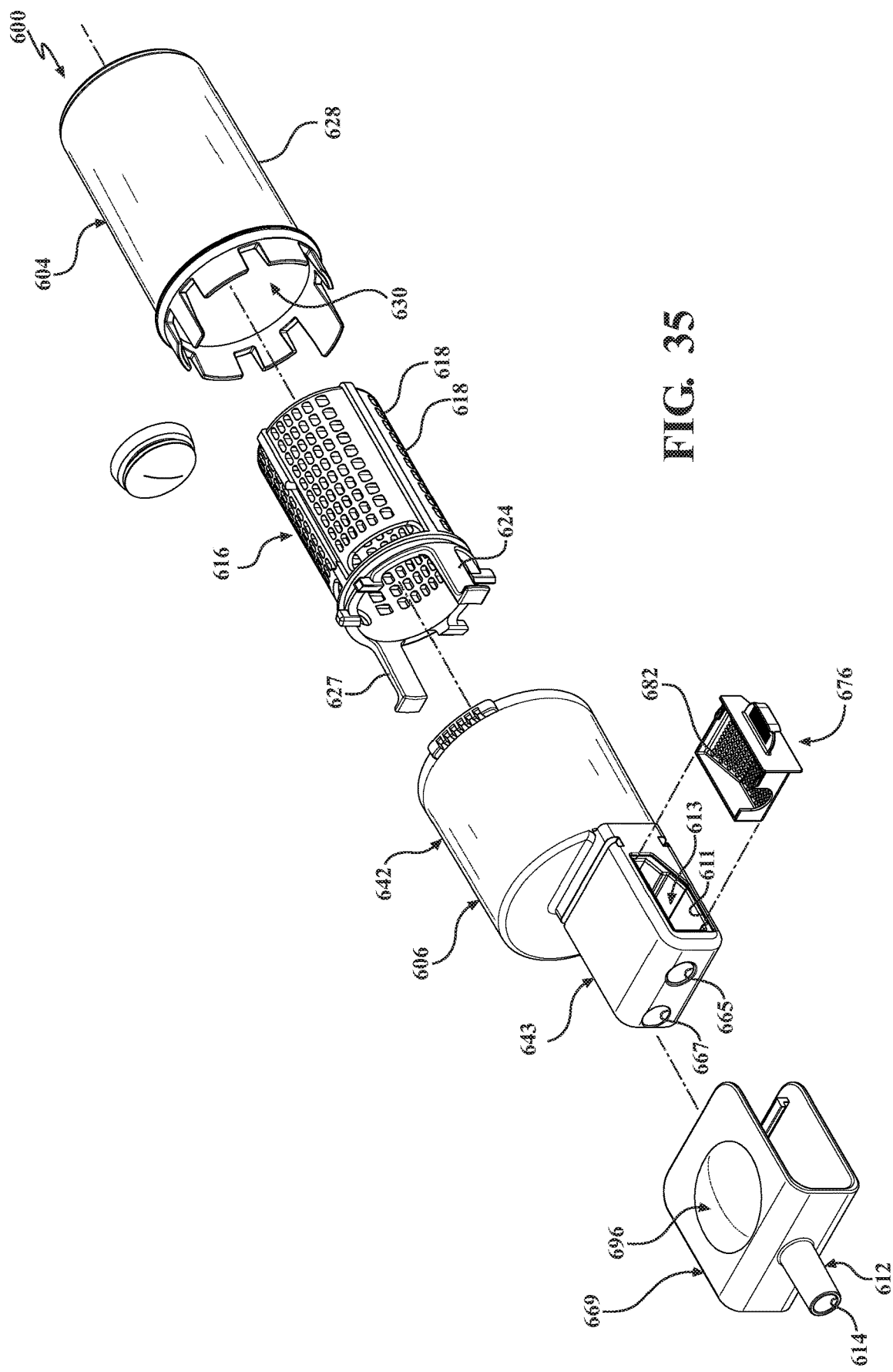
FIG. 35 is an exploded view of the manifold of FIG. 34.
Figure 36:
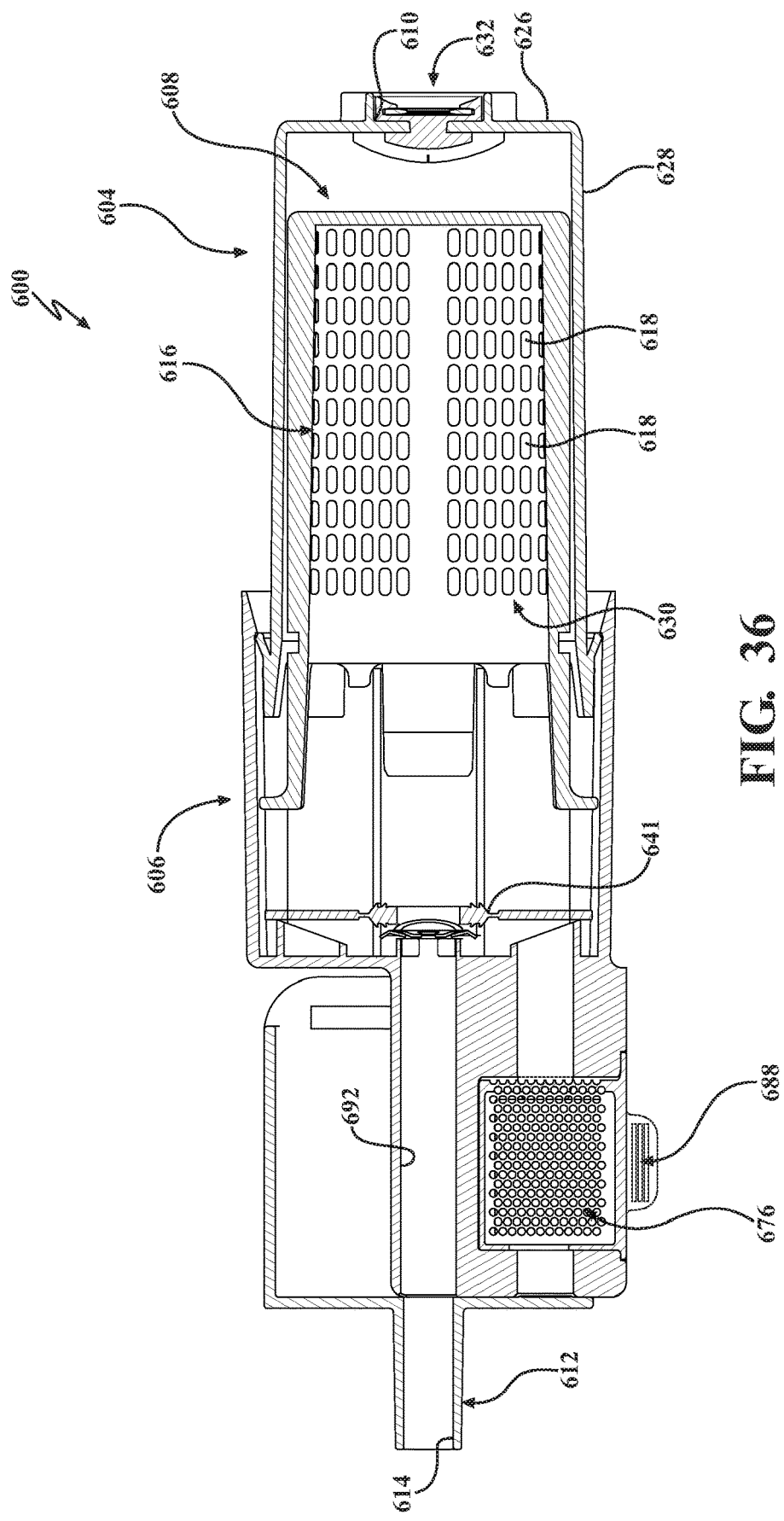
FIG. 36 is a sectional view of the manifold of FIG. 34 taken along section lines 36-36.

Referring now to FIGS. 34-36, another manifold 600 is illustrated that is, in at least some respects, similar to those previously described (and certain like components being indicated by like numerals plus one hundred (100)). The manifold 600 includes the housing 602 adapted to be removably engaged with the manifold receiver 54. The housing 602 includes the body portion 604 and the cap portion 606. As previously expressed, the cap portion 606 may be coupled to the body portion 604 with removable or permanent joining means, or the body and cap portions 604, 606 may be formed as a single piece of unitary construction. In one example, the body and cap portions 604, 606 are spin welded at an interface to prevent reuse. As best shown in FIG. 36, the housing 602 defines the manifold volume 608, and the outlet opening 610 in fluid communication with the manifold volume 608. The body portion 604 may include the proximal base 626 and the side 628 extending distally from the proximal base 626 to define the cavity 630 including a portion of the manifold volume 608. The drip valve 632 may be positioned within the outlet opening 610 to, in manners previously described, prevent egress of fluid from the outlet opening 610 when the housing 602 is disengaged from the manifold receiver 54 and provide fluid communication between the manifold volume 608 and the suction inlet 52 of the medical waste collection assembly 50 when the housing 602 is engaged with the manifold receiver 54.

The manifold 600 may include a filter element 616 disposed within the housing 602 and in the suction path. The filter element 616 defines porous features 618 adapted to capture the semisolid and solid matter entrained within the stream being aspirated along the suction path. With concurrent reference to FIGS. 37 and 38, the cap portion 606 includes the cap head 642 and a support frame 643. The cap head 642 may include one or more orientation features 652, for example one or more pairs of rails extending radially inwardly from an inner annular surface. The rails receive the tabs 627 of the filter element 616 to prevent rotation of the filter element 616 relative to the cap portion 606. The cap head 642 includes at least one sidewall 654 extending distally and terminating at the distal face 656. A first aperture 658 and a second aperture 657 extend through the distal face 656 with functions to be described. A valve 641 may be disposed within the cap head 642 seated over the first and second apertures 657, 658 to prevent backflow of the fluid from the cap head 642.

Figure 37:
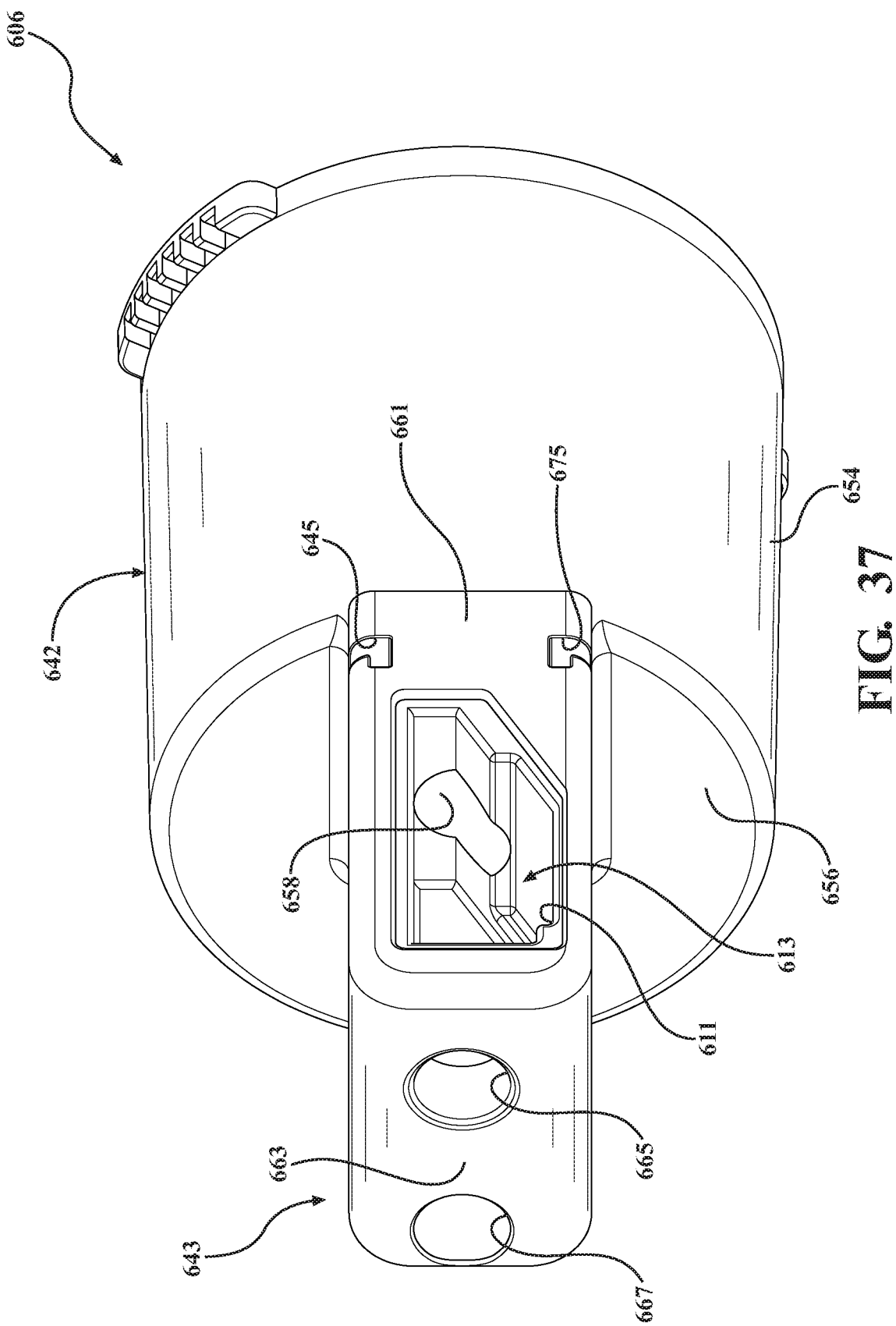
FIG. 37 is a front perspective view of a cap portion of the manifold of FIG. 34.
Figure 38:
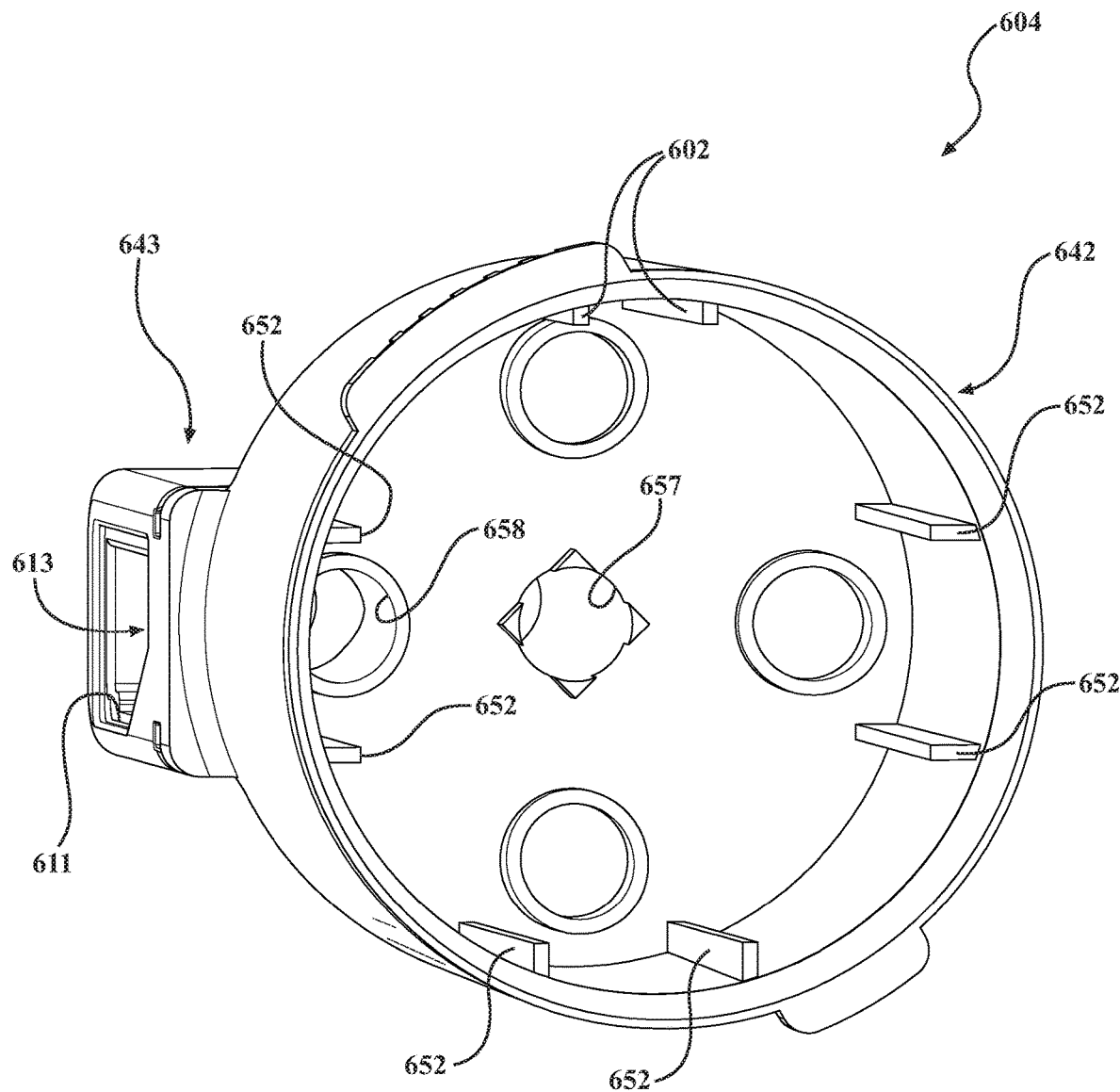
FIG. 38 is a rear perspective view of the cap portion of FIG. 37.

The support frame 643 may be integrally formed with or removably coupled to the cap head 642. The support frame 643 includes opposing lateral sides 661 and a front side 663 separated by upper and lower surfaces. The housing 602 further defines an accessory opening 611 opening into an accessory sleeve 613. The accessory sleeve 613 is in fluid communication with the manifold volume 608 through the first and second apertures 657, 658 extending through the distal face 656. The accessory sleeve 613 is disposed within the support frame 643 of the cap body 606. More particularly, the accessory opening 611 is within one of the opposing sides 661 of the support frame 643 with the accessory sleeve 613 extending inwardly from the accessory opening 611. The accessory sleeve 613 is shaped to complement a side profile of the tray 676 such that the accessory sleeve 613 removably receives the tray 676 in a manner to be described. The front side 663 of the support frame 643 further defines a first opening 665 and a bypass opening 667 separate from the first opening 665. The first opening 665 may be coaxial and in fluid communication with the first aperture 658 and separated by the accessory sleeve 613, and the bypass opening 667 may be coaxial and in fluid communication with the second aperture 657 to define the bypass channel 692, as shown in FIG. 37.

The manifold 600 includes a slide member 669 slidably coupled to the support frame 643. The slide member 669 includes upper and lower surfaces 671, 673 separated by a gap sized approximately to a thickness of the support frame 643 defined between the upper and lower surfaces of the support frame 643. The gap between the upper and lower surfaces 671, 673 slidably receives the support frame 643. Each of the support frame 643 and the slide member 669 include complementary track features 675 to limit movement of the slide member 669 relative to the support frame 643 to one degree of freedom. In particular, the track features 675 of the support frame 643 include elongate slots oriented parallel to the front side 663, and the track features 675 of the slide member 669 are elongate rails oriented to engage the slots. The movement of the slide member 669 relative to the support frame 643 may be considered lateral movement when viewing the front of the manifold 600.

Figure 39:
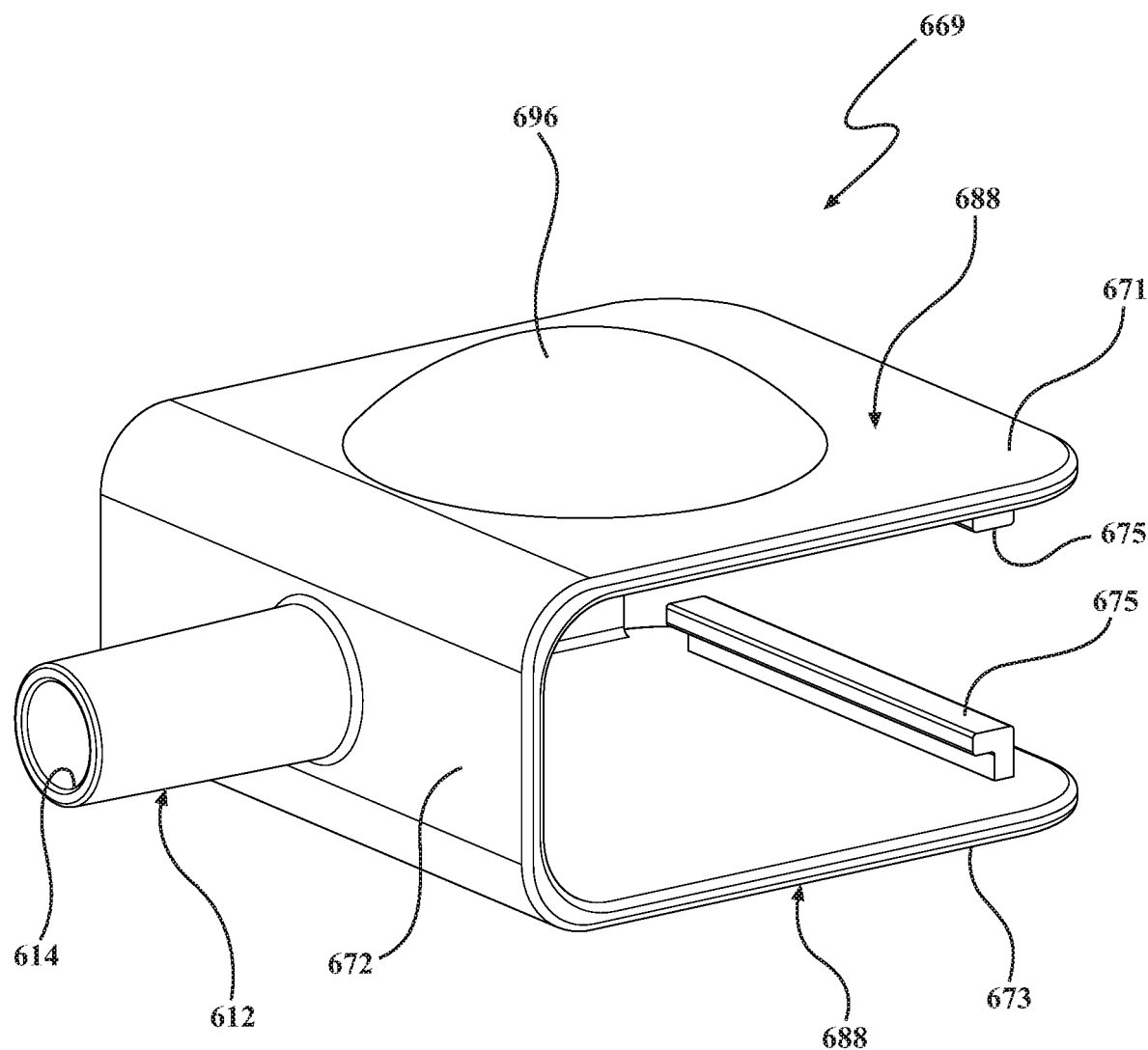
FIG. 39 is a perspective view of a slide member of the manifold of FIG. 34.

The slide member 669 includes the inlet fitting 612 defining the inlet bore 614. FIG. 39 shows the inlet fitting 612 extending distally from a front surface 672 of the slide member 669 separating the upper and lower surfaces 671, 673. The inlet fitting 612 is adapted to receive the suction line 52. The slide member 669 further includes a control surface 688 adapted to receive the input from the user with resulting function to be described. The control surface 688 may include the upper and lower surfaces 671, 673 adapted to be grasped or pinched by fingers of the user to impart sliding of the slide member 669 relative to the support frame 643.

Figure 40:
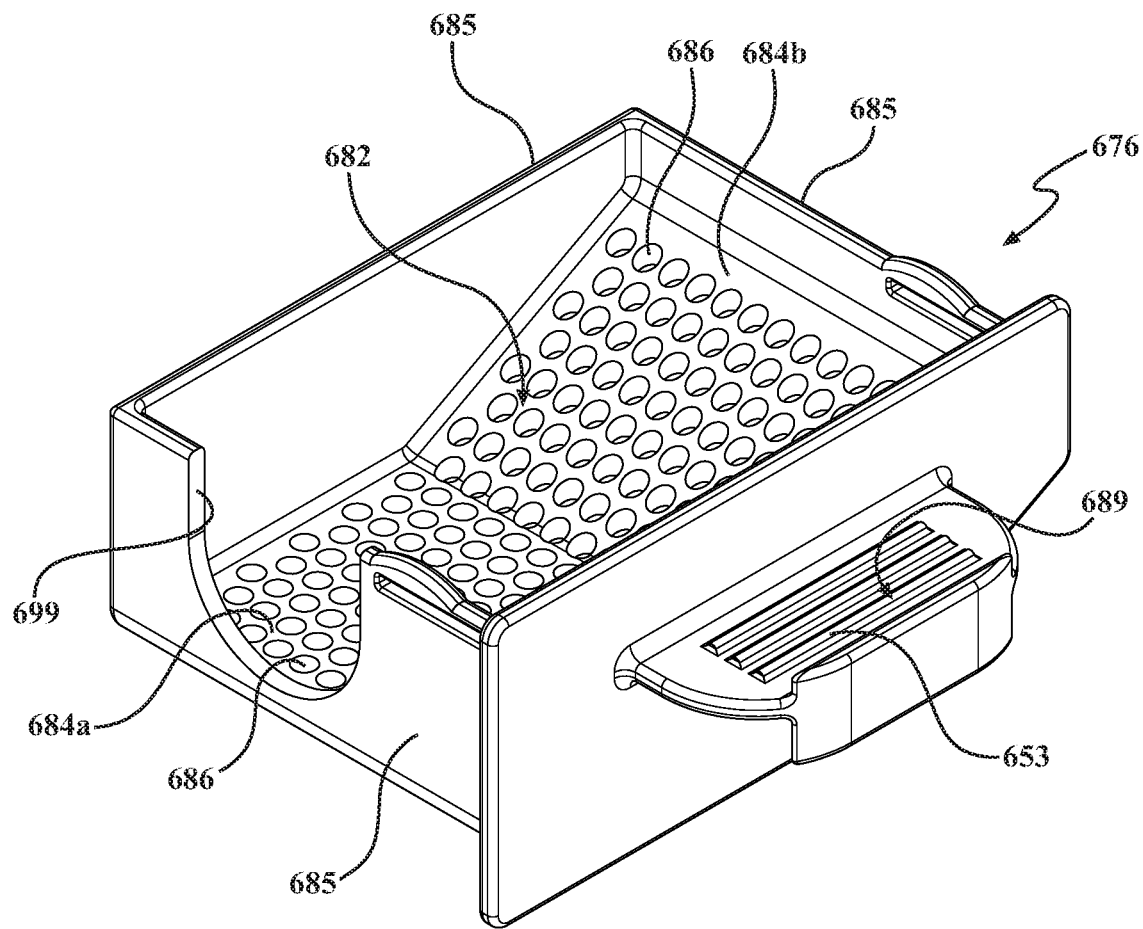
FIG. 40 is a perspective view of a tray of the manifold of FIG. 40 with the tray defining a tissue collecting cavity.

As mentioned, the accessory sleeve 613 of the support frame 643 is configured to removably receive the tray 676. With reference to FIG. 40, the tray 676 may be generally box-shaped, but other suitable geometries are contemplated. The tray 676 includes a screen surface 684 and the pair of opposing sides 685 extending from the screen surface 684 to define the tissue collection cavity 682. One of the pairs of opposing sides 685 may define a front wall opposite a rear wall. The screen surface 684 of the tray 676 defines porous features 686. The screen surface 684 may include a first screen surface 684a and a second screen surface 684b inclined relative to the first screen surface 684a. The second screen surface 684b is inclined upwardly towards the rear wall. In addition to being more effectively positioned in the suction path, the inclined second screen surface 684b provides a trapezoidal shape to the side profile of the tray 676 to function as an orientation feature for inserting and removing the tray 676 from the accessory sleeve 613. In other words, the corresponding shape of the side profile of the tray 676 and the accessory opening 611 requires that the tray 676 be in the predetermined orientation to be disposed or seated within the accessory sleeve 613. FIG. 40 also shows the tray 676 including a cutout 699 within the front wall, and a grip 674 extending from one of the sides 685. The cutout 699 is aligned with the inlet bore 614 of the inlet fitting 612 (and the first aperture 688) when the tray 676 is disposed within the accessory sleeve 613. The grip 674 may include gripping features 653 to facilitate confident manipulation of the tray 676.

In operation, should the user wish to collect the tissue sample within the tissue collecting cavity 682 of the tray 676, the user provides the input to the control surface 688 to move the slide member 669 to the tissue collection position. The slide member 669 is moved such that the inlet bore 614 of the inlet fitting 612 is positioned in fluid communication with the tissue collecting cavity 682 when the tray 676 is disposed within the accessory sleeve 613. The suction path is established from the inlet bore 614 to the suction inlet 52 through each of the first opening 665, the tissue collection cavity 682, the first aperture 658, the manifold volume 608, the filter element 616, and the outlet opening 610. The porous features 686 of the tray 676 are in the suction path and collect the tissue sample. In one example, moving the inlet bore 614 in fluid communication with the tissue collecting cavity 682 includes axially aligning the inlet bore 614 with the first opening 665. It is understood that when the tissue collecting cavity 682 is in the suction path, the bypass channel 692 is not within the suction path.

Once the desired tissue sample is collected and/or the user prefers to operate the manifold 600 without collecting the tissue sample, another input is provided to the control surface 688 to move the slide member 669 to the bypass position. The slide member 669 is moved such that the inlet bore 614 of the inlet fitting 612 is positioned in fluid communication with the bypass channel 692. The suction path is established from the inlet bore 614 to the suction inlet 52 through each of the bypass opening 667, the bypass channel 692, the second aperture 657, the manifold volume 608, the filter element 616, and the outlet opening 610. In one example, moving the inlet bore 614 in fluid communication with the bypass channel 692 includes axially aligning the inlet bore 614 with the bypass opening 667. It is understood that when the bypass channel 692 is in the suction path, the tissue collecting cavity 682 is not within the suction path.

With the slide member 669 in the bypass position such that the tissue collecting cavity 682 is not within the suction path, the tray 676 may be removed from the accessory sleeve 613 without disrupting the operation of the medical waste collection assembly 50. For example, the user may remove the tray 676 to retrieve the collected tissue sample while another user continues with other aspects of the surgical operation requiring suction provided by the medical waste collection assembly 50. If the retrieved tissue sample is unsatisfactory and/or another tissue sample is desired, another tray 676 may be quickly disposed within the accessory sleeve 613 without undue disruption such as loss of suction.

The manifold 600 accommodates visualization for an improved tissue collection experience for the user. Referring to FIGS. 34 and 39, the slide member 669 includes the lens 696 providing magnification within the tissue collecting cavity 682 when the tray 676 is within the accessory sleeve 613 and when the slide member 669 is in the tissue collection position. It is contemplated that lighting may be provided to illuminate the tissue collecting cavity 682.

Exemplary methods for collecting the tissue sample with the manifold 600 are also contemplated. The manifold 600 is coupled to the medical waste collection assembly 50 such that the outlet opening 610 is in fluid communication with the suction inlet 58 of the medical waste collection assembly 50. The suction line 52 is coupled to the inlet fitting 612 of the manifold 600. The medical waste collection assembly 50 is operated with the slide member 669 in the bypass position. The inlet bore 614 of the inlet fitting 612 is in fluid communication with the bypass channel 692 such that fluid is permitted to flow through the suction path without the tray 676 collecting the tissue sample. The user applies the input to the control surface 688 to move the slide member 669 from the bypass position to the tissue collecting position. In the tissue collection position, the inlet bore 614 of the inlet fitting 612 is in fluid communication with the tissue collecting cavity 682 such that the porous features 686 are in the suction path. The medical waste collection assembly 50 is operated with the slide member 669 in the tissue collection position to collect the tissue sample. Another input may be applied to the control surface 688 to return the slide member 669 to the bypass position, for example, subsequent to collecting the tissue sample within the tissue collecting cavity 682. The prior input may include applying a lateral force to the control surface 688 in a first linear direction, and the later input may include applying another lateral force to the control surface 688 in a second linear direction opposite the first linear direction to return the slide member 669 to the bypass position. The tissue collecting cavity may be viewed through the lens 696 when the slide member 669 is in the tissue collection position. The tray 676 may be removed from the accessory sleeve 613 with the slide member 669 in the bypass position. Another tray (not shown) may be provided and positioned within the accessory sleeve 613 of the slide member 669 with the slide member 669 in the bypass position.

Figure 41:
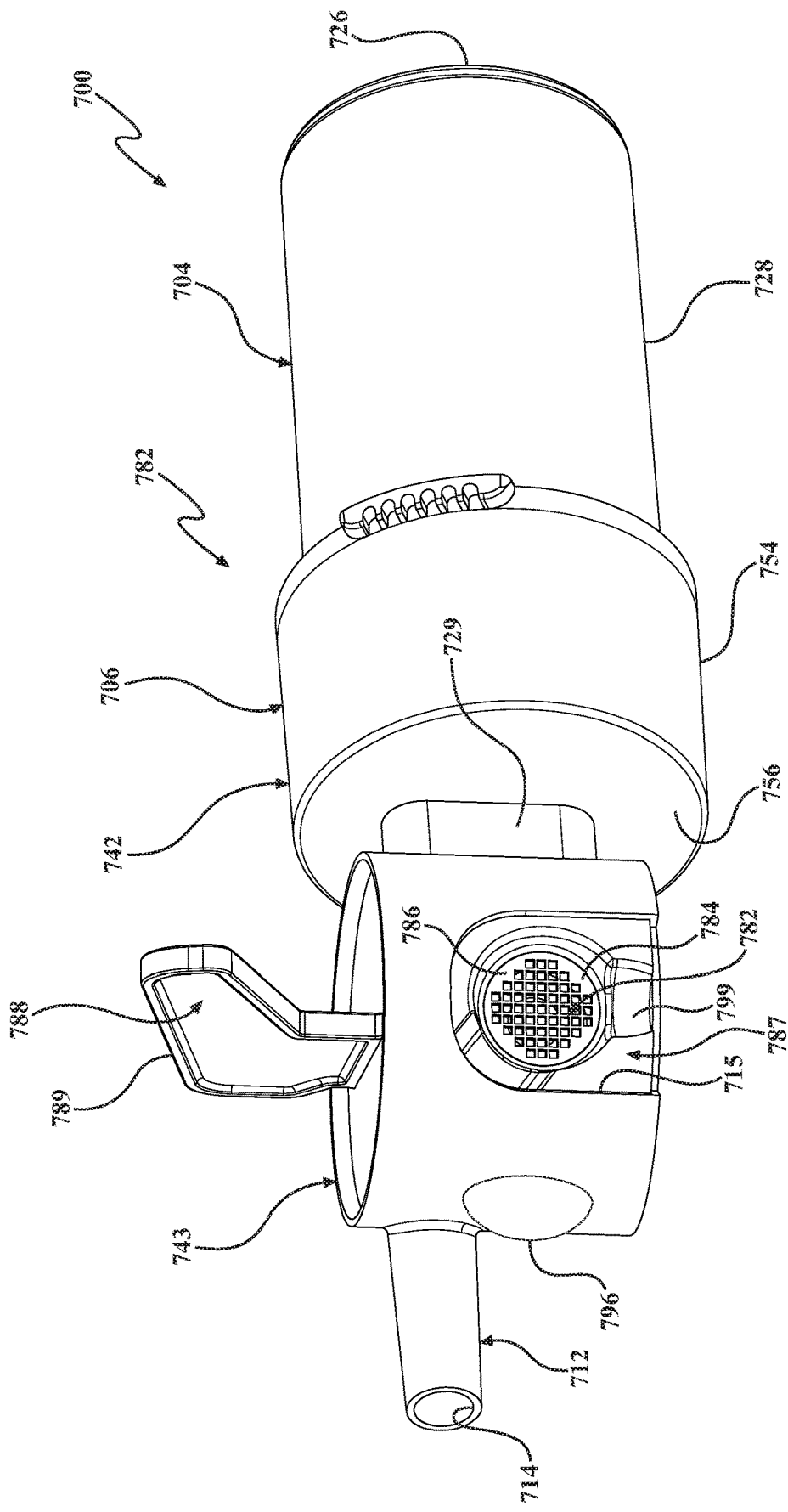
FIG. 41 is a perspective view of a manifold.
Figure 42:
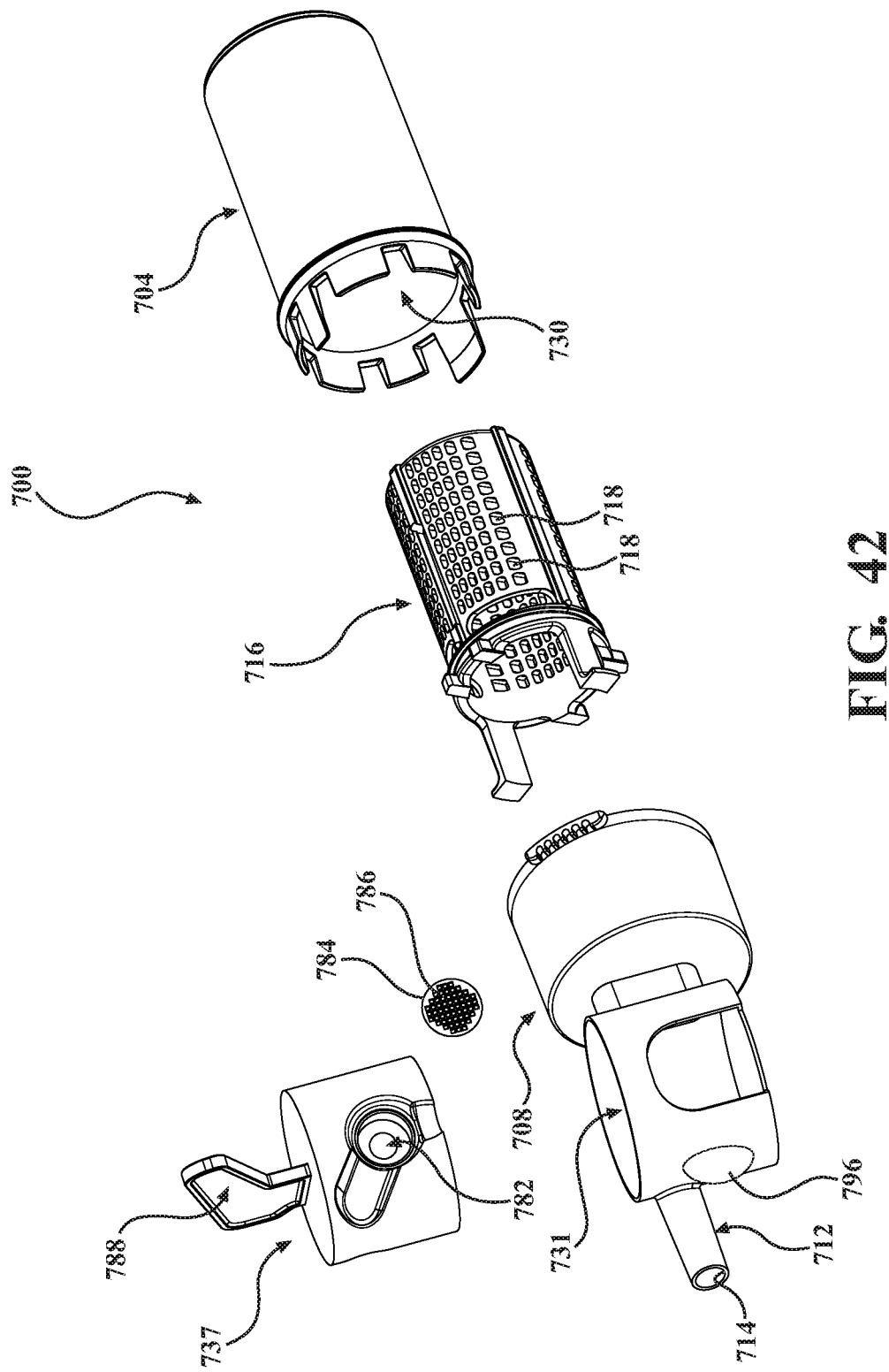
FIG. 42 is an exploded view of the manifold of FIG. 41.
Figure 43:
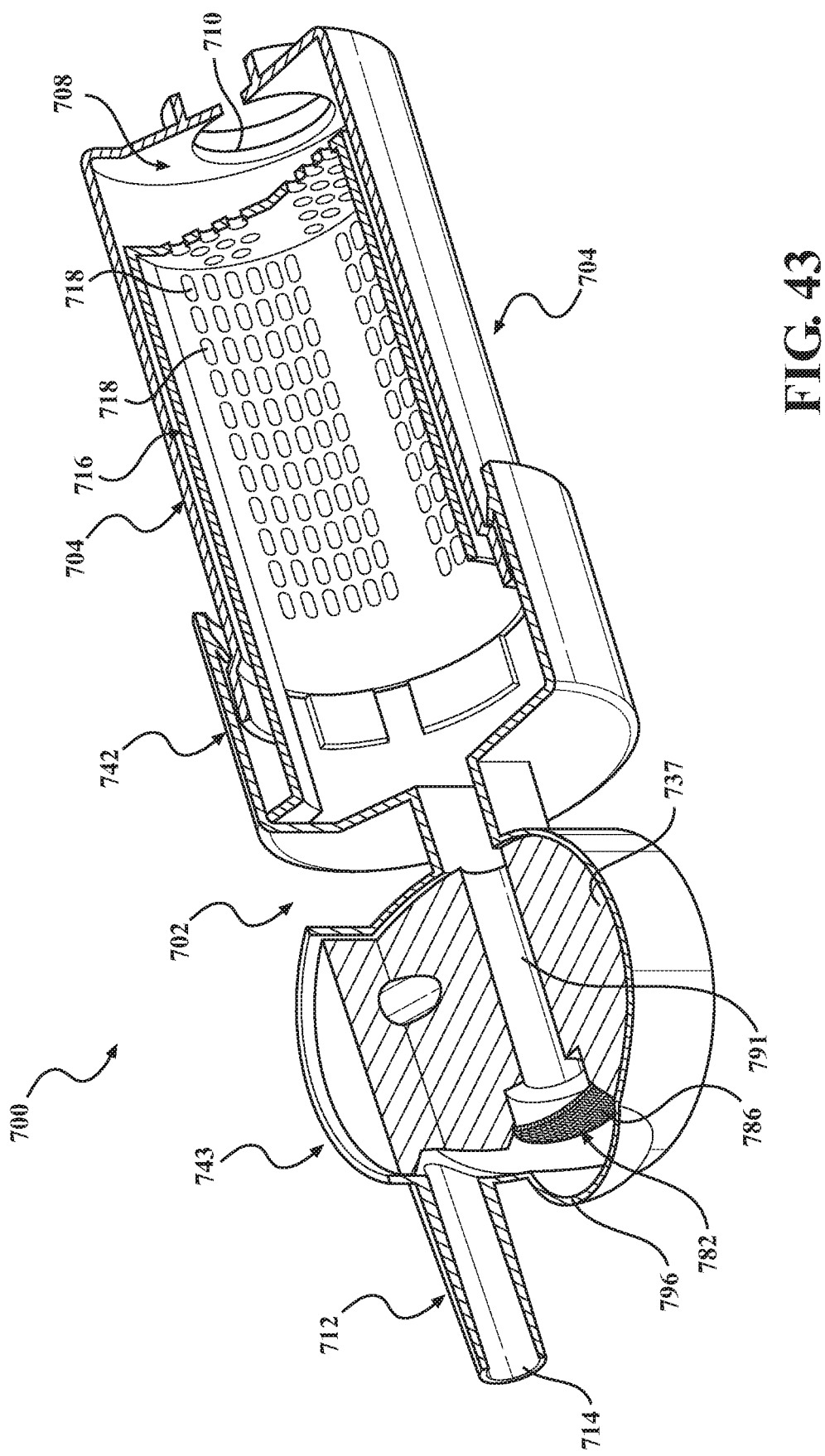
FIG. 43 is a sectional view of the manifold of FIG. 41 with the rotor in a tissue collecting position.

Referring now to FIGS. 41-46, another manifold 700 is illustrated that is, in at least some respects, similar to those previously described (and certain like components being indicated by like numerals plus one hundred (100)). The manifold 700 includes a housing 702 adapted to be removably engaged with the manifold receiver 54. The housing 702 includes a body portion 704 and a cap portion 706. As previously expressed, the cap portion 706 may be coupled to the body portion 704 with removable or permanent joining means, or the body and cap portions 704, 706 may be formed as a single piece of unitary construction. In one example, the body and cap portions 704, 706 are spin welded at an interface to prevent reuse. As best shown in FIG. 43, the housing 702 defines a manifold volume 708 and an outlet opening 710 in fluid communication with the manifold volume 708. The body portion 704 may include a proximal base 726 and a side 728 extending distally from the proximal base 726 to define a cavity 730 including a portion of the manifold volume 708. A drip valve (not shown) may be positioned within the outlet opening 710 to, in manners previously described, prevent egress of fluid from the outlet opening 710 when the housing 702 is disengaged from the manifold receiver 54 and provide fluid communication between the manifold volume 708 and the suction inlet 58 of the medical waste collection assembly 50 when the housing 702 is engaged with the manifold receiver 54.

The manifold 700 may include a filter element 716 disposed within the housing 702 and in the suction path to be described. The filter element 716 defines porous features 718 adapted to capture the semisolid and solid matter entrained within the stream being aspirated along the suction path. With concurrent reference to FIG. 41, the cap portion 706 includes a cap head 742 and a support frame 743. The support frame 743 of the manifold 700 is a stator and referred to as such hereinafter. The cap head 742 is coupled with the body portion 704. The cap head 742 includes at least one sidewall 754 extending distally and terminating at a distal face 756. The aperture 758 extends through the distal face 756.

Figure 47:
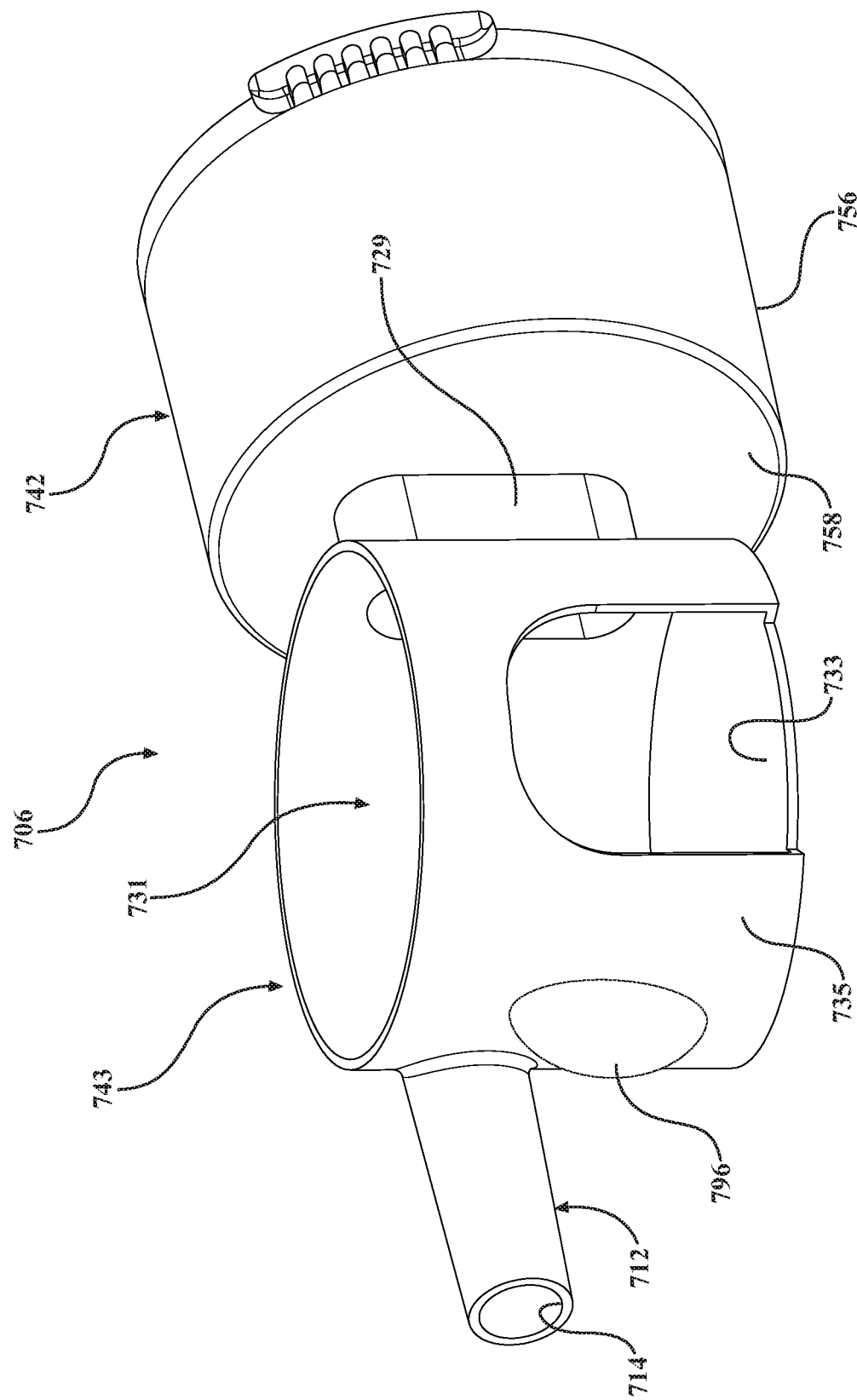
FIG. 47 is a front perspective view of a cap portion of the manifold of FIG. 41 including a stator defining a window.

The stator 743 may be integrally formed with the cap head 742, or the stator 743 may be coupled to the cap head 742 with a suitable joining process. FIG. 47 shows the stator 743 coupled to the cap head 742 with a throat member 729. The throat member 729 extends distally from the distal face 756 of the cap head 742 and proximally from an aspect of the stator 743. The stator 743 defines a void space 731 in communication with the aperture 758 through a lumen defined by the throat member 729. Referring to FIGS. 42 and 47, the void space 731 of the stator 734 may be defined by a base 733 and at least one sidewall 735 extending from the base 733. The void space 731 is shown as a cylinder, but other suitable geometries are contemplated. The stator 743 of the housing 702 includes the inlet fitting 712 adapted to receive the suction line 52. The inlet fitting 712 defines the inlet bore 714 in fluid communication with the void space 731.

Figure 48:
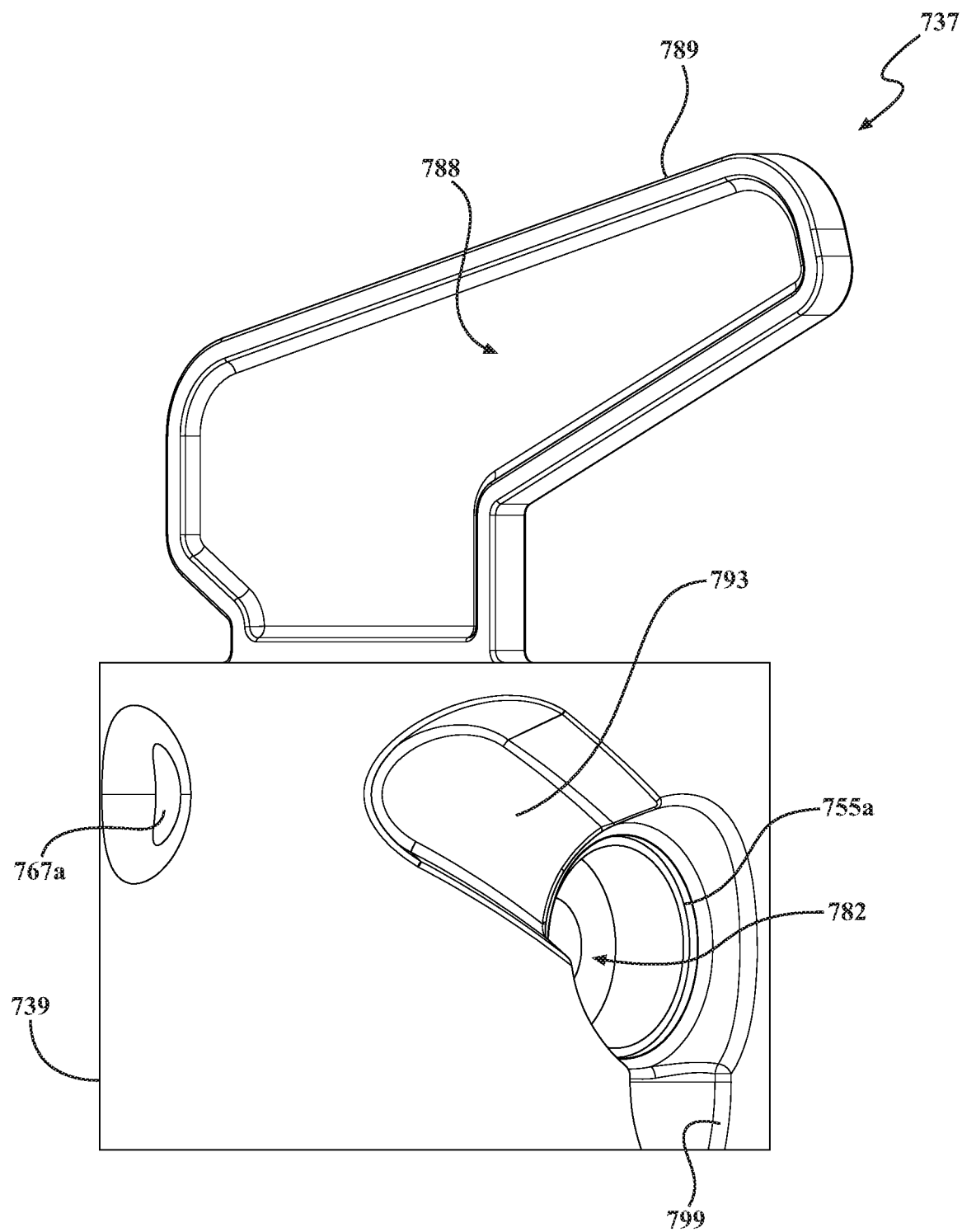
FIG. 48 is a first perspective view of a rotor of the manifold of FIG. 41 with the rotor defining a tissue collecting cavity.
Figure 49:
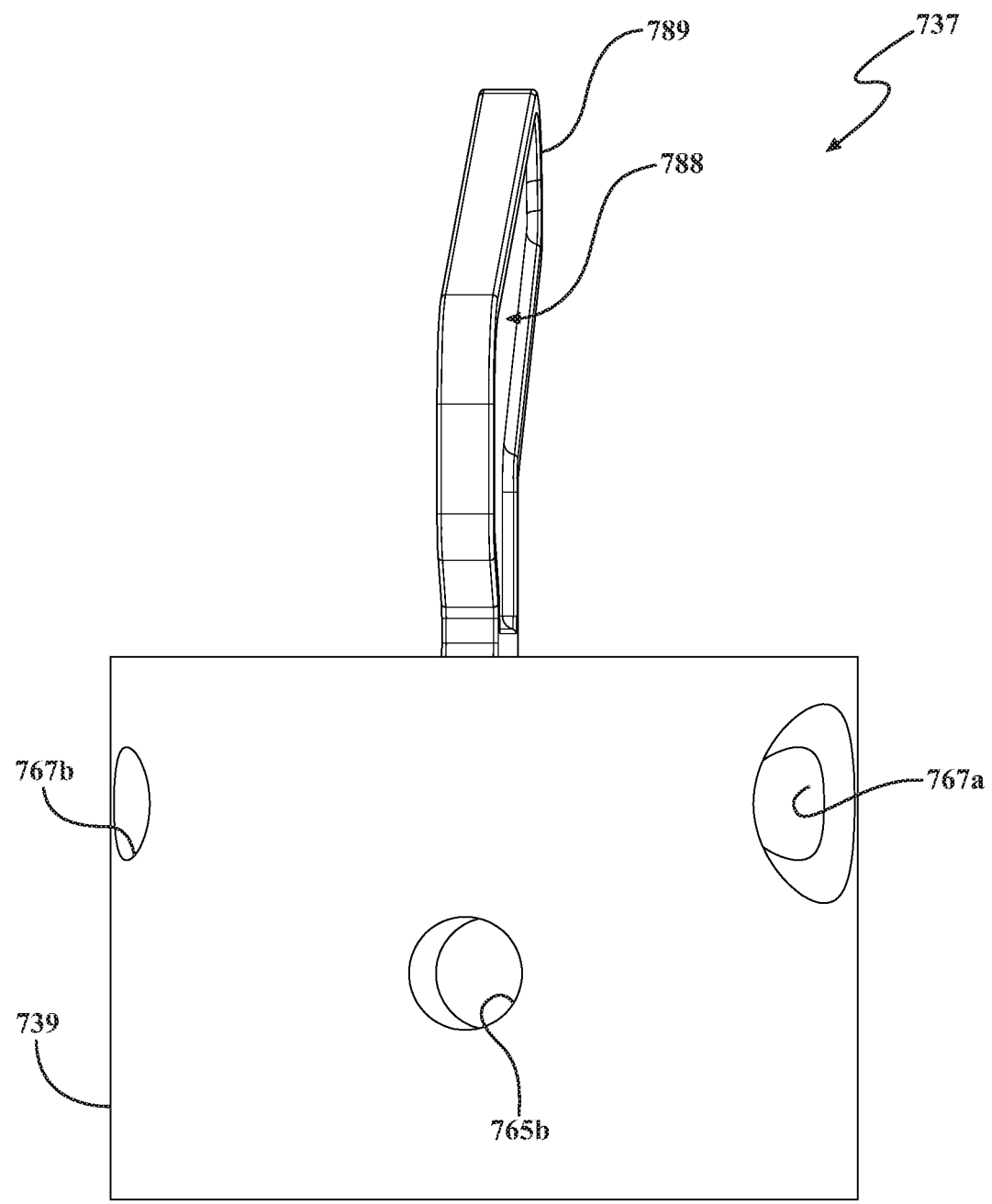
FIG. 49 is a second perspective view of the rotor of FIG. 44.

The manifold 700 includes a rotor 737 rotatably disposed within the stator 743. The rotor 737 is supported on the base 733 of the stator 743 when disposed within the void space 731. With reference to FIGS. 48 and 49, the rotor 737 includes an annular outer wall 739 with an outer diameter generally approximating but slightly less than an inner diameter of an inner annular wall of the rotor 737. The rotor 737 defines a pair of first openings 765a, 765b and a pair of bypass openings 767a, 767b. Each of the pair of first openings 765a, 765b are defined by the outer wall 739 and in fluid communication with one another to define a tissue channel 791, and each of the pair of bypass openings 767a, 767b are defined by the outer wall 739 and in fluid communication with one another to define the bypass channel 792 (see FIGS. 45 and 46). One of the first openings 765a may be considered the inlet of the tissue channel 791, and the other one of the first openings 765b may be considered the outlet of the tissue channel 791. Likewise, one of the bypass openings 767a may be considered the inlet of the bypass channel 792, and the other one of the bypass openings 767b may be considered the outlet of the bypass channel 792. The bypass channel 792 is separate from the tissue channel 791 and the tissue collecting cavity 782.

The rotor 737 defines the tissue collecting cavity 782 and the porous features 786 within the tissue collecting cavity 782. The porous features 786 may be defined by the screen surface 784 removably coupled to the rotor 737. In another version of the rotor 737, the screen surface 784 is integrally formed with the rotor 737. The tissue collecting cavity 782 is associated with the inlet opening 765*a* such that the inlet opening 765*a* of the tissue channel 791 opens into the tissue collecting cavity 782.

The rotor 737 may also include the control surface 788 adapted to receive the input from the user. The control surface 788 associated with a handle 789 extending from an upper surface of the rotor 737. The control surface 788 receives the input to switch the manifold 700 between the tissue collection position and the bypass position to be described. It is contemplated that the control surface may be an electronic input (e.g., a button) with a resulting signal sent to a controller to actuate the rotor 737.

Figure 44:
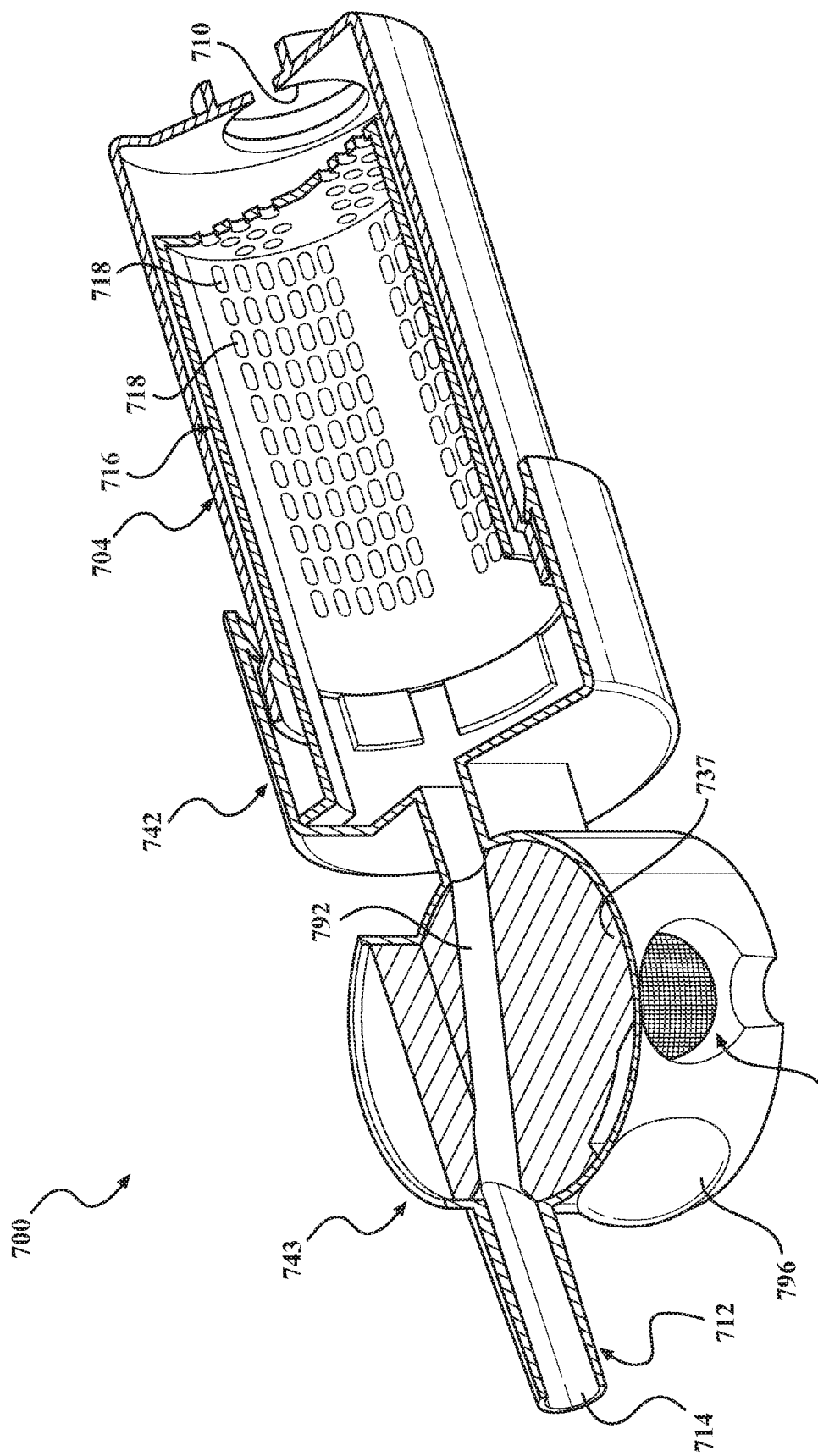
FIG. 44 is a sectional view of the manifold of FIG. 41 with the rotor in a bypass position.

In operation, should the user wish to collect the tissue sample in the tissue collecting cavity 782 of the tray 776, the user provides the input to the control surface 788 to rotate the rotor 737 within the stator 743 the tissue collection position. The rotor 737 is rotated such that the tissue collecting cavity 782 is in fluid communication with the inlet bore 714. The porous features 786 are in the suction path to collect the tissue sample. FIGS. 43 and 44 show the manifold 700 with the rotor 737 in the tissue collection position. It is observed that the suction path between the inlet bore 714 and the tissue collecting cavity is somewhat tortuous for a reason to be identified. To facilitate the illustrated suction path, the rotor 737 includes a recess 793 within the outer wall 739. As best shown in FIG. 48, the recess 793 extends radially from the inlet opening 765*a* for a designed distance. The designed distance is such that, when the rotor 737 is rotated to the tissue collection position, an end of the recess 793 opposite the opening 765*a* is substantially aligned with the inlet bore 714. With the rotor 737 in the tissue collection position, the suction path is established from the inlet bore 714 to the suction inlet 52 through each of the inlet opening 765*a*, the recess 793, the tissue collecting cavity 782, the tissue channel 791, the outlet opening 765*b*, the aperture 758, the manifold volume 708, the filter element 716, and the outlet opening 710. It is understood that when the tissue collecting cavity 782 is in the suction path, the bypass channel 792 is not within the suction path.

Once the desired tissue sample is collected and/or the user prefers to operate the manifold 700 without collecting the tissue sample, another the input to the control surface 788 to rotate the rotor 737 within the stator 743 the bypass position. FIGS. 44 and 46 show the manifold 700 with the rotor 737 in the bypass position. The rotor 737 is rotated such that the bypass channel 792 is in fluid communication with the inlet bore 714, and the tissue collecting cavity 782 is not in the suction path. The suction path is established from the inlet bore 714 to the suction inlet 52 through each of the inlet opening 767*a*, the bypass channel 792, the outlet opening 767*b*, the aperture 758, the manifold volume 708, the filter element 716, and the outlet opening 710.

With the rotor 737 in the bypass position such that the tissue collecting cavity 682 is not within the suction path, the manifold 700 advantageously provides for retrieval of the collected tissue sample without disrupting the operation of the medical waste collection assembly 50. With reference to FIG. 41, the stator 743 defines a window 715 extending through the sidewall 735. The window 715 may be positioned circumferentially about the stator 743 to be aligned with the tissue collecting cavity 782 when the rotor 737 is in the bypass position. Further, the window 715 includes a height and a width to expose the tissue collecting cavity 782 to permit retrieval of the tissue sample. For example, the user may position a container (e.g., a formalin jar) beneath the exposed tissue collecting cavity 782 and use an instrument (e.g., a spatula) to scrape the tissue sample from the porous features 786 and into the container. A cutout 799 within the rotor 737 beneath the tissue collecting cavity 782 provides a straight drop from the tissue collecting cavity 782 to the container. As the tissue sample is being retrieved, another user may continue with other aspects of the surgical operation requiring suction provided by the medical waste collection assembly 50. If the retrieved tissue sample is unsatisfactory and/or another tissue sample is desired, the rotor 737 may be promptly rotated back to the tissue collection position.

The manifold 700 accommodates visualization for an improved tissue collection experience for the user. The stator 743 may include a lens 796 positioned to be aligned with and provide magnification within the tissue collecting cavity 782 when the rotor 737 is in the tissue collection position. This is accomplished in part with the somewhat tortuous suction path between the inlet bore 714 and the tissue collecting cavity, as previously mentioned. With the inlet fitting 712 offset and the recess 793 within the rotor 737, the lens 796 is coaxially aligned with the tissue collecting cavity 782 when the rotor 737 is in the tissue collection position. Further, with the lens 796 at a front of the manifold 700, the user may glance at the manifold 700 from a reasonable distance and without undue maneuvering about the manifold 700 to quickly ascertain whether a suitable tissue sample has been captured. It is contemplated that lighting may be provided to illuminate the tissue collecting cavities 782.

Exemplary methods for collecting the tissue sample with the manifold 700 are also contemplated. The housing 702 of the manifold 700 is coupled to the medical waste collection assembly 50 such that the outlet opening 710 is in fluid communication with the suction inlet 58 of the medical waste collection assembly 50. The suction line 52 is coupled to the inlet fitting 712 to provide the suction path from the inlet bore 714 of the inlet fitting 712 to the suction inlet 58. The medical waste collection assembly 50 is operated with the manifold 700 in the bypass position. The bypass channel 792 is in the suction path and the tissue collecting cavity 782 is not in the suction path. The control surface 788 is actuated to rotate the rotor 737 within the stator 743 from the bypass position to the tissue collection position. For example, the control surface 788 is rotated in a first rotational direction. The tissue collecting cavity 782 is in the suction path and the bypass channel 792 is removed from the suction path. The medical waste collection assembly 50 is operated with the manifold 700 in the tissue collection position to collect the tissue sample with porous features 786 of the tissue collecting cavity 782. The tissue collecting cavity 782 may be viewed through the lens 796 when the rotor 797 is in the tissue collection position. The control surface 788 may be actuated to return the rotor 737 to the bypass position after collection of the tissue sample. For example, the control surface 788 is rotated in a second rotational direction opposite the first rotational direction. The tissue sample may be retrieved from the tissue collecting cavity 782 while the rotor 737 is in the bypass position. For example, the tissue example may be retrieved from the exposed tissue collecting cavity 382 through the window 715 of the stator 743, such as with an instrument scraping the porous features 786 to dislodge the tissue sample.

In the aforementioned implementation of the manifold 700, the rotor 737 is rotatably disposed with the stator 743 fixed relative to the body portion 704. It is contemplated that the reverse configuration may be implemented in which the "rotor" is fixed relative to the body portion 704, and the "stator" rotates or pivots about the "rotor." Moreover, the aforementioned implementation of the manifold 700 includes the rotor 737 rotating about a vertical axis. It is contemplated that each of the rotor 737 and the stator 743 may be oriented about a horizontal axis.

Figure 50:
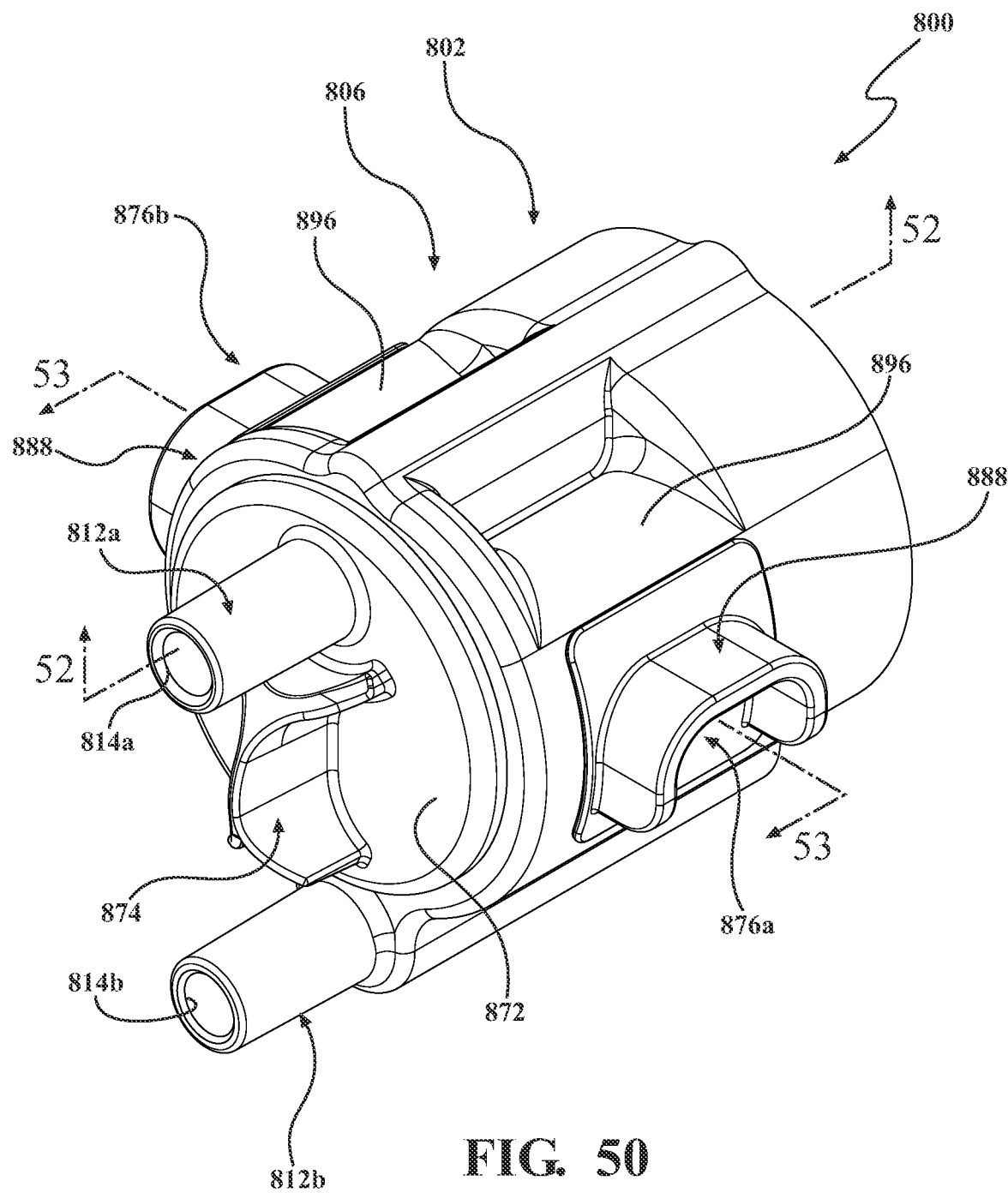
FIG. 50 is a perspective view of a manifold.
Figure 51:
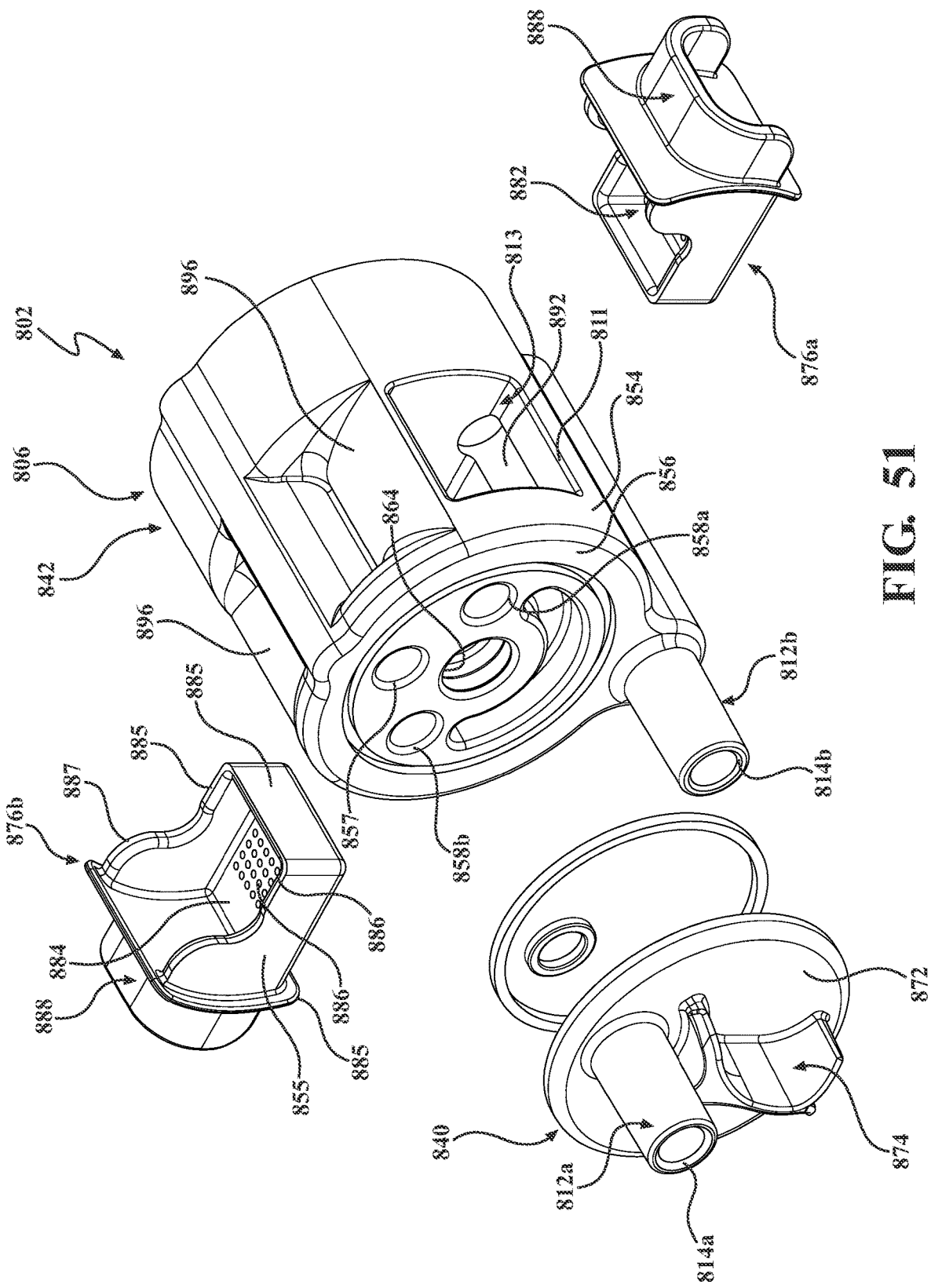
FIG. 51 is an exploded view of the manifold of FIG. 50.
Figure 52:
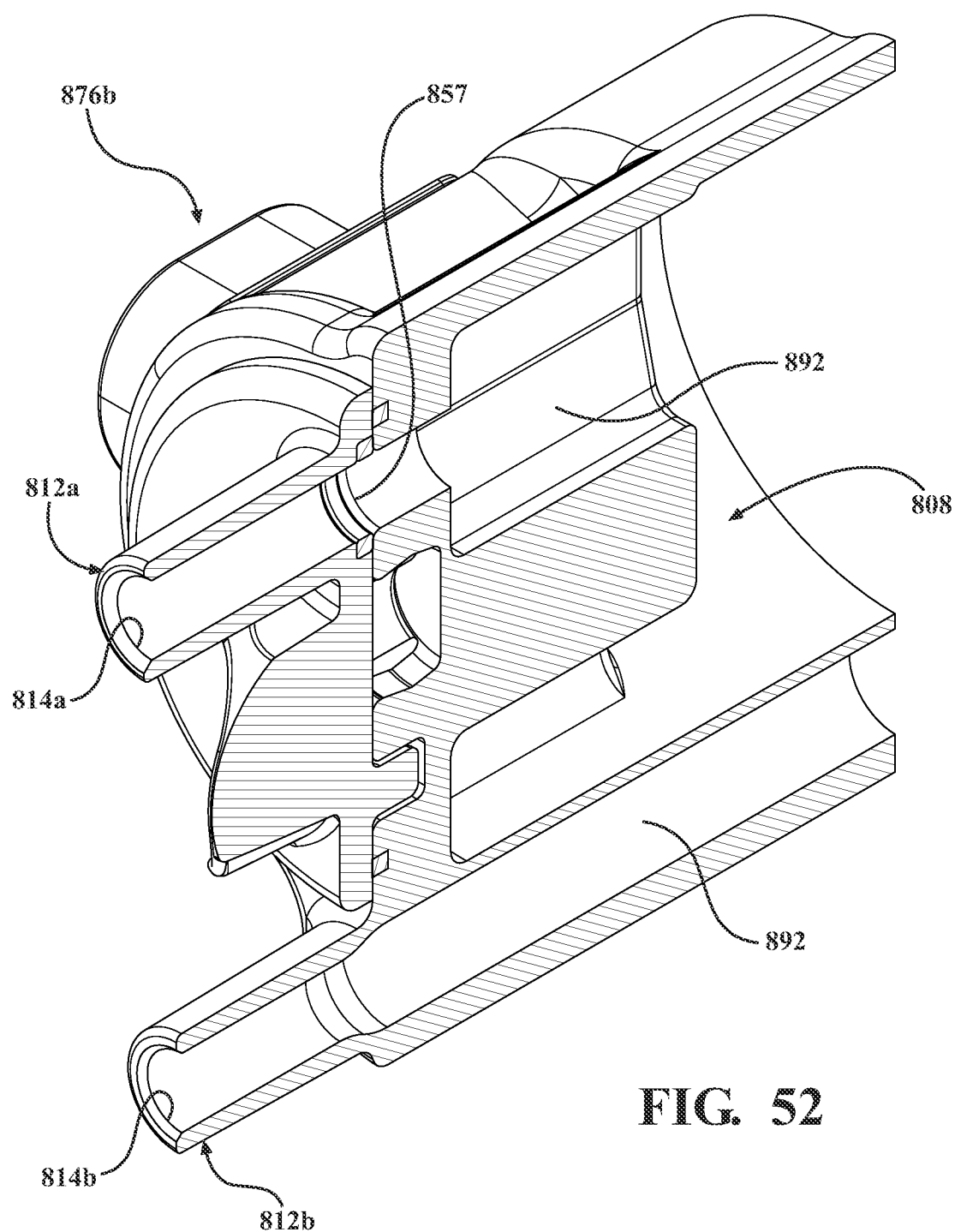
FIG. 52 is a sectional view of the manifold of FIG. 50 taken along section lines 52-52.

Referring now to FIGS. 50 and 51, another manifold 800 is illustrated that is, in at least some respects, similar to those previously described (and certain like components being indicated by like numerals plus one hundred (100)). The manifold 800 includes the housing 802 adapted to be removably engaged with the manifold receiver 54. The housing 802 includes the cap portion 806 and the body portion (not shown), which may include any of those described in the present disclosure. As previously expressed, the cap portion 806 may be coupled to the body portion with removable or permanent joining means, or the body portion and the cap portions 806, may be formed as a single piece of unitary construction, for example, spin welded at an interface to prevent reuse. As best shown in FIG. 52, a manifold volume 808 is defined, and an outlet opening (not shown) is in fluid communication with the manifold volume 808. The housing 802 includes the first inlet fitting 812a defining the first inlet bore 814a in fluid communication with the manifold volume 808. The housing 802 includes a second inlet fitting 812b defining a second inlet bore 814b in fluid communication with the manifold volume 808 in a manner to be described. As previously mentioned, the outlet opening is adapted to be in fluid communication with the suction inlet 52 of the medical waste collection assembly 50 when the housing 802 is engaged with the manifold receiver 54 such that a suction path is provided from the inlet bore 514 to the suction inlet 58. The drip valve (not shown) may be positioned within the outlet opening to, in manners previously described, prevent egress of fluid from the outlet opening when the housing 802 is disengaged from the manifold receiver 54 and provide fluid communication between the manifold volume 808 and the suction inlet 58 of the medical waste collection assembly 50 when the housing 802 is engaged with the manifold receiver 54. The manifold 800 may include the filter element (not shown) disposed within the housing 802 and in the suction path to be described. The filter element defines the porous features adapted to capture the semisolid and solid matter entrained within the stream being aspirated along the suction path.

Figure 54:
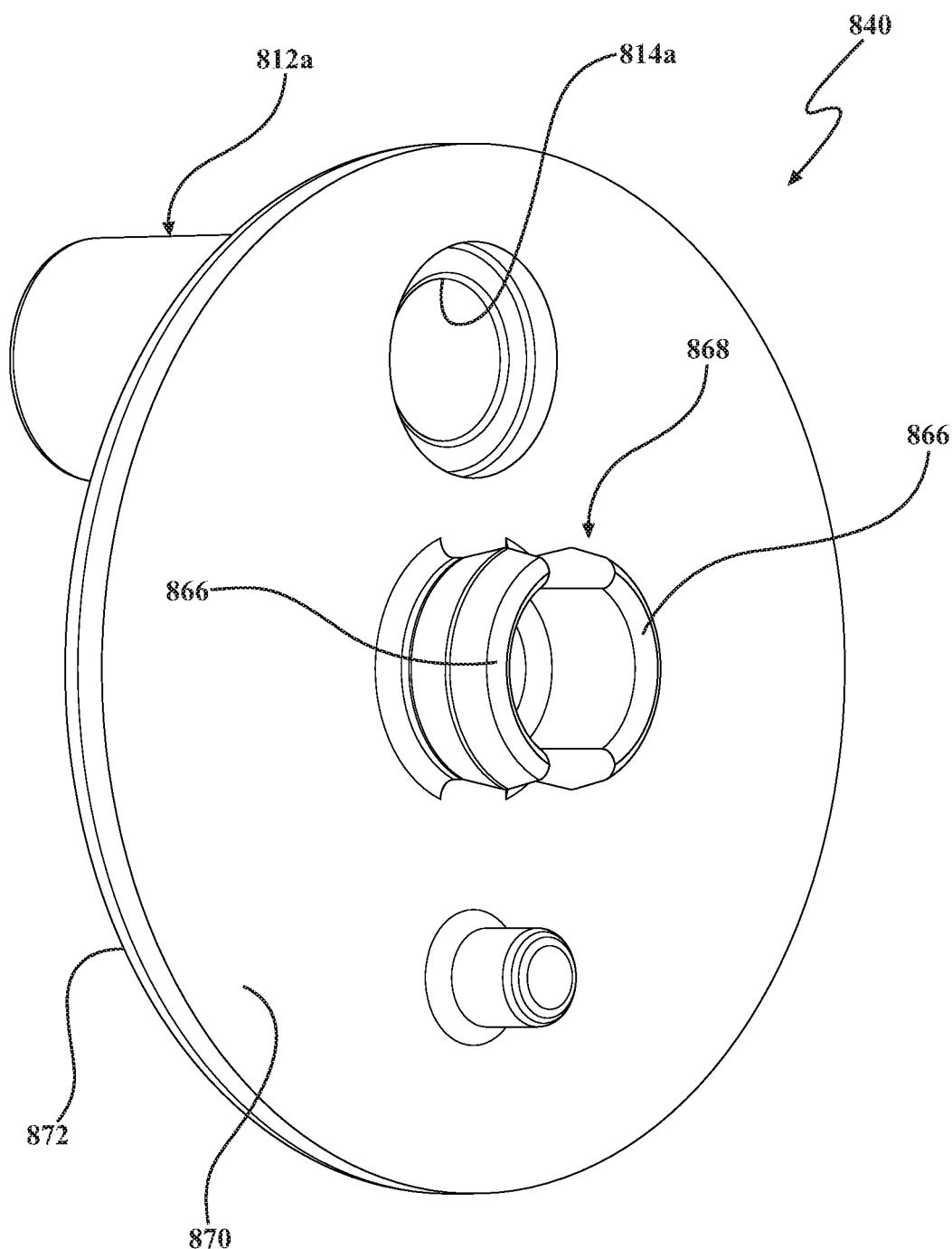
FIG. 54 is a rear perspective view of a cap faceplate of the manifold of FIG. 50.

FIG. 51 shows the cap portion 806 including the cap faceplate 840 and a cap head 842. The cap head 842 includes at least one sidewall 854 extending distally and terminating at a distal face 856. The apertures 858a, 858b extend through the distal face 856 of the cap head 852 and each open into tissue collecting channels 891 extending through the cap head 842. With concurrent reference to FIG. 54, the cap faceplate 840 may be disc-shaped including the proximal face 870 and the distal face 872 opposite the proximal face 870. The coupling features 864 may be a pair of slots arranged to provide a bayonet mount with complementary coupling features 866 of the cap faceplate 840, as shown in FIGS. 51 and 54. The complementary coupling features 866 of the cap faceplate 840 are posts circumferentially arranged to be received within the slots. Of course, other coupling features are contemplated. A tubular portion 868 extends proximally from the proximal face 870. To facilitate operating the manifold 800 in a manner to be described, the cap faceplate 840 may include a control surface 874 adapted to be manipulated by the user (e.g., pinched).

The cap faceplate 840 of the cap portion 806 includes the first inlet fitting 812a. As shown in FIGS. 50 and 51, the first inlet fitting 812a extends distally from the distal face 872 of the cap faceplate 840 with the inlet bore 814a extending through the cap faceplate 840. As a result, with the manifold 800 assembled, the first inlet fitting 812a is rotatable relative to the body portion, i.e., it orbits around the longitudinal axis of the housing. It is contemplated that the first inlet fitting may be movable in other ways. The second inlet fitting 812b may extend distally from the distal face 856 of the cap head 852. The second inlet fitting 812b is not directly connected to the cap faceplate 840. Whereas the first inlet fitting 812a is rotatable relative to the body portion, the second inlet fitting 812b is fixed relative to the cap head 852 and the body portion. The second inlet bore 814b defined by the second inlet fitting 812b is in communication with the second aperture 857b to be described to define one of the bypass channels 892. The second inlet fitting may also be part of the housing instead.

The housing 802 further defines at least one of the accessory openings 811 each opening into the accessory sleeve 813. The accessory sleeve 813 is in fluid communication with the manifold volume 808. The accessory sleeve 813 is disposed within the cap body 806. FIG. 40 shows one of the accessory openings 811 positioned at a lateral aspect of the cap head 842 with the accessory sleeve 813 opening radially inwardly into the manifold volume 808. Another one of the accessory openings 811 may be positioned diametrically opposite the other access opening 811 relative to the cap body 806.

The manifold 800 includes at least one tray 876a, 876b configured to be removably positioned within the accessory sleeve 813. With reference to FIG. 51, the tray 876a, 876b defines the tissue collecting cavity 882 and the porous features 886 within the tissue collecting cavity 882. With the tray 876a, 876b positioned within the accessory sleeve 813, the porous features 582 may be within the suction path to collect the tissue sample, which is further based on a rotatable position of the first inlet bore 814a in a manner to be described. Once it is desired to retrieve the collected tissue sample, the tray 876a, 876b may be slidably removed from the accessory sleeve 813 with the tissue sample disposed within the tissue collecting cavity 882. It is to be understood that the tray 876a, 876b is optional, and the manifold 800 may be operated without the tray 876 within the accessory sleeve 813.

The tray 876a, 876b may be formed from a single piece or multiple components. With continued reference to FIG. 51, the tray 876a, 876b includes opposing pairs of sides 885 extending from a screen surface 884 defining the porous features 886. The sides 885 and the screen surface 884 collectively define the tissue collecting cavity 882 of the tray 876a, 876b. The tray 876a, 876b may further include orientation features (not shown) configured to engage complementary orientation features (not shown) of the accessory sleeve 813 to position the tray 876a, 876b within the accessory sleeve 813 in a predetermined orientation relative to the distal barrier 803. The tray 876 includes the control surface 888 adapted to receive the input from the user. The control surface 888 may be formed as a handle to be pinched between fingers of the user. The tray 876a, 876b further includes a sealing surface 855 adapted to be in sealing engagement with the housing 802 when the tray 876a, 876b is within the accessory sleeve 813. In particular, the tray 876 may include a flange defining the sealing surface 855 with the sealing surface 855 adapted to contact a perimeter of the accessory opening 811. With the tray 876a, 876b within the accessory sleeve 813 and the sealing surface 855 covering the accessory opening 811, suction is maintained through the suction path during operation of the medical waste collection assembly 50. Likewise, a cap (not shown) may be provided and sized to cover the accessory opening 811 to maintain suction through the suction path in the absence of the tray 876a, 876b. Still further, the tray 876a, 876b may include the retention feature (not shown) adapted to defeatably engage a complementary retention feature of the housing 802, for example, a detent to provide a tactile and/or audible feedback to the user such that the user is confident the tray 876a, 876b is fully disposed or seated within the accessory sleeve 813. Once the tissue sample is collected within the tissue collecting cavity 882 and the user wishes to remove the tray 876a, 876b, an input of sufficient force is provided to the control surface 888 of the tray 876a, 876b to disengage the retention feature and the complementary retention feature (e.g., overcome the interference engagement between the detent and the housing 802).

With concurrent reference to FIG. 51, the cap head 842 of the housing 802 defines at least one of the apertures 858a, 858b and the second apertures 857. Each of the apertures 858a, 858b may open into a respective one of the tissue collecting channels 891. The tissue collecting channels 891 may be coaxial and in fluid communication with the accessory sleeve 813. The bypass opening 857 may open into the bypass channel 892 (shown in FIG. 51). The second inlet bore 814b is in fluid communication with another one of the bypass channels 892.

In operation, should the user wish to collect the tissue sample in one or both of the tissue collecting cavities 882 of the trays 876, the user provides the input to the control surface 874 to rotate the first inlet fitting 812a align the first inlet bore 814a with one of the apertures 858a, 858b. Further, the user positions one of the trays 876a, 876b in one of the accessory sleeves 813. With the first inlet bore 814a aligned with one of the apertures 858a, 858b and the tray 876a, 876b positioned within the accessory sleeve 813, a respective one of the tissue collecting cavities 882 is in the suction path, and the tissue sample being aspirated through the suction path encounters the porous features 886 within the tissue collecting cavity 882. The manifold 800 may be considered in the tissue collecting position. Should another tissue sample be desired, the user may simply provide another input to the control surface 844 to rotate the first inlet fitting 812a to align the first inlet bore 814a with the one of the apertures 858a, 858b. The user positions another one of the trays 876a, 876b in one of the accessory sleeves 813. With the first inlet bore 814a aligned with the other one of the apertures 858a, 858b and the tray 876a, 876b positioned within the other accessory sleeve 813, the other one of the tissue collecting cavities 882 is in the suction path, and the tissue sample being aspirated through the suction path encounters the porous features 886 within the tissue collecting cavity 882.

Should the user wish to not collect a tissue sample with the manifold 800 yet maintain suction, the bypass channels 892 permit fluid to flow through the manifold 800 without collecting the tissue sample during operation of the medical waste collection assembly 50. Two bypass channels 892 are shown. The first inlet bore 812a is adapted to be rotated be selectively aligned with the bypass opening 857. In particular, the user provides the input to the control surface 844 to rotate the first inlet bore 814a in alignment with the bypass opening 857. The manifold 800 may be considered in the bypass position. With the bypass channel 892 is in fluid communication with the first inlet bore 814a, it is considered that the tissue collecting cavities 882 are not in fluid communication with the inlet bore 814. Additionally or alternatively, a second suction line may be coupled to the second inlet fitting 812b defining the second inlet bore 814b. In such an exemplary operation, the waste material entering the second inlet bore 814b is directed through the other one of the bypass channels 892. Of course, additional inlet fittings are also contemplated where certain features described above are replicated, such as three or four inlet fittings.

With the manifold 800 in the bypass position such that the tissue collecting cavity 882 is not within the suction path, the manifold 800 advantageously provides for retrieval of the collected tissue sample without disrupting the operation of the medical waste collection assembly 50. The bypass channels 892 permit the user to continue to aspirate the surgical site without needing to first retrieve the tissue sample from the manifold 800 and without compromising the quality of the tissue sample as initially collected. As a result, the manifold 800 may remain engaged with the medical waste collection assembly 50 until the conclusion of the surgical procedure. With the manifold 800 in the bypass position (or with the manifold 800 in the tissue collection position utilizing the other tray 876a, 876b), the user provides an input to the control surface 888 of the tray 876a, 876b to remove the tray 876a, 876b from its respective accessory sleeve 813. A replacement one of the trays 876a, 876b may be positioned within the accessory sleeve 813 without disrupting the operation of the medical waste collection assembly 50.

Figure 53:
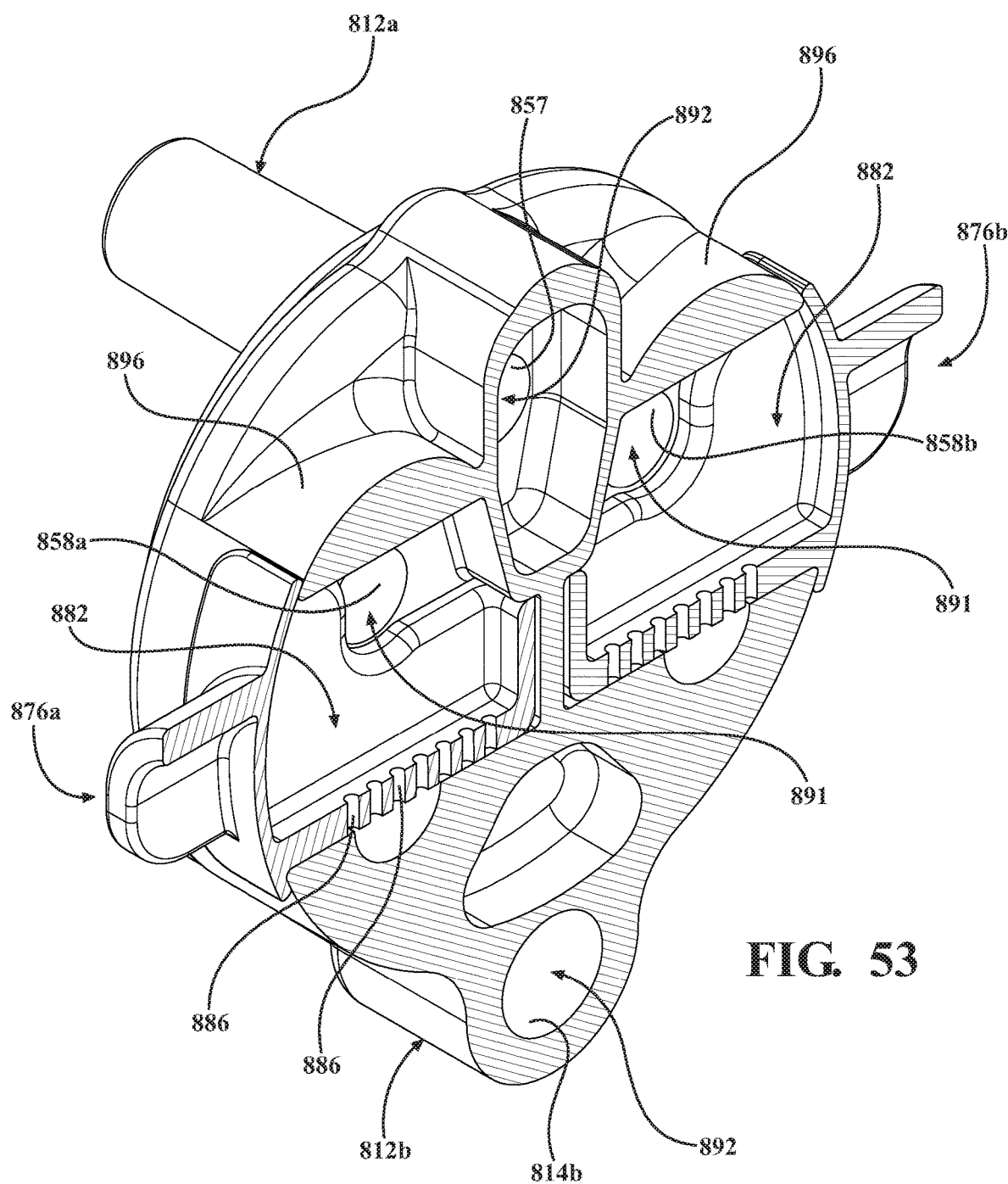
FIG. 53 is a sectional view of the manifold of FIG. 50 taken along section lines 53-53.

As previously described, the manifold 800 accommodates visualization for an improved tissue collection experience for the user. Referring to FIGS. 51 and 53, the tissue collecting cavity 882 of the tray 876 opens towards a top of the manifold 800, and the manifold 800 includes the lens 896 providing magnification within the tissue collecting cavity when the tray is within the accessory sleeve 813. Further, with the lens 896 at the top of the manifold 800 positioned horizontally within the medical waste collection assembly 50, the user may glance at the manifold 800 from a reasonable distance and without undue maneuvering about the manifold 800 to quickly ascertain whether a suitable tissue sample has been captured. It is contemplated that lighting may be provided to illuminate the tissue collecting cavities 882.

Referring now to FIGS. 55-61, another manifold 900 is illustrated that is, in at least some respects, similar to those previously described (and certain like components being indicated by like numerals plus one hundred (100)). The manifold 900 includes the housing 902 adapted to be removably engaged with the manifold receiver 54. The housing 902 includes the cap portion 906 and the body portion 904. As previously expressed, the cap portion 906 may be coupled to the body portion with removable or permanent joining means, or the body portion and the cap portions 904, may be formed as a single piece of unitary construction, for example, spin welded at an interface to prevent reuse. The housing 902 defines the manifold volume (not identified). The outlet opening (not shown) is in fluid communication with the manifold volume. The housing 902 includes the first inlet fitting 912a defining the first inlet bore 914a in fluid communication with the manifold volume, and the second inlet fitting 912b defining a second inlet bore 914b in fluid communication with the manifold volume. As previously mentioned, the outlet opening is adapted to be in fluid communication with the suction inlet 52 of the medical waste collection assembly 50 when the housing 902 is engaged with the manifold receiver 54 such that a suction path is provided from the inlet bores 914a, 914b to the suction inlet 52. The drip valve (not shown) may be positioned within the outlet opening to, in manners previously described, prevent egress of fluid from the outlet opening when the housing 902 is disengaged from the manifold receiver 54 and provide fluid communication between the manifold volume and the suction inlet 52 of the medical waste collection assembly 50 when the housing 902 is engaged with the manifold receiver 54. The manifold 900 may include the filter element (not shown) disposed within the housing 902 and in the suction path to be described. The filter element defines the porous features adapted to capture the semisolid and solid matter entrained within the stream being aspirated along the suction path.

Figure 55:
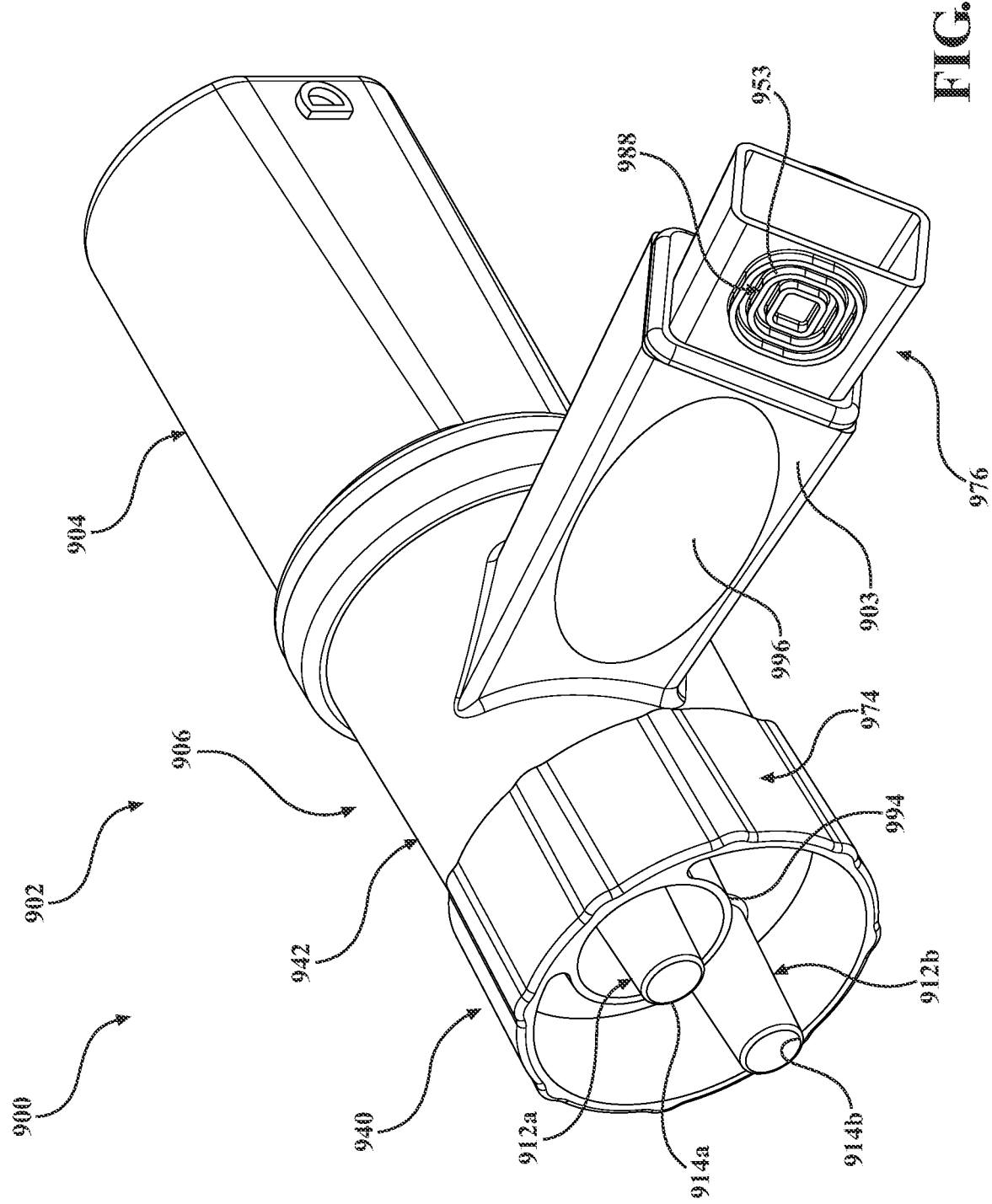
FIG. 55 is a perspective view of a manifold.

FIG. 55 shows the cap portion 906 including the cap faceplate 940 and a cap head 942. With concurrent reference to FIG. 56, the cap head 942 includes at least one sidewall 954 extending distally and terminating at the distal face 956. With concurrent reference to FIG. 57, the cap faceplate 940 may be disc-shaped including the proximal face 970 and the distal face 972 opposite the proximal face 970. Coupling features 964 may be arranged to provide a bayonet mount with complementary coupling features 966 of the cap faceplate 940. The tubular portion 968 extends proximally from the proximal face 970. Of course, other coupling features may be used. To facilitate operating the manifold 900 in a manner to be described, the cap faceplate 940 may include the control surface 974 adapted to be manipulated by the user.

Figure 56:
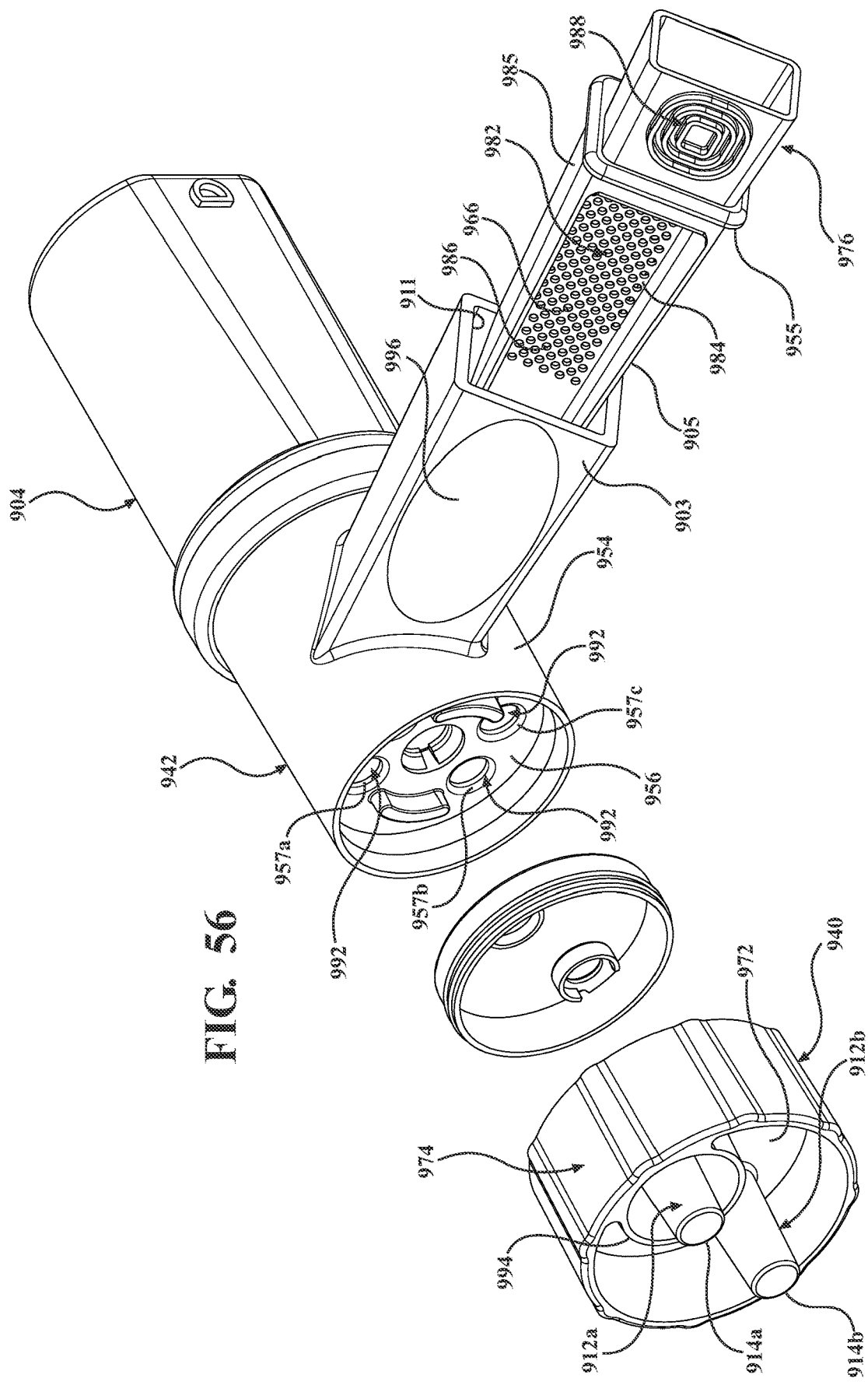
FIG. 56 is an exploded view of the manifold of FIG. 55.
Figure 57:
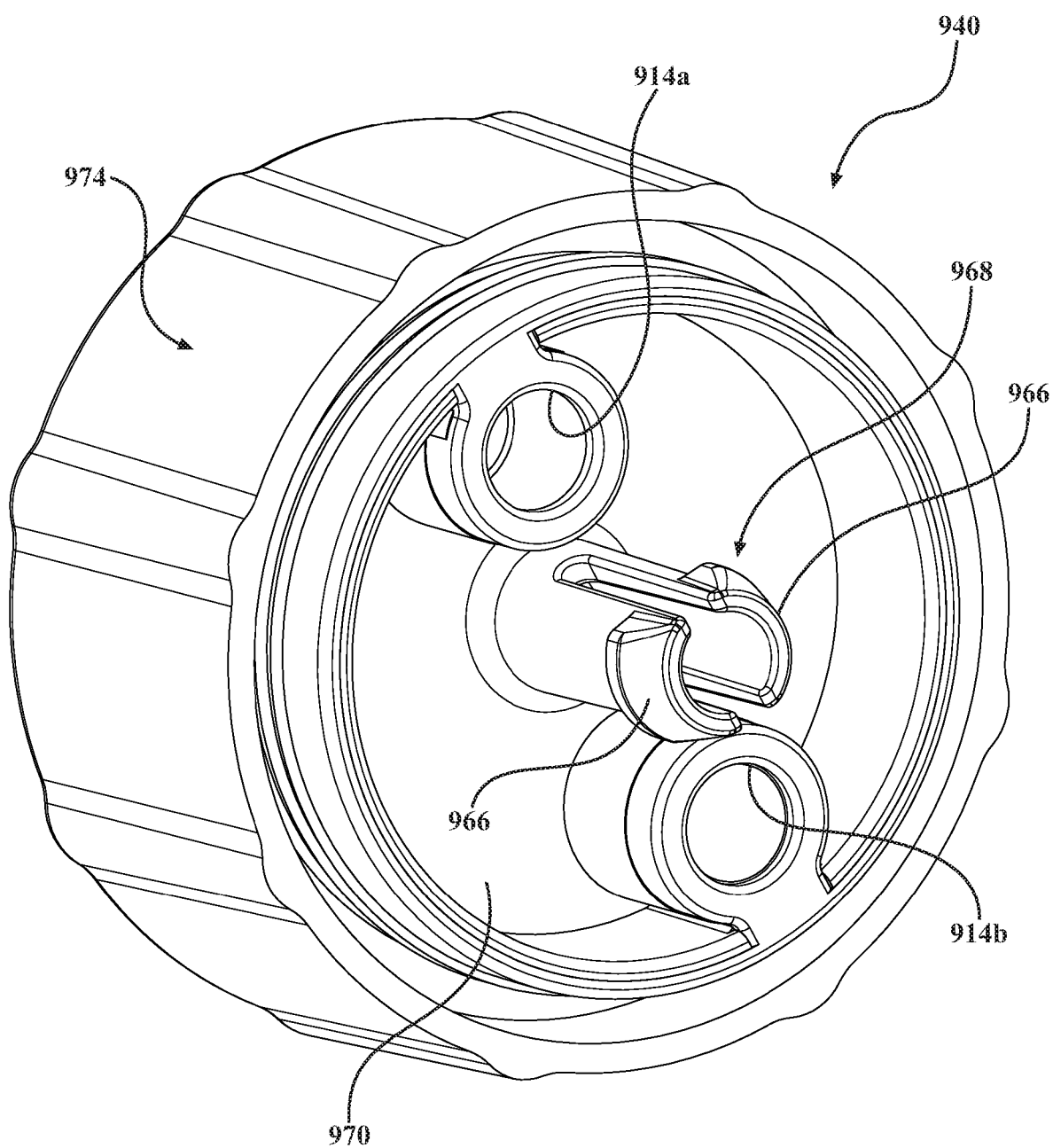
FIG. 57 is a rear perspective view of a cap faceplate of the manifold of FIG. 55.

The cap faceplate 940 of the cap portion 906 includes the first inlet fitting 912a. As shown in FIG. 56, each of the first inlet fitting 912a and the second inlet fitting 912b extend distally from the distal face 972 of the cap faceplate 940 with the inlet bores 914a, 914b extending through the cap faceplate 940. As a result, with the manifold 900 assembled, the first and second inlet fittings 912a, 912b are rotatable relative to the body portion 904, i.e., orbit relative to the longitudinal axis of the body portion and are configured to be rotated between the tissue collecting position and the bypass position. It is also contemplated that the first and second inlet fittings may move in a different fashion relative to the housing. Indicia 994 may be provided to indicate which is the first inlet fitting 912a, as the first inlet fitting 912a serves as the port for tissue collection. The indicia 994 illustrated in FIGS. 55 and 56 include a ring encircling the first inlet fitting 912a to provide visual as well as tactile indication without undue effort. Other types of indicia are also contemplated, such as tabs or protrusions.

The housing 902 further defines the accessory opening 911 opening into the accessory sleeve 913. The accessory sleeve 913 is in fluid communication with the manifold volume 908. The accessory sleeve 913 is disposed within the cap body 906. FIG. 56 shows the accessory opening 911 positioned at a lateral aspect of the cap head 942 with the accessory sleeve 913 inclined upwardly in a manner to be described. It is contemplated that another one of the accessory sleeves (not shown) may be positioned diametrically opposite relative to the cap body 806.

The manifold 900 includes the tray 976 configured to be removably positioned within the accessory sleeve 913. With reference to FIG. 56, the tray 976 defines the tissue collecting cavity 982 and the porous features 986 within the tissue collecting cavity 982. With the tray 976 positioned within the accessory sleeve 913, the porous features 986 may be within the suction path to collect the tissue sample, which is further based on a rotatable position of the first inlet bore 914a in a manner to be described. Once it is desired to retrieve the collected tissue sample, the tray 976 may be slidably removed from the accessory sleeve 913 with the tissue sample disposed within the tissue collecting cavity 982. It is to be understood that the tray 976 is optional, and the manifold 900 may be operated without the tray 976 within the accessory sleeve 913.

As best shown in FIG. 56, the tray 976 may be formed from a single piece or multiple components. With continued reference to FIG. 56, the tray 976 includes opposing pairs of sides 985 extending from a screen surface 984 defining the porous features 986. The sides 985 and the screen surface 984 collectively define the tissue collecting cavity 982 of the tray 976. The tray 976 may further include orientation features (not shown) configured to engage complementary orientation features (not shown) of the accessory sleeve 913 to position the tray 976 within the accessory sleeve 913 in a predetermined orientation relative to the distal barrier 903. The tray 976 includes the control surface 988 adapted to receive the input from the user. The control surface 988 may be formed as a handle to be pinched between fingers of the user. The tray 976 further includes a sealing surface 955 adapted to be in sealing engagement with the housing 902 when the tray 976 is within the accessory sleeve 913. In particular, the tray 976 may include a flange defining the sealing surface 955 with the sealing surface 955 adapted to contact a perimeter of the accessory opening 911. With the tray 976 within the accessory sleeve 913 and the sealing surface 955 covering the accessory opening 911, suction is maintained through the suction path during operation of the medical waste collection assembly 50. Likewise, a cap (see, e.g., FIG. 29) may be provided and sized to cover the accessory opening 911 to maintain suction through the suction path in the absence of the tray 976. Still further, the tray 976 may include the retention feature (not shown) adapted to defeatably engage a complementary retention feature of the housing 902, for example, a detent to provide a tactile and/or audible feedback to the user such that the user is confident the tray 976 is fully disposed or seated within the accessory sleeve 913. Once the tissue sample is collected within the tissue collecting cavity 982 and the user wishes to remove the tray 976, an input of sufficient force is provided to the control surface 988 of the tray 976 to disengage the retention feature and the complementary retention feature (e.g., overcome the interference engagement between the detent and the housing 902).

Figure 58:
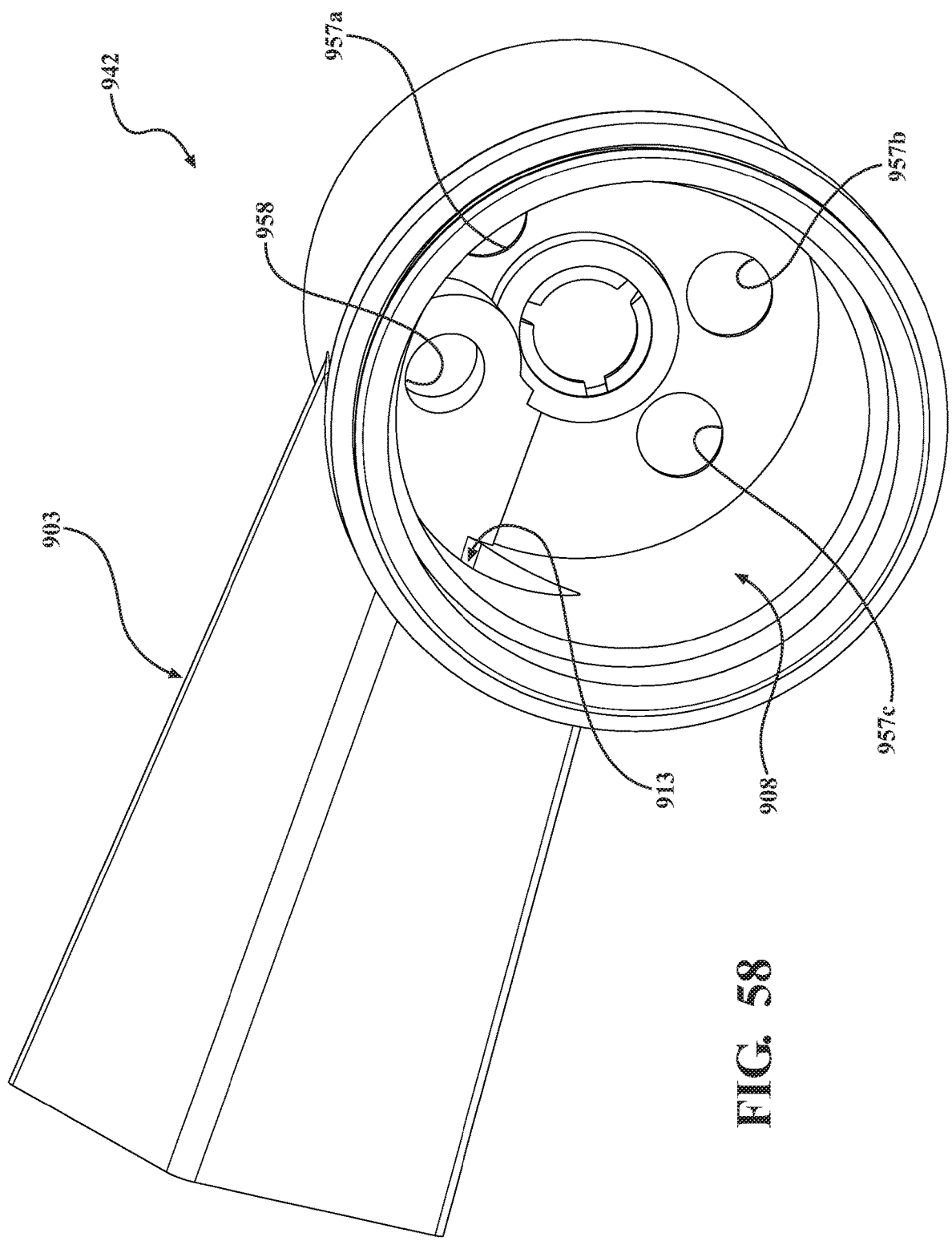
FIG. 58 is a rear perspective view of a cap head of the manifold of FIG. 55.
Figure 61:
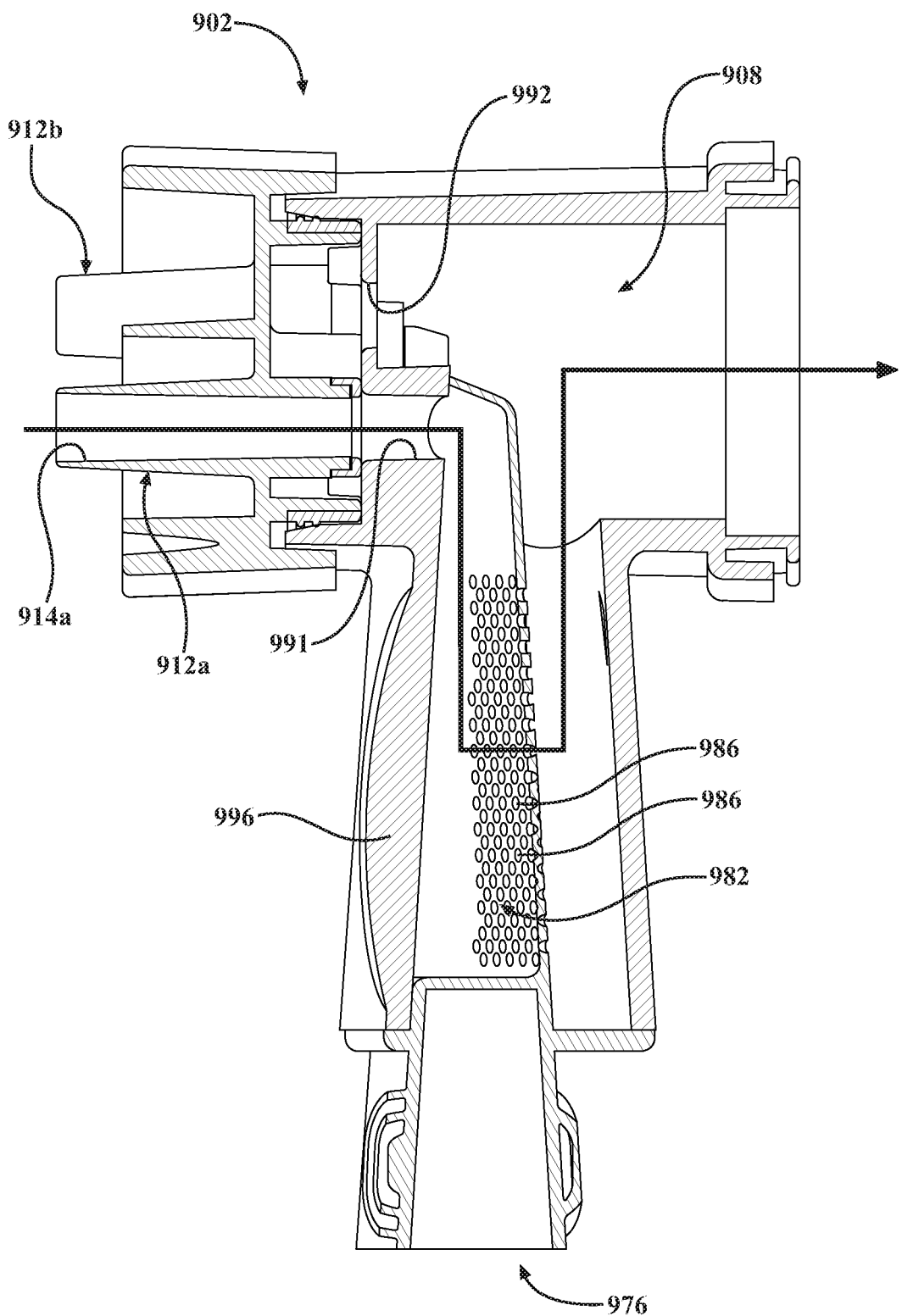
FIG. 61 is a sectional elevation view of the manifold of FIG. 55 with a schematic representation of a flow path through the manifold in the tissue collecting position.

With concurrent reference to FIGS. 58 and 60, the cap head 942 of the housing 902 may define the aperture 958 and at least one of the bypass openings 957. The aperture 958 opens into the tissue collecting channel 991. The tissue collecting channel 991 is in fluid communication with the accessory sleeve 913. FIG. 58 shows three bypass openings 957a, 957b, 957c each opening into a respective bypass channel 992 in a manner to be described. In a variant to be described, one of the bypass openings 957a may be removed in order to remove suction to the suction line 52 when the manifold 900 is in the bypass position.

In operation, should the user wish to collect the tissue sample in the tissue collecting cavity 982 of the tray 976, the user provides the input to the control surface 974 to rotate the first inlet fitting 912a (and consequently the second inlet fitting 912b) to the tissue collecting position shown in FIG. 59. The input may include providing a torque to the control surface 974 of the cap faceplate 940 in a first rotational direction, $D_1$. In the tissue collecting position shown in FIG.

59, the first inlet bore 914a is in communication, for example coaxially aligned, with the aperture 958 proximal to which the tissue collecting cavity 982 is aligned when the tray 976 is positioned within the accessory sleeve 913. At the same time, the second inlet bore 914b is in communication, for example coaxially aligned, with the one of the bypass openings 957b opening into the manifold volume 908.

The user positions the tray 976 in the accessory sleeve 913. With the first inlet bore 914a aligned with the aperture 958 and the tray 976 positioned within the accessory sleeve 913, a suction path is established as shown in FIG. 49. In particular, the tissue collecting cavity 982 is in the suction path, and the tissue sample being aspirated through the suction path encounters the porous features 986 within the tissue collecting cavity 982. The manifold 900 may be considered in the tissue collecting position, and simultaneously provide for separate aspiration of waste material through the second inlet fitting 912b in communication with the one of the bypass openings 957b.

Should the user wish to retrieve the tissue sample collected in the tray 976 and/or remove the tray 976 from the suction path, the user provides another input to the control surface 974 to rotate the first inlet fitting 912a (and consequently the second inlet fitting 912b) to the bypass position shown in FIG. 60. The input may include providing another torque to the control surface 974 in a second rotational direction, $D_2$, opposite the first rotational direction. In the bypass position shown in FIG. 60, the first inlet bore 914a is in communication, for example coaxially aligned, with one of the bypass openings 957a and the second inlet bore 914b is in communication with, for example coaxially aligned, with another one of the bypass openings 957c.

In the aforementioned variant, the bypass opening 957a is removed such that, in the bypass position, the first inlet bore 914a is aligned with a portion of the distal face 856 of the cap head 942. Suction through the first inlet bore 914a is removed, thereby removing the risk of further tissue samples or waste material being drawn through the suction line 52 and the first inlet bore 914a.

The tray 976 may be removed from the accessory sleeve 913 with the manifold 900 in the tissue collecting position and/or the bypass position. Upon doing so, a decrease in suction may occur secondary to the accessory opening 911 no longer being in sealing engagement with the sealing surface 955 of the tray 976. With the manifold 900 in the tissue collecting and/or the bypass position, the user provides an input to the control surface 988 of the tray 976 to remove the tray 976 from the accessory sleeve 913. Should another tissue sample be desired, a replacement tray 976 may be positioned within the accessory sleeve 913 without disrupting the operation of the medical waste collection assembly 50.

The manifold 900 accommodates visualization for an improved tissue collection experience for the user. The tissue collecting cavity 982 of the tray 976 opens towards the distal barrier 903, and the manifold 900 includes the lens 996 providing magnification within the tissue collecting cavity when the tray is within the accessory sleeve 913. The distal barrier 903 and other barriers defining the external of the accessory sleeve 913 are "clocked" relative to the longitudinal axis of the manifold 900 such that the distal barrier 903 including the lens 996 is oriented distally and upwardly relative to the longitudinal axis. Based on the orientation of the manifold 900 within the medical waste collection assembly 50, the lens 996 is positioned at the top of the manifold 900. The user may glance at the manifold 900 from a reasonable distance and without undue maneuvering about the manifold 900 to quickly ascertain whether a suitable tissue sample has been captured. It is contemplated that lighting may be provided to illuminate the tissue collecting cavity 982.

Figure 62:
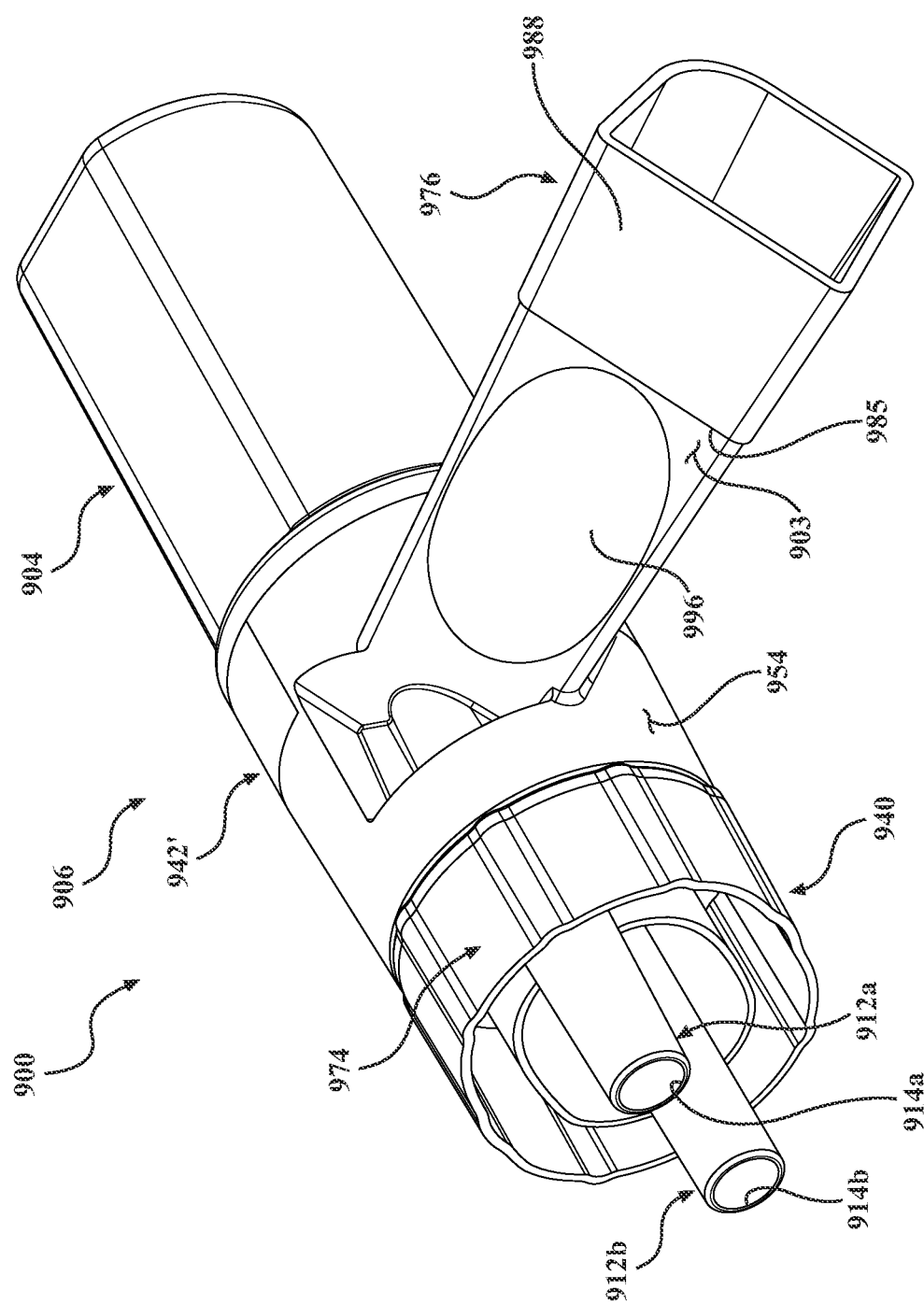
FIG. 62 is a perspective view of a variant of the manifold of FIG. 55.
Figure 63:
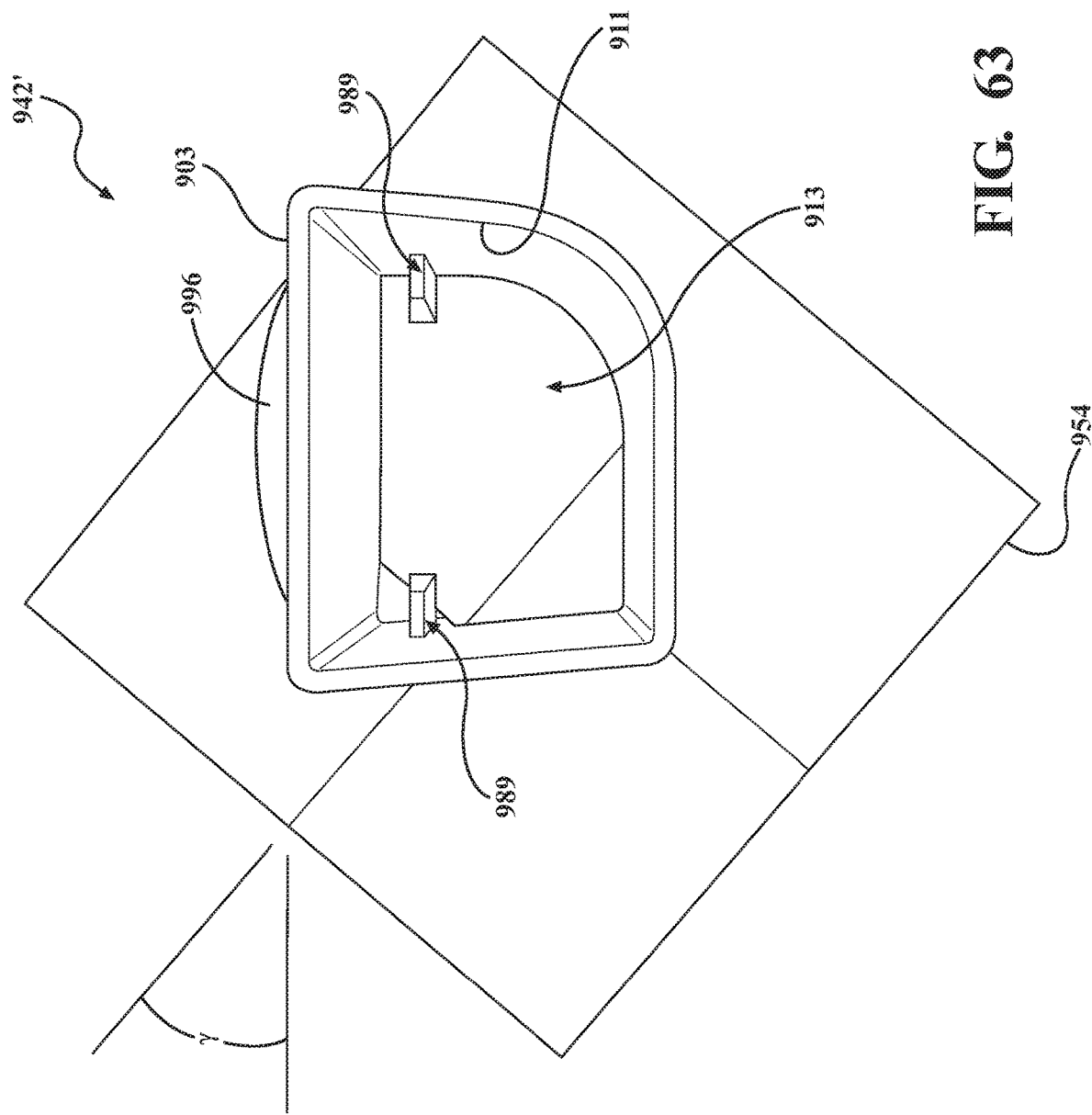
FIG. 63 is a side elevation view of a cap head of the manifold of FIG. 55 including orientation and/or locating features.
Figure 64:
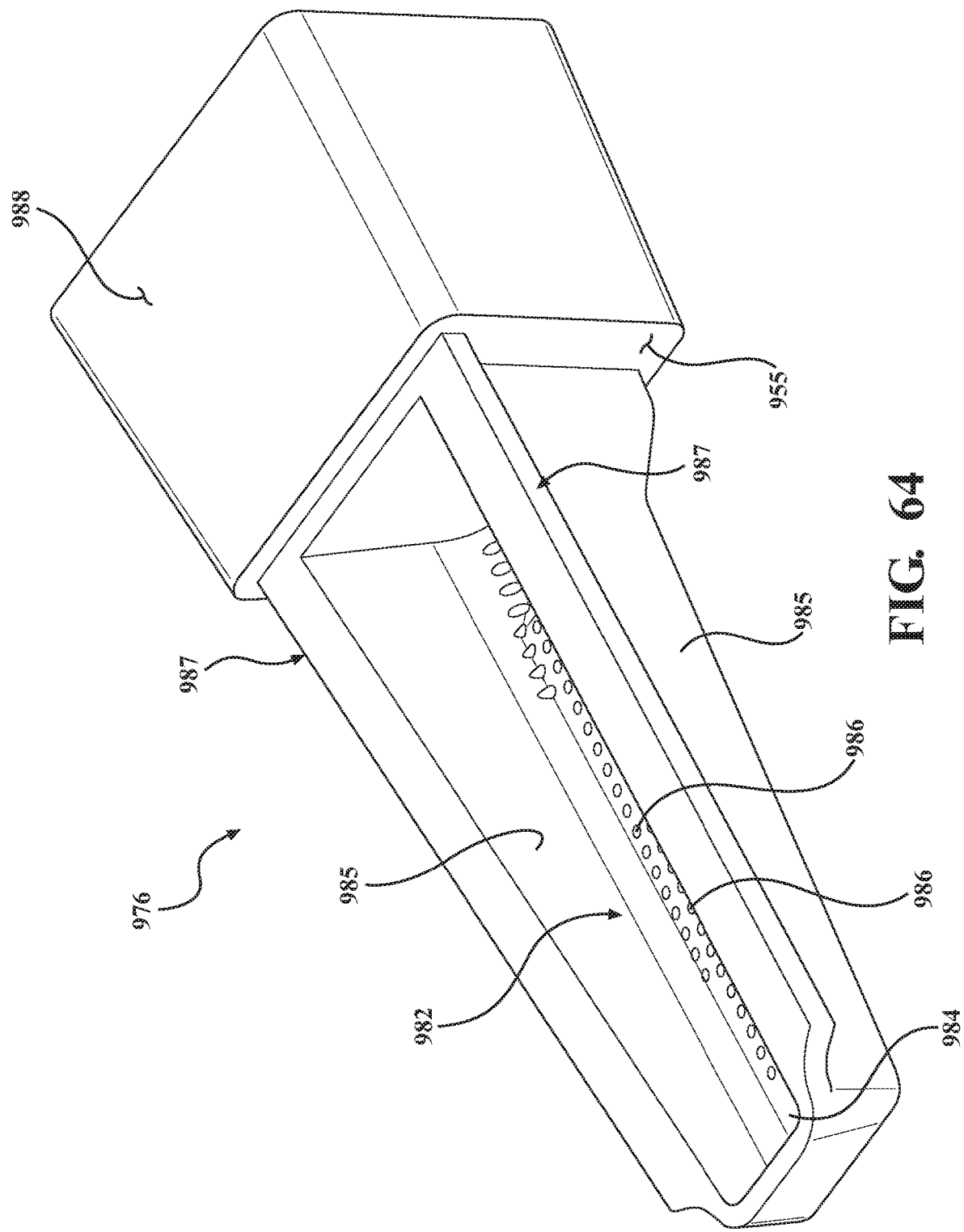
FIG. 64 is a tray of the manifold of FIG. 62 with the tray including complimentary orientation and/or locating features.

FIGS. 62-64 illustrates a variant of the manifold 900 of FIGS. 55-61 with certain alternative or additional features to be described, and in particular features directed to orienting and/or locating the tray 976 within the accessory sleeve 913. Description not repeated relative to the manifold 900 of FIGS. 55-61 is in the interest of brevity and should be considered incorporated by reference. The manifold 900 includes the cap portion 906 and the body portion 904 collectively forming the housing 902. The housing 902 includes the first inlet fitting 912a defining the first inlet bore 914a in fluid communication with the manifold volume, and the second inlet fitting 912b defining a second inlet bore 914b in fluid communication with the manifold volume. The manifold 900 may include the filter element (not shown) disposed within the housing 902 and in the suction path.

FIG. 62 shows the cap portion 906 including the cap faceplate 940 and a cap head 942'. The cap faceplate 940 of the cap portion 906 includes the first inlet fitting 912a and the second inlet fitting 912b rotatable relative to the body portion 904, i.e., orbit relative to the longitudinal axis of the body portion and are configured to be rotated between the tissue collecting position and the bypass position.

With concurrent reference to FIG. 63, the cap head 942' includes at least one sidewall 954 extending distally and terminating at the distal face (not shown). The housing 902 further defines the accessory opening 911 opening into the accessory sleeve 913. The accessory sleeve 913 is in fluid communication with the manifold volume 908. The accessory sleeve 913 is disposed within the cap portion 906. FIG. 63 shows the accessory opening 911 positioned at a lateral aspect of the cap head 942' with the accessory sleeve 913 inclined upwardly in a manner to be described.

The manifold 900 includes the tray 976 configured to be removably positioned within the accessory sleeve 913. With reference to FIG. 64, the tray 976 defines the tissue collecting cavity 982 and the porous features 986 within the tissue collecting cavity 982. With the tray 976 positioned within the accessory sleeve 913, the porous features 986 may be within the suction path to collect the tissue sample, which is further based on a rotatable position of the first inlet bore 914a in a manner previously described. Once it is desired to retrieve the collected tissue sample, the tray 976 may be slidably removed from the accessory sleeve 913 with the tissue sample disposed within the tissue collecting cavity 982.

With continued reference to FIG. 64, the tray 976 may include opposing pairs of sides 985 extending from a screen surface 984 defining the porous features 986. The sides 985 and the screen surface 984 collectively define the tissue collecting cavity 982 of the tray 976. The tray 976 includes the control surface 988 adapted to receive the input from the user. The control surface 988 may be formed as a handle to be pinched between fingers of the user. The tray 976 further includes a sealing surface 955 adapted to be in sealing engagement with the housing 902 when the tray 976 is within the accessory sleeve 913. In particular, the tray 976 may include a flange defining the sealing surface 955 with the sealing surface 955 adapted to contact a perimeter of the accessory opening 911. With the tray 976 within the accessory sleeve 913 and the sealing surface 955 covering the accessory opening 911, suction is maintained through the suction path during operation of the medical waste collection assembly 50. Once the tissue sample is collected within the tissue collecting cavity 982 and the user wishes to remove the tray 976, an input of sufficient force is provided to the control surface 988 of the tray 976 to remove the tray 976 from the accessory sleeve 913.

Referring to FIG. 64, the tray 976 may further include orientation features 987 configured to engage complementary orientation features 989 of the accessory sleeve 913 (shown in FIG. 63) to position the tray 976 within the accessory sleeve 913 in a single orientation relative orientation, and in particular relative to the upper barrier 903. The orientation features 989 of the tray accessory sleeve 913 may be tabs. The tabs extend inwardly from opposing barriers at least partially defining the accessory sleeve 913 and are oriented generally parallel to the direction of the accessory sleeve 913, for example parallel to the upper barrier 903. FIG. 63 shows the tabs extending only partially between the accessory opening 911 and an interface opening within the sidewall 954 of the cap head 942' opposite the accessory opening 911. It is contemplated that the orientation features 989 may extend between along substantially an entirety of the accessory sleeve 913 such that the orientation features 999 are more akin to elongate rails. The orientation features 989 are spaced closer to the distal barrier 903 than a barrier at least partially defining the accessory sleeve 913 opposite the upper barrier 903, thereby requiring the coupling of the tray 976 with the housing 902 in the singular orientation.

The complementary orientation features 987 of the tray 976 may be rails configured to movably engage the tabs of the accessory sleeve 913. FIG. 64 shows the rails extending outwardly from the sealing surface 955 to a position near an end of the tray 976 opposite the sealing surface 955. More particularly, the orientation features 987 extending laterally outwardly from the opposing sides 985 at least partially defining the tissue collecting cavity 982. The orientation features 987 are positioned at upper edge of the sides 985, in other words at the edge of the sides 985 opposite the screen surface 984. The position of the orientation features 987 relative to the screen surface 984 and of the orientation features 989 relative to the upper barrier 903 requires the tray 976 be inserted into the accessory sleeve 913 in the single orientation. The rails movably engage the tabs such that the tissue collecting cavity 982 opens towards the first inlet bore 914a.

The orientation features 987, 989 may also function as locating features to provide a second suction path beneath the tray 976 (i.e., adjacent the screen surface 984 opposite the tissue collecting cavity 982). The second suction path may be utilized to at least partially lessen or break suction ("bleed") between the inlet bores 912a, 912b and the outlet opening secondary to the accessory opening 911 no longer being in sealing engagement with the sealing surface 955 of the tray 976. The locating features and second suction path are to be described in greater detail. In short, upon initiating removal of the tray 976 from the accessory sleeve 913, a corresponding fluid flow occurs through the accessory sleeve 913 in a path of least resistance based on fluid dynamics. With the second suction path being beneath the tray 976 as the tray 976 is being removed from the accessory sleeve 913, the likelihood that the fluid flow through the accessory sleeve 913 inadvertently and undesirably ejects the tissue sample collected in the tissue collecting cavity 982 is lessened. The orientation features 987, 989 may suspend the screen surface 984 above the lower barrier at least partially defining the accessory sleeve 913 to define a gap. With the upper surfaces of the orientation features 987 (e.g., the rails) positioned adjacent to the upper barrier 903 at partially defining the accessory sleeve 913, the gap may be the path of least resistance such that a majority of the fluid is directed beneath the tray 976 and does not come into contact with the tissue sample collected in the tissue collecting cavity 982. With negligible fluid flow entering the tissue collecting cavity 982, the associated forces are minimal and the likelihood the collected tissue sample is siphoned out of the tissue collecting cavity 982 and into the manifold volume is lessened or eliminated.

The manifold 900 accommodates visualization for an improved tissue collection experience for the user. Referring to FIGS. 63 and 64, the tissue collecting cavity 982 of the tray 976 opens towards the upper barrier 903, and the manifold 900 includes the lens 996 providing magnification within the tissue collecting cavity when the tray is within the accessory sleeve 913. The upper barrier 903 and other barriers defining the external of the accessory sleeve 913 are "clocked" relative to the longitudinal axis of the manifold 900 such that the upper barrier 903 including the lens 996 is oriented distally and upwardly relative to the longitudinal axis. In particular, FIG. 63 shows the upper barrier 903 on which the lens 996 is disposed is positioned at an angle, γ, relative to a plane including the longitudinal axis of the manifold 900. The angle γ may be between approximately 10 and 45 degrees, more particularly between approximately 20 and 35 degrees, and even more particularly at approximately 25 degrees. Based on the orientation of the manifold 900 within the medical waste collection assembly 50, the lens 996 is positioned at the top of the manifold 900 at generally oriented horizontally relative to ground. The user may glance at the manifold 900 from a reasonable distance and without undue maneuvering about the manifold 900 to quickly ascertain whether a suitable tissue sample has been captured. It is contemplated that lighting may be provided to illuminate the tissue collecting cavity 982.

Referring now to FIGS. 65-68, cap portion 1106, 1206 for a manifold 1100, 1200 includes the cap head 1142, 1242 and a support frame 1143, 1243. The cap portion 1106, 1206 defines an upper barrier 1103, 1203. The housing includes a first inlet fitting 1112a, 1212a and a second inlet fitting 1112b, 1212b. More particularly the support frame 1143, 1243 of the cap portion 1106, 1206 includes a first inlet fitting 1112a, 1212a, and the cap head 1142, 1242 includes a second inlet fitting 1112b, 1212b. The first inlet fitting 1112a, 1212a extends upwardly away from the upper barrier 1103, 1203 with the first inlet bore 1114a, 1214a extending through the first inlet fitting 1112a, 1212a and the upper barrier 1103, 1203. The second inlet fitting 1112b, 1212b extends distally from the cap head 1142, 1242 with the second inlet bore 1114b, 1214b extending through the cap head 1142, 1242. The housing of the manifold 1100, 1200 further defines the accessory opening 1111, 1211 opening into an accessory sleeve 1113, 1213. The accessory sleeve 1113, 1213 may be at least partially defined by the upper barrier 1103, 1203 a lower barrier 1122, 1222, and opposing side barriers 1123, 1223 extending between the upper barrier 1103, 1203 and the lower barrier 1122, 1222. The accessory sleeve 1113, 2113 is in fluid communication with the manifold volume through a bore 1125, 1225.

The manifold 1100, 1200 includes the tray 1176, 1276 configured to be removably positioned within the accessory sleeve 1113, 1213. The tray 1176, 1276 may be the same as that previously described. The operation of the manifold 1100, 1200, including moving the manifold 1100, 1200 between the sealing configuration and the bleed configuration, is the same as that previously described.

Figure 65:
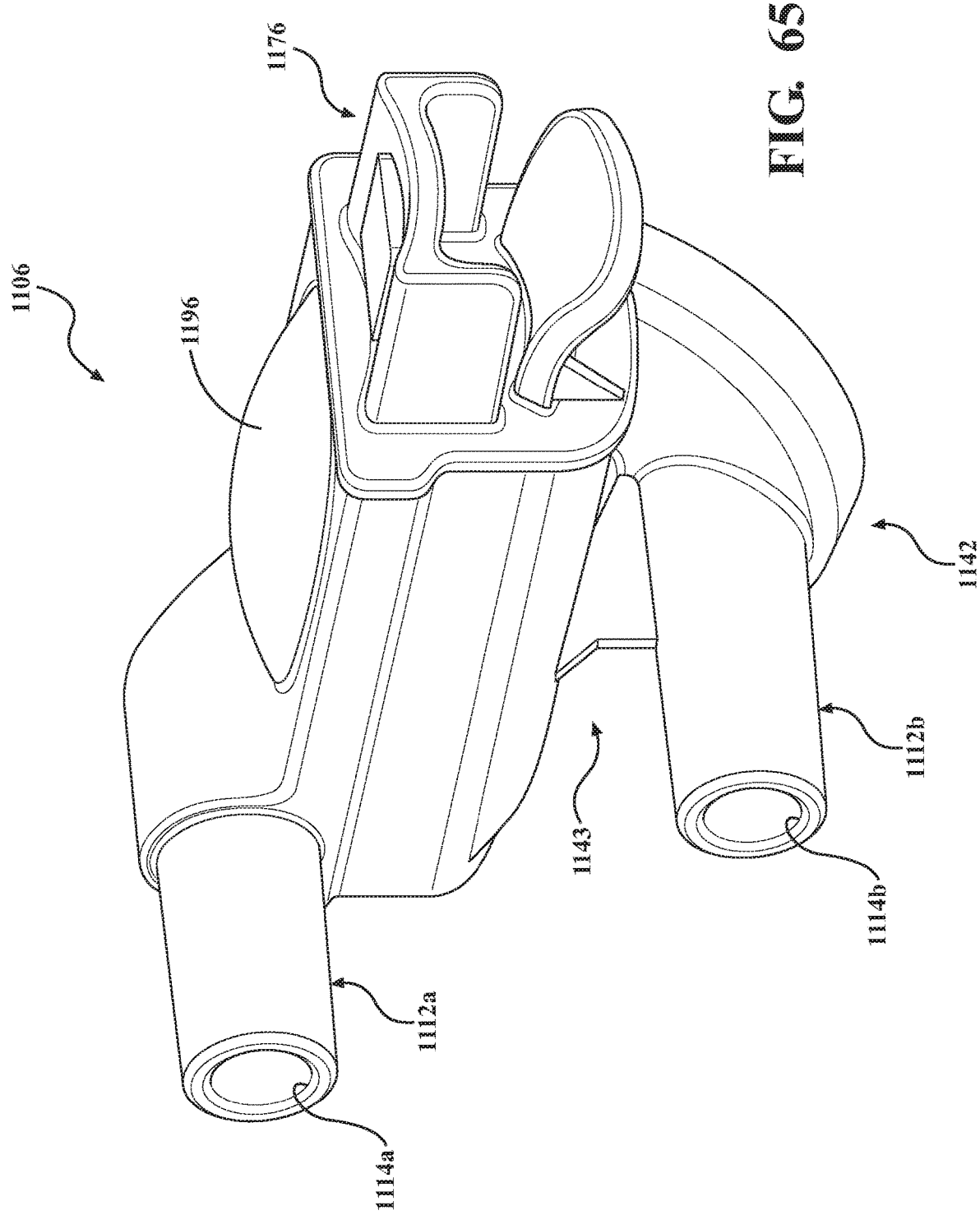
FIG. 65 is a perspective view of a cap portion of a manifold.
Figure 66:
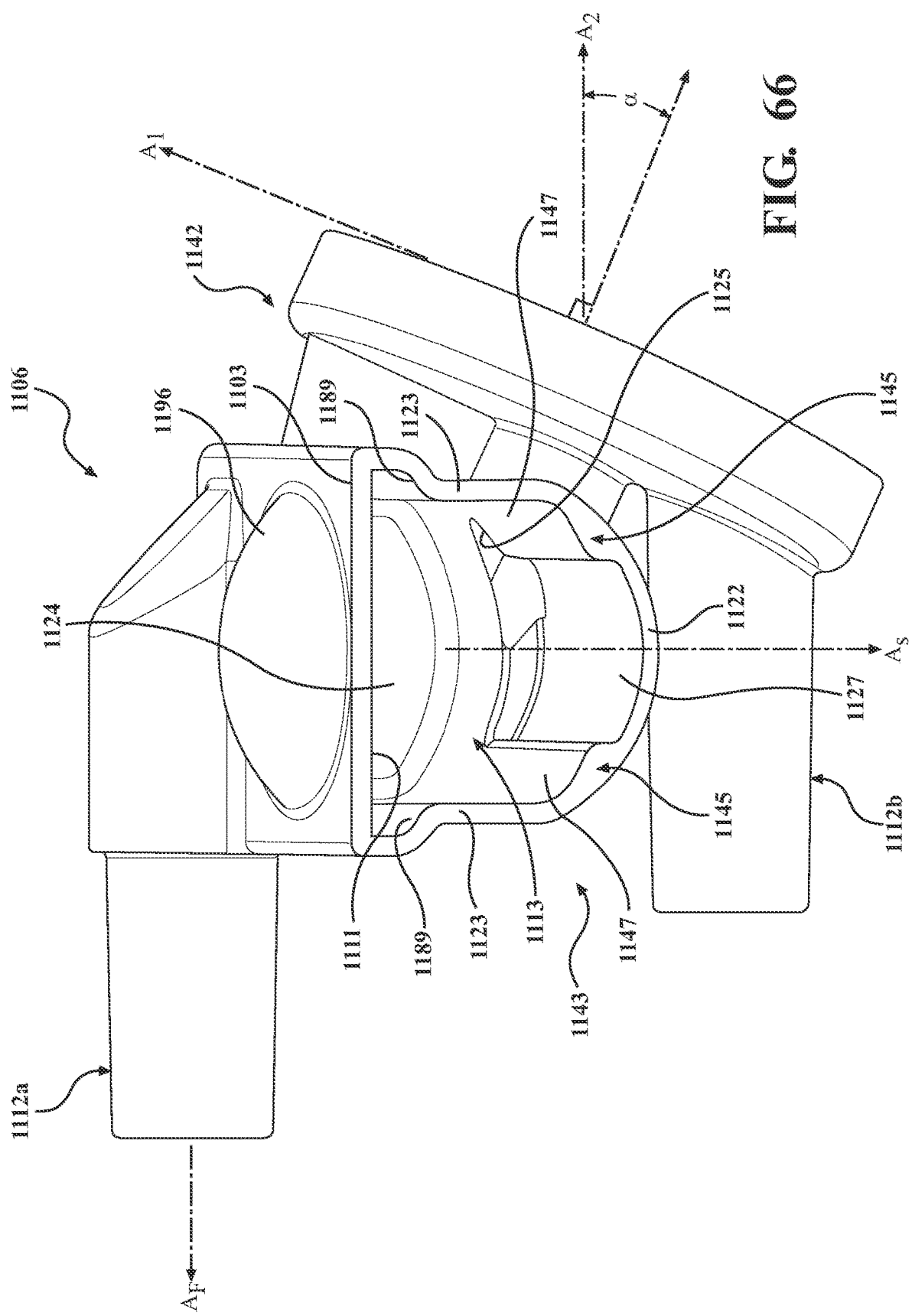
FIG. 66 is a side elevation view of the cap portion of FIG. 65 with the tray removed.
Figure 67:
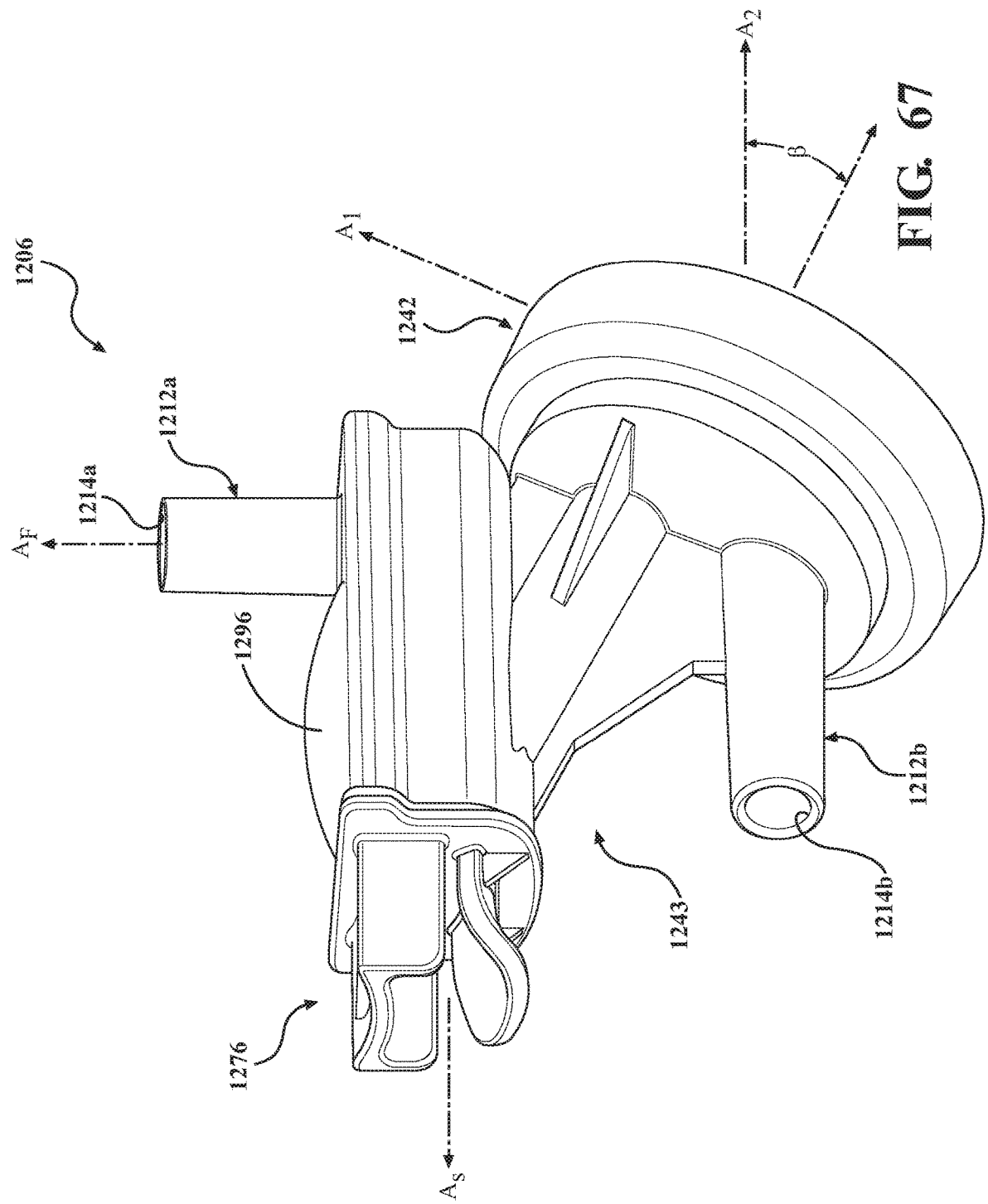
FIG. 67 is a perspective view of a cap portion of a manifold.
Figure 68:
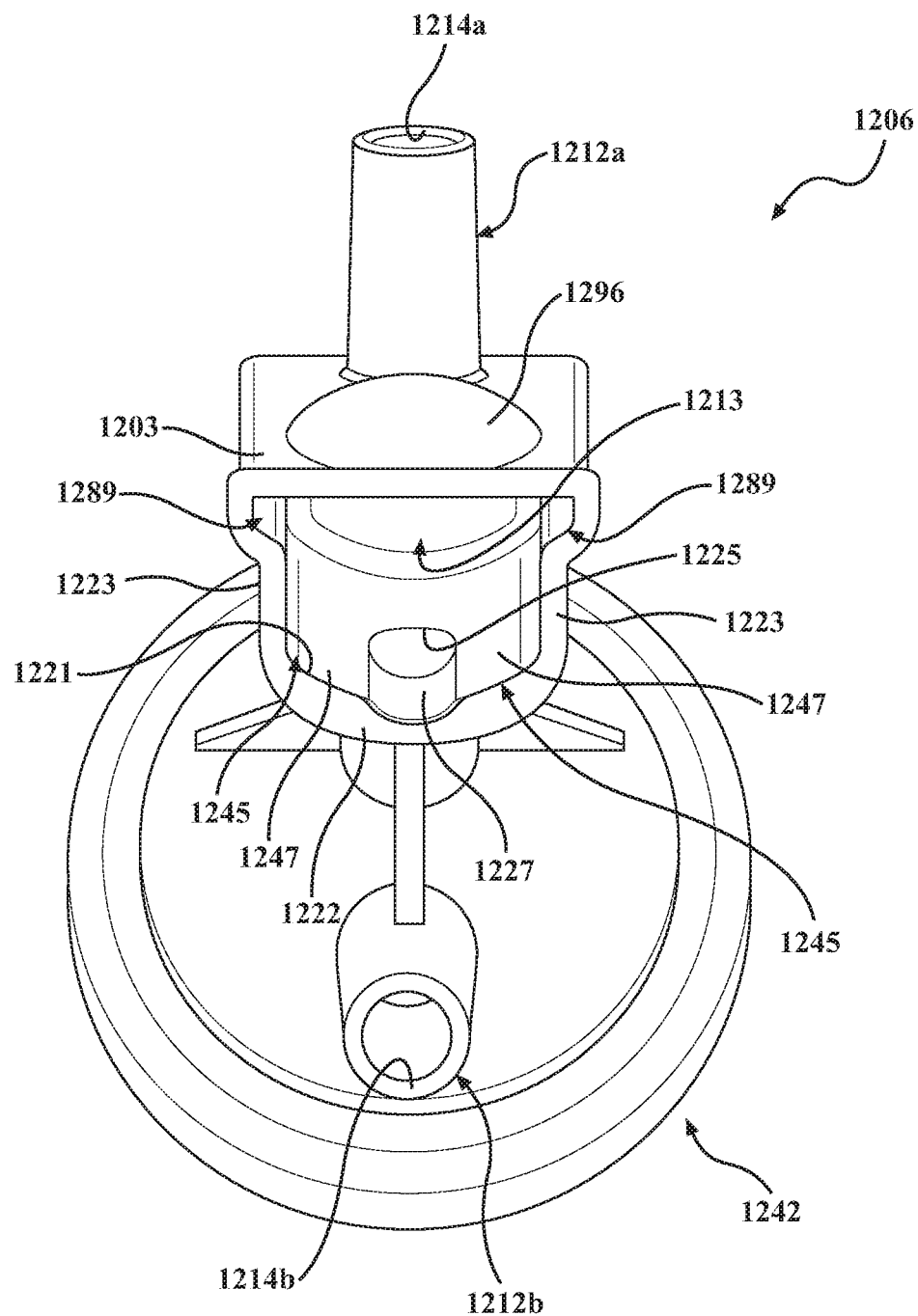
FIG. 68 is a side elevation view of the cap portion of FIG. 66 with the tray removed.

It is readily appreciated from FIGS. 65 and 66, the cap portion 1106 may be considered "side load," whereas the cap portion 1206 may be considered a "front load"; i.e., the tray 1176, 1276 is loaded from a front and a side of the manifold 1100, 1200, respectively. FIGS. 67 and 68 are side elevation views of the front load cap portion 1206. The cap portion 1106, 1206 include the cap faceplate 1140, 1240 and the cap head 1142, 1242 coupled to the cap faceplate 1140, 1240. As shown in FIGS. 66 and 67, the cap faceplate 1140, 1240 is oriented on a first axis ($A_1$). The cap head 1142, 1242 includes the upper barrier 1103, 1203 at least partially defining the accessory sleeve 1113, 1213, as previously described. The upper barrier 1103, 1203 is oriented on a second axis ($A_2$) angled relative to the first axis ($A_1$). As illustrated in FIGS. 62 and 63, a line perpendicular to the first axis ($A_1$) is at an angle, $\alpha, \beta$, relative to the second axis ($A_2$). The angle, $\alpha, \beta$ may be between approximately 10 and 45 degrees, more particularly between approximately 20 and 35 degrees, and even more particularly at approximately 25 degrees. Consequently, in constructions of the medical waste collection assembly 50 where the void 56 of the manifold receiver 54 is oriented at an angle, and in particular, the angle, $\alpha, \beta$, the orientation of the upper barrier 1103, 1203 relative to the cap faceplate 1140, 1240 (coupled to the body portion 1104, 1204 inserted within the void 156) results in the upper barrier 1103, 1203 being generally horizontal. Moreover, the accessory sleeve 1113, 1213 is similarly horizontal to facilitate ease of use for insertion and removal of the tray 1176, 1276 to and from the accessory sleeve 1113, 1213, respectively. Still further, the bore (not identified) extending between the accessory sleeve 1113, 1213 and the manifold volume is oriented at the angle, $\alpha, \beta$ relative to horizontal, which facilitates prevention of backflow of the waste material from the manifold volume to the accessory sleeve 1113, 1213. In other words, it is less likely the waste material overcome the forces of gravity to move from the manifold volume to the accessory sleeve 1113, 1213 through the inclined bore 1125, 1225.

The side load cap portion 1106 of FIG. 65 shows the first inlet fitting 1112a oriented on a fitting axis ($A_F$) in a proximal-to-distal direction. More specifically, the first inlet fitting 1112a extends distally from the upper barrier 1103 near a distal one of the side portions 1125 at least partially defining the accessory sleeve 1113. The first inlet fitting 1112a may define a distal end of the manifold 1100. The accessory sleeve 1113 may be defined on a sleeve axis ($A_S$) (considered into and out of FIG. 67). The sleeve axis ($A_S$) may be orthogonal to the fitting axis ($A_F$) such that the accessory sleeve 1113 is oriented in a side-to-side direction, hence the "side load" cap portion 1106. When viewing the cap portion 1106 from the front (see FIG. 65), the accessory opening 1111 may be positioned on a right-hand side and defines a lateral end of the manifold 1100. Such an arrangement may be more convenient for right-hand users approaching the manifold 1100 from the front. Of course, it is understood that an alternative configuration is contemplated in which the accessory opening 1111 is positioned on the left-hand side. The cap portion 1106 may further include the second inlet fitting 1112b coupled to the cap faceplate 1140 and defining a second inlet bore 1114b providing a bypass suction path from the second inlet bore 1114b to the manifold volume without passing through the accessory sleeve 1113.

The front load cap portion 1206 of FIGS. 67 and 68 shows the first inlet fitting 1212a oriented on a fitting axis ($A_F$) in a vertical direction. More specifically, the first inlet fitting 1212a extends upwardly from the upper barrier 1203 at least partially defining the accessory sleeve 1113. The accessory sleeve 1213 may be defined on a sleeve axis ($A_S$) with the accessory opening 1211 defining a distal end of the manifold 1200. The sleeve axis ($A_S$) may be perpendicular to the fitting axis ($A_F$) such that the accessory sleeve 1213 is oriented in a proximal-to-distal direction, hence the "front load" cap portion 1206. The cap portion 1206 may further include the second inlet fitting 1212b coupled to the cap faceplate 1240 and defining a second inlet bore 1214b providing a bypass suction path from the second inlet bore 1214b to the manifold volume without passing through the accessory sleeve 1213.

Complementary to the orientation of the upper barrier 1103, 1203 relative to the cap faceplate 1140, 1240 resulting in the upper barrier 1103, 1203 being generally horizontal during operation is the presence of the lens 1196, 1296. As mentioned, it is desirable to visualize the tissue collecting cavity 1182, 1282 during collection of the tissue sample. The quick visual confirmation afforded to the user once the tissue sample is within the tissue collecting cavity 1182, 1382 permits the user to move onto any other aspects of the surgical procedure. The manifold 1100, 1200 accommodates visualization for an improved tissue collection experience for the user. The tissue collecting cavity 1182, 1282 of the tray 1176, 1276 opens towards the upper barrier 1103, 1203, when the tray 1176, 1276 is within the accessory sleeve 1113, 1213. The lens 1196, 1296 is disposed on the upper barrier 1103, 1203 for providing magnification within the tissue collecting cavity 1182, 1282, as shown in FIGS. 53-63. The lens 1196, 1296 is oval-shaped, but other suitable geometries are contemplated. The lens 1196, 1296 may be shaped to maximize visualization of the tissue collecting cavity 1182, 1282 and to provide magnification to the same. As a result, the user to glance at the manifold 1100, 1200 from a reasonable distance and without undue maneuvering about the manifold 1100, 1200 to quickly ascertain whether a suitable tissue sample has been captured. It is contemplated that lighting may be provided to illuminate the tissue collecting cavity 1182, 1282.

Figure 69:
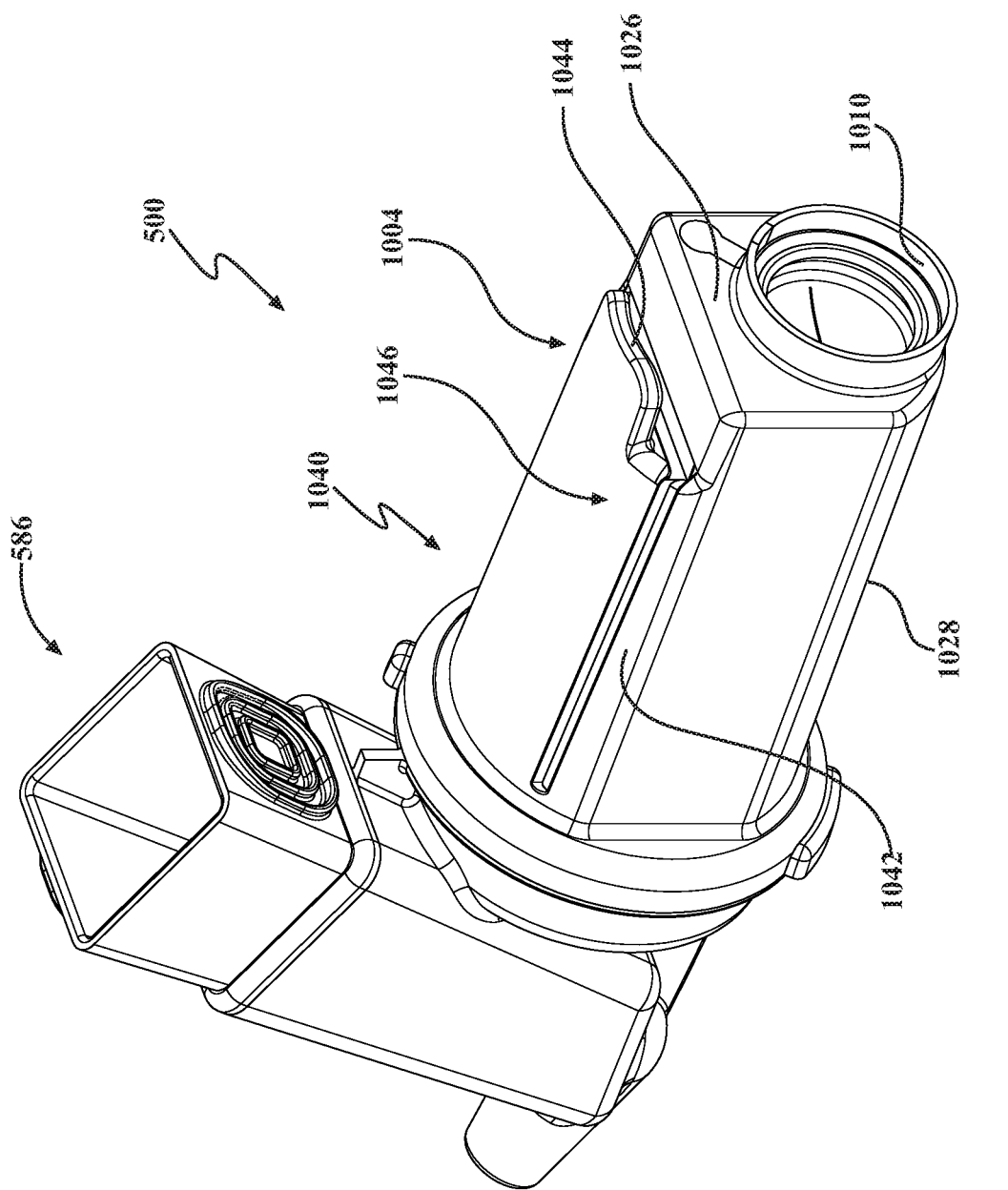
FIG. 69 is a rear perspective view of a manifold including an access feature to be permanently mutilated to provide access to a filter element within the manifold.
Figure 70:
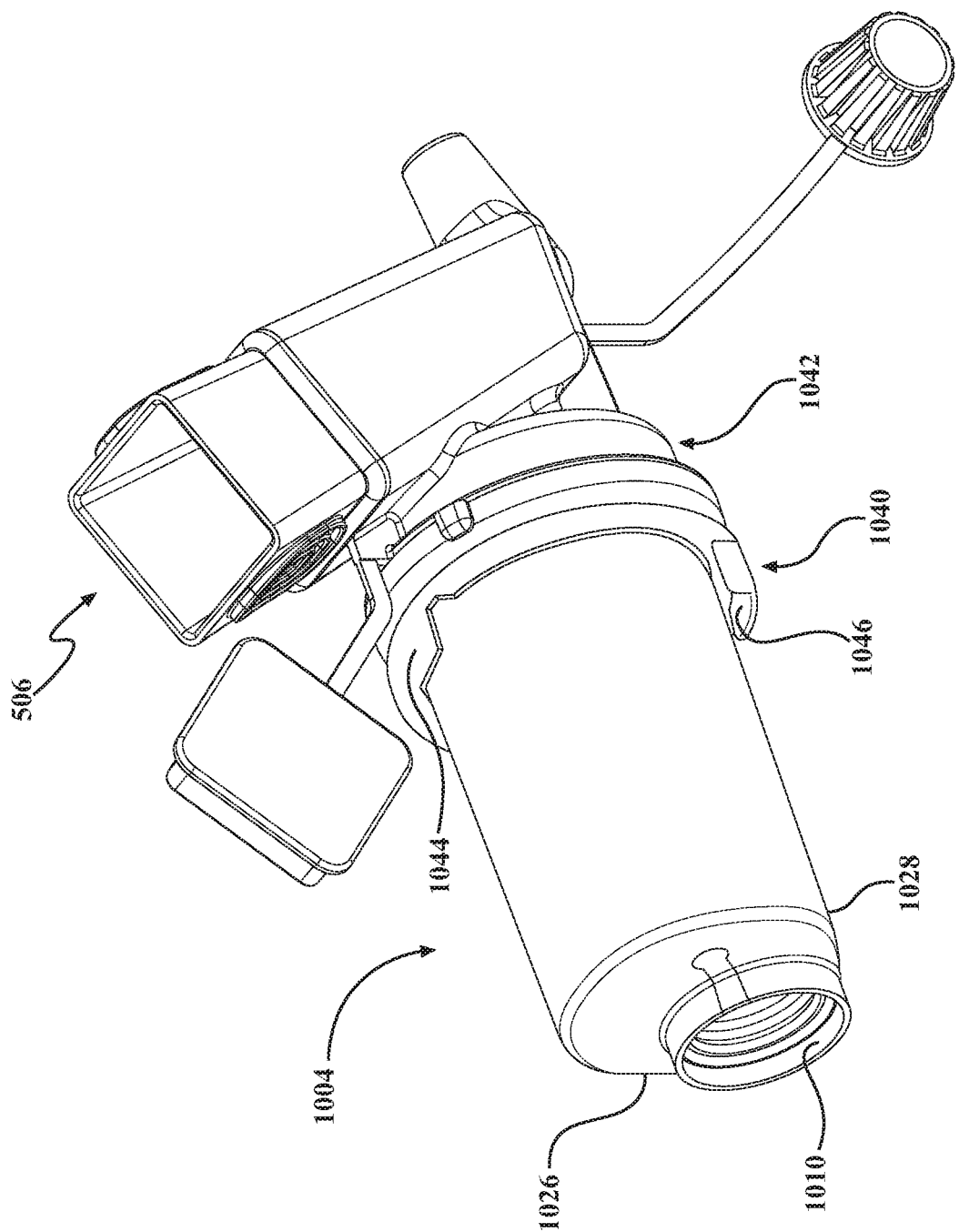
FIG. 70 is a rear perspective view of a manifold including an access feature to be permanently mutilated to provide access to a filter element within the manifold.
Figure 71:
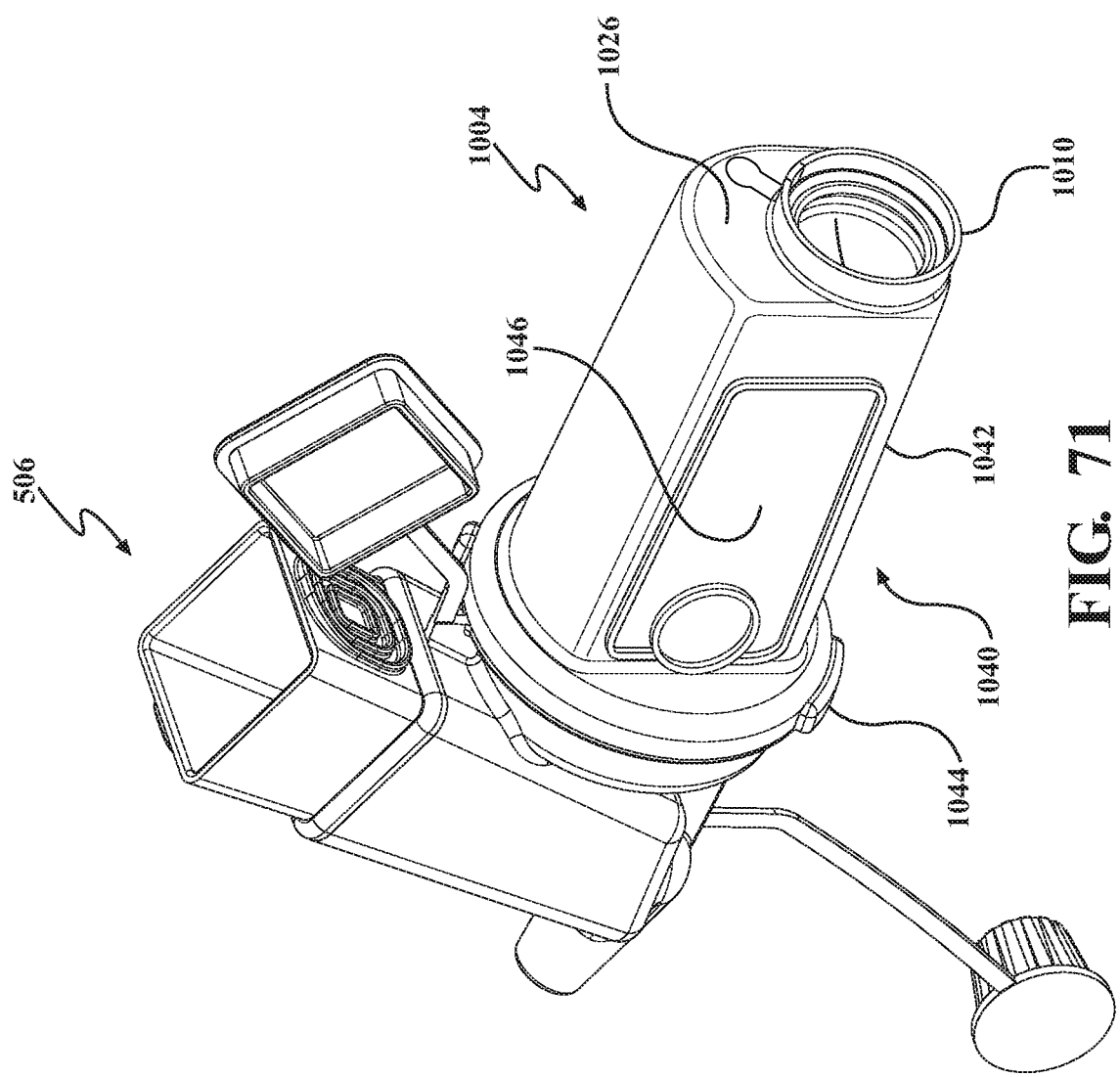
FIG. 71 is a rear perspective view of a manifold including an access feature to be permanently mutilated to provide access to a filter element within the manifold.

As mentioned and as previously described, the stream is filtered through the filter element 216-716 of the manifold 100-900, 1100, 1200 regardless of whether the tissue sample is being collected with, for example, the tray 176-676, 876, 976, 1176, 1276. For any number of reasons it may be desirable to access the filter element 216-716. In one example, the manifold 100-900, 1100, 1200 was advertently operating in "bypass mode" when the desired tissue sample was aspirated from the patient. Referring now to FIGS. 69-71, FIG. 69 shows one of implementation of the manifold 500 previously described. FIGS. 70 and 71 show the cap portion 506 of the manifold 500. Each of the manifolds of FIGS. 69-71 include an access feature 1040 to enable access to the filter element 1016 within the body portion 1004. In manners to be described, access features 1040 are configured to receive an input of the user to permanently mutilate the manifold, thereby providing access to the filter element 1016. It is to be understood that the access features 1040 may be included on any of the implementations of the manifold 100-900, 1100, 1200 as well as compatible manifolds not described herein.

Figure 72:
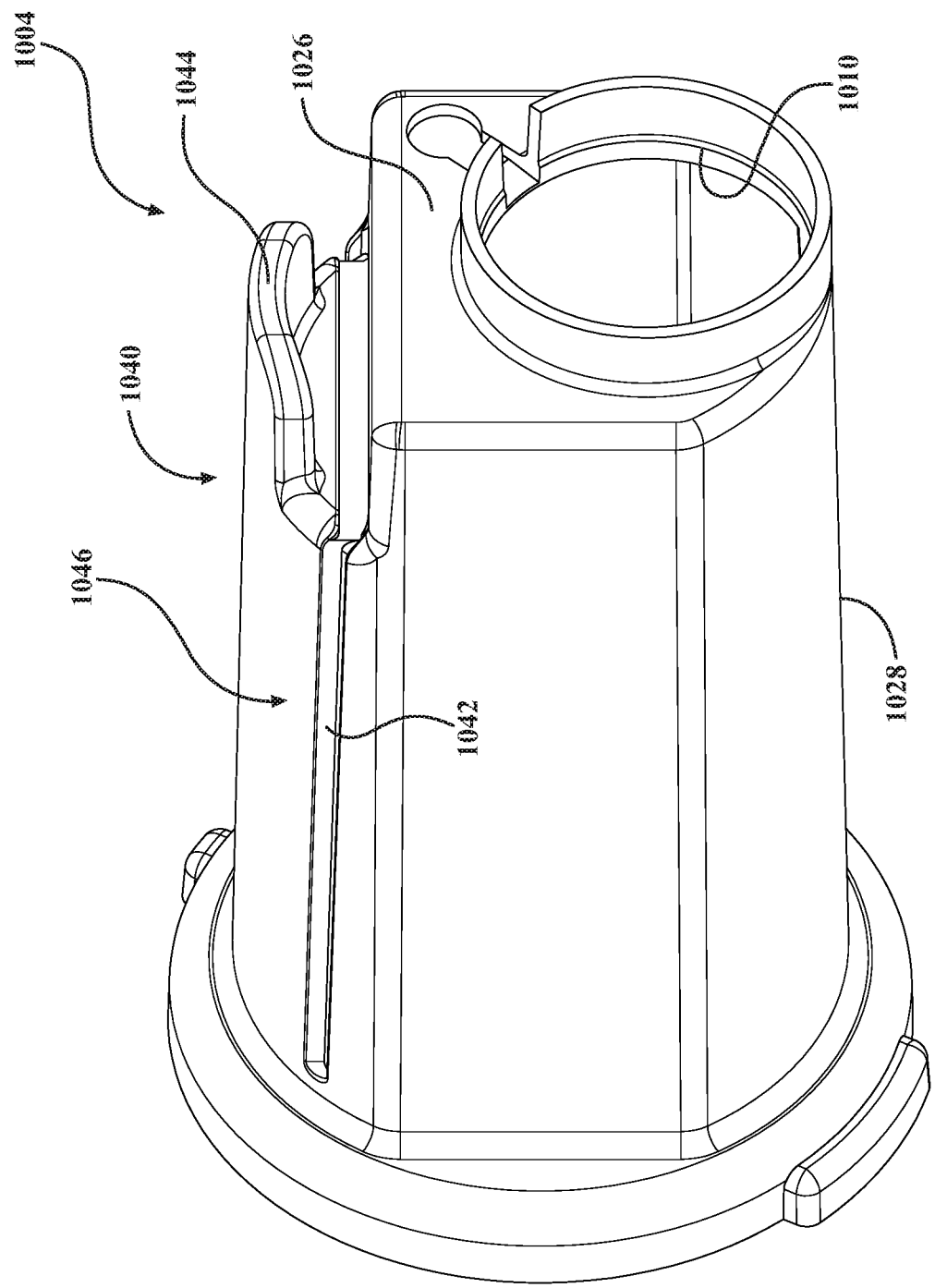
FIG. 72 is a rear perspective view of the body portion of FIG. 69.

With reference to FIG. 72, the body portion 1004 includes the proximal base 1026 and at least one side 1028 extending from the proximal base 1026. The outlet opening 1010 is defined within the proximal base 1026. The access feature 1040 may include a frangible boundary 942. The frangible boundary 942 of the version of the access feature 1040 illustrated in FIG. 67 includes thinned material disposed at an interface between lateral and top portions of the side 1028 to define at least partially detachable portion 1046 of the side 1026. The access feature 1040 further includes a grip 1044. FIG. 72 shows the grip 1044 including a tab-like structure defining a gap sized to receive at least one finger of the user. The user pinches the grip 1044, for example, and peels the portion 1046 of the side 1026 such that the frangible boundary 942 ruptures. The portion 1046 is peeled to expose the filter element 1016 within the body portion 1004.

FIG. 73 shows the filter element 1016 that is well suited for use with the access feature 1040 previously described. The filter element 1016 includes at least one sidewall 1022 extending from the base wall 1020 to form a basket defining a cavity 1025. FIG. 73 shows opposing sidewalls 1022 separated by a top wall 1023 and a bottom wall 1025. The sidewalls 1022 may define the porous features 1018, and in other versions the base wall 1020 may also define the porous features 1018. The filter element 1016 defines a window 1050 extending through at least one of the sidewalls 1022. FIG. 73 shows the window 1050 consuming nearly an entirely of the top wall 1023. The window 1050 is aligned with the access feature 1040, and more particularly the detachable portion 1046, when the filter element 1016 is disposed within the body portion 1004. Consequently, subsequent to permanently mutilating the access feature 1040, for example peeling the portion 1046 to expose the filter element 1016, the window 1050 is sized to permit retrieval of the tissue sample from within the filter element 1016. In one example, forceps may be directed within the cavity 1025 of the filter element 1016 through the window 1050 to retrieve the tissue sample without requiring removal of the filter element 1016 from the body portion 1004.

Referring now to FIG. 70, another version of the access feature 1040 is shown. The access feature 1040 includes the frangible boundary 1042 that is the at least partially detachable portion 1046, illustrated as a ring, coupled to the grip 1044. The user pinches the grip 1044, for example, and peels the removable ring 1044 about a circumference of the body portion 1004 to rupture an interface between the cap portion 1006 and the body portion 1004. The cap portion 506 decouples from the body portion 1004, thereby exposing the mouth 1024 of the filter element 1016 in communication with the cavity 1025. In one example, forceps may be directed within the cavity 1025 of the filter element 1016 through the mouth 1024 to retrieve the tissue sample without requiring removal of the filter element 1016 from the body portion 1004.

FIG. 71 shows still another version of the access feature 1040. The access feature 1040 of FIG. 71 includes a closed perimeter of the frangible boundary 1024 to define the detachable portion 1046. The closed perimeter may be entirely within one of the sidewalls 1028 of the body portion 1004. The access feature 1040 includes the grip 1044 coupled to the detachable portion 1026, for example, the ring. The user manipulates the grip 1044 and peels the portion 1046 of the side 1026 such that the frangible boundary 942 ruptures. The closed perimeter of the frangible boundary 1024 may provide for complete removal of the detachable portion 1026. A filter element similar to that of FIG. 73 may be provided with the window 1050 aligned with the closed perimeter disposed within the sidewall 1028. It should be appreciated that the access features, both those discussed above and otherwise, may be on at least one of the body portion 1004, as shown in FIGS. 69-71, and the cap portion 106.

Exemplary Clauses

Clause 1—A manifold for collecting a tissue sample with a medical waste collection assembly including a manifold receiver and a suction inlet, the manifold including: an inlet fitting adapted to receive a suction line and defining an inlet bore; a housing adapted to be removably engaged with the manifold receiver and defining a manifold volume and an outlet opening adapted to be in fluid communication with the suction inlet of the medical waste collection assembly when the housing is engaged with the manifold receiver to provide a suction path from the inlet bore to the suction inlet through the manifold volume; a filter element disposed within the housing in the suction path; and a flow director defining a tissue collecting cavity and porous features within the tissue collecting cavity and a bypass channel separate from the tissue collecting cavity, and including a control surface adapted to receive an input from a user to move the flow director between a tissue collection position in which the tissue collecting cavity is in fluid communication with the inlet bore such that the porous features are in the suction path and the bypass channel is out of the suction path, and a bypass position in which the bypass channel is in fluid communication with the inlet bore in the suction path and the tissue collecting cavity is out of the suction path.

Clause 2—A manifold for collecting a tissue sample with a medical waste collection assembly including a manifold receiver and a suction inlet, the manifold including: a housing adapted to be removably engaged with the manifold receiver and defining a manifold volume with the housing including an inlet fitting defining an inlet bore and adapted to receive a suction line, and defining an outlet opening adapted to be in fluid communication with the suction inlet of the medical waste collection assembly when the housing is engaged with the manifold receiver to provide a suction path from the inlet bore to the suction inlet through the manifold volume; a filter element disposed within the housing in the suction path; and a tray rotatably coupled to the housing and defining a plurality of tissue collecting cavities and porous features within each of the tissue collecting cavities, and including a control surface adapted to receive an input from a user to rotate the tray about an axis to selectively align one of the tissue collecting cavities with the inlet bore such that the porous features are in the suction path to collect the tissue sample.

Clause 3—The manifold of clause 2, wherein the tray further defines a bypass channel separate from the tissue collecting cavities with the tray further adapted to be rotated about the axis to selectively align the bypass channel with the inlet bore such that fluid is permitted to flow through the suction path without the tray collecting the tissue sample.

Clause 4—The manifold of clause 3, wherein the bypass channel includes a plurality of bypass channels, wherein the tissue collecting cavities and the bypass channels are arranged in an alternating manner angularly about the axis.

Clause 5—The manifold of clause 4, wherein the tissue collecting cavities and the bypass channels are angularly spaced equally about the axis.

Clause 6—The manifold of clause 2, wherein the tray further includes a plurality of lenses circumferentially arranged about the control surface with each of the lenses aligned with one of the tissue collecting cavities and each shaped to provide magnification within one of the tissue collecting cavities.

Clause 7—The manifold of clause 2, wherein the housing further includes a lens positioned to provide magnification within one of the tissue collecting cavities.

Clause 8—The manifold of clause 2, wherein the housing further includes a cap portion, and a body portion coupled to the cap portion with the cap portion with the tray positioned proximal to a faceplate of the cap portion.

Clause 9—The manifold of clause 8, wherein one of the cap portion and the body portion includes an orientation feature adapted to rotatably fix the cap portion relative to the body portion.

Clause 10—The manifold of clause 8, wherein the cap portion includes an opening with the control surface arranged to be manipulated through the opening.

Clause 11—The manifold of clause 2, further including a carrier defining a void space sized to removably receive the tray with the carrier removably coupled to the housing.

Clause 12—The manifold of clause 2, wherein the housing further includes a bypass inlet fitting adapted to removably receive the suction line with the bypass inlet fitting defining a fluid channel bypassing the tray without being in fluid communication with the tissue collecting cavities.

Clause 13—The manifold of clause 1, wherein the housing further including a cap portion including the inlet fitting, and a body portion coupled to the cap portion.

Clause 14—A manifold for collecting a tissue sample with a medical waste collection assembly including a manifold receiver and a suction inlet, the manifold including: a cap portion including a cap faceplate, and an inlet fitting adapted to receive a suction line and defining an inlet bore; a body portion coupled to cap portion and being rotatably fixed relative to the cap portion to collectively define a manifold volume with the body portion adapted to be removably engaged with the manifold receiver and defining an outlet opening adapted to be in fluid communication with the suction inlet of the medical waste collection assembly when the body portion is engaged with the manifold receiver to provide a suction path from the inlet bore to the suction inlet through the manifold volume; a filter element at least partially disposed within the body portion in the suction path; and a tray disposed proximal to the cap faceplate of the cap portion and defining a plurality of tissue collecting cavities and porous features with each of the tissue collecting cavities, and a bypass channel separate from the tissue collecting cavities, wherein the manifold is adapted to be operated in a tissue collection position in which one of the tissue collecting cavities is in fluid communication with the inlet bore such that the porous features are in the suction path to collect the tissue sample, and a bypass position in which the bypass channel is in fluid communication with the inlet bore in the suction path such that fluid is permitted to flow through the suction path without the tray collecting the tissue sample.

Clause 15—The manifold of clause 14, wherein the tray is rotatably coupled to the housing and adapted to receive an input from a user to rotate about an axis relative to the cap portion and the body portion to selectively switch the manifold between the tissue collection position and the bypass position.

Clause 16—The manifold of clause 14, wherein the cap portion is removably coupled to the tray to provide access to the tissue collecting cavities.

Clause 17—A manifold for collecting a tissue sample with a medical waste collection assembly including a manifold receiver and a suction inlet with the manifold including a front and a rear, the manifold including: a housing defining a manifold volume, including an inlet fitting on the front of the housing and defining an inlet bore in fluid communication with the manifold volume with the inlet fitting adapted to removably receive a suction line, and further defining an outlet opening on the rear of the housing adapted to be in fluid communication with the suction inlet of the medical waste collection assembly when the housing is engaged with the manifold receiver to provide a suction path from the inlet bore to the suction inlet through the manifold volume; a filter element disposed within the housing in the suction path; the housing further defining an accessory sleeve in fluid communication with the manifold volume with the accessory sleeve oriented on an axis angled away from a longitudinal axis of the housing; and a tray adapted to be removably positioned within the accessory sleeve and defining a tissue collecting cavity and porous features within the tissue collecting cavity with the tissue collecting cavity opening towards the front of the manifold when the tray is within the accessory sleeve such that the porous features are in the suction path to collect the tissue sample.

Clause 18—The manifold of clause 17, wherein the housing further includes a distal barrier at least partially defining the accessory sleeve with the distal barrier including a lens adapted to provide magnification within the tissue collecting cavity when the tray is within the accessory sleeve.

Clause 19—The manifold of clause 17, wherein the tray further includes a control surface adapted to receive an input from a user, and a sealing surface adapted to be in sealing engagement with the housing when the tray is within the accessory sleeve.

Clause 20—The manifold of clause 17, wherein the accessory sleeve is oriented on an axis angled proximally away from the front of the housing.

Clause 21—The manifold of clause 17, wherein the inlet bore is oriented on an axis angled distally upward relative to the longitudinal axis of the housing.

Clause 22—The manifold of clause 17, further including a valve coupled to the housing and positioned within the accessory sleeve.

Clause 23—The manifold of clause 17, wherein the tray further includes a retention feature adapted to defeatably engage a complementary retention feature of the housing to facilitate retention of the tray within the accessory sleeve.

Clause 24—The manifold of clause 17, wherein the housing further includes a body portion with the filter element at least partially disposed within the body portion, a cap portion coupled to the body portion and including the inlet fitting, and an access feature adapted to receive an input of a user to permanently mutilate the manifold to access the filter element within the body portion.

Clause 25—The manifold of clause 24, wherein the access feature further includes a frangible boundary, and a grip coupled to the frangible boundary and adapted to receive the input of the user to rupture the frangible boundary to access to the filter element within the body portion.

Clause 26—The manifold of clause 25, wherein the filter element includes at least one sidewall extending from a base wall, porous features extending through the sidewall, and a window extending through the sidewall, aligned with the access feature, and sized to permit retrieval of the tissue sample from within the filter element subsequent to permanently mutilating the manifold to access the filter element.

Clause 27—A manifold for collecting a tissue sample with a medical waste collection assembly including a manifold receiver and a suction inlet with the manifold including a front and a rear, the manifold including: a housing defining a manifold volume, including an inlet fitting on the front of the housing and defining an inlet bore in fluid communication with the manifold volume with the inlet fitting adapted to removably receive a suction line, and further defining an outlet opening on the rear of the housing adapted to be in fluid communication with the suction inlet of the medical waste collection assembly when the housing is engaged with the manifold receiver to provide a suction path from the inlet bore to the suction inlet through the manifold volume; a filter element disposed within the housing in the suction path; the housing further including a distal barrier defining an accessory sleeve in fluid communication with the manifold volume; a tray defining a tissue collecting cavity and porous features within the tissue collecting cavity with the tray adapted to be removably disposed within the accessory sleeve; and the distal barrier including a lens shaped to provide magnification within the tissue collecting cavity when the tray is disposed within the accessory sleeve such that the porous features are in the suction path to collect the tissue sample.

Clause 28—The manifold of clause 27, wherein the accessory sleeve further includes orientation features adapted to engage complementary orientation features of the tray to position the tray within the accessory sleeve in a predetermined orientation relative to the distal barrier.

Clause 29—A manifold for collecting a tissue sample with a medical waste collection assembly including a manifold receiver and a suction inlet, the manifold including: a cap portion including an inlet fitting adapted to receive a suction line; a body portion coupled to cap portion to collectively define a manifold volume with the body portion adapted to be removably engaged with the manifold receiver, and further defining an outlet opening adapted to be in fluid communication with the suction inlet of the medical waste collection assembly when the body portion is engaged with the manifold receiver to provide a suction path from the inlet fitting to the suction inlet through the manifold volume; and a filter element at least partially disposed within the body portion in the suction path, wherein at least one of the body portion and the cap portion including an access feature adapted to receive an input of a user to permanently mutilate the manifold to enable access to the filter element.

Clause 30—The manifold of clause 29, wherein the access feature further includes a frangible boundary, and a grip coupled to the frangible boundary and adapted to receive an input of the user to rupture the frangible boundary.

Clause 31—The manifold of clause 30, wherein the frangible boundary is a removable ring coupled to one of the body portion and the cap portion and adapted to rupture an interface between the cap portion and the body portion.

Clause 32—The manifold of clause 30, wherein the frangible boundary further includes a closed perimeter within the body portion and formed from thinned material such that the frangible boundary ruptures along the closed perimeter.

Clause 33—The manifold of clause 29, wherein the filter element at least one sidewall extending from a base wall, porous features extending through at least one sidewall, and a window extending through the sidewall, aligned with the access feature, and sized to permit retrieval of the tissue sample from within the filter element subsequent to permanently mutilating the manifold to access the filter element.

Clause 34—The manifold of clause 29, further including a tray adapted to be removably coupled to the manifold and defining a tissue collecting cavity and porous features within the tissue collecting cavity and adapted to collect the tissue sample when the tray is positioned within the suction path.

Clause 35—A manifold for collecting a tissue sample with a medical waste collection assembly including a manifold receiver and a suction inlet, the manifold including: a housing adapted to be removably engaged with the manifold receiver with the housing defining a manifold volume, an outlet opening adapted to be in fluid communication with the suction inlet of the medical waste collection assembly when the housing is engaged within the manifold receiver, and a bypass channel, wherein the housing including a support frame defining an accessory sleeve separate from the bypass channel; a filter element disposed within the housing; a tray defining a tissue collection cavity and porous features within the tissue collection cavity with the tray sized to be removably disposed within the accessory sleeve of the support frame; and a slide member slidably coupled to the support frame and including an inlet fitting defining an inlet bore and adapted to removably receive a suction line with the slide member including a control surface adapted to receive an input from a user to move the slide member between a tissue collection position in which the inlet bore of the inlet fitting is in fluid communication with the tissue collecting cavity when the tray is disposed within the accessory sleeve such that the porous features are in the suction path to collect the tissue sample, and a bypass position in which the inlet bore of the inlet fitting is in fluid communication such that fluid is permitted to flow through the suction path without the tray collecting the tissue sample.

Clause 36—The manifold of clause 35, wherein the slide member further includes a lens shaped to provide magnification within the tissue collection cavity of the tray when the tray is disposed within the accessory sleeve and the slide member is in the tissue collection position.

Clause 37—The manifold of clause 35, wherein the support frame further includes opposing sides separated by a front side with the accessory sleeve extending inwardly from one of the opposing sides, and the bypass channel extending inwardly from the front side.

Clause 38—The manifold of clause 35, wherein the slide member further includes track features adapted to engage complementary track features of the support frame to limit movement of the slide member relative to the support frame to one degree of freedom.

Clause 39—The manifold of clause 35, wherein the tray further includes a front wall opposite a rear wall and separated by opposing sidewalls, and a base including the porous features with the front wall including a cutout adapted to be aligned with the inlet bore of the inlet fitting when the slide member is in the tissue collection position.

Clause 40—The manifold of clause 39, wherein the base of the tray further includes an inclined surface inclined upwardly towards the rear wall.

Clause 41—A method for collecting a tissue sample with a manifold for a medical waste collection assembly with the manifold including a housing defining a manifold volume, an outlet opening, and a support frame defining an accessory sleeve and a bypass channel separate from the accessory sleeve, the manifold further including a filter element disposed within the housing, a slide member slidably coupled to the support frame and including an inlet fitting defining an inlet bore, and a tray positionable within the tissue collecting cavity and defining a tissue collecting cavity and porous features within the tissue collecting cavity, the method including the steps of: coupling the manifold to the medical waste collection assembly such that the outlet opening is in fluid communication with a suction inlet of the medical waste collection assembly; coupling a suction line to the inlet fitting; operating the medical waste collection assembly with the slide member in a bypass position in which the inlet bore of the inlet fitting is in fluid communication with the bypass channel such that fluid is permitted to flow through the suction path without the tray collecting the tissue sample; applying an input to the control surface to move the slide member from the bypass position to a tissue collecting position in which the inlet bore of the inlet fitting is in fluid communication with the tissue collecting cavity such that the porous features are in the suction path; and operating the medical waste collection assembly with the slide member in the tissue collection position to collect the tissue sample.

Clause 42—The method of clause 41, further including applying another input to the control surface to return the slide member to the bypass position.

Clause 43—The method of clause 41, wherein the slide member further includes a lens shaped to provide magnification, the method further including viewing the tissue collecting cavity through the lens when the slide member is in the tissue collection position.

Clause 44—The method of clause 41, further including removing the tray from the accessory sleeve with the slide member in the bypass position.

Clause 45—The method of clause 44, further including replacing another tray within the accessory sleeve of the slide member with the slide member in the bypass position.

Clause 46—The method of clause 41, wherein the step of applying the input to the control surface to move the slide member to the tissue collection position further includes applying a lateral force to the control surface in a first linear direction.

Clause 47—The method of clause 45, further including applying another lateral force to the control surface in a second linear direction opposite the first linear direction to return the slide member to the bypass position.

Clause 48—A manifold for collecting a tissue sample with a medical waste collection assembly including a manifold receiver and a suction inlet, the manifold including: a housing adapted to be removably engaged with the manifold receiver and defining a manifold volume with the housing including a stator, including an inlet fitting adapted to receive a suction line and defining an inlet bore, and the housing defining an outlet opening adapted to be in fluid communication with the suction inlet of the medical waste collection assembly when the housing is engaged with the manifold receiver to provide a suction path from the inlet bore to the suction inlet through the manifold volume; a filter element disposed within the housing in the suction path; and a rotor rotatably disposed within the stator and defining a tissue collecting cavity and porous features within the tissue collecting cavity, and including a control surface adapted to receive an input from a user to rotate the rotor within the stator to selectively establish fluid communication between the inlet bore and the tissue collecting cavity such that the porous features are in the suction path to collect the tissue sample.

Clause 49—The manifold of clause 48, wherein the rotor further defines a bypass channel separate from the tissue collecting cavity with the control surface further adapted to receive the input from the user to rotate the rotor within the stator to selectively establish fluid communication between the inlet bore and the bypass channel such that fluid is permitted to flow through the suction path without collection of the tissue sample.

Clause 50—The manifold of clause 48, wherein the stator further includes a sidewall defining a window positioned such that, when the bypass channel of the rotor is in the suction path, the tissue collecting cavity is aligned with the window.

Clause 51—The manifold of clause 50, wherein the sidewall of the stator further includes a lens shaped to provide magnification and positioned to be aligned with the lens when the tissue collecting cavity is in the suction path.

Clause 52—The manifold of clause 48, wherein the rotor further includes a cylindrical outer wall with the tissue collecting cavity and the bypass channel each defined between two openings within the outer wall.

Clause 53—A manifold for collecting a tissue sample with a medical waste collection assembly including a manifold receiver and a suction inlet, the manifold including: a housing adapted to be removably engaged with the manifold receiver and defining a manifold volume with the housing including a stator, an inlet fitting adapted to receive a suction line and defining an inlet bore extending through the stator, and with the housing defining an outlet opening adapted be in fluid communication with the suction inlet of the medical waste collection assembly when the housing is engaged with the manifold receiver; and a rotor rotatably disposed within the stator and defining a tissue collecting cavity and porous features within the tissue collecting cavity adapted to collect the tissue sample, and a bypass channel separate from the tissue collecting cavity, wherein the manifold is adapted to be operated in one of a tissue collection position in which the tissue collecting cavity is in fluid communication with the inlet bore such the porous features are in the suction path to collect the tissue sample, and a bypass position in which the bypass channel is in fluid communication with the inlet bore such that fluid is permitted to flow through the suction path without collection of the tissue sample.

Clause 54—The manifold of clause 53, wherein the rotor includes an outer wall with the tissue collecting cavity and the bypass channel each defined between two openings within the sidewall.

Clause 55—The manifold of clause 53, wherein the rotor further includes a control surface adapted to receive an input from a user to switch the manifold to be operated between the tissue collection position and the bypass position.

Clause 56—The manifold of clause 53, wherein the stator further includes a sidewall defining a window positioned to be aligned with and expose the tissue collecting cavity when the manifold is operated in the bypass position so as to permit retrieval of the tissue sample.

Clause 57—The manifold of clause 53, wherein the stator further includes a lens shaped to provide magnification and positioned to be aligned with the tissue collecting cavity when the manifold is operated in the tissue collection position.

Clause 58—A method for collecting a tissue sample with a manifold for a medical waste collection assembly with the manifold including a housing defining a manifold volume, an outlet opening, and a stator and an inlet fitting, the manifold further including a filter element disposed within the housing, and a rotor rotatably disposed within the stator and including a control surface, the method including the steps of: coupling the housing to the medical waste collection assembly such that the outlet opening is in fluid communication with a suction inlet of the medical waste collection assembly; coupling a suction line to the inlet fitting to provide a suction path from an inlet bore of the inlet fitting to the suction inlet; operating the medical waste collection assembly with the manifold in a bypass position in which a bypass channel defined within the rotor is in the suction path and a tissue collecting cavity defined within of the rotor is not in the suction path; actuating the control surface to rotate the rotor within the stator from the bypass position to a tissue collection position in which the tissue collecting cavity is in the suction path and the bypass channel is removed from the suction path; and operating the medical waste collection assembly with the manifold in the tissue collection position to collect the tissue sample with porous features of the tissue collecting cavity.

Clause 59—The method of clause 58, further including actuating the control surface to return the rotor to the bypass position after collection of the tissue sample.

Clause 60—The method of clause 59, further including retrieving the tissue sample from the tissue collecting cavity while the rotor is in the bypass position.

Clause 61—The method of clause 59, wherein the stator includes a sidewall defining a window, wherein the step of actuating the control surface to return the rotor to the bypass position further includes aligning the tissue collecting cavity with the window of the stator, thereby exposing the tissue collecting cavity; and retrieving the tissue sample from the exposed tissue collecting cavity through the window of the stator.

Clause 62—The method of clause 58, wherein the stator further includes a lens shaped to provide magnification, the method further including viewing the tissue collecting cavity through the lens when the rotor is in the tissue collection position.

Clause 63—The method of clause 60, wherein the step of retrieving the tissue sample from the tissue collecting cavity further includes scraping the porous features with an instrument to dislodge the tissue sample.

Clause 64—The method of clause 59, wherein the step of actuating the control surface to move the rotor from the bypass position to the tissue collection position further includes rotating the control surface in a first rotational direction.

Clause 65—The method of clause 64, wherein the step of actuating the control surface to return the rotor to the bypass position further includes rotating the control surface in a second rotational direction opposite the first rotational direction.

Clause 66—A manifold for collecting a tissue sample with a medical waste collection assembly including a manifold receiver and a suction inlet, the manifold including: a housing adapted to be removably engaged with the manifold receiver and defining a manifold volume, an accessory sleeve in fluid communication with the manifold volume, a tissue collecting channel, a bypass channel separate from the tissue collecting channel, and an outlet opening adapted to be in fluid communication with the suction inlet of the medical waste collection assembly when the housing is engaged with the manifold receiver; a filter element disposed within the housing; and an inlet fitting rotatable relative to the housing and adapted to receive a suction line and defining an inlet bore; a tray adapted to be removably positioned within the accessory sleeve and defining a tissue collecting cavity and porous features in communication with the tissue collecting passage when the tray is positioned within the accessory sleeve; and a control surface adapted to receive an input from a user to rotate the inlet fitting between a tissue collection configuration in which the inlet bore is in communication with tissue collecting channel and the porous features when the tray is positioned within the accessory sleeve, and a bypass configuration in which the inlet bore is in communication with the bypass channel.

Clause 67—The manifold of clause 66, wherein the housing further includes a lens positioned to provide magnification within tissue collecting cavity.

Clause 68—The manifold of clause 66, wherein the housing further defines a second accessory sleeve in fluid communication with the manifold volume with the manifold further including a second tray to be removably positioned within the second accessory sleeve and defining a second tissue collecting cavity and second porous features.

Clause 69—The manifold of clause 68, wherein the first and second accessory sleeves are diametrically positioned opposite the housing.

Clause 70—The manifold of clause 66, wherein the housing further includes a bypass inlet fitting adapted to removably receive another suction line with the bypass inlet fitting defining a fluid channel bypassing the tray without being in fluid communication with the tissue collecting cavity.

Clause 71—A manifold for collecting a tissue sample with a medical waste collection assembly including a manifold receiver and a suction inlet, the manifold including: a housing adapted to be removably engaged with the manifold receiver and defining a manifold volume and an outlet opening adapted to be in fluid communication with the suction inlet of the medical waste collection assembly when the housing is engaged with the manifold receiver; a filter element disposed within the housing; and a first inlet fitting movable relative to the housing and adapted to receive a first suction line and defining a first inlet bore; a second inlet fitting fixed relative to the housing and adapted to receive a first suction line and defining a first inlet bore with each of the first and inlet bores in fluid communication with the manifold volume; a tray adapted to be removably couple to the housing defining a tissue collecting cavity and porous features in communication with the tissue collecting passage when the tray is positioned within the accessory sleeve; and a control surface adapted to receive an input from a user to move the first inlet fitting between a tissue collection configuration in which the first inlet bore is in communication with the porous features when the tray is positioned within the accessory sleeve and a bypass configuration in which the first inlet bore is out of communication with the porous features.

Clause 72—The manifold of clause 71, wherein the second inlet bore is not in fluid communication with the tissue collecting cavity in the tissue collecting configuration.

Clause 73—The manifold of clause 71, wherein the housing further defines an accessory sleeve in fluid communication with the manifold volume with the tray configured to be removably positioned within the accessory sleeve.

Clause 74—A manifold for collecting a tissue sample with a medical waste collection assembly including a manifold receiver and a suction inlet, the manifold including: a housing adapted to be removably engaged with the manifold receiver and defining a manifold volume, an aperture, a bypass openings separate from the aperture, and an outlet opening adapted to be in fluid communication with the suction inlet of the medical waste collection assembly when the housing is engaged with the manifold receiver; a filter element disposed within the housing; and a first inlet fitting rotatable relative to the housing and adapted to receive a first suction line and defining a first inlet bore; a second inlet fitting rotatable relative to the housing and adapted to receive a second suction line and defining a second inlet bore; a control surface adapted to receive an input from a user to rotate the first and second inlet fittings between a tissue collection configuration in which the first inlet bore is in communication with the aperture and the second inlet bore is in communication with the one of bypass openings, and a bypass configuration in which the first inlet bore and the second inlet bore are each in communication a separate one of with the bypass openings.

Clause 75—The manifold of clause 74, wherein the housing further defines an accessory sleeve in communication with the manifold volume with the tray configured to be removably positioned within the accessory sleeve.

Clause 76—The manifold of clause 75, wherein the tissue collecting cavity of the tray is in communication with the aperture.

Clause 77—The manifold of clause 66, wherein the housing further includes orientation features within the accessory sleeve and the tray further includes complementary orientation features configured to removably engage the orientation features to permit coupling of the tray with the housing in a singular orientation.

Clause 78—The manifold of clause 77, wherein the orientation features of the housing are tabs and the complementary orientation features of the tray are rails extending from the side portions and configured to movably engage the tabs.

Clause 79—A manifold for collecting a tissue sample through a suction line, the manifold including: a housing defining a manifold volume, an inlet bore in fluid communication with the manifold volume and adapted to be in fluid communication with the suction line, an accessory sleeve in fluid communication with the manifold volume, and an outlet opening adapted to be in fluid communication with a suction source to provide a suction path from the suction line to the outlet opening through the accessory sleeve and the manifold volume; a filter element disposed within the housing in the suction path; a tray defining a tissue collecting cavity and porous features within the tissue collecting cavity with the tray adapted to be removably positioned within the accessory sleeve with the porous features in the suction path to collect the tissue sample; and a backflow prevention valve within the suction path between the tray and the filter element.

Clause 80—The manifold of clause 79, wherein the housing further defines a transfer bore having a first end opening into the accessory sleeve and a second end opening into the manifold volume, wherein the backflow prevention valve selectively covers the second end of the transfer bore to permit the flow of waste material from the accessory opening to the manifold volume.

Clause 81—The manifold of clause 80, wherein the housing further defines a bypass bore in fluid communication with the outlet opening bypassing the accessory sleeve to provide a bypass suction path from the bypass bore to the outlet opening through the manifold volume, wherein the backflow prevention valve selectively covers the second end of the transfer bore and an end of the bypass bore.

Clause 82—The manifold of clause 81, wherein the backflow prevention valve is a flapper valve unit.

Clause 83—The manifold of clause 82, wherein the flapper valve unit includes a first flapper selectively covering the second end of the transfer bore and a second flapper selectively covering the end of the bypass bore.

Clause 84—The manifold of clause 81, wherein the housing further includes a cap portion and a body portion coupled to the cap portion with the cap portion including a cap faceplate at least partially defining the manifold volume with the body portion, wherein the transfer bore extends through the cap faceplate and wherein the backflow prevention valve is coupled to the cap faceplate.

Clause 85—The manifold of clause 84, wherein the housing further includes a bypass fitting defining the bypass bore and adapted to receive another suction line with the bypass fitting coupled to the cap faceplate.

Clause 86—A manifold for collecting a tissue sample through a suction line, the manifold including: a housing defining a manifold volume, an inlet bore in fluid communication with the manifold volume and adapted to be in fluid communication with the suction line, an accessory sleeve in fluid communication with the manifold volume, and an outlet opening adapted to be in fluid communication with a suction source to provide a suction path from the suction line to the outlet opening through the accessory sleeve and the manifold volume, wherein the housing includes a body portion, and a cap portion coupled to the body portion and at least partially defining the manifold volume with the cap portion including a cap faceplate oriented on a first axis, and an upper barrier coupled to the cap faceplate and at least partially defining the accessory sleeve with the upper barrier oriented on a second axis angled relative to the first axis; and a tray defining a tissue collecting cavity and porous features within the tissue collecting cavity with the tray adapted to be removably positioned within the accessory sleeve with the porous features in the suction path to collect the tissue sample.

Clause 87—The manifold of clause 86, further including a lens coupled to the upper barrier and shaped to provide magnification within the accessory sleeve.

Clause 88—The manifold of clause 86, further including a filter element disposed within the manifold volume and in the suction path.

Clause 89—The manifold of clause 86, wherein the housing further defines an accessory opening into the accessory sleeve with the accessory opening defining a distal end of the manifold such that the accessory sleeve is oriented in a proximal-to-distal direction.

Clause 90—The manifold of clause 89, wherein the housing further includes an inlet fitting defining the inlet bore with the inlet fitting sized to receive the suction line, wherein the inlet fitting is coupled to and extending upwardly from the upper barrier.

Clause 91—The manifold of clause 86, wherein the housing further defines an accessory opening into the accessory sleeve with the accessory opening defining a lateral end of the manifold such that the accessory sleeve is oriented in a side-to-side direction.

Clause 92—The manifold of clause 91, wherein the housing further includes an inlet fitting defining the inlet bore with the inlet fitting sized to receive the suction line, wherein the inlet fitting is coupled to and extending distally from the upper barrier to define a distal end of the manifold.

Clause 93—The manifold of clause 86, wherein the housing further defines a bypass fitting coupled to the cap faceplate and defining a bypass bore in fluid communication with the outlet opening bypassing the accessory sleeve to provide a bypass suction path from the bypass bore to the outlet opening through the manifold volume.

Clause 94—A manifold for collecting a tissue sample through a suction line, the manifold including: a housing defining a manifold volume, an inlet bore in fluid communication with the manifold volume and adapted to be in fluid communication with the suction line, an accessory sleeve in fluid communication with the manifold volume, and an outlet opening adapted to be in fluid communication with a suction source to provide a suction path from the suction line to the outlet opening through the accessory sleeve and the manifold volume, wherein the housing includes an inlet fitting defining the inlet bore with the inlet fitting oriented on a first axis in a proximal-to-distal direction, and wherein the accessory sleeve is disposed about a second axis orthogonal to the first axis such that the accessory sleeve is oriented in a side-to-side direction; and a tray defining a tissue collecting cavity and porous features within the tissue collecting cavity with the tray adapted to be removably positioned within the accessory sleeve with the porous features in the suction path to collect the tissue sample.

Clause 95—The manifold of clause 94, further including a filter element disposed within the housing in the suction path.

Clause 96—A manifold for collecting a tissue sample through a suction line, the manifold includes: a housing defining a manifold volume, an inlet bore in fluid communication with the manifold volume and adapted to be in fluid communication with the suction line, and an outlet opening adapted to be in fluid communication with a suction source to provide a suction path from the suction line to the outlet opening through the manifold volume; a tray defining a tissue collecting cavity and porous features in communication with the tissue collecting cavity, the tray adapted to be removably coupled with the housing; and a filter element disposed within the housing in the suction path, wherein the housing includes a cap portion and a body portion removably coupled to one another such that the filter element is accessible to retrieve the tissue sample.

Clause 97—The manifold of clause 96, wherein each of the cap portion and body portion includes complementary coupling features for removably coupling the cap portion and the body portion.

Clause 98—The manifold of clause 97, wherein the complementary coupling features include at least one key and at least one keyway configured to removably engage one another by interference engagement.

Clause 99—The manifold of clause 98, wherein the at least one key and the at least one keyway comprise three keys and three keyways.

Clause 100—The manifold of clause 98, wherein the at least one keyway includes an insertion portion and a locking portion in communication with the insertion portion, wherein the insertion portion is wider than the locking portion.

Clause 101—A manifold for collecting a tissue sample through a suction line, the manifold comprising: a housing defining a manifold volume, an inlet bore in fluid communication with the manifold volume and adapted to be in fluid communication with the suction line, an accessory opening into an accessory sleeve in fluid communication with the manifold volume, and an outlet opening adapted to be in fluid communication with a suction source to provide a first suction path from the suction line to the outlet opening through the accessory sleeve and the manifold volume, wherein the housing comprises locating features disposed within the accessory sleeve; and a tray comprising a control surface, a sealing surface coupled to the control surface, a base portion, and side portion coupled to the base portion with the base and the side portions extending from the sealing surface and defining a tissue collecting cavity, and porous features within the base portion, wherein the control surface of the tray is adapted to receive an input from a user to move the sealing surface away from a portion of the accessory opening near the lower barrier to provide and locate a second suction path from the accessory opening to the outlet opening through the gap between the base portion of the tray and a lower barrier of the housing defining the accessory sleeve.

Clause 102—A manifold for collecting a tissue sample through a suction line, the manifold comprising: a housing defining a manifold volume, an inlet bore in fluid communication with the manifold volume and adapted to be in fluid communication with the suction line, an accessory opening into an accessory sleeve in fluid communication with the manifold volume, and an outlet opening adapted to be in fluid communication with a suction source to provide a first suction path from the suction line to the outlet opening through the accessory sleeve and the manifold volume, wherein the housing comprises locating features disposed within the accessory sleeve; and a tray comprising a sealing surface, a base portion, and side portion coupled to the base portion with the base and the side portions extending from the sealing surface and defining a tissue collecting cavity, and porous features within the base portion, wherein the tray is adapted to be removably coupled with the housing such that (i) the sealing surface seals the accessory opening, (ii) the tissue collecting cavity is positioned within the accessory sleeve and opening towards the inlet bore, and (iii) the base portion and/or the side portion engages the locating features within the accessory sleeve to provide a gap between the base portion of the tray and a lower barrier of the housing defining the accessory sleeve.

The foregoing description is not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

What is claimed is:

1. A manifold for collecting a tissue sample through a suction line, said manifold comprising:
    a housing defining a manifold volume, an inlet bore in fluid communication with said manifold volume and adapted to be in fluid communication with the suction line, an accessory opening opening into an accessory sleeve in fluid communication with said manifold volume, and an outlet opening adapted to be in fluid communication with a suction source to provide a first suction path from the suction line to said outlet opening through said accessory sleeve and said manifold volume, wherein said housing comprises locating features disposed within said accessory sleeve; and
    a tray comprising a sealing surface formed from resiliently flexible material, a base portion, and side portion coupled to said base portion with said base portion and said side portions extending from said sealing surface and defining a tissue collecting cavity, and porous features within said base portion, wherein said tray is adapted to be removably coupled with said housing such that (i) said sealing surface seals said accessory opening, (ii) said tissue collecting cavity is positioned within said accessory sleeve and opening towards said inlet bore, and (iii) at least one of said base portion and said side portion engages said locating features within said accessory sleeve to provide a gap between said base portion of said tray and a lower barrier of said housing defining said accessory sleeve,
    wherein said tray further comprises an upper control surface extending from said sealing surface opposite said tissue collecting cavity, and a lower control surface extending from said sealing surface opposite said tissue collecting cavity,
    wherein said lower control surface of said tray is adapted to receive an input from a user to be pivoted towards said upper control surface by said resiliently flexible material of said sealing surface to move a lower portion of said sealing surface away from said accessory opening near said lower barrier, wherein an upper portion of said sealing surface is configured to remain in contact with said accessory opening near an upper barrier of said housing defining said accessory sleeve for said manifold to provide and locate a second suction path from said accessory opening to said outlet opening through said gap between said base portion of said tray and said lower barrier of said housing defining said accessory sleeve.

2. The manifold of claim 1, wherein said housing further defines a bore having a first end within said lower barrier and a second end opening into said manifold volume.

3. The manifold of claim 1, wherein said locating features comprise plateaus defining a trough with said gap further defined between said base portion of said tray and said trough.

4. The manifold of claim 3, wherein said tray further comprises a foot extending from said base portion in a direction opposite said tissue collecting cavity, wherein said foot is positioned adjacent said plateaus when said tray is coupled with said housing.

5. The manifold of claim 1, wherein said housing further comprises orientation features within said accessory sleeve and said tray further comprises complementary orientation features configured to removably engage said orientation features to permit coupling of said tray with said housing in a singular relative orientation.

6. The manifold of claim 5, wherein said orientation features of said housing are grooves and said complementary orientation features of said tray are rails extending from said side portions.

7. The manifold of claim 3, wherein said trough extends to and defines a portion of said accessory opening.

* * * * *